United States Patent
Arnott et al.

(10) Patent No.: US 10,011,654 B2
(45) Date of Patent: Jul. 3, 2018

(54) ANTIBODIES DIRECTED TO IL-17A/IL-17F HETERODIMERS

(71) Applicant: GENENTECH, INC., South San Francisco, CA (US)

(72) Inventors: David P. Arnott, San Mateo, CA (US); Austin L. Gurney, Belmont, CA (US); Philip E. Hass, Moss Beach, CA (US); James M. Lee, San Bruno, CA (US); Yan Wu, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 14/491,641

(22) Filed: Sep. 19, 2014

(65) Prior Publication Data

US 2015/0232551 A1 Aug. 20, 2015

Related U.S. Application Data

(60) Continuation of application No. 11/953,733, filed on Dec. 10, 2007, now abandoned, which is a division of application No. 10/860,824, filed on Jun. 2, 2004, now abandoned.

(60) Provisional application No. 60/486,457, filed on Jul. 11, 2003, provisional application No. 60/485,599, filed on Jul. 8, 2003.

(51) Int. Cl.
| | | |
|---|---|---|
| *A61K 39/395* | (2006.01) | |
| *C07K 16/24* | (2006.01) | |
| *C07K 14/54* | (2006.01) | |
| *G01N 33/68* | (2006.01) | |

(52) U.S. Cl.
CPC .......... *C07K 16/244* (2013.01); *C07K 14/54* (2013.01); *G01N 33/6869* (2013.01); *C07K 2317/24* (2013.01); *C07K 2317/32* (2013.01); *C07K 2317/565* (2013.01); *C07K 2317/622* (2013.01); *C07K 2317/75* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 6,043,344 A | 3/2000 | Jacobs et al. | |
| 6,274,711 B1 | 8/2001 | Golstein et al. | |
| 6,486,303 B1 | 11/2002 | Moyle | |
| 6,902,735 B1 | 6/2005 | Jacobs et al. | |
| 7,790,163 B2 | 3/2010 | Jaspers et al. | |
| 7,790,862 B2 | 8/2010 | West et al. | |
| 8,003,099 B2 | 8/2011 | Auer et al. | |
| 8,609,093 B2 | 12/2013 | Masternak et al. | |
| 8,715,669 B2 | 5/2014 | Masternak et al. | |
| 2002/0177188 A1 | 11/2002 | Chen et al. | |
| 2002/0182673 A1 | 12/2002 | Chen et al. | |
| 2002/0187206 A1 | 12/2002 | Mirkov et al. | |
| 2003/0049255 A1 | 3/2003 | Sims et al. | |
| 2007/0160576 A1 | 7/2007 | Arnott et al. | |
| 2007/0218065 A1 | 9/2007 | Jaspers et al. | |
| 2009/0317400 A1 | 12/2009 | Masternak et al. | |
| 2010/0055103 A1 | 3/2010 | Chen et al. | |
| 2010/0080812 A1 | 4/2010 | Auer et al. | |
| 2011/0318301 A1 | 12/2011 | Arnott et al. | |
| 2012/0141492 A1 | 6/2012 | Masternak et al. | |

FOREIGN PATENT DOCUMENTS

| | | |
|---|---|---|
| AU | 2007226627 B2 | 3/2007 |
| AU | 2006294511 A1 | 4/2007 |
| AU | 2007311689 B2 | 4/2008 |
| EP | 0451 216 | 1/1996 |
| EP | 1326 974 | 12/2006 |
| JP | 11-1510045 A | 9/1999 |
| JP | 2000-186046 A | 7/2000 |
| WO | WO 1995/018826 | 7/1995 |
| WO | WO 1997/004097 | 2/1997 |
| WO | WO 1999/061617 | 12/1999 |
| WO | WO 2000/020593 | 4/2000 |
| WO | WO 2000/069463 | 11/2000 |
| WO | WO 2001/004304 | 1/2001 |
| WO | WO 2001/016318 | 3/2001 |
| WO | WO 2001/046420 | 6/2001 |
| WO | WO-2001/059120 A2 | 8/2001 |

(Continued)

OTHER PUBLICATIONS

Brüggemann et al. Comparison of the effector functions of human immunoglobulins using a matched set of chimeric antibodies. J Exp Med. Nov. 1, 1987;166(5):1351-61.*
Opposition by Ablynx, N.V. to EP Patent No. EP-B-1 641 822 (Genentech, Inc.) Feb. 14, 2014 (31 pages).
Opposition by Merck Patent GmbH. to EP Patent No. EP-B-1 641 822 (Genentech, Inc.), Feb. 14, 2014 (49 pages).
Opposition by Novartis AG to EP Patent No. EP-B-1 641 822( Genentech, Inc.), Feb. 14, 2014 (45 pages).
Opposition by Janssen Biotech, Inc. to EP Patent No. EP-B-1 641 822 (Genentech, Inc.), Feb. 17, 2014 (23 pages).
Opposition by Harvey Vaughan John Adams. to EP Patent No. EP-B-1 641 822 (Genentech, Inc.), Feb. 17, 2014 (28 pages).

(Continued)

*Primary Examiner* — Dong Jiang
(74) *Attorney, Agent, or Firm* — Morrison & Foerster LLP

(57) ABSTRACT

The present invention is directed to a novel naturally occurring human cytokine that is comprised of a heterodimer of interleukin-17 and interleukin-17F designated herein as interleukin 17A/F (IL-17A/F). Also provided herein are vectors and host cells comprising those nucleic acid sequences, chimeric polypeptide molecules comprising the polypeptides of the present invention fused to heterologous polypeptide sequences, specific antibodies which bind to the polypeptides of the present invention and to methods for producing the polypeptides of the present invention. Further provided herein are methods for treating degenerative cartilaginous disorders and other inflammatory diseases.

7 Claims, 17 Drawing Sheets

(56) References Cited

FOREIGN PATENT DOCUMENTS

| WO | WO-2001/059120 A3 | 8/2001 |
|---|---|---|
| WO | WO 2001/068848 | 9/2001 |
| WO | WO 2001/090358 | 11/2001 |
| WO | WO 2002/000690 | 1/2002 |
| WO | WO 2002/008284 | 1/2002 |
| WO | WO-02/058717 A2 | 8/2002 |
| WO | WO-02/058717 A3 | 8/2002 |
| WO | WO 2002/064739 | 8/2002 |
| WO | WO 2002/068452 | 9/2002 |
| WO | WO 2002/0177188 | 11/2002 |
| WO | WO 2004/042009 | 5/2004 |
| WO | WO 2005/000897 | 1/2005 |
| WO | WO 2005/010044 | 2/2005 |
| WO | WO 2005/051422 | 6/2005 |
| WO | WO 2006/088833 | 8/2006 |
| WO | WO 2006/132788 | 12/2006 |
| WO | WO 2007/038703 | 4/2007 |
| WO | WO 2007/106769 | 9/2007 |
| WO | WO 2008/047134 | 10/2007 |
| WO | WO 2008/067223 | 6/2008 |
| WO | WO 2009/082624 A2 | 7/2009 |
| WO | WO 2010/025400 | 3/2010 |

OTHER PUBLICATIONS

Proprietor's response to Notices of Oppositions to EP Patent No. EP-B-1 641 822 (Genentech, Inc.) Mar. 2, 2015 (51 pages).
Declaration of Sarah Hymowitz, Ph.D. dated Feb. 27, 2015 filed with Proprietor's Response to Notices of Opposition to EP Patent No. EP-B-1 641 822 (Genentech, Inc.), with Exhibits, Mar. 2, 2015 (14 pages).
Declaration of Philip Hass dated Feb. 27, 2015 filed with Proprietor's Response to Notices of Opposition to EP Patent No. EP-B-1 641 822 (Genentech, Inc.), with Exhibits, Mar. 2, 2015 (12 pages).
Declaration of Wenjun Ouyang dated Feb. 27, 2015 filed with Proprietor's Response to Notices of Opposition to EP Patent No. EP-B-1 641 822 (Genentech, Inc.), with Exhibits, Mar. 2, 2015 8 pages).
Kawaguchi et al., "IL-17 cytokine family", 2004, J. Allergy Clin. Immunol., vol. 114, No. 6, pp. 1265-1273.
Tan, et. al., "'Superhumanized' Antibodies: Reduction of Immunogenic Potential by Complementarity-Determining Region Grafting with Human Germline Sequences: Application to an Anti-CD28", Journal of Immunology, 2002, vol. 169, No. 2, pp. 1119-1125.
De Jager, et. al., "Simultaneous Detection of 15 Human Cytokines in a Single Sample of Stimulated Peripheral Blood Mononuclear Cells", Clinical and Diagnostic Laboratory Immunology, Jan. 2003, vol. 10, No. 1, pp. 133-139, filed as exhibit in Opposition by Harvey Vaughan John Adams. to EP Patent No. EP-B-1 641 822 (Genetech, Inc.), Feb. 17, 2014.
Excerpt Wikipedia entry "Multiprotein complex" (5 pages) filed as exhibit in Opposition by Merck Patent GmbH. to EP Patent No. EP-B-1 641 822 (Genentech, Inc.) , Feb. 14, 2014.
Honorati, et. al., "IL-17 enhances the susceptibility of U-2 OS osteosarcoma cells to NK cell lysis", Clin Exp Immunol, 2003, vol. 133, pp. 344-349, filed as exhibit in Opposition by Merck Patent GmbH. to EP Patent No. EP-B-1 641 822 (Genentech, Inc.) , Feb. 14, 2014.
Janeway, et. al., Immunologie, 2002, vol. 5, pp. 107-112, filed as exhibit in Opposition by Merck Patent GmbH. to EP Patent No. EP-B-1 641 822 (Genentech, Inc.), Feb. 14, 2014.
Minireview R&D Systems, 1998, filed as exhibit in Opposition by Merck Patent GmbH. to EP Patent No. EP-B-1 641 822 (Genentech, Inc.), Feb. 14, 2014.
Sequence alignment using the Basic Alignment Search Tool (NCBI): IL17A vs. AL355513.11 (8 pages), filed as exhibit in Opposition by Merck Patent GmbH. to EP Patent No. EP-B-1 641 822 (Genentech, Inc.) , Feb. 14, 2014.

Sequence alignment using the Basic Alignment Search Tool (NCBI): IL17F vs. AL355513.11 (13 pages), filed as exhibit in Opposition by Merck Patent GmbH. to EP Patent No. EP-B-1 641 822 (Genentech, Inc.) , Feb. 14, 2014.
Statement of Grounds and Particulars of Opposition by Amgen, Inc. to AU Patent Application No. 2007325316 (Genentech, Inc.), Nov. 8, 2013 (31 pages).
Applicant's Response Letter to Opposition by Amgen, Inc. to AU Patent Application No. 2007325316 ( Genentech, Inc.), May 21, 2014 (5 pages).
Applicant's Letter to Notice of Opposition by Amgen, Inc. to AU Patent Application No. 2007325316 (Genentech, Inc.) Jul. 16, 2014 (9 pages).
Applicant's Response to Examination report re EP Application No. 07864668, dated Oct. 15, 2012.
Declaration by Wenjun Ouyang for European Patent No. 1 641 822, European Opposition, for Proprietor, Genentech, Inc. and Opponents, Ablynx NV, et al., dated Feb. 27, 2015, 8 pages.
Annex GRH-1, "Practice Note CM 7 in Expert Witness Proceedings in the Federal Court of Australia" dated Jun. 4, 2013, filed as annex in Declaration of Geoffrey R. Hill dated Feb. 6, 2014 filed with Evidence of Support by Amgen, Inc. to AU Patent Application No. 2007325316 (Genentech, Inc.), Feb. 10, 2014 (3 pages), total pp. 4.
Annex GRH-2, Curriculum Vitae of Geoffrey R. Hill filed as annex in Declaration of Geoffrey R. Hill dated Feb. 6, 2014 filed with Evidence of Support by Amgen, Inc. to AU Patent Application No. 2007325316 (Genentech, Inc.), Feb. 10, 2014 (30 pages), total pp. 32.
Annex GRH-3, "CIB Track Record Statement: Geoffrey R. Hill", dated Feb. 6, 2014 filed with Evidence of Support by Amgen, Inc. to AU Patent Application No. 2007325316 (Genentech, Inc.), Feb. 10, 2014 (7 pages), total pp. 8.
Annex GRH-8, U.S. Appl. No. 10/000,157, (filed Oct. 30, 2001, Jian Chen, et al., "IL-17 homologous polypeptides and therapeutic uses thereof") (160 pages), filed as annex in Declaration of Geoffrey R. Hill dated Feb. 6, 2014 filed with Evidence of Support by Amgen, Inc. to AU Patent Application No. 2007325316 (Genentech, Inc.), Feb. 10, 2014, Total pp. 162.
Annex GRH-9, U.S. Appl. No. 11/606,192, (filled Nov. 29, 2006, David P. Arnott, et al., "L-17A/F heterologous polypeptides and Therapeutic uses thereof") (126 pages), filed as annex in Declaration of Geoffrey R. Hill dated Feb. 6, 2014 filed with Evidence of Support by Amgen, Inc. to AU Patent Application No. 2007325316 (Genentech, Inc.), Feb. 10, 2014, total pp. 195.
Annex GRH-10, Australian application No. 2007325316 (filed Nov. 20, 2007, David P. Arnott, et al., "L-17A/F heterodimeric polypeptides and therapeutic uses thereof") (annotated) (205 pages), filed as annex in Declaration of Geoffrey R. Hill dated Feb. 6, 2014 filed with Evidence of Support by Amgen, Inc. to AU Patent Application No. 2007325316 (Genentech, Inc.), Feb. 10, 2014, total pp. 207.
Annex AFL-1, "Practice Note CM 7 in Expert Witness Proceedings in the Federal Court of Australia" dated Jun. 4, 2013, filed as an annex in Declaration of Angel Francisco Lopez dated Feb. 7, 2014 filed with Evidence of Support by Amgen, Inc. to AU Patent Application No. 2007325316 (Genentech, Inc.), Feb. 10, 2014 (4 pages), total pp. 4.
Annex AFL-2, Australian application No. 2007325316 (filed Nov. 20, 2007, David P. Arnott, et al., "IL-17A/F heterodimeric polypeptides and therapeutic uses thereof") (205 pages), filed as an annex in Declaration of Angel Francisco Lopez dated Feb. 7, 2014 filed with Evidence of Support by Amgen, Inc. to AU Patent Application No. 2007325316 (Genentech, Inc.), Feb. 10, 2014, total pp. 207.
Annex AFL-3, Curriculum Vitae of Angel Francisco Lopez filed as an annex in Declaration of Angel Francisco Lopez dated Feb. 7, 2014 filed with Evidence of Support by Amgen, Inc. to AU Patent Application No. 2007325316 (Genentech, Inc.), Feb. 10, 2014 (18 pages), total pp. 21.
Annex LMK-1, Australian application No. 2004259638 (filed Jun. 2, 2004, James Lee, et al., "IL-17 A/F heterologous polypeptides and therapeutic uses thereof") (192 pages), filed as an annex in Declaration of Linda May Kennaugh dated Feb. 6, 2014 filed with

(56) References Cited

OTHER PUBLICATIONS

Evidence of Support by Amgen, Inc. to AU Patent Application No. 2007325316 (Genentech, Inc.), Feb. 10, 2014, total pp. 192.
Annex LMK-2, Australian application No. 2006214473 (filed Feb. 14, 2006, Beatriz M. Carreno, et al., "Interleukin-17f antibodies and other IL-17f signaling antagonists and uses therefor") (189 pages)(WO-2006/088833), filed as an annex in Declaration of Linda May Kennaugh dated Feb. 6, 2014 filed with Evidence of Support by Amgen, Inc. to AU Patent Application No. 2007325316 (Genentech, Inc.), Feb. 10, 2014, total pp. 190.
Annex LMK-3, Australian application No. 2006294511 (filing date Sep. 28, 2006, Steven D. Levin, et al., "IL-17A and IL-17F antagonists and methods of using the same") (300 pages), filed as an annex in Declaration of Linda May Kennaugh dated Feb. 6, 2014 with Evidence of Support by Amgen, Inc. to AU Patent Application No. 2007325316 (Genentech, Inc.), Feb. 10, 2014, total pp. 303.
Annex LMK-4, Australian application No. 2007226627 (filed Mar. 12, 2007, Scott R. Presnell, et al., "Antibodies that bind both IL-17A and IL-17F and methods of using the same") (87 pages), filed as an annex in Declaration of Linda May Kennaugh dated Feb. 6, 2014 with Evidence of Support by Amgen, Inc. to AU Patent Application No. 2007325316 (Genentech, Inc.), Feb. 10, 2014, total pp. 87.
Annex LMK-7, Australian application No. 2007311689, ( filed Oct. 18, 2007, Andrew George Popplewell, et al., "Antibody molecules which bind IL-17A and IL-17F", (47 pages), filed as an annex in Declaration of Linda May Kennaugh dated Feb. 6, 2014 with Evidence of Support by Amgen, Inc. to AU Patent Application No. 2007325316 (Genentech, Inc.), Feb. 10, 2014, total pp. 47.
Annex LMK-8, Australian application No. 2007325316 (filed Nov. 20, 2007, David P. Arnott, et al., "IL-17A/F heterodimeric polypeptides and therapeutic uses thereof") (206 pages), filed as an annex in Declaration of Linda May Kennaugh dated Feb. 6, 2014 with Evidence of Support by Amgen, Inc. to AU Patent Application No. 2007325316 (Genentech, Inc.), Feb. 10, 2014, total pp. 207.
Annex GRH-4, Ye et al., "Requirement of interleukin 17 receptor signaling for lung CXC chemokine and granulocyte colony-stimulating factor expression, neutrophil recruitment, and host defense", J. Exp. Med., 2001, vol. 194, No. 4, pp. 519-527, filed as annex in Declaration of Geofferey R. Hill dated Feb. 6, 2014 filed with Evidence of Support by Amgen, Inc. to AU Patent Application No. 2007325316 (Genentech, Inc.), Feb. 10, 2014, total pp. 10.
Annex GRH-5, Kennedy, et al., "The Addition of Interleukin-6 Inhibition to Standard Gvhd Prophylaxis Prevents Acute Gvhd: Interim Results of a Phase I/II Clinical Study", Abstract 908, American Society of Hematology, 201, filed as annex in Declaration of Geoffrey R. Hill dated Feb. 6, 2014 filed with Evidence of Support by Amgen, Inc. to AU Patent Application No. 2007325316 (Genentech, Inc.), Feb. 10, 2014, total 2 pages.
Annex GRH-6, Serody, et al., "The IL-17 differentiation pathway and its role in transplant outcome", Biol Blood Marrow Transplant, 2012, vol. 18, pp. S56-S61, filed as annex in Declaration of Geoffrey R. Hill dated Feb. 6, 2014 filed with Evidence of Support by Amgen, Inc. to AU Patent Application No. 2007325316 (Genentech, Inc.), Feb. 10, 2014, total 7 pages.,
Annex GRH-7, Bowman E., et al., "Rationale and safety of anti-interleukin-23 and anti-interleukin-17A therapy", Current Opinion on Infectious Diseases, Current Sciences, 2006, vol. 19, No. 3, pp. 245-252, filed as annex in Declaration of G Geoffrey R. Hill dated Feb. 6, 2014 filed with Evidence of Support by Amgen, Inc. to AU Patent Application No. 2007325316 (Genentech, Inc.), Feb. 10, 2014 , total 9 pages.
Annex AFL-4, Kolls et al. "Interleukin-17 family members and inflammation", Immunity, 2004, vol. 21, No. 4, pp. 467-476, filed as an annex in Declaration of Angel Francisco Lopez dated Feb. 7, 2014 filed with Evidence of Support by Amgen, Inc. to AU Patent Application No. 2007325316 (Genentech, Inc.), Feb. 10, 2014, total 11 pages.
Annex AFL-5, Dumont et al., "IL-17 cytokine/receptor families: Emerging targets for the modulation of inflammatory responses", Expert Opinion on Therapeutic Patents, 2003, vol. 13, pp. 287-303, filed as an annex in Declaration of Angel Francisco Lopez dated Feb. 7, 2014 filed with Evidence of Support by Amgen, Inc. to AU Patent Application No. 2007325316 (Genentech, Inc.), Feb. 10, 2014, total 18 pages.
Annex AFL-6, Aggarwal, et al., "IL-17: prototype member of an emerging cytokine family" Journal of Leukocyte Biology, 2002, vol. 71, pp. 1-8, filed as an annex in Declaration of Angel Francisco Lopez dated Feb. 7, 2014 filed with Evidence of Support by Amgen, Inc. to AU Patent Application No. 2007325316 (Genentech, Inc.), Feb. 10, 2014, total 9 pages.
Annex AFL-7, Hymowitz et al., "IL-17s adopt a cystine knot fold: structure and activity of a novel cytokine, IL-17F, and implications for receptor binding", The EMBO Journal 2001, vol. 20, No. 19, pp. 5332-5341, filed as an annex in Declaration of Angel Francisco Lopez dated Feb. 7, 2014 filed with Evidence of Support by Amgen, Inc. to AU Patent Application No. 2007325316 (Genentech, Inc.), Feb. 10, 2014, total 11 pages.
Annex LMK-5, Chang et al. "A novel heterodimeric cytokine consisting of IL-17 and IL-17F regulates inflammatory responses", Cell Research, 2007, vol. 17, pp. 435-440, filed as an annex in Declaration of Linda May Kennaugh dated Feb. 6, 2014 with Evidence of Support by Amgen, Inc. to AU Patent Application No. 2007325316 (Genentech, Inc.), Feb. 10, 2014, total 7 pages.
Annex LMK-6, Kuestner, et al., "Identification of the IL-17 receptor related molecule IL-17RC as the receptor for IL-17F", The Journal of Immunology, 2007, vol. 179, pp. 5462-5473, filed as an annex in Declaration of Linda May Kennaugh dated Feb. 6, 2014 with Evidence of Support by Amgen, Inc. to AU Patent Application No. 2007325316 (Genentech, Inc.), Feb. 10, 2014, total 14 pages.
Declaration of Angel Francisco Lopez dated Feb. 7, 2014 with exhibits filed with Evidence of Support by Amgen, Inc. to AU Patent Application No. 2007325316 (Genentech, Inc.), Feb. 10, 2014 (30 pages).
Declaration of Linda May Kennaugh dated Feb. 6, 2014 with exhibits filed with Evidence of Support by Amgen, Inc. to AU Patent Application No. 2007325316 (Genentech, Inc.), Feb. 10, 2014 (1047 pages), total pp. 1049.
U.S. Appl. No. 60/085,579, filed May 15, 1998, Wood, W.I.
U.S. Appl. No. 60/087,340, filed May 29, 1998, Ebner et al.
U.S. Appl. No. 60/099,805, filed Sep. 10, 1998, Ebner et al.
U.S. Appl. No. 60/113,621, filed Dec. 23, 1998, Wood, W.I.
U.S. Appl. No. 60/131,965, filed Apr. 30, 1999, Ebner et al.
"qk39g09.x1 NCI_CGAP_Co8 *Homo sapiens* cDNA clone Image:1871392 3', mRNA sequence." XP002154807, (1998).
$1^{st}$ Declaration of Dr. Stefan Pflanz.
$2^{nd}$ Declaration of Dr. Stefan Pflanz.
Aarvak et al. "IL-17 is produced by some proinflammatory ThI/Th0 cells but not by Th2 cells", J. Immunology162:1246-1251,1999.
Aggarwal et al. "IL-17: prototype member of an emerging cytokine family", Journal of Leukocyte Biology71:1-8, 2002.
Aggarwal et al. "Interleukin-23 promotes a distinct CD4 T cell activation state characterized by the production of interleukin-17", Journal of Biological Chemistry 278:1910-1914, 2003.
Albanesi et al. "Interleukin-17 is produced by both Th1 and Th2 lymphocytes and modulates interferon-γ- and interleukin-4-induced activation of human keratinocytes" J Investigative Dermatology 115(1):81-87, 2000.
Alderson et al. "Molecular and biological characterization of human 4-1BB and its ligand", European Journal of Immunology 24(9):2219-2227, 1994.
Anglade et al. "Interleukin-10 immunoadhesin production by a replication-defective adenovirus", J. Immunology Methods 202:41-48, 1997.
Appendix A: Experiment: Stimulation of THP-1 cells with hIL-17C, 131, 17B, hL-17A, LPS.
Appendix B: Figures 1-4.
Appendix C: R & D Systems.
Avramescu et al. "Mixed-matrix membranes absorbers for protein separation", J. Chromatology A 1006:171-183, 2003.
Balsa et al "IL-15 and the initiation of cell contact-dependent synovial fibroblast-T lymphocyte cross-talk in rheumatoid arthritis: effect of methotrexate", J. Immunology 173:1463-1476, 2004.

(56) References Cited

OTHER PUBLICATIONS

Becher et al. "Experimental autoimmune encephalitis and inflammation in the absence of interleukin-12", Journal of Clinical Investigation 110(4):493-497, 2002.
Becher et al. "IL-23 produced by CNS-resident cells controls T cell encephalitogenicity during the effector phase of experimental autoimmune encephalomyelitis", Journal of Clinical Investigation 112(8):1186-1191, 2003.
Boder et al. "Directed evolution of antibody fragments with monovalent femtomolar antigen-binding affinity", Proc. Natl. Acad. Sci. USA 97:10701-10705, 2000.
Bowman et al. "Rationale and safety of anti-interleukin-23 and anti-interleukin-17A therapy", Current Opinion Infectious Diseases 19(3):245-252, 2006.
Brizzard et al. "Epitope tagging of recombinant proteins", Current Protocols in Neuroscience 5.8: (5.8.1-5.8.10), 1997.
Burchill et al. "Inhibition of interleukin-17 prevents the development of arthritis in vaccinated mice challenged with Borrelia burgdorferi", Infection and Immunity 71(6):3437-3442, 2003.
Bush et al. "Reduction of joint inflammation and bone erosion in a rat adjuvant arthritis by treatment with interieukin-17 receptor IgG1 Fc fusion protein", Arthritis Rheumatism 46(3):802-805, 2002.
Cai et al. "Regulation of granulocyte colony-stimulating factor gene expression by interleukin-17", Immunology Letters 62:51-58, 1998.
Carrano et. al. "Measurement and purification of human chromosomes by flow cytometry and sorting", Proc. Natl. Acad. Sci. USA 76(3):1382-1384, 1979.
Chang et al. "A novel heterodimeric cytokine consisting of IL-17 and IL-17F regulates inflammatory responses", Cell Research 17:435-440, 2007.
Chabaud et al. "Enhancing effect of IL-17 on IL-1-induced IL-6 and leukemia inhibitory factor production by rheumatoid arthritis snyoviocytes and its regulations by Th2 Cytokines" Journal of Immunology 161:409-414, 1998.
Chabaud et al. "Human interleukin-17: a T cell-derived proinflammatory cytokine produced by the rheumatoid synovium", Arthrtis & Rheumatism 42(5):963-970, 1999.
Chabaud et al. "IL-17 derived from juxta-articular bone andsynovium contributes to joint degradation in rheumatoid arthritis", Arthritis Research 3:168-177, 2001.
Chaly et al. "Expression of IL-8 gene in human monocytes and lymphocytes: differential regulation by TNF and IL-1", Cytokine 12(6):636-643, 2000.
Chambers et al. "Co-stimulation in T cell responses", Current Opinion Immunology. 9(3):396-404, 1997.
Chen et al. "In vitro scanning saturation mutagenesis of all the specificity determining residues in an antibody binding site", Protein Engineering 12:349-356, 1999.
Constantinescu et al. "Antibodies against IL-12 prevent superantigen-induced and spontaneous relapses of experimental autoimmune encephalomyelitis", Journal lmmunology 161:5097-5104, 1998.
Cua et al. "Interleukin-23 rather than interleukin-12 is the critical cytokine for autoimmune inflammation of the brain", Nature 421(6924):744-748, 2003.
Declaration by Wenjun Ouyang under 37 C.F.R. 1.132.
Declaration of Dr. Stefan Pflanz.
Declaration of Ellen Filvaroff.
Declaration of Richard Vandlen.
Declaration of Roland Grenningloh and Julie DeMartino; Experimental Test Report: MAB317 binding and neutralization.
Declaration of Geoffrey R. Hill dated Feb. 6, 2014 with Exhibits.
Declaration of Angel Francisco Lopez dated Feb. 7, 2014 with Exhibits AFL-1 to AFL-7.
Declaration of Linda May Kennaugh dated Feb. 6, 2014 with Exhibits LMK-1 to LMK-7.
De Jager et al. "Simultaneous detection of 15 human cytokines in a single sample of stimulated peripheral blood mononuclear cells", Clinical and Diagnostic Laboratory Immunology10(1):133-139, 2003.

De Smet et al. "The activation of human gene MAGE-1 in tumor cells is correlated with genome-wide demethylation", Proc. Natl. Acad. Sci. USA 93(14):7149-7153, 1996.
Dubowchik et al. "Receptor-mediated and enzyme-dependent targeting of cytotoxic anticancer drugs", Pharmacology Therapeutics 83(2):67-123, 1999.
Dumont et al. "IL-17 cytokine/receptor families: Emerging targets for the modulation of inflammatory responses,", Expert Opinion on Therapeutic Patents 13:287-303, 2003.
Except Wikipedia entry "Multiprotein complex".
Ely et al. "Structural basis of receptor sharing by inerleukin 17 cytokines", Nature Immunology 10(12):1245-1252, 2009.
Ferretti et al. "IL-17, produced by lymphocytes and neutrophils, is necessary for lipopolysaccharide-induced airway neutrophilia: IL-15 as a possible trigger", Journal of Immunology 170(4):2106-2112, 2003.
Finn et al. "Introduction third keystone symposium on cellular immunology and the immunotherapy of cancer", Journal of Immunotherapy 21(2):114-118, 1998.
Fleit et al. "The human monocyte-like cell line THP-1 expresses FcγRI and FcγRII", Journal of Leukocyte Biology 49:556-565,1991.
Fossiez et al. "T cell interleukin-17 induces stromal cells to produce proinflammatory and hematopoietic cytokines", Journal of Experimental Medicine 183(6):2593-2603, 1996.
Fujino et al. "Increased expression of interleukin 17 in inflammatory bowel disease", Gut 52:65-70, 2003.
Gaffen, SL."Structure and signaling in the IL-17 receptor superfamily", Nature Reviews Immunology 9:556-567, 2009.
Genbank Accession No. AAC50341, Jan. 16, 1996.
Genbank Accession No. AAK83350, Oct. 12, 2001.
Genbank Accession No. NM_002190, 1999.
Gerhardt et al. "Structure of IL-17A in complex with a potent, fully human neutralizing antobody", J. Mol. Biol. 394(5):905-921, 2009.
Gerstner et al. "Sequence plasticity in the antigen-binding site of therapeutic Anti-HER2 antibody", J. Mol. Biol. 321:851-862, 2002.
Goodin et al. "Disease modifying therapies in multiple sclerosis", Neurology 170(58):169-178, 2001.
Gubler et al. "Co expression of two distinct genes is required to generate secreted bioactive cytotoxic lymphocyte maturation factor", Proc. Natl. Acad. Sci. USA 88:4143-4147, 1991.
Haak et al. "IL-17A and IL-17F do not contribute vitally to autoimmune neuro-inflammation in mice", Journal of Clinical Investigation 119(1):61-69, 2009.
Hellings et. al. "Interleukin-17 orchestrates the granulocyte influx into airways after allergen inhalation in a mouse model of allergic asthma", American Journal of Respiratory Cell and Molecular Biology 28:42-50, 2003.
Hellstrom et al. "T cell immunity to tumor antigens." Critical Reviews in Immunology 18(1-2): 1-6,1998.
Homey et al. "Up-regulation of macrophage inflammatory protein-3a/CCL20 and CC chemokine receptor 6 in psoriasis", Journal of Immunology 164(12):6621-6632, 2000.
Honorati et al. "IL-17 enhances the susceptibility of U-2 OS osteosarcoma cells to NK cell lysis", Clin. Exp Immunology133:344-349, 2003.
Hornbeck, P. "Assays for antibody production", Current Protocols in Immunology 1(2):.2.1.1-2.1.22,1991.
Hurst et al. "New IL-17 family members promote Th1 or Th2 responses in the lung: in vivo function of the novel cytokine IL-25", Journal of Immunology 169:443-453, 2002.
Hymowitz et al. "IL-17s adopt a cystine knot fold: structure and activity of a novel cytokine, IL-17F, and implications for receptor binding", EMBO Journal 20(19):5332-5341, 2001.
Janeway et al. "The immune system in health and disease $5^{th}$ ed.", Immunologie 5:107-112, 2002.
Janeway et al. "Immun Biology 5, The Immune system in Health and Disease", pp. 102-103 2001.
Jenkins, M. "The ups and downs of T cell costimulation", Immunity 1(6):443-446, 1994.
Jonker et al. "Autoimmunity in non-human primates: the role of major histocompatibility complex and T cells, and implications for therapy", Human Immunology 32:31-40, 1991.

(56) References Cited

OTHER PUBLICATIONS

Joosten et al. "Dual role of IL-12 in early and late stages of murine collagen type II arthritis", Journal of Immunology 159:4094-4102, 1997.

Jovanovic et al. "IL-17 stimulates the production and expression of proinflammatory cytokines, IL-13 and TNF-a, by human macrophages", J. Immunology 160: 3513-3521, 1998.

June et al. "The B7 and CD28 receptor families", Immunology Today 15(7): 321-331, 1994.

Kennedy et al. "Mouse IL-17: A cytokine preferentially expressed by apTCR+CD4-CD8-T cells" Journal of Interferon and Cytokine Research 16(8): 611-617, 1996.

Kennedy et al. "The addition of interleukin-6 inhibition to standard Gvhd prophylaxis prevents acute Gvhd: Interim results of a Phase I/II clinical study", Abstract 908, American Society of Hematology, 2013.

Kolls et al. "Interleukin-17 family members and inflammation", Immunity 21(4):467-476, 2004.

Kotake et al. "IL-17 in synovial fluids from patients with rheumatoid arthritis is a potent stimulator of osteoclastogenesis", Journal of Clinical Investigation 103(9): 1345-1352, 1999.

Kuestner et al. "Identification of the IL-17 receptor related molecule IL-17RC as the receptor for IL-17F". Journal of Immunology 179: 5462-5473, 2007.

Kurasawa et al. "Increased interleukin-17 production in patients with systemic sclerosis" Arthritis and Rheumatism 43(11): 2455-2463, 2000.

Kwon et al. "Manipulation of T cell costimulatory and inhibitory signals for immunotherapy of prostate cancer", Proc. Natl. Acad. Sci. USA 94(15): 8099-8103, 1997.

Laan et al. "Neutrophil recruitment by human IL-17 via C-X-C-chemokine release in the airways", Journal of Immunology, 162: 2347-2352, 1999.

Lee et al. "IL-17E, a novel proinflarnmatory ligand for the IL-17 receptor homolog IL-17Rh1", Journal of Biological Chemistry 276(2):1660-1664, 2001.

Li et al. "Cloning and characterization of IL-17B and IL-17C two new members of the IL-17 cytokine family", PNAS 97(2):773-778, 2000.

Lippens et. al. "Therapeutic efficacy of IL-17A versus IL-17F neutralization in mCIA, a mouse model of rheumatoid arthritis", Novimmune S.A. 1228 Plan Les Ouates, Geneva Switzerland.

Linden et al. "Airway neutrophils and interleukin-17", Eur Respir. J. 15:973-977, 2000.

Linsley et al. "The role of the CD28 receptor during T cell responses to antigen", Annu. Rev. Immunol. 11:191-212, 1993.

Lock et al. "Gene-microarray analysis of multiple sclerosis lesions yields new targets validated in autoimmune encephalomyelitis", Nature Medicine 8(5):500-508, 2002.

Lonberg et al. "Human antibodies from transgenic mice", Intern. Rev. Immunology 13:65-93, 1995.

Lu et al. "Acquired antagonistic activity of a bispecific diabody directed against two different epitopes on vascular endothelial growth factor receptor 2," J. Immunol. Meth. 230:159-171, 1999.

Lubberts et al. "IL-1-independent role of IL-17 in synovial inflammation and joint destruction during collagen-induced arthritis", Journal of Immunology 167:1004-1013, 2001.

Lynch et al. "Flt3 ligand induces tumor regression and antitumor immune responses in vivo." Nature Medicine 3(6): 625-631, 1997.

Mabry et al. "Engineering of stable bispecific antibodies targeting IL-17A and IL-123," Protein Engineering Design and Selection 23:115-127, 2010.

Matusevicius et al. "Interleukin-17 mRNA expression in blood and CSF mononuclear cells is augmented in multiple sclerosis", Multiple Sclerosis 5:101-104, 1999.

McCafferty et al. "Phage antibodies: filamentous phage displaying antibody variable domains", Nature 348:552-554, 1990.

McDonald et al. "A structural super family of growth factors containing a cystine knot motif", Cell 73:421-424, 1993.

Melero et al. "Monoclonal antibodies against the 4-1BB T-cell activation molecule eradicate establsihed tumors", Nature Medicine 3(6):682-685,1997.

Minireview R&D Systems, 1998.

Miyamoto et al. "Endogenous IL-17 as a mediator of neutrophil recruitment caused by endotoxin exposure in mouse airways", Journal of Immunology 170(9):4665-4472, 2003.

Moseley et al. "Interleukin-17 family and IL-17 receptors", Cytokine and Growth Factor Reviews 14(2):155-174, 2003.

Nakae et al. "Antigen-specific T cell sensitization is impaired in IL-14-deficient mice, causing suppresiion of allergic cellular and humoral responses", Immunity17:375-387, 2002.

Nakae et al. "Suppression of immune induction of collagen-induced arthritis in IL-17-deficient mice", Journal of Immunology 171:6173-6177, 2003.

Nelson et. al. "Demystified monoclonal antibodies", Journal of Clinical Pathology 53:111-117, 2002.

Nielsen et al. "Identification of prokaryotic and eukaryotic signal peptides and prediction of their cleavage sites", Protein Engineering 16(1):1-6, 1997.

Numasaki et al. "Interleukin-17 promotes angiogenesis and tumor growth", Blood 101(7):2620-2627, 2003.

Ogawa et al. "Purification and characterization of transforming growth factor-82.3 and -81.2 heterodimers from bovine bone", Journal of Biological Chemistry 27(4):2325-2328, 1992.

Okuda et al. "IL-6 plays a crucial role in the induction phase of meylin oligodendrocyte glycoprotein 35-55 induced experimental autoimmune encephalomyelitis", Journal of Neuroimmunology101:188-196, 1999.

Oppman et al. "Novel p19 protein engages IL-12p40 to form a cytokine, IL-23, with biological activities similar as well as distinct from IL-12", Immunity13:715-725, 2000.

Ozenci et al. "Cytokines in multiple sclerosis: methodological aspects and pathogenic implications", Multiple Sclerosis 8:396-404, 2002.

Page et al. "Plasma cell-like morphology of Th1-cytokine-producing cells associated with the loss ofCD3 expression", Am. J. Path. 164:409-417, 2004.

Peterson et al. "Immunization with melan-A peptide-pulsed peripheral blood mononuclear cells plus recombinant human interleukin-12 induces clinical activity and T-cell responses in advanced melanoma", Journal of Clinical Oncology 21(12):2342-2348, 2003.

Product Data Sheet.

Product information sheet of R&D systems Inc. dated Mar. 5, 1998 on Monoclonal Anti-human IL-17 antibody MAB317.

Product sheet from Dendritics Monoclonal Anti-Human IL-17A Product Reference: DDX0330-DDX0339.

Product sheet from R7D "Human IL-17 Antibody", Catalog No. AF-317-NA.

R&D Systems 2003 Catalog.

R&D Systems catalog entry for MAB317 (1998) (revised 2012).

R&D Systems Online Product Search: IL-17 antibodies.

Rickel et al. "Identification of functional roles for both IL-17RB and IL-17RA in mediating IL-25-induced activities", Journal of Immunology 181:4299-4310, 2008.

Rohn et al. "Vaccination against IL-17 suppresses autoimmune arthritis and encephalomyelitis", Eur. J. Immunology 36:2857-2867, 2006.

Sabat et al. "IL-22 and IL-17; an overview", IL-17, IL-22 and their producing cells: role in inflammation and autoimmunity (EDS), V. Quesniaux et al. Springer Basel, 2013, pp. 11-35.

Schwartz, R. "Costimulation of T lymphocytes: the role of CD28, CTLA-4, and B7/BB1 in interleukin-2 production and immunotherapy", Cell. 71(7):1065-1068, 1992.

Sequence alignment using the Basic Alignment Search Tool (NCBI): IL17A vs. AL355513.11.

Sequence alignment usin the Basic Alignment Search Tool (NCBI): ILI7F vs. AL355513.11.

Serody et al."The IL-17 differentiation pathway and its role in transplant outcome", Biology of Blood Marrow Transplantation 18:S56-S61, 2012.

(56) References Cited

OTHER PUBLICATIONS

Shalom-Barak et al. "Interleukin-17-induced gene expression in articular chondrocytes is associated with activation of mitogen-activated protein kinases and NF-KB" Journal of Biological Chemistry 273(42):27467-27473, 1998.
Singh et al. "The paradigm of Th1 and Th2 cytokines", Immunologic Research 20:147-161, 1999.
Starnes et al. "Cutting edge: IL-17F, a novel cytokine selectively expressed in activated T cells ant-monocytes, regulates angiogenesis and endothelial cell cytokine production", J. Immunology 167:4137-4140, 2001.
Supplement I to Table 1, Overview of Antibody Properties, pp. 1-2.
Supplement 2 to Table 1, Overview of Antibody Properties, pp, 1-8.
Supplement 3 to Table 1, Overview of Antibody Properties, pp. 1-6.
Table I, Overview of Antibody Properties.
Takei et al, "5'-,3'-inverted thymidine-modified antisense oligodeoxynucleotide targeting midkine: Its design and application for cancer therapy", Journal of Biological Chemistry 277(26): 23800-23806, 2002.
Tarner et al, "Gene therapy in autoimmune disease", Current Opinion in Immunology13:676-682, 2001.
Teunissen et al. "Interleukin-17 and interferon-y synergize in the enhancement of proinflammatory cytokine production by human keratinocytes", J. Invest. Dermatol. 111:645-649, 1998.
Thiele et al. "Cell-cell contact of human T cells with fibroblasts, changes lymphocytic mRNA expression: Increase mRNA expression of interleukin 17-A and interleukin-17-receptor", European Cytokine Network 11(1) :53-58, 2000.
Thurner et al."Vaccination with mage-3A1 peptide-pulsed mature, monocyte-derived dendritic cells expands specific cytotoxic T cells and induces regression of some metastases in advanced stage IV melanoma", Journal of Experimental Medicine 190: 1669-1678, 1999.
Tompkins et al. "An array of possibilities for multiple sclerosis", Nature Medicine 8(5):451.453, 2002.
Toy et al. "Cutting edge: interleukin 17 signals through a heteromeric receptor complex", Journal of Immunology177:36-39, 2006.
Uyttenhove et al. "Development of an anti-IL-17A auto-vaccine that prevents experimental auto-immune encephalomyelitis", Eur. J, Immunol. 36:2868-2874, 2006.
Valjakka et al. "Crystal structure of an in vitro affinity- and specificity-matured anti-testosterone fab in complex with testosterone", Journal Biological Chemistry 277:44021-44027, 2002.
Van Bezooijen et al. "Interleukin-17: a new hone acting cytokine in vitro", Journal of Bone and Mineral Research 14(9):1513-1521, 1999.
Van Kooten et al. "Interleukin-17 activates human renal epithelial cells in vitro and is expressed during renal allograft rejection", J. Am Soc Nephrol 9:1526-1534, 1998.
Von Heijne, G. "A new method for predicting signal sequence cleavage sites", Nucleic Acids. Research 14(11): 4683-4690, 1986.
Walunas et al. "CTLA-4 can function as a negative regulator of T cell activation", Immunity1(5):405-413, 1994.
Wiendl et al. "Therapeutic approaches in multiple sclerosis", Biodrugs 16(3):183-200, 2002.
Witowski et al, "IL-17 stimulates intraperitoneal neutrophil infiltration through the release of GROα chemokine from mesothelial cells", Journal of Immunology 165:5814-5821, 2000.
Woltman et al."Interleukin-17 and CD40-ligand synergistically enhance cytokine and chemokine production by renal epithelial cells", J Am Soc Nephrol.11:2044-2055, 2000.
Wright et al. "Identification of an interleukin 17F/17A heterodimer in activated human CD4+ T cells", Journal of Biological Chemistry 282(18): 13447-13455, 2007.
Wright et al. "The human IL-17F/IL-17A heterodimeric cytokine signals through the IL-17RA/IL-17RC receptor complex", J. Immunology 181:2799-2805, 2008.

Xiong et al. "Regulation of IL-8 expression by nitric oxide in human pancreatic adenocarcinoma", J. Interferon Cytokine Res. 21(7):529-537, 2001.
Yamaguchi et al. "O:-17B and IL-17c are associated with TNF-α production and contribute to the exacerbation of inflammatory arthritis", Journal of Immunology179:7128-7136, 2007.
Yao et al. "Herpesvirus saimiri encodes a new cytokine, IL-17, which binds to a novel cytokine receptor", Immunity 3:811-821, 1995.
Yao et al. "Human IL-17: a novel cytokine derived from T Cells", Journal of Immunology 155(12): 5483-5486, 1995.
Yao et al. "Molecular characterization of the human interleukin (IL)-17 receptor", Cytokine 9(11): 794-800, 1997.
Yayon et al. "Isolation of peptides that inhibit binding of basic fibroblast growth factor to its receptor from a random phage-epitope library," Proc. Natl. Acad. Sci. USA 90:10643-10547, 1993.
Yazaki et al. "Humanization of the anti-CEA T84.66 antibody based on crystal structure data", Protein Engineering Design&Selection17(5):481-489, 2004.
Ye et al. "Interleukin-17 and lung host defense against klebsiella pneumoniae infection", American Journal of Respiratory Cell and Molecular Biology 25:335-340, 2001.
Ye et al. "Requirement of interleukin 17 receptor signaling for lung CXC chemokine and granulocyte colony-stimulating factor expression, neutrophil recruitment, and host defense", J. Exp. Med. 194(4):519-527, 2001.
Zenepax Product Insert 1997 Version.
Zhang et al. "Induction of experimental autoimmune encephalomyelitis in IL-I2 receptor-β2-deficient mice:IL-12 responsiveness is not required in the pathogenesis of inflammatory demyelination in the central nervous system", The Journal of Immunology170:2153-2160, 2003.
Delagrave et al. "Effects of Humanization by Variable Domains Resurfacing on the Antiviral Activity of a Single-Chain Antibody Against Respiratory Syncytial Virus," *Protein Engineering* 12(4):357-362, (1999).
Kawaguchi et al. "Identification of a Novel Cytokine, ML-1, and Its Expression in Subjects With Asthma," *The Journal of Immunology* 167:4430-4435, (2001).
Kelley et al. "Antigen Binding Thermodynamics and Antiproliferative Effects of Chimeric and Humanized Anti-p185$^{HER2}$ Antibody Fab Fragments," *Biochemistry* 31:5434-5441, (1992).
Harding, F.A. et al. (May/Jun. 2010). "The Immunogenicity of Humanized and Fully Human Antibodies. Residual Immunogenicity Resides in the CDR Regions," *mABS* 2(3):256-265.
Marks, J.D. et al. (1991). "By-Passing Immunization. Human Antibodies from V-Gene Libraries Displayed on Phage," *J. Mol. Biol.* 222:581-597.
Molet, S. et al. (2001). "IL-17 is Increased in Asthmatic Airways and Induces Human Bronchial Fibroblasts to Produce Cytokines," *J. Allergy Clin. Immunol.* 108(3):430-438.
Wong, C.K. et al. (2000). "Elevation of Proinflammatory Cytokine (IL-18, IL-17, IL-12) and Th2 Cytokine (IL-4) Concentrations in Patients with Systemic Lupus Erythematosus," *Lupus* 9:589-593.
Notice of Entitlement for Australian patent Application No. 2008229758, dated Dec. 19, 2011, 1 page.
Assignment details for U.S. Appl. No. 11/606,192, filed Nov. 29, 2006, 1 page.
European Patent Office Form 1002, Sep. 23, 2010), for European Applicants Reference No. CMD/FP6716997, IL-17 A/F Heterologous Polypeptides and Therapeutic Uses Thereof, 1 page.
U.S. Appl. No. 11/762,738, "IL1-7 and IL-23 Antagonists and Methods of Using the Same," filed Jun. 13, 2007, 175 pages.
Declaration of Dr. Seon Hee Chang dated Aug. 11, 2016, for European Opposition for EP 1 641 822-B1 Proprietor Genentech, Inc., Opponents Ablynx NV, et al., 13 pages.
Suzuki, M. et al. (2000). "The Role of p38 Mitogen-Activated Protein Kinase in IL-6 and IL-8 Production From the TNF-α- or IL-1β-Stimulated Rheumatiod Synovial Fibroblasts," *FEBS Letter* 465:23-27.

(56) References Cited

OTHER PUBLICATIONS

Umland, S.P. et al. (Oct. 1997). "The Inhibitory Effects of Topically Active Glucocorticoids on Il-4, Il-5, and Interferon-γ Production by Cultured Primary CD4+ T Cells," *J. Allergy Clin. Immunol.* 100(4):511-519.
Nakae, S. et al. (Sep. 2002). "Antigen-Specific T Cell Sensitization is Impaired in Il-17 Deficient Mice, Causing Suppression of Allergic Cellular and Humoral Responses," *Immunity* 17:375-387.
Response to Final Office action for U.S. Appl. No. 11/606,192, filed Nov. 29, 2006, dated Nov. 3, 2009, Request for Continued Examination, 10 pages.
Excerpt from AACR regulations concerning public availability of antibodies, European Opposition for European Patent No. 1 641 822-B1, p. 265.
Email from Sadie Buckallew to Sebastian Hoepfner, dated Jul. 7, 2016, from AACR Journals about author agreements, 3 pages.
Tartour, E. et al. (Aug. 1, 1999). "Interleukin 17, a T-Cell-Derived Cytokine, Promotes Tumorigenicity of Human Cervical Tumors in Nude Mice," *Cancer Research* 59:3698-3704.
E-mail from Frank Mortari to Tung-Gia Du, dated Jan. 22, 2014, Confirmation of R&D Systems on MAB317 sales data and product data sheet, 1 page.
Request for Continued Examination of U.S. Appl. No. 13/039,201, filed Mar. 2, 2011, dated Nov. 7, 2012, in the Examination of U.S. Publication No. US-2011/0256126-A1, 12 pages.
Response to Final Office Action dated May 3, 2010, for U.S. Appl. No. 11/606,192, filed Nov. 29, 2006, 13 pages.
Response to Non-Final Office Action dated Jan. 22, 2009, for U.S. Appl. No. 11/606,192, filed Nov. 29, 2006, 10 pages.
Final Office Action dated Oct. 2, 2008, for U.S Appl. No. 11/606,192, filed Nov. 29, 2006, 10 pages.
Declaration of Dr. Wenjun Ouyang, Ph.D. filed in U.S. Appl. No. 11/606,192, filed Nov. 29, 2006, 2 pages.
Experimental report from Darko Skegro, dated Aug. 8, 2016, in European Patent No. 1641822, 6 pages.
Experimental report from Max Wisetschläger, Aug. 11, 2016, in European Patent No. 1 641 822, 5 pages.
Pham, V. et al. (2006, e-pub. Feb. 21, 2006). "De Novo Proteomic Sequencing of a Monoclonal Antibody Raised Against OX40 Ligand," *Analytical Biochemistry* 352:77-86.
Protest Under 37 C.F.R. § 1.291(a), mailed on Aug. 21, 2015, for U.S. Appl. No. 14/718,039, filed May 20, 2015, 16 Pages.
Request for Notification Regarding Third Party Preissuance Submission, mailed on Jul. 19, 2017, for U.S. Appl. No. 14/718,039, filed May 20, 2015, Third Party Submission Under 35 U.S.C. 35 U.S.C. §122(e) and 37 C.F.R. § 1.290, 34 pages.
Product sheet from R&D Systems "Human/Primate IL-17/IL-17A Antibody, Monoclonal Mouse IgG$_{2B}$ Clone #41809," Catalog No. MAB317, dated Rev. Sep. 6, 2016, 1 page.
Protest Under 37 C.F.R. 1.291(a), mailed on Dec. 31, 2016, for U.S. Appl. No. 15/360,803, filed May 20, 2015, 22 pages.
Certified copy of Assignment for U.S. Appl. No. 60/485,599, filed Jul. 8, 2003, Submitted in European Patent Opposition for European Patent No. 1 641 822-B1, 146 pages.
Certified copy of Assignment for U.S. Appl. No. 60/486,457, filed Jul. 11, 2003, Submitted in European Patent Opposition for European Patent No. 1 641 822-B1, 160 pages.
Lebecque, S. et al. (2001). "IL-Receptor," in *Cytokine Reference, A Compendium of Cytokines and Other Mediators of Host Defense*, Oppenheim, J.J. et al. (eds.), Academic Press, San Diego, CA, pp. 1541-1546.
Matsumoto, K. et al. (2002). "Increased Urinary Excretion of Interleukin-17 in Nephrotic Patients," *Nephron* 91(2):243-249.
Letter to the dated Jul. 27, 2016, to the EPO from Ablynx NX (O1), for European Patent No. 1 641 822, Comments on the Summons Jan. 4, 2016, 14 pages.
Letter dated Aug. 4, 2016, to the EPO from Bird & Bird, for EP Patent No. 1 641 822 B1, Patent Proprietor: Genentech, Inc., Opponent 1: Ablynx N.V., Opponent 2: Merck Patent GmbH,
Opponent 3: Novartis Ag, Opponent Janssen Biotech, Inc., Opponent 5: Adams, Harvey Vaughan John, In Response to the Preliminary Opinion of Jan. 4, 2016 and In Preparation of the Oral Proceedings Scheduled for Oct. 12-14, 34 pages.
Letter dated Aug. 12, 2016 to EPO from Proprietor Genentech, Inc., Opponent Ablynx NV (O1), et al. for European Patent No. 1 641 822 B1, 16 pages.
Letter dated Aug. 12, 2016 to EPO from Carpmaels & Ransford LLP, for European Patent No. 1 641 822 B1, Further Submission from O3, 2 pages.
Letter dated Oct. 3, 2016, to the EPO, Proprietor Genentech, Inc., Opponent Ablynx NV (O1), et al., Letter in Response to Opponents' Submissions under Rule 116 EPC, 10 pages.
Letter dated Oct. 6, 2016, to the EPO, Carpmales & Ransford, for European Patent No. 1 641 822, Response to Submission of Oct. 3, 2016, 1 page.
Provision of the minutes in accordance with Rule 124(4) EPC, and Decision from the EPO concerning the Revocation of the Patent for European Patent Application No. 1 641 822 B1, dated Nov. 24, 2016, 25 pages.
European Patent Office Notice of Appeal Filed on Jan. 31, 2017, Proprietor Genentech, Inc., opponents: Ablynx NV (O1) et al., for European Patent No. 1 641 822, 4 pages.
Letter to the EPO dated Apr. 4, 2017, for European Patent Application No. 1 641 822, Vossius & Partner, Patentee: Genentech, Inc., Opposition by Ablynx, N.V.; Merck Patent GmbH; Novartis AG; Janssen Biotech, Inc.; Harvey Vaughan John Adams, 36 pages.
Letter dated Aug. 15, 2017, Response of Opponent 03 (Novartis AG) to the Patentee's Appeal, for European Patent No. 1 641 822 B1, 10 pages.
Letter from Bird and Bird dated Aug. 18, 2017, for European Patent No. 1 641 822, Opponent 2: Merck Patent GmbH, Response to the Grounds of Appeal, 32 pages.
Eli Lilly and Company et al. and Genentech, Inc. (Jul. 3, 2017). "Grounds of UK Patent Invalidity," Claim No. HP-2017-000041, in the High Court of Justice Chancery Division Patents Court, 6 pages.
Busse, W.W. et al. (Dec. 1, 2013, e-pub. Nov. 7, 2013). "Randomized, Double-Blind, Placebo-Controlled Study of Brodalumab, a Human Anti-IL-17 Receptor Monoclonal Antibody, in Moderate to Severe Asthma," *Am. J. Respir. Crit. Care Med.* 188(11):1294-1302.
Deforge, L.E. et al. (2010, e-pub. Sep. 9, 2010). "Evaluation of Heterophilic Antibody Blocking Agents in Reducing False Positive Intervention in Immunoassays for IL-17AA, IL-17FF, and IL-17AF," *Journal of Immunological Methods* 316:70-81.
Griffiths, C.E.M. et al. (Aug. 8, 2015). "Comparison of Ixekizumab With Etanercept or Placebo in Moderate-to-Severed Psoriasis (Uncover-2 and Uncover-3): Results from Two Phase 3 Randomised Trials," *Lancet* 386:541-551.
Liu, L. et al. (2016). "Generation and Characterization of Ixekizumab, A Humanized Monoclonal Antibody that Neutralized Interleukin-17A," *Journal of Inflammation Research* 9:39-50.
European Examination Report, dated Dec. 7, 2017, for European Patent Application No. 14163686,0, filed Apr. 7, 2014, 7 pages.
Eli Lilly and Company et al. and Genentech, Inc. (Jan. 5, 2018). "Defense and Counterclaim," Claim No. HP-2017-000041, in the High Court of Justice Business and Property Courts of England and Wales Intellectual Property List (ChD) Patents Court, 5 pages.
European Patent Board of Appeals, dated Apr. 10, 2018, for European Patent Application No. 04754234.5, Appeal No. T0304/17-3. 3.04, Opponent No. 6, Eli Lilly and Company, Proprietor of the Patent Genentech, Inc., Art. 105 EPC Notice of Intervention Opposition Statement, 36 pages.
Preparation for Oral Proceeding, Dated Jan. 4, 2016, filed in Opposition Against European Patent No. 1 641 822, 6 pages.
Further Submissions From Opponent O3 (Novartis AG), dated Jun. 22, 2016, filed Opposition Against European Patent No. 1 641 822, 5 pages.

\* cited by examiner

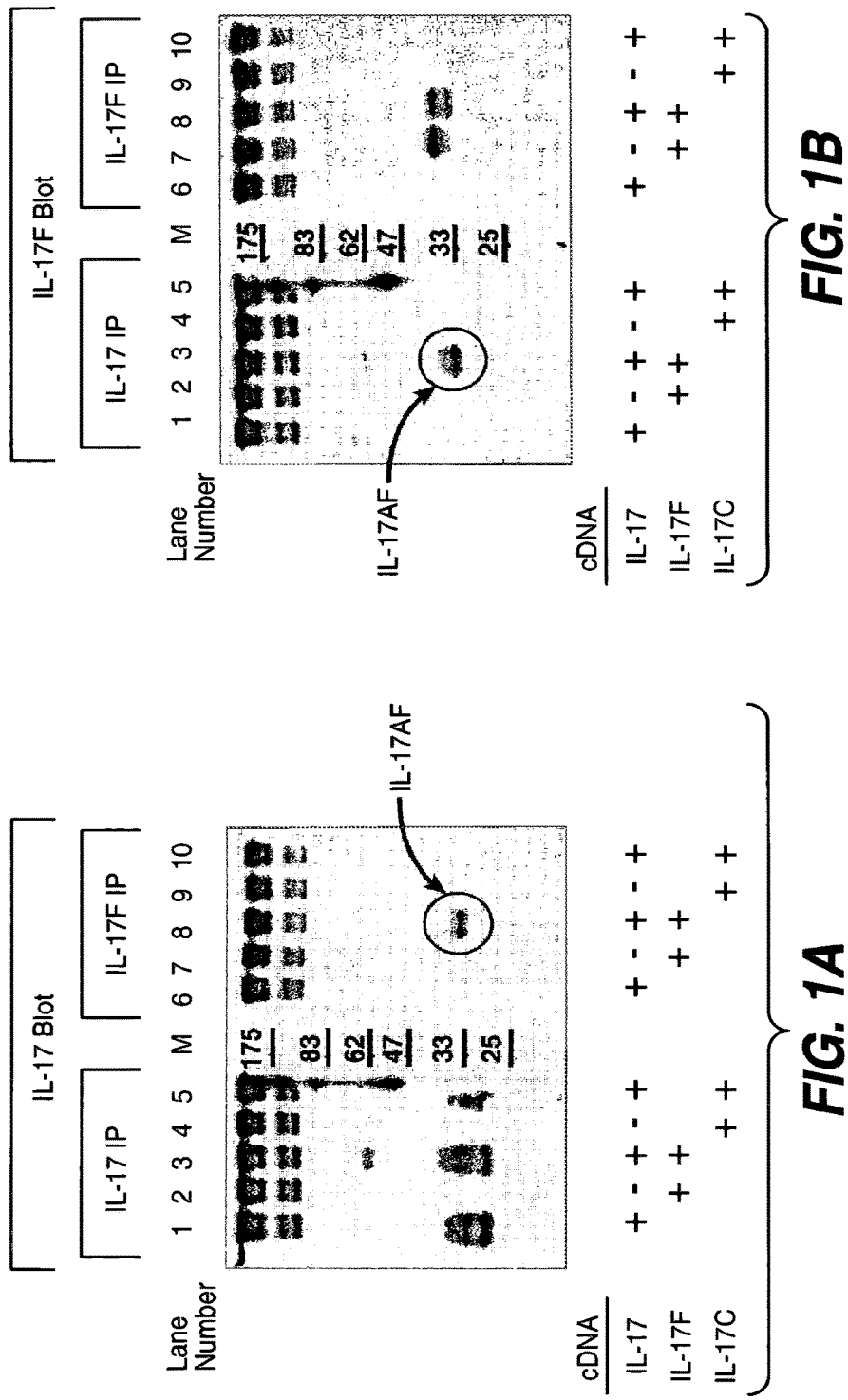

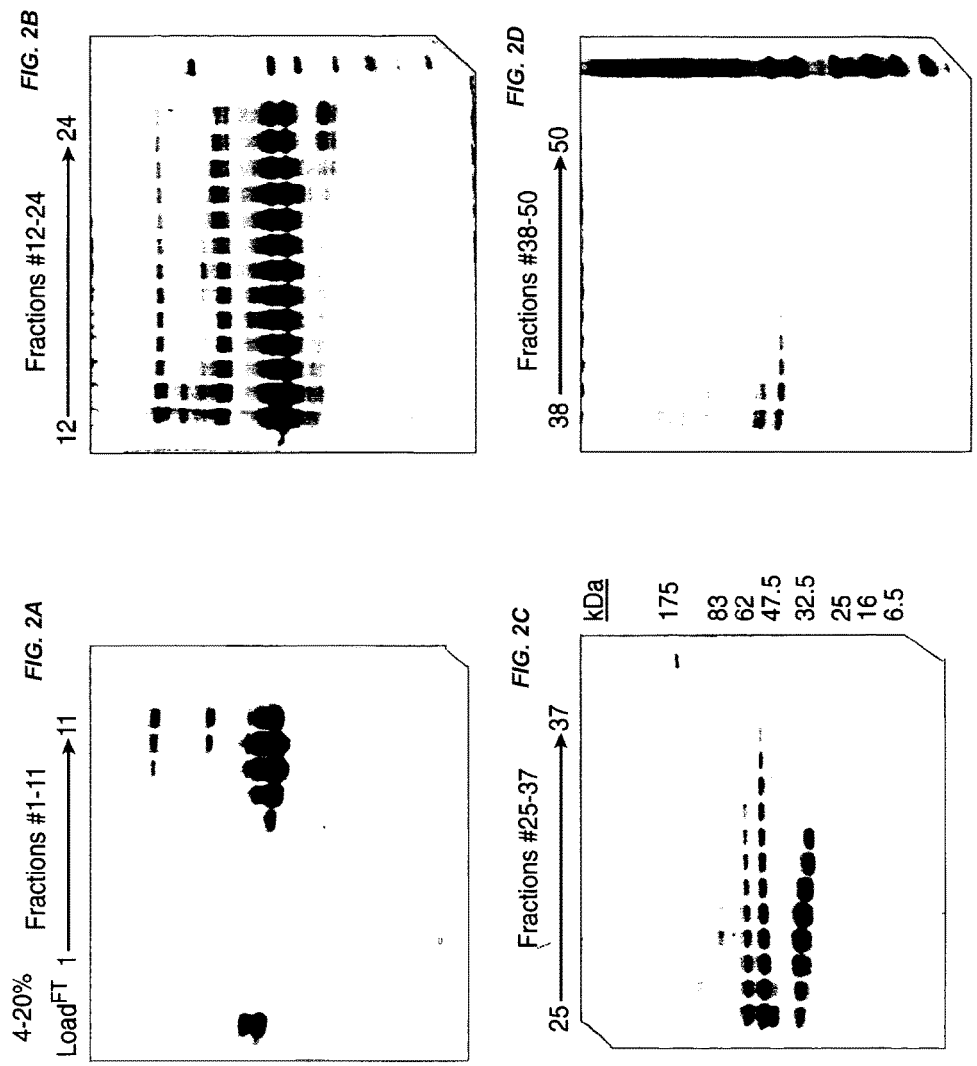

Sequence Data Results

| SEQ ID NO: | Cycle / Run | 1/3 | 2/4 | 3/5 | 4/6 | 5/7 | 6/8 | 7/9 | 8/10 | 9/11 | 10/12 | 11/13 | 12/14 |
|---|---|---|---|---|---|---|---|---|---|---|---|---|---|
| SEQ ID NO:1 | Sequence 1 | G 11.353 | I 16.037 | T 6.719 | I 16.620 | P 10.757 | R 3.563 | N 4.106 | P 8.529 | G 4.488 | C 0.076 | P 7.599 | N 3.502 |
| SEQ ID NO:2 | Sequence 2 | R 16.186 | K 3.857 | I 25.186 | P 6.655 | K 2.679 | V 7.060 | G 2.385 | H 3.082 | T 2.395 | F 3.263 | (F) 7.163 | Q 4.522 |

MTPGKTSLVSLLLLLSLEAIVKAGITIPRNPGCPNSEDKNFPRTVMVNLNIHNRNTNTN
PKRSSDYYNRSTSPWNLHRNEDPERYPSVIWEAKCRHLGCINADGNVDYHMNSVPIQQEI
LVLRREPPHCPNSFRLEKILVSVGCTCVTPIVHHVA (SEQ ID NO:3)

IL-17F

MTVKTLHGPAMVKYLLLSILGLAFLSEAAARKIPKVGHTFFQKPESCPPVPGGSMKL
DIGIINENQRVSMSRNIESRSTSPWNYTVTWDPNRYPSEVVQAQCRNLGCINAQGKEDISM
NSVPIQQETLVVRRKHQGCSVSFQLEKVLVTVGCTCVTPVIHHVQ (SEQ ID NO:4)

FIG. 3C

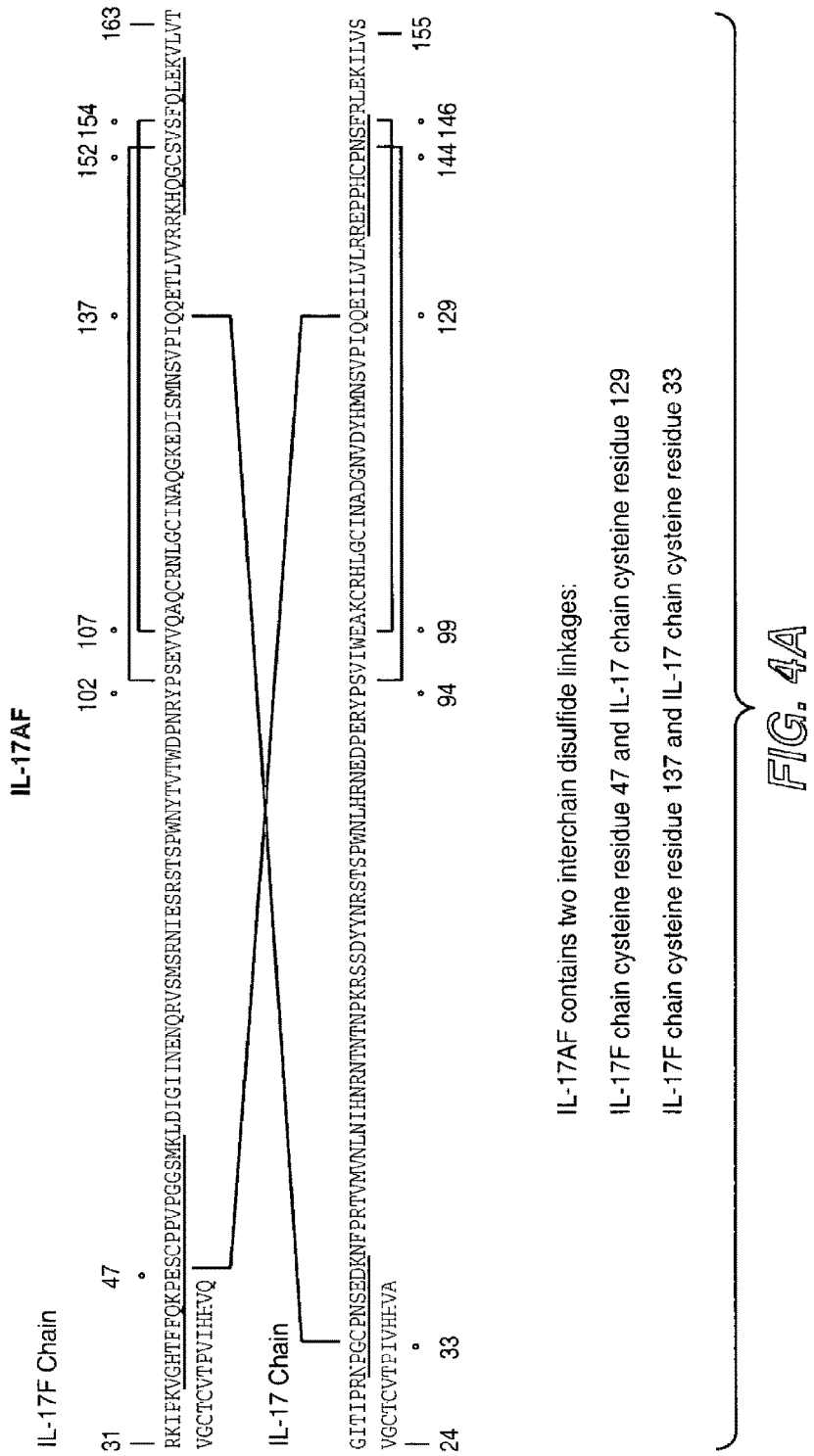

IL-17AF Disulfide Bond Fragment #1

VGHTFFQKPESCPPVPGGSMK  (IL-17F chain trypsin digest peptide amino acids 36-56)
           |
      EPPHCPNSFR        (IL-17F chain trypsin digest peptide amino acids 125-134)

monoisotopic [M+H]$^+$ = 3410.58 Da

IL-17AF Disulfide Bond Fragment #2

HQGCSVSFQLEK  (IL-17F chain trypsin digest peptide amino acids 134-145)
   |
NPGCPNSEDK    (IL-17 chain trypsin digest peptide amino acids 30-39)

monoisotopic [M+H]$^+$ = 2420.05 Da

FIG. 4B

Amino Acid Sequence of Region of Heavy Chain Variable Region Containing CDR H1-H3 from Fab that Bind IL-17AF

| Clone # | CDR-H1 CDR-H2 CDR-H3 |
|---|---|
| 1 | LSCAASGFTISDSAIHWVRQAPGKGLEWVAGITPYSGYTDYADSVKGRFTISADTSKNTAYLQMNSLRAEDTAVYYCAKEAREGYDVGYAMDYWGQ |
| 2 | LSCAASGFTISDSYIHWVRQAPGKGLEWVAEISPPGGDTYYADSVKGRFTISADTSKNTAYLQMNSLRAEDTAVYYCARLLWWWDGAMDYWGQ |
| 3 | LSCAASGFTITNTWIHWVRQAPGKGLEWVAVITPYGGATYYADSVKGRFTISADTSKNTAYLQMNSLRAEDTAVYYCARESMWSKFDYWGQ |
| 4 | LSCAASGFTINSSAIHWVRQAPGKGLEWVGYITPDNGDTNYADSVKGRFTISADTSKNTAYLQMNSLIAEDTAVYYCARGHGNFYGTWAAMDYWGQ |
| 5 | LSCAASGFTISGSDIHWVRQAPGKGLEWVAYINPYGGSTDYADSVKGRFTISADTSKNTAYLQMNSLRAEDTAVYYCARAYEMWYVMDYWGQ |
| 6 | LSCAASGFTITNSWIHWVRQAPGKGLEWVGVITPSSGSTYYADSVKGRFTISADTSKNTAYLQMNSLRAEDTAVYYCAREVFPDIGDCSNAYCYAMDYWGQ |
| 7 | LSCAASGFTITSTYIHWVRQAPGKGLEWVAWISPYSGYTDYADSVKGRFTISADTSKNTAYLQMNSLRAEDTAVYYCAREVGWGDSYAMDYWGQ |
| 8 | LSCAASGFTISGSWIHWVRQAPGKGLEWVAGIYPYDGYTYYADSVKGRFTISADTSKNTAYLQMNSLRAEDTAVYYCAREAEGLYQSGIYDAGMDYWGQ |
| 9 | LSCAASGFTITSYYIHWVRQAPGKGLEWVAWIYPADGATYYADSVKGRFTISADTSKNTAYLQMNSLRAEDTAVYYCARGSYFGGYDMDYWGQ |
| 10 | LSCAASGFTINDSDIHWVRQAPGKGLEWVGIIYPYDGYTYYADSVKGRFTISADTSKNTAYLQMNSLRAEDTAVYYCARSNLDNNLFDYWGQ |
| 11 | LSCAASGFTINGYWIHWVRQAPGKGLEWVADINPNGGSTNYADSVKGRFTISADTSKNTAYLQMNSLRAEDTAVYYCARAYRCGGLADWAGAMDYWGQ |
| 12 | LSCAASGFTISGSWIHWVRQAPGKGLEWVAIITPSGGNTDYADSVKGRFTISADTSKNTAYLQMNSLRAEDTAVYYCAREVFAVSTAGYPWVMDYWGQ |
| 13 | LSCAASGFTITDSWIHWVRQAPGKGLEWVGSITPYNGNTDYADSVKGRFTISADTSKNTAYLQMNSLRAEDTAVYYCARRGESDEAYAAVMDYWGQ |
| 14 | LSCAASGFTISSSDIHWVRQAPGKGLEWVGTINPASGSTDYADSVKGRFTISADTSKNTAYLQMNSLRAEDTAVYYCARGANSSFYALQYVMDYWGQ |
| 15 | LSCAASGFTITDNYIHWVRQAPGKGLEWVGWISPYSGYTYYADSVKGRFTISADTSKNTAYLQMNSLRAEDTAVYYCARETLFYDKDQYSYVMDYWGQ |
| 16 | LSCAASGFTISSSYIHWVRQAPGKGLEWVAWISPYSGYTDYADSVKGRFTISADTSKNTAYLQMNSLRAEDTAVYYCAREGLLRWGYAMDYWGQ |
| 17 | LSCAASGFTITDNGIHWVRQAPGKGLEWVGWITPTSGYTNYADSVKGRFTISADTSKNTAYLQMNSLRAEDTAVYYCARDGDTWKWDAPYVMDYWGQ |
| 18 | LSCAASGFTITNTYIHWVRQAPGKGLEWVAWISPYSGYTDYADSVKGRFTISADTSKNTAYLQMNSLRAEDTAVYYCAREILLDYGSAGYAMDYWGQ |
| 19 | LSCAASGFTITSTWIHWVRQAPGKGLEWVGVITPTNGSTYYADSVKGRFTISADTSKNTAYLQMNSLRAEDTAVYYCAREVWWWGDGHGYVMDYWGQ |
| 20 | LSCAASGFTISSSAIHWVRQAPGKGLEWVGGITPASGYTYYADSVKGRFTISADTSKNTAYLQMNSLRAEDTAVYYCARSPGGVFVDGGVMDYWGQ |
| 21 | LSCAASGFTINSTDIHWVRQAPGKGLEWVGRINPSGGSTNYADSVKGRFTISADTSKNTAYLQMNSLRAEDTAVYYCARTSAYTTWAVDWFIGYVMDYWGQ |
| 22 | LSCAASGFTITGYGIHWVRQAPGKGLEWVAWISPSNGYTYYADSVKGRFTISADTSKNTAYLQMNSLRAEDTAVYYCARRVSYYVYRHDWVRGYVMDYWGQ |
| 23 | LSCAASGFTITDTWIHWVRQAPGKGLEWVGVITPYGGYTYYADSVKGRFTISADTSKNTAYLQMNSLRAEDTAVYYCARDGGFFDYWGQ |
| 24 | LSCAASGFTISDSSIHWVRQAPGKGLEWVAFIYPTSGSTYYANSVKGRFTISADTSKNTAYLQMNSLRAEDTAVYYCARASYGVSKWTFDYWGQ |
| 25 | LSCAASGFTITGYGIHWVRQAPGKGLEWVAWISPSNGYTYYADSVKGRFTISAYTSKNTAYLQMNSLRAEDTAVYYCARRVSYYVYRHDWVRGYVMDYQGQ |
| 26 | LSCAASGFTITGTYIHWVRQAPGKGLEWVAWISPYSGYTNYADSVKGRFTISADTSKNTAYLQMNSLRAEDTAVYYCAREARSSLSADYAMDYWGQ |
| 27 | LSCAASGFTITDNYIHWVRQAPGKGLEWVAWISPYSGYTYYADSVKGRFTISADTSKNTAYLQMNSLRAEDTAVYYCARESGFSACNTRAYAMDYWGQ |
| 28 | LSCAASGFTITDSWIHWVRQAPGKGLEWVGSITPYNGNTDYADSVKGRFTISADTSKNTAYLQMNSLRAEDTAVYYCARRGESDEAYPAVMDYWGQ |
| 29 | LSCAASGFTITSTAIHWVRQAPGKGLEWVAWITPYDGYTDYADSVKGRFTISADTSKNTAYLLMNSLRAEDTAVYYCARTWFTLASAMELLGSA |
| 30 | LSCAASGFTITGNGIHWVRQAPGKGLEWVAWISPTNGSTYYADSVKGRFTISADTSKNTAYLQMNSLRAEDTAVYYCARRVDYQVYHDRFEEGYAMDYWGQ |
| 31 | LSCAASGFTINSYWIHWVRQAPGKGLEWVGWISPDNGATNYADSVKGRFTISADTSKNTAYLQMNSLRAEDTAVYYCARKFWGWDWGGMDYWGQ |
| 32 | LSCAASGFTISDSYIHWVRQAPGKGLEWVGDITPTDGYTDYADSVKGRFTISADTSKNTAYLQMNSLRAEDTAVYYCARNLMWWDSSAMDYWGQ |
| 33 | LSCAASGFTISDSGIHWVRQAPGKGLEWVGFIYPNGGSTYYADSVKGRFTISADTSKNTAYLQMNSLRAEDTAVYYCARMSLIGFSYAMDYWGQ |
| 34 | LSCAASGFTINSTWIHWVRQAPGKGLEWVAWINPYNGSTYYADSVKGRFTISADTSKNTAYLQMNSLRAEDTAVYYCARDLYDYDIGFDYWGQ |

*FIG. 6*

GCAGGCACAAACTCATCCATCCCCAGTTGATTGGAAGAAACAACGATGACTCCTGGGAAG
ACCTCATTGGTGTCACTGCTACTGCTGCTGAGCCTGGAGGCCATAGTGAAGGCAGGAATC
ACAATCCCACGAAATCCAGGATGCCCAAATTCTGAGGACAAGAACTTCCCCGGACTGTG
ATGGTCAACCTGAACATCCATAACCGGAATACCAATACCAATCCCAAAAGGTCCTCAGAT
TACTACAACCGATCCACCTCACCTTGGAATCTCCACCGCAATGAGGACCCTGAGAGATAT
CCCTCTGTGATCTGGGAGGCAAAGTGCCGCCACTTGGGCTGCATCAACGCTGATGGGAAC
GTGGACTACCACATGAACTCTGTCCCCATCCAGCAAGAGATCCTGGTCCTGCGCAGGGAG
CCTCCACACTGCCCCAACTCCTTCCGGCTGGAGAAGATACTGGTGTCCGTGGGCTGCACC
TGTGTCACCCCGATTGTCCACCATGTGGCCTAAGAGCTCTGGGGAGCCCACACTCCCCAA
AGCAGTTAGACTATGGAGAGCCGACCCAGCCCCTCAGGAACCCTCATCCTTCAAAGACAG
CCTCATTTCGGACTAAACTCATTAGAGTTCTTAAGGCAGTTTGTCCAATTAAAGCTTCAG
AGGTAACACTTGGCCAAGATATGAGATCTGAATTACCTTTCCCTCTTTCCAAGAAGGAAG
GTTTGACTGAGTACCAATTTGCTTCTTGTTTACTTTTTTAAGGGCTTTAAGTTATTTATG
TATTTAATATGCCCTGAGATAACTTTGGGGTATAAGATTCCATTTTAATGAATTACCTAC
TTTATTTTGTTTGTCTTTTTAAAGAAGATAAGATTCTGGGCTTGGGAATTTTATTATTTA
AAAGGTAAAACCTGTATTTATTTGAGCTATTTAAGGATCTATTTATGTTTAAGTATTTAG
AAAAAGGTGAAAAAGCACTATTATCAGTTCTGCCTAGGTAAATGTAAGATAGAATTAAAT
GGCAGTGCAAAATTTCTGAGTCTTTACAACATACGGATATAGTATTTCCTCCTCTTTGTT
TTTAAAAGTTATAACATGGCTGAAAAGAAAGATTAAACCTACTTTCATATGTATTAATTT
AAATTTTGCAATTTGTTGAGGTTTTACAAGAGATACAGCAAGTCTAACTCTCTGTTCCAT
TAAACCCTTATAATAAAATCCTTCTGTAATAATAAAGTTTCAAAAGAAATGTTTATTTG
TTCTCATTAAATGTATTTTAGCAAACTCAGCTCTTCCCTATTGGGAAGAGTTATGCAAAT
TCTCCTATAAGCAAAACAAAGCATGTCTTTGAGTAACAATGACCTGGAAATACCCAAAAT
TCCAAGTTCTCGATTTCACATGCCTTCAAGACTGAACACCGACTAAGGTTTTCATACTAT
TAGCCAATGCTGTAGACAGAAGCATTTTGATAGGAATAGAGCAAATAAGATAATGGCCCT
GAGGAATGGCATGTCATTATTAAAGATCATATGGGGAAAATGAAACCCTCCCCAAAATAC
AAGAAGTTCTGGGAGGAGACATTGTCTTCAGACTACAATGTCCAGTTTCTCCCCTAGACT
CAGGCTTCCTTTGGAGATTAAGGCCCCTCAGAGATCAACAGACCAACATTTTTCTCTTCC
TCAAGCAACACTCCTAGGGCCTGGCTTCTGTCTGATCAAGGCACCACACAACCCAGAAAG
GAGCTGATGGGGCAGAACGAACTTTAAGTATGAGAAAGTTCAGCCCAAGTAAAATAAAA
ACTCAATCACATTCAATTCCAGAGTAGTTTCAAGTTTCACATCGTAACCATTTTCGCCC

FIG. 7

MTPGKTSLVSLLLLLSLEAIVKAGITIPRNPGCPNSEDKNFPRTVMVNLNIHNRNTNTNP
KRSSDYYNRSTSPWNLHRNEDPERYPSVIWEAKCRHLGCINADGNVDYHMNSVPIQQEIL
VLRREPPHCPNSFRLEKILVSVGCTCVTPIVHHVA

FIG. 8

CAACTGCACCTCGGTTCTATCGATAGCCACCAGCGCAACATGACAGTGAAGACCCTGCAT
GGCCCAGCCATGGTCAAGTACTTGCTGCTGTCGATATTGGGGCTTGCCTTTCTGAGTGAG
GCGGCAGCTCGGAAAATCCCCAAAGTAGGACATACTTTTTTCCAAAAGCCTGAGAGTTGC
CCGCCTGTGCCAGGAGGTAGTATGAAGCTTGACATTGGCATCATCAATGAAAACCAGCGC
GTTTCCATGTCACGTAACATCGAGAGCCGCTCCACCTCCCCCTGGAATTACACTGTCACT
TGGGACCCCAACCGGTACCCTCGGAAGTTGTACAGGCCCAGTGTAGGAACTTGGGCTGC
ATCAATGCTCAAGGAAAGGAAGACATCTCCATGAATTCCGTTCCCATCCAGCAAGAGACC
CTGGTCGTCCGGAGGAAGCACCAAGGCTGCTCTGTTTCTTTCCAGTTGGAGAAGGTGCTG
GTGACTGTTGGCTGCACCTGCGTCACCCCTGTCATCCACCATGTGCAGTAAGAGGTGCAT
ATCCACTCAGCTGAAGAAG

FIG. 9

MTVKTLHGPAMVKYLLLSILGLAFLSEAAARKIPKVGHTFFQKPESCPPVPGGSMKLDIG
IINENQRVSMSRNIESRSTSPWNYTVTWDPNRYPSEVVQAQCRNLGCINAQGKEDISMNS
VPIQQETLVVRRKHQGCSVSFQLEKVLVTVGCTCVTPVIHHVQ

Signal sequence:         Amino acids 1-30
N-glycosylation site:    Amino acids 83-86
N-myristoylation sites:  Amino acids
                         106-111;136-141

FIG. 10

SEQUENCE LISTING

```
<160> NUMBER OF SEQ ID NOS: 80

<210> SEQ ID NO 1
<211> LENGTH: 12
<212> TYPE: PRT
<213> ORGANISM: Homo sapiens
<220> FEATURE:
<221> NAME/KEY: Unsure
<222> LOCATION: 10
<223> OTHER INFORMATION: Unknown amino acid

<400> SEQUENCE: 1

Gly Ile Thr Ile Pro Arg Asn Pro Gly Xaa Pro Asn
                5                   10

<210> SEQ ID NO 2
<211> LENGTH: 12
<212> TYPE: PRT
<213> ORGANISM: Homo sapiens

<400> SEQUENCE: 2

Arg Lys Ile Pro Lys Val Gly His Thr Phe Phe Gln
                5                   10

<210> SEQ ID NO 3
<211> LENGTH: 155
<212> TYPE: PRT
<213> ORGANISM: Homo sapiens

<400> SEQUENCE: 3

Met Thr Pro Gly Lys Thr Ser Leu Val Ser Leu Leu Leu Leu Leu
  1               5                   10                  15

Ser Leu Glu Ala Ile Val Lys Ala Gly Ile Thr Ile Pro Arg Asn
                 20                  25                  30

Pro Gly Cys Pro Asn Ser Glu Asp Lys Asn Phe Pro Arg Thr Val
                 35                  40                  45

Met Val Asn Leu Asn Ile His Asn Arg Asn Thr Asn Thr Asn Pro
                 50                  55                  60

Lys Arg Ser Ser Asp Tyr Tyr Asn Arg Ser Thr Ser Pro Trp Asn
                 65                  70                  75

Leu His Arg Asn Glu Asp Pro Glu Arg Tyr Pro Ser Val Ile Trp
                 80                  85                  90

Glu Ala Lys Cys Arg His Leu Gly Cys Ile Asn Ala Asp Gly Asn
                 95                 100                 105

Val Asp Tyr His Met Asn Ser Val Pro Ile Gln Gln Glu Ile Leu
```

```
                        110                 115                 120

Val Leu Arg Arg Glu Pro Pro His Cys Pro Asn Ser Phe Arg Leu
            125                 130                 135

Glu Lys Ile Leu Val Ser Val Gly Cys Thr Cys Val Thr Pro Ile
            140                 145                 150

Val His His Val Ala
            155

<210> SEQ ID NO 4
<211> LENGTH: 163
<212> TYPE: PRT
<213> ORGANISM: Homo sapiens

<400> SEQUENCE: 4

Met Thr Val Lys Thr Leu His Gly Pro Ala Met Val Lys Tyr Leu
  1               5                  10                  15

Leu Leu Ser Ile Leu Gly Leu Ala Phe Leu Ser Glu Ala Ala Ala
             20                  25                  30

Arg Lys Ile Pro Lys Val Gly His Thr Phe Phe Gln Lys Pro Glu
             35                  40                  45

Ser Cys Pro Pro Val Pro Gly Gly Ser Met Lys Leu Asp Ile Gly
             50                  55                  60

Ile Ile Asn Glu Asn Gln Arg Val Ser Met Ser Arg Asn Ile Glu
             65                  70                  75

Ser Arg Ser Thr Ser Pro Trp Asn Tyr Thr Val Thr Trp Asp Pro
             80                  85                  90

Asn Arg Tyr Pro Ser Glu Val Val Gln Ala Gln Cys Arg Asn Leu
             95                 100                 105

Gly Cys Ile Asn Ala Gln Gly Lys Glu Asp Ile Ser Met Asn Ser
            110                 115                 120

Val Pro Ile Gln Gln Glu Thr Leu Val Val Arg Arg Lys His Gln
            125                 130                 135

Gly Cys Ser Val Ser Phe Gln Leu Glu Lys Val Leu Val Thr Val
            140                 145                 150

Gly Cys Thr Cys Val Thr Pro Val Ile His His Val Gln
            155                 160

<210> SEQ ID NO 5
<211> LENGTH: 1859
<212> TYPE: DNA
<213> ORGANISM: Homo sapiens

<400> SEQUENCE: 5
gcaggcacaa actcatccat ccccagttga ttggaagaaa caacgatgac         50
tcctgggaag acctcattgg tgtcactgct actgctgctg agcctggagg        100
ccatagtgaa ggcaggaatc acaatccac gaaatccagg atgcccaaat         150
tctgaggaca agaacttccc ccggactgtg atggtcaacc tgaacatcca        200
taaccggaat accaatacca atcccaaaag gtcctcagat tactacaacc        250
gatccacctc accttggaat ctccaccgca atgaggaccc tgagagatat        300
ccctctgtga tctgggaggc aaagtgccgc cacttgggct gcatcaacgc        350
tgatgggaac gtggactacc acatgaactc tgtccccatc cagcaagaga       400
tcctggtcct gcgcagggag cctccacact gccccaactc cttccggctg       450
gagaagatac tggtgtccgt gggctgcacc tgtgtcaccc cgattgtcca       500
```

| | |
|---|---|
| ccatgtggcc taagagctct ggggagccca cactccccaa agcagttaga | 550 |
| ctatggagag ccgacccagc ccctcaggaa ccctcatcct tcaaagacag | 600 |
| cctcatttcg gactaaactc attagagttc ttaaggcagt ttgtccaatt | 650 |
| aaagcttcag aggtaacact tggccaagat atgagatctg aattaccttt | 700 |
| ccctctttcc aagaaggaag gtttgactga gtaccaattt gcttcttgtt | 750 |
| tactttttta agggctttaa gttatttatg tatttaatat gccctgagat | 800 |
| aactttgggg tataagattc cattttaatg aattacctac tttattttgt | 850 |
| ttgtcttttt aaagaagata agattctggg cttgggaatt ttattattta | 900 |
| aaaggtaaaa cctgtattta tttgagctat ttaaggatct atttatgttt | 950 |
| aagtatttag aaaaaggtga aaaagcacta ttatcagttc tgcctaggta | 1000 |
| aatgtaagat agaattaaat ggcagtgcaa aatttctgag tctttacaac | 1050 |
| atacggatat agtatttcct cctctttgtt tttaaaagtt ataacatggc | 1100 |
| tgaaaagaaa gattaaacct actttcatat gtattaattt aaattttgca | 1150 |
| atttgttgag gttttacaag agatacagca agtctaactc tctgttccat | 1200 |
| taaacccttaa taataaaatc cttctgtaat aataaagttt caaaagaaaa | 1250 |
| tgtttatttg ttctcattaa atgtatttta gcaaactcag ctcttcccta | 1300 |
| ttgggaagag ttatgcaaat tctcctataa gcaaaacaaa gcatgtcttt | 1350 |
| gagtaacaat gacctggaaa tacccaaaat tccaagttct cgatttcaca | 1400 |
| tgccttcaag actgaacacc gactaaggtt ttcatactat tagccaatgc | 1450 |
| tgtagacaga agcattttga taggaataga gcaaataaga taatggccct | 1500 |
| gaggaatggc atgtcattat taaagatcat atggggaaaa tgaaaccctc | 1550 |
| cccaaaatac aagaagttct gggaggagac attgtcttca gactacaatg | 1600 |
| tccagtttct cccctagact caggcttcct ttggagatta aggcccctca | 1650 |
| gagatcaaca gaccaacatt tttctcttcc tcaagcaaca ctcctagggc | 1700 |
| ctggcttctg tctgatcaag gcaccacaca acccagaaag gagctgatgg | 1750 |
| ggcagaacga actttaagta tgagaaaagt tcagcccaag taaaataaaa | 1800 |
| actcaatcac attcaattcc agagtagttt caagtttcac atcgtaacca | 1850 |
| ttttcgccc | 1859 |

<210> SEQ ID NO 6
<211> LENGTH: 559
<212> TYPE: DNA
<213> ORGANISM: Homo sapiens

<400> SEQUENCE: 6

| | |
|---|---|
| caactgcacc tcggttctat cgatagccac cagcgcaaca tgacagtgaa | 50 |
| gaccctgcat ggcccagcca tggtcaagta cttgctgctg tcgatattgg | 100 |
| ggcttgcctt tctgagtgag gcggcagctc ggaaaatccc caaagtagga | 150 |
| catactttt tccaaaagcc tgagagttgc ccgcctgtgc caggaggtag | 200 |
| tatgaagctt gacattggca tcatcaatga aaaccagcgc gtttccatgt | 250 |
| cacgtaacat cgagagccgc tccacctccc cctggaatta cactgtcact | 300 |
| tgggacccca accggtaccc ctcggaagtt gtacaggccc agtgtaggaa | 350 |

```
cttgggctgc atcaatgctc aaggaaagga agacatctcc atgaattccg       400
ttcccatcca gcaagagacc ctggtcgtcc ggaggaagca ccaaggctgc       450
tctgtttctt tccagttgga gaaggtgctg gtgactgttg gctgcacctg       500
cgtcacccct gtcatccacc atgtgcagta agaggtgcat atccactcag       550
ctgaagaag                                                     559
```

<210> SEQ ID NO 7
<211> LENGTH: 21
<212> TYPE: PRT
<213> ORGANISM: Homo sapiens

<400> SEQUENCE: 7

Val Gly His Thr Phe Phe Gln Lys Pro Glu Ser Cys Pro Pro Val
 1               5                  10                  15

Pro Gly Gly Ser Met Lys
                20

<210> SEQ ID NO 8
<211> LENGTH: 12
<212> TYPE: PRT
<213> ORGANISM: Homo sapiens

<400> SEQUENCE: 8

His Gln Gly Cys Ser Val Ser Phe Gln Leu Glu Lys
 1               5                  10

<210> SEQ ID NO 9
<211> LENGTH: 96
<212> TYPE: PRT
<213> ORGANISM: Artificial sequence
<220> FEATURE:
<223> OTHER INFORMATION: synthetic polypeptides

<400> SEQUENCE: 9

Leu Ser Cys Ala Ala Ser Gly Phe Thr Ile Ser Asp Ser Ala Ile
 1               5                  10                  15

His Trp Val Arg Gln Ala Pro Gly Lys Gly Leu Glu Trp Val Ala
                20                  25                  30

Gly Ile Thr Pro Tyr Ser Gly Tyr Thr Asp Tyr Ala Asp Ser Val
                35                  40                  45

Lys Gly Arg Phe Thr Ile Ser Ala Asp Thr Ser Lys Asn Thr Ala
                50                  55                  60

Tyr Leu Gln Met Asn Ser Leu Arg Ala Glu Asp Thr Ala Val Tyr
                65                  70                  75

Tyr Cys Ala Lys Glu Ala Arg Glu Gly Tyr Asp Val Gly Tyr Ala
                80                  85                  90

Met Asp Tyr Trp Gly Gln
                95

<210> SEQ ID NO 10
<211> LENGTH: 93
<212> TYPE: PRT
<213> ORGANISM: Artificial sequence
<220> FEATURE:
<223> OTHER INFORMATION: synthetic polypeptides

<400> SEQUENCE: 10

Leu Ser Cys Ala Ala Ser Gly Phe Thr Ile Ser Asp Ser Tyr Ile
 1               5                  10                  15

His Trp Val Arg Gln Ala Pro Gly Lys Gly Leu Glu Trp Val Ala
            20                  25                  30

Glu Ile Ser Pro Pro Gly Gly Asp Thr Tyr Tyr Ala Asp Ser Val
            35                  40                  45

Lys Gly Arg Phe Thr Ile Ser Ala Asp Thr Ser Lys Asn Thr Ala
            50                  55                  60

Tyr Leu Gln Met Asn Ser Leu Arg Ala Glu Asp Thr Ala Val Tyr
            65                  70                  75

Tyr Cys Ala Arg Leu Leu Trp Trp Asp Gly Ala Met Asp Tyr
            80                  85                  90

Trp Gly Gln

<210> SEQ ID NO 11
<211> LENGTH: 91
<212> TYPE: PRT
<213> ORGANISM: Artificial sequence
<220> FEATURE:
<223> OTHER INFORMATION: synthetic polypeptides

<400> SEQUENCE: 11

Leu Ser Cys Ala Ala Ser Gly Phe Thr Ile Thr Asn Thr Trp Ile
 1               5                  10                  15

His Trp Val Arg Gln Ala Pro Gly Lys Gly Leu Glu Trp Val Ala
            20                  25                  30

Val Ile Thr Pro Tyr Gly Gly Ala Thr Tyr Tyr Ala Asp Ser Val
            35                  40                  45

Lys Gly Arg Phe Thr Ile Ser Ala Asp Thr Ser Lys Asn Thr Ala
            50                  55                  60

Tyr Leu Gln Met Asn Ser Leu Arg Ala Glu Asp Thr Ala Val Tyr
            65                  70                  75

Tyr Cys Ala Arg Glu Ser Met Trp Ser Lys Phe Asp Tyr Trp Gly
            80                  85                  90

Gln

<210> SEQ ID NO 12
<211> LENGTH: 96
<212> TYPE: PRT
<213> ORGANISM: Artificial sequence
<220> FEATURE:
<223> OTHER INFORMATION: synthetic polypeptides

<400> SEQUENCE: 12

Leu Ser Cys Ala Ala Ser Gly Phe Thr Ile Asn Ser Ser Ala Ile
 1               5                  10                  15

His Trp Val Arg Gln Ala Pro Gly Lys Gly Leu Glu Trp Val Gly
            20                  25                  30

Tyr Ile Thr Pro Asp Asn Gly Asp Thr Asn Tyr Ala Asp Ser Val
            35                  40                  45

Lys Gly Arg Phe Thr Ile Ser Ala Asp Thr Ser Lys Asn Thr Ala
            50                  55                  60

Tyr Leu Gln Met Asn Ser Leu Ile Ala Glu Asp Thr Ala Val Tyr
            65                  70                  75

Tyr Cys Ala Arg Gly His Gly Asn Phe Tyr Gly Thr Trp Ala Ala
            80                  85                  90

Met Asp Tyr Trp Gly Gln
            95

```
<210> SEQ ID NO 13
<211> LENGTH: 92
<212> TYPE: PRT
<213> ORGANISM: Artificial sequence
<220> FEATURE:
<223> OTHER INFORMATION: synthetic polypeptides

<400> SEQUENCE: 13

Leu Ser Cys Ala Ala Ser Gly Phe Thr Ile Ser Gly Ser Asp Ile
  1               5                  10                  15

His Trp Val Arg Gln Ala Pro Gly Lys Gly Leu Glu Trp Val Ala
             20                  25                  30

Tyr Ile Asn Pro Tyr Gly Gly Ser Thr Asp Tyr Ala Asp Ser Val
         35                  40                  45

Lys Gly Arg Phe Thr Ile Ser Ala Asp Thr Ser Lys Asn Thr Ala
     50                  55                  60

Tyr Leu Gln Met Asn Ser Leu Arg Ala Glu Asp Thr Ala Val Tyr
 65                  70                  75

Tyr Cys Ala Arg Ala Tyr Glu Met Trp Tyr Val Met Asp Tyr Trp
                 80                  85                  90

Gly Gln

<210> SEQ ID NO 14
<211> LENGTH: 101
<212> TYPE: PRT
<213> ORGANISM: Artificial sequence
<220> FEATURE:
<223> OTHER INFORMATION: synthetic polypeptides

<400> SEQUENCE: 14

Leu Ser Cys Ala Ala Ser Gly Phe Thr Ile Thr Asn Ser Trp Ile
  1               5                  10                  15

His Trp Val Arg Gln Ala Pro Gly Lys Gly Leu Glu Trp Val Gly
             20                  25                  30

Val Ile Thr Pro Ser Ser Gly Ser Thr Tyr Tyr Ala Asp Ser Val
         35                  40                  45

Lys Gly Arg Phe Thr Ile Ser Ala Asp Thr Ser Lys Asn Thr Ala
     50                  55                  60

Tyr Leu Gln Met Asn Ser Leu Arg Ala Glu Asp Thr Ala Val Tyr
 65                  70                  75

Tyr Cys Ala Arg Glu Val Phe Pro Asp Ile Gly Asp Cys Ser Asn
                 80                  85                  90

Ala Tyr Cys Tyr Ala Met Asp Tyr Trp Gly Gln
                 95                 100

<210> SEQ ID NO 15
<211> LENGTH: 94
<212> TYPE: PRT
<213> ORGANISM: Artificial sequence
<220> FEATURE:
<223> OTHER INFORMATION: synthetic polypeptides

<400> SEQUENCE: 15

Leu Ser Cys Ala Ala Ser Gly Phe Thr Ile Thr Ser Thr Tyr Ile
  1               5                  10                  15

His Trp Val Arg Gln Ala Pro Gly Lys Gly Leu Glu Trp Val Ala
             20                  25                  30

Trp Ile Ser Pro Tyr Ser Gly Tyr Thr Asp Tyr Ala Asp Ser Val
         35                  40                  45
```

-continued

Lys Gly Arg Phe Thr Ile Ser Ala Asp Thr Ser Lys Asn Thr Ala
            50                  55                  60

Tyr Leu Gln Met Asn Ser Leu Arg Ala Glu Asp Thr Ala Val Tyr
            65                  70                  75

Tyr Cys Ala Arg Glu Val Gly Trp Gly Asp Ser Tyr Ala Met Asp
            80                  85                  90

Tyr Trp Gly Gln

<210> SEQ ID NO 16
<211> LENGTH: 99
<212> TYPE: PRT
<213> ORGANISM: Artificial sequence
<220> FEATURE:
<223> OTHER INFORMATION: synthetic polypeptides

<400> SEQUENCE: 16

Leu Ser Cys Ala Ala Ser Gly Phe Thr Ile Ser Gly Ser Trp Ile
  1               5                  10                  15

His Trp Val Arg Gln Ala Pro Gly Lys Gly Leu Glu Trp Val Ala
            20                  25                  30

Gly Ile Tyr Pro Tyr Asp Gly Tyr Thr Tyr Tyr Ala Asp Ser Val
            35                  40                  45

Lys Gly Arg Phe Thr Ile Ser Ala Asp Thr Ser Lys Asn Thr Ala
            50                  55                  60

Tyr Leu Gln Met Asn Ser Leu Arg Ala Glu Asp Thr Ala Val Tyr
            65                  70                  75

Tyr Cys Ala Arg Glu Ala Glu Gly Leu Tyr Gln Ser Gly Ile Tyr
            80                  85                  90

Asp Ala Gly Met Asp Tyr Trp Gly Gln
                  95

<210> SEQ ID NO 17
<211> LENGTH: 93
<212> TYPE: PRT
<213> ORGANISM: Artificial sequence
<220> FEATURE:
<223> OTHER INFORMATION: synthetic polypeptides

<400> SEQUENCE: 17

Leu Ser Cys Ala Ala Ser Gly Phe Thr Ile Thr Ser Tyr Tyr Ile
  1               5                  10                  15

His Trp Val Arg Gln Ala Pro Gly Lys Gly Leu Glu Trp Val Ala
            20                  25                  30

Trp Ile Tyr Pro Ala Asp Gly Ala Thr Tyr Tyr Ala Asp Ser Val
            35                  40                  45

Lys Gly Arg Phe Thr Ile Ser Ala Asp Thr Ser Lys Asn Thr Ala
            50                  55                  60

Tyr Leu Gln Met Asn Ser Leu Arg Ala Glu Asp Thr Ala Val Tyr
            65                  70                  75

Tyr Cys Ala Arg Gly Ser Tyr Phe Gly Gly Tyr Asp Met Asp Tyr
            80                  85                  90

Trp Gly Gln

<210> SEQ ID NO 18
<211> LENGTH: 92
<212> TYPE: PRT
<213> ORGANISM: Artificial sequence
<220> FEATURE:
<223> OTHER INFORMATION: synthetic polypeptides

<400> SEQUENCE: 18

```
Leu Ser Cys Ala Ala Ser Gly Phe Thr Ile Asn Asp Ser Asp Ile
  1               5                  10                  15

His Trp Val Arg Gln Ala Pro Gly Lys Gly Leu Glu Trp Val Gly
                 20                  25                  30

Ile Ile Tyr Pro Tyr Asp Gly Tyr Thr Tyr Tyr Ala Asp Ser Val
                 35                  40                  45

Lys Gly Arg Phe Thr Ile Ser Ala Asp Thr Ser Lys Asn Thr Ala
                 50                  55                  60

Tyr Leu Gln Met Asn Ser Leu Arg Ala Glu Asp Thr Ala Val Tyr
                 65                  70                  75

Tyr Cys Ala Arg Ser Asn Leu Asp Asn Asn Leu Phe Asp Tyr Trp
                 80                  85                  90

Gly Gln
```

<210> SEQ ID NO 19
<211> LENGTH: 98
<212> TYPE: PRT
<213> ORGANISM: Artificial sequence
<220> FEATURE:
<223> OTHER INFORMATION: synthetic polypeptides

<400> SEQUENCE: 19

```
Leu Ser Cys Ala Ala Ser Gly Phe Thr Ile Asn Gly Tyr Trp Ile
  1               5                  10                  15

His Trp Val Arg Gln Ala Pro Gly Lys Gly Leu Glu Trp Val Ala
                 20                  25                  30

Asp Ile Asn Pro Asn Gly Gly Ser Thr Asn Tyr Ala Asp Ser Val
                 35                  40                  45

Lys Gly Arg Phe Thr Ile Ser Ala Asp Thr Ser Lys Asn Thr Ala
                 50                  55                  60

Tyr Leu Gln Met Asn Ser Leu Arg Ala Glu Asp Thr Ala Val Tyr
                 65                  70                  75

Tyr Cys Ala Arg Ala Tyr Arg Cys Gly Gly Leu Ala Asp Trp Ala
                 80                  85                  90

Gly Ala Met Asp Tyr Trp Gly Gln
                 95
```

<210> SEQ ID NO 20
<211> LENGTH: 98
<212> TYPE: PRT
<213> ORGANISM: Artificial sequence
<220> FEATURE:
<223> OTHER INFORMATION: synthetic polypeptides

<400> SEQUENCE: 20

```
Leu Ser Cys Ala Ala Ser Gly Phe Thr Ile Ser Gly Ser Trp Ile
  1               5                  10                  15

His Trp Val Arg Gln Ala Pro Gly Lys Gly Leu Glu Trp Val Ala
                 20                  25                  30

Ile Ile Thr Pro Ser Gly Gly Asn Thr Asp Tyr Ala Asp Ser Val
                 35                  40                  45

Lys Gly Arg Phe Thr Ile Ser Ala Asp Thr Ser Lys Asn Thr Ala
                 50                  55                  60

Tyr Leu Gln Met Asn Ser Leu Arg Ala Glu Asp Thr Ala Val Tyr
                 65                  70                  75
```

Tyr Cys Ala Arg Glu Val Phe Ala Val Ser Thr Ala Gly Tyr Pro
            80                  85                  90

Trp Val Met Asp Tyr Trp Gly Gln
                95

<210> SEQ ID NO 21
<211> LENGTH: 96
<212> TYPE: PRT
<213> ORGANISM: Artificial sequence
<220> FEATURE:
<223> OTHER INFORMATION: synthetic polypeptides

<400> SEQUENCE: 21

Leu Ser Cys Ala Ala Ser Gly Phe Thr Ile Thr Asp Ser Trp Ile
 1               5                  10                  15

His Trp Val Arg Gln Ala Pro Gly Lys Gly Leu Glu Trp Val Gly
                20                  25                  30

Ser Ile Thr Pro Tyr Asn Gly Asn Thr Asp Tyr Ala Asp Ser Val
                35                  40                  45

Lys Gly Arg Phe Thr Ile Ser Ala Asp Thr Ser Lys Asn Thr Ala
                50                  55                  60

Tyr Leu Gln Met Asn Ser Leu Arg Ala Glu Asp Thr Ala Val Tyr
                65                  70                  75

Tyr Cys Ala Arg Arg Gly Glu Ser Asp Glu Ala Tyr Ala Ala Val
                80                  85                  90

Met Asp Tyr Trp Gly Gln
                95

<210> SEQ ID NO 22
<211> LENGTH: 97
<212> TYPE: PRT
<213> ORGANISM: Artificial sequence
<220> FEATURE:
<223> OTHER INFORMATION: synthetic polypeptides

<400> SEQUENCE: 22

Leu Ser Cys Ala Ala Ser Gly Phe Thr Ile Ser Ser Ser Asp Ile
 1               5                  10                  15

His Trp Val Arg Gln Ala Pro Gly Lys Gly Leu Glu Trp Val Gly
                20                  25                  30

Thr Ile Asn Pro Ala Ser Gly Ser Thr Asp Tyr Ala Asp Ser Val
                35                  40                  45

Lys Gly Arg Phe Thr Ile Ser Ala Asp Thr Ser Lys Asn Thr Ala
                50                  55                  60

Tyr Leu Gln Met Asn Ser Leu Arg Ala Glu Asp Thr Ala Val Tyr
                65                  70                  75

Tyr Cys Ala Arg Gly Ala Asn Ser Ser Phe Tyr Ala Leu Gln Tyr
                80                  85                  90

Val Met Asp Tyr Trp Gly Gln
                95

<210> SEQ ID NO 23
<211> LENGTH: 98
<212> TYPE: PRT
<213> ORGANISM: Artificial sequence
<220> FEATURE:
<223> OTHER INFORMATION: synthetic polypeptides

<400> SEQUENCE: 23

Leu Ser Cys Ala Ala Ser Gly Phe Thr Ile Thr Asp Asn Tyr Ile

```
  1               5                  10                 15
His Trp Val Arg Gln Ala Pro Gly Lys Gly Leu Glu Trp Val Gly
                 20                 25                 30

Trp Ile Ser Pro Tyr Ser Gly Tyr Thr Tyr Tyr Ala Asp Ser Val
                 35                 40                 45

Lys Gly Arg Phe Thr Ile Ser Ala Asp Thr Ser Lys Asn Thr Ala
                 50                 55                 60

Tyr Leu Gln Met Asn Ser Leu Arg Ala Glu Asp Thr Ala Val Tyr
                 65                 70                 75

Tyr Cys Ala Arg Glu Thr Leu Phe Tyr Asp Lys Asp Gln Tyr Ser
                 80                 85                 90

Tyr Val Met Asp Tyr Trp Gly Gln
                 95
```

<210> SEQ ID NO 24
<211> LENGTH: 94
<212> TYPE: PRT
<213> ORGANISM: Artificial sequence
<220> FEATURE:
<223> OTHER INFORMATION: synthetic polypeptides

<400> SEQUENCE: 24

```
Leu Ser Cys Ala Ala Ser Gly Phe Thr Ile Ser Ser Ser Tyr Ile
  1               5                  10                 15

His Trp Val Arg Gln Ala Pro Gly Lys Gly Leu Glu Trp Val Ala
                 20                 25                 30

Trp Ile Ser Pro Tyr Ser Gly Tyr Thr Asp Tyr Ala Asp Ser Val
                 35                 40                 45

Lys Gly Arg Phe Thr Ile Ser Ala Asp Thr Ser Lys Asn Thr Ala
                 50                 55                 60

Tyr Leu Gln Met Asn Ser Leu Arg Ala Glu Asp Thr Ala Val Tyr
                 65                 70                 75

Tyr Cys Ala Arg Glu Gly Leu Leu Arg Trp Gly Tyr Ala Met Asp
                 80                 85                 90

Tyr Trp Gly Gln
```

<210> SEQ ID NO 25
<211> LENGTH: 96
<212> TYPE: PRT
<213> ORGANISM: Artificial sequence
<220> FEATURE:
<223> OTHER INFORMATION: synthetic polypeptides

<400> SEQUENCE: 25

```
Leu Ser Cys Ala Ala Ser Gly Phe Thr Ile Ser Ser Ser Ala Ile
  1               5                  10                 15

His Trp Val Arg Gln Ala Pro Gly Lys Gly Leu Glu Trp Val Gly
                 20                 25                 30

Gly Ile Thr Pro Ala Ser Gly Tyr Thr Tyr Tyr Ala Asp Ser Val
                 35                 40                 45

Lys Gly Arg Phe Thr Ile Ser Ala Asp Thr Ser Lys Asn Thr Ala
                 50                 55                 60

Tyr Leu Gln Met Asn Ser Leu Arg Ala Glu Asp Thr Ala Val Tyr
                 65                 70                 75

Tyr Cys Ala Arg Ser Pro Gly Gly Val Phe Val Asp Gly Gly Val
                 80                 85                 90

Met Asp Tyr Trp Gly Gln
```

<210> SEQ ID NO 26
<211> LENGTH: 97
<212> TYPE: PRT
<213> ORGANISM: Artificial sequence
<220> FEATURE:
<223> OTHER INFORMATION: synthetic polypeptides

<400> SEQUENCE: 26

```
Leu Ser Cys Ala Ala Ser Gly Phe Thr Ile Thr Asn Thr Tyr Ile
 1               5                  10                  15
His Trp Val Arg Gln Ala Pro Gly Lys Gly Leu Glu Trp Val Ala
            20                  25                  30
Trp Ile Ser Pro Tyr Ser Gly Tyr Thr Asp Tyr Ala Asp Ser Val
        35                  40                  45
Lys Asp Arg Phe Thr Ile Ser Ala Asp Thr Ser Lys Asn Thr Ala
    50                  55                  60
Tyr Leu Gln Met Asn Ser Leu Arg Ala Glu Asp Thr Ala Val Tyr
65                  70                  75
Tyr Cys Ala Arg Glu Ile Leu Leu Asp Tyr Gly Ser Ala Gly Tyr
                80                  85                  90
Ala Met Asp Tyr Trp Gly Gln
                95
```

<210> SEQ ID NO 27
<211> LENGTH: 97
<212> TYPE: PRT
<213> ORGANISM: Artificial sequence
<220> FEATURE:
<223> OTHER INFORMATION: synthetic polypeptides

<400> SEQUENCE: 27

```
Leu Ser Cys Ala Ala Ser Gly Phe Thr Ile Thr Ser Thr Trp Ile
 1               5                  10                  15
His Trp Val Arg Gln Ala Pro Gly Lys Gly Leu Glu Trp Val Gly
            20                  25                  30
Val Ile Thr Pro Thr Asn Gly Ser Thr Tyr Tyr Ala Asp Ser Val
        35                  40                  45
Lys Gly Arg Phe Thr Ile Ser Ala Asp Thr Ser Lys Asn Thr Ala
    50                  55                  60
Tyr Leu Gln Met Asn Ser Leu Arg Ala Glu Asp Thr Ala Val Tyr
65                  70                  75
Tyr Cys Ala Arg Glu Val Trp Trp Gly Asp Gly His Gly Tyr
                80                  85                  90
Val Met Asp Tyr Trp Gly Gln
                95
```

<210> SEQ ID NO 28
<211> LENGTH: 96
<212> TYPE: PRT
<213> ORGANISM: Artificial sequence
<220> FEATURE:
<223> OTHER INFORMATION: synthetic polypeptides

<400> SEQUENCE: 28

```
Leu Ser Cys Ala Ala Ser Gly Phe Thr Ile Ser Ser Ser Ala Ile
 1               5                  10                  15
His Trp Val Arg Gln Ala Pro Gly Lys Gly Leu Glu Trp Val Gly
            20                  25                  30
```

Gly Ile Thr Pro Ala Ser Gly Tyr Thr Tyr Tyr Ala Asp Ser Val
            35                  40                  45

Lys Gly Arg Phe Thr Ile Ser Ala Asp Thr Ser Lys Asn Thr Ala
            50                  55                  60

Tyr Leu Gln Met Asn Ser Leu Arg Ala Glu Asp Thr Ala Val Tyr
            65                  70                  75

Tyr Cys Ala Arg Ser Pro Gly Gly Val Phe Val Asp Gly Gly Val
            80                  85                  90

Met Asp Tyr Trp Gly Gln
            95

<210> SEQ ID NO 29
<211> LENGTH: 101
<212> TYPE: PRT
<213> ORGANISM: Artificial sequence
<220> FEATURE:
<223> OTHER INFORMATION: synthetic polypeptides

<400> SEQUENCE: 29

Leu Ser Cys Ala Ala Ser Gly Phe Thr Ile Asn Ser Thr Asp Ile
  1               5                  10                  15

His Trp Val Arg Gln Ala Pro Gly Lys Gly Leu Glu Trp Val Gly
            20                  25                  30

Arg Ile Asn Pro Ser Gly Gly Ser Thr Asn Tyr Ala Asp Ser Val
            35                  40                  45

Lys Gly Arg Phe Thr Ile Ser Ala Asp Thr Ser Lys Asn Thr Ala
            50                  55                  60

Tyr Leu Gln Met Asn Ser Leu Arg Ala Glu Asp Thr Ala Val Tyr
            65                  70                  75

Tyr Cys Ala Arg Thr Ser Ala Tyr Thr Thr Trp Ala Val Asp Trp
            80                  85                  90

Phe Ile Gly Tyr Val Met Asp Tyr Trp Gly Gln
            95                  100

<210> SEQ ID NO 30
<211> LENGTH: 101
<212> TYPE: PRT
<213> ORGANISM: Artificial sequence
<220> FEATURE:
<223> OTHER INFORMATION: synthetic polypeptides

<400> SEQUENCE: 30

Leu Ser Cys Ala Ala Ser Gly Phe Thr Ile Thr Gly Tyr Gly Ile
  1               5                  10                  15

His Trp Val Arg Gln Ala Pro Gly Lys Gly Leu Glu Trp Val Ala
            20                  25                  30

Trp Ile Ser Pro Ser Asn Gly Tyr Thr Tyr Tyr Ala Asp Ser Val
            35                  40                  45

Lys Gly Arg Phe Thr Ile Ser Ala Asp Thr Ser Lys Asn Thr Ala
            50                  55                  60

Tyr Leu Gln Met Asn Ser Leu Arg Ala Glu Asp Thr Ala Val Tyr
            65                  70                  75

Tyr Cys Ala Arg Arg Val Ser Tyr Tyr Val Tyr Arg His Asp Trp
            80                  85                  90

Val Arg Gly Tyr Val Met Asp Tyr Trp Gly Gln
            95                  100

```
<210> SEQ ID NO 31
<211> LENGTH: 90
<212> TYPE: PRT
<213> ORGANISM: Artificial sequence
<220> FEATURE:
<223> OTHER INFORMATION: synthetic polypeptides

<400> SEQUENCE: 31

Leu Ser Cys Ala Ala Ser Gly Phe Thr Ile Thr Asp Thr Trp Ile
 1               5                  10                  15

His Trp Val Arg Gln Ala Pro Gly Lys Gly Leu Glu Trp Val Gly
                20                  25                  30

Val Ile Thr Pro Tyr Gly Gly Tyr Thr Tyr Tyr Ala Asp Ser Val
                35                  40                  45

Lys Gly Arg Phe Thr Ile Ser Ala Asp Thr Ser Lys Asn Thr Ala
                50                  55                  60

Tyr Leu Gln Met Asn Ser Leu Arg Ala Glu Asp Thr Ala Val Tyr
                65                  70                  75

Tyr Cys Ala Arg Asp Gly Gly Phe Phe Asp Tyr Trp Gly Gln
                80                  85                  90

<210> SEQ ID NO 32
<211> LENGTH: 94
<212> TYPE: PRT
<213> ORGANISM: Artificial sequence
<220> FEATURE:
<223> OTHER INFORMATION: synthetic polypeptides

<400> SEQUENCE: 32

Leu Ser Cys Ala Ala Ser Gly Phe Thr Ile Ser Asp Ser Tyr Ile
 1               5                  10                  15

His Trp Val Arg Gln Ala Pro Gly Lys Gly Leu Glu Trp Val Gly
                20                  25                  30

Asp Ile Thr Pro Thr Asp Gly Tyr Thr Asp Tyr Ala Asp Ser Val
                35                  40                  45

Lys Gly Arg Phe Thr Ile Ser Ala Asp Thr Ser Lys Asn Thr Ala
                50                  55                  60

Tyr Leu Gln Met Asn Ser Leu Arg Ala Glu Asp Thr Ala Val Tyr
                65                  70                  75

Tyr Cys Ala Arg Asn Leu Met Trp Trp Asp Ser Ser Ala Met Asp
                80                  85                  90

Tyr Trp Gly Gln

<210> SEQ ID NO 33
<211> LENGTH: 101
<212> TYPE: PRT
<213> ORGANISM: Artificial sequence
<220> FEATURE:
<223> OTHER INFORMATION: synthetic polypeptides

<400> SEQUENCE: 33

Leu Ser Cys Ala Ala Ser Gly Phe Thr Ile Thr Gly Tyr Gly Ile
 1               5                  10                  15

His Trp Val Arg Gln Ala Pro Gly Lys Gly Leu Glu Trp Val Ala
                20                  25                  30

Trp Ile Ser Pro Ser Asn Gly Tyr Thr Tyr Tyr Ala Asp Ser Val
                35                  40                  45

Lys Gly Arg Phe Thr Ile Ser Ala Tyr Thr Ser Lys Asn Thr Ala
                50                  55                  60
```

```
Tyr Leu Gln Met Asn Ser Leu Arg Ala Glu Asp Thr Ala Val Tyr
                65                  70                  75

Tyr Cys Ala Arg Arg Val Ser Tyr Tyr Val Tyr Arg His Asp Trp
            80                  85                  90

Val Arg Gly Tyr Val Met Asp Tyr Trp Gly Gln
        95                  100
```

<210> SEQ ID NO 34
<211> LENGTH: 96
<212> TYPE: PRT
<213> ORGANISM: Artificial sequence
<220> FEATURE:
<223> OTHER INFORMATION: synthetic polypeptides

<400> SEQUENCE: 34

```
Leu Ser Cys Ala Ala Ser Gly Phe Thr Ile Thr Gly Thr Tyr Ile
  1               5                  10                  15

His Trp Val Arg Gln Ala Pro Gly Lys Gly Leu Glu Trp Val Ala
                20                  25                  30

Trp Ile Ser Pro Tyr Ser Gly Tyr Thr Asn Tyr Ala Asp Ser Val
            35                  40                  45

Lys Gly Arg Phe Thr Ile Ser Ala Asp Thr Ser Lys Asn Thr Ala
        50                  55                  60

Tyr Leu Gln Met Asn Ser Leu Arg Ala Glu Asp Thr Ala Val Tyr
                65                  70                  75

Tyr Cys Ala Arg Glu Ala Arg Ser Ser Leu Ser Ala Asp Tyr Ala
            80                  85                  90

Met Asp Tyr Trp Gly Gln
                95
```

<210> SEQ ID NO 35
<211> LENGTH: 98
<212> TYPE: PRT
<213> ORGANISM: Artificial sequence
<220> FEATURE:
<223> OTHER INFORMATION: synthetic polypeptides

<400> SEQUENCE: 35

```
Leu Ser Cys Ala Ala Ser Gly Phe Thr Ile Thr Asp Asn Tyr Ile
  1               5                  10                  15

His Trp Val Arg Gln Ala Pro Gly Lys Gly Leu Glu Trp Val Ala
                20                  25                  30

Trp Ile Ser Pro Tyr Ser Gly Tyr Thr Tyr Tyr Ala Asp Ser Val
            35                  40                  45

Lys Gly Arg Phe Thr Ile Ser Ala Asp Thr Ser Lys Asn Thr Ala
        50                  55                  60

Tyr Leu Gln Met Asn Ser Leu Arg Ala Glu Asp Thr Ala Val Tyr
                65                  70                  75

Tyr Cys Ala Arg Glu Ser Gly Phe Ser Ala Cys Asn Thr Arg Ala
            80                  85                  90

Tyr Ala Met Asp Tyr Trp Gly Gln
                95
```

<210> SEQ ID NO 36
<211> LENGTH: 96
<212> TYPE: PRT
<213> ORGANISM: Artificial sequence
<220> FEATURE:
<223> OTHER INFORMATION: synthetic polypeptides

<400> SEQUENCE: 36

Leu Ser Cys Ala Ala Ser Gly Phe Thr Ile Thr Asp Ser Trp Ile
1               5                   10                  15

His Trp Val Arg Gln Ala Pro Gly Lys Gly Leu Glu Trp Val Gly
                20                  25                  30

Ser Ile Thr Pro Tyr Asn Gly Asn Thr Asp Tyr Ala Asp Ser Val
                35                  40                  45

Lys Gly Arg Phe Thr Ile Ser Ala Asp Thr Ser Lys Asn Thr Ala
            50                  55                  60

Tyr Leu Gln Met Asn Ser Leu Arg Ala Glu Asp Thr Ala Val Tyr
            65                  70                  75

Tyr Cys Ala Arg Arg Gly Glu Ser Asp Glu Ala Tyr Pro Ala Val
            80                  85                  90

Met Asp Tyr Trp Gly Gln
                95

<210> SEQ ID NO 37
<211> LENGTH: 94
<212> TYPE: PRT
<213> ORGANISM: Artificial sequence
<220> FEATURE:
<223> OTHER INFORMATION: synthetic polypeptides

<400> SEQUENCE: 37

Leu Ser Cys Ala Ala Ser Gly Phe Thr Ile Thr Ser Thr Ala Ile
1               5                   10                  15

His Trp Val Arg Gln Ala Pro Gly Lys Gly Leu Glu Trp Val Ala
                20                  25                  30

Trp Ile Thr Pro Tyr Asp Gly Tyr Thr Asp Tyr Ala Asp Ser Val
                35                  40                  45

Lys Gly Arg Phe Thr Ile Ser Ala Asp Thr Ser Lys Asn Thr Ala
            50                  55                  60

Tyr Leu Leu Met Asn Ser Leu Arg Ala Glu Asp Thr Ala Val Tyr
            65                  70                  75

Tyr Cys Ala Arg Thr Trp Phe Thr Leu Ala Ser Ala Met Glu Leu
            80                  85                  90

Leu Gly Ser Ala

<210> SEQ ID NO 38
<211> LENGTH: 101
<212> TYPE: PRT
<213> ORGANISM: Artificial sequence
<220> FEATURE:
<223> OTHER INFORMATION: synthetic polypeptides

<400> SEQUENCE: 38

Leu Ser Cys Ala Ala Ser Gly Phe Thr Ile Thr Gly Asn Gly Ile
1               5                   10                  15

His Trp Val Arg Gln Ala Pro Gly Lys Gly Leu Glu Trp Val Ala
                20                  25                  30

Trp Ile Ser Pro Thr Asn Gly Ser Thr Tyr Tyr Ala Asp Ser Val
                35                  40                  45

Lys Gly Arg Phe Thr Ile Ser Ala Asp Thr Ser Lys Asn Thr Ala
            50                  55                  60

Tyr Leu Gln Met Asn Ser Leu Arg Ala Glu Asp Thr Ala Val Tyr
            65                  70                  75

Tyr Cys Ala Arg Arg Val Asp Tyr Gln Val Tyr His Asp Arg Phe

Glu Glu Gly Tyr Ala Met Asp Tyr Trp Gly Gln
                95                 100

<210> SEQ ID NO 39
<211> LENGTH: 94
<212> TYPE: PRT
<213> ORGANISM: Artificial sequence
<220> FEATURE:
<223> OTHER INFORMATION: synthetic polypeptides

<400> SEQUENCE: 39

Leu Ser Cys Ala Ala Ser Gly Phe Thr Ile Asn Ser Tyr Trp Ile
 1               5                  10                  15

His Trp Val Arg Gln Ala Pro Gly Lys Gly Leu Glu Trp Val Gly
                20                  25                  30

Trp Ile Ser Pro Asp Asn Gly Ala Thr Asn Tyr Ala Asp Ser Val
                35                  40                  45

Lys Gly Arg Phe Thr Ile Ser Ala Asp Thr Ser Lys Asn Thr Ala
                50                  55                  60

Tyr Leu Gln Met Asn Ser Leu Arg Ala Glu Asp Thr Ala Val Tyr
                65                  70                  75

Tyr Cys Ala Arg Lys Phe Trp Gly Trp Asp Trp Gly Met Asp
                80                  85                  90

Tyr Trp Gly Gln

<210> SEQ ID NO 40
<211> LENGTH: 94
<212> TYPE: PRT
<213> ORGANISM: Artificial sequence
<220> FEATURE:
<223> OTHER INFORMATION: synthetic polypeptides

<400> SEQUENCE: 40

Leu Ser Cys Ala Ala Ser Gly Phe Thr Ile Ser Asp Ser Tyr Ile
 1               5                  10                  15

His Trp Val Arg Gln Ala Pro Gly Lys Gly Leu Glu Trp Val Gly
                20                  25                  30

Asp Ile Thr Pro Thr Asp Gly Tyr Thr Asp Tyr Ala Asp Ser Val
                35                  40                  45

Lys Gly Arg Phe Thr Ile Ser Ala Asp Thr Ser Lys Asn Thr Ala
                50                  55                  60

Tyr Leu Gln Met Asn Ser Leu Arg Ala Glu Asp Thr Ala Val Tyr
                65                  70                  75

Tyr Cys Ala Arg Asn Leu Met Trp Trp Asp Ser Ser Ala Met Asp
                80                  85                  90

Tyr Trp Gly Gln

<210> SEQ ID NO 41
<211> LENGTH: 94
<212> TYPE: PRT
<213> ORGANISM: Artificial sequence
<220> FEATURE:
<223> OTHER INFORMATION: synthetic polypeptides

<400> SEQUENCE: 41

Leu Ser Cys Ala Ala Ser Gly Phe Thr Ile Ser Asp Ser Gly Ile
 1               5                  10                  15

His Trp Val Arg Gln Ala Pro Gly Lys Gly Leu Glu Trp Val Gly

```
                20                  25                  30

Phe Ile Tyr Pro Asn Gly Gly Ser Thr Tyr Tyr Ala Asp Ser Val
                35                  40                  45

Lys Gly Arg Phe Thr Ile Ser Ala Asp Thr Ser Lys Asn Thr Ala
                50                  55                  60

Tyr Leu Gln Met Asn Ser Leu Arg Ala Glu Asp Thr Ala Val Tyr
            65                  70                  75

Tyr Cys Ala Arg Met Ser Leu Ile Gly Phe Ser Tyr Ala Met Asp
            80                  85                  90

Tyr Trp Gly Gln

<210> SEQ ID NO 42
<211> LENGTH: 93
<212> TYPE: PRT
<213> ORGANISM: Artificial sequence
<220> FEATURE:
<223> OTHER INFORMATION: synthetic polypeptides

<400> SEQUENCE: 42

Leu Ser Cys Ala Ala Ser Gly Phe Thr Ile Asn Ser Thr Trp Ile
1               5                   10                  15

His Trp Val Arg Gln Ala Pro Gly Lys Gly Leu Glu Trp Val Ala
                20                  25                  30

Trp Ile Asn Pro Tyr Asn Gly Ser Thr Tyr Tyr Ala Asp Ser Val
                35                  40                  45

Lys Gly Arg Phe Thr Ile Ser Ala Asp Thr Ser Lys Asn Thr Ala
                50                  55                  60

Tyr Leu Gln Met Asn Ser Leu Arg Ala Glu Asp Thr Ala Val Tyr
            65                  70                  75

Tyr Cys Ala Arg Asp Leu Tyr Asp Tyr Asp Ile Gly Phe Asp Tyr
            80                  85                  90

Trp Gly Gln

<210> SEQ ID NO 43
<211> LENGTH: 288
<212> TYPE: DNA
<213> ORGANISM: Artificial sequence
<220> FEATURE:
<223> OTHER INFORMATION: synthetic polynucleotides

<400> SEQUENCE: 43
ttgtcctgtg cagcttctgg cttcaccatt agtgattccg ctatacactg          50
ggtgcgtcag gccccgggta agggcctgga atgggttgct gggattactc         100
cttatagcgg ttatactgac tatgccgata gcgtcaaggg ccgtttcact         150
ataagcgcag acacatccaa aaacacagcc tacctacaaa tgaacagctt         200
aagagctgag acactgccg tctattattg tgcaaaagag gcccgcgagg          250
gctacgacgt cggctacgct atggactact ggggtcaa                     288

<210> SEQ ID NO 44
<211> LENGTH: 279
<212> TYPE: DNA
<213> ORGANISM: Artificial sequence
<220> FEATURE:
<223> OTHER INFORMATION: synthetic polynucleotides

<400> SEQUENCE: 44
ttgtcctgtg cagcttctgg cttcaccatt agtgattcct atatacactg          50
```
ggtgcgtcag gccccgggta agggcctgga atgggttgct gaaatttctc          100
ctcctggcgg cgatacttac tatgccgata gcgtcaaggg ccgtttcact          150
ataagcgcag acacatccaa aaacacagcc tacctacaaa tgaacagctt          200
aagagctgag gacactgccg tctattattg tgctcgtctc ttgtggtggt          250
gggacggggc tatggactac tggggtcaa                                 279

<210> SEQ ID NO 45
<211> LENGTH: 273
<212> TYPE: DNA
<213> ORGANISM: Artificial sequence
<220> FEATURE:
<223> OTHER INFORMATION: synthetic polynucleotides

<400> SEQUENCE: 45
ttgtcctgtg cagcttctgg cttcaccatt actaatactt ggatacactg           50
ggtgcgtcag gccccgggta agggcctgga atgggttgct gttattactc          100
cttatggcgg tgctacttac tatgccgata gcgtcaaggg ccgtttcact          150
ataagcgcag acacatccaa aaacacagcc tacctacaaa tgaacagctt          200
aagagctgag gacactgccg tctattattg tgcaagagag agtatgtgga          250
gtaagttcga ctactggggt caa                                       273

<210> SEQ ID NO 46
<211> LENGTH: 288
<212> TYPE: DNA
<213> ORGANISM: Artificial sequence
<220> FEATURE:
<223> OTHER INFORMATION: synthetic polynucleotides

<400> SEQUENCE: 46
ttgtcctgtg cagcttctgg cttcaccatt aatagttctg ctatacactg           50
ggtgcgtcag gccccgggta agggcctgga atgggttggt tatattactc          100
ctgataacgg tgatactaac tatgccgata gcgtcaaggg ccgtttcact          150
ataagcgcag acacatccaa aaacacagcc tacctacaaa tgaacagctt          200
aatagctgag gatactgccg tctattattg tgctcgcggc cacggcaact          250
tctacggtac ctgggcggct atggactact ggggtcaa                       288

<210> SEQ ID NO 47
<211> LENGTH: 276
<212> TYPE: DNA
<213> ORGANISM: Artificial sequence
<220> FEATURE:
<223> OTHER INFORMATION: synthetic polynucleotides

<400> SEQUENCE: 47
ttgtcctgtg cagcttctgg cttcaccatt agtggttctg atatacactg           50
ggtgcgtcag gccccgggta agggcctgga atgggttgct tatattaatc          100
cttatggcgg ttctactgac tatgccgata gcgtcaaggg ccgtttcact          150
ataagcgcag acacatccaa aaacacagcc tacctacaaa tgaacagctt          200
aagagctgag gacactgccg tctattattg tgctcgtgcg tacgagatgt          250
ggtacgttat ggactactgg ggtcaa                                    276

<210> SEQ ID NO 48

```
<211> LENGTH: 303
<212> TYPE: DNA
<213> ORGANISM: Artificial sequence
<220> FEATURE:
<223> OTHER INFORMATION: synthetic polynucleotides

<400> SEQUENCE: 48
ttgtcctgtg cagcttctgg cttcaccatt actaattcct ggatacactg        50
ggtgcgtcag gccccgggta agggcctgga atgggttggt gttattactc       100
cttctagcgg ttctacttac tatgccgata gcgtcaaggg ccgtttcact       150
ataagcgcag acacatccaa aaacacagcc tacctacaaa tgaacagctt       200
aagagctgag gacactgccg tctattattg tgctcgtgag gtcttccccg       250
acatcgggga ctgcagcaac gcctactgct acgctatgga ctactggggt       300
caa                                                          303

<210> SEQ ID NO 49
<211> LENGTH: 282
<212> TYPE: DNA
<213> ORGANISM: Artificial sequence
<220> FEATURE:
<223> OTHER INFORMATION: synthetic polynucleotides

<400> SEQUENCE: 49
ttgtcctgtg cagcttctgg cttcaccatt actagtactt atatacactg        50
ggtgcgtcag gccccgggta agggcctgga atgggttgct tggatttctc       100
cttatagcgg ttatactgac tatgccgata gcgtcaaggg ccgtttcact       150
ataagcgcag acacatccaa aaacacagcc tacctacaaa tgaacagctt       200
aagagctgag gacactgccg tctattattg tgctcgtgag gtggggtggg       250
gggactcgta cgctatggac tactggggtc aa                          282

<210> SEQ ID NO 50
<211> LENGTH: 297
<212> TYPE: DNA
<213> ORGANISM: Artificial sequence
<220> FEATURE:
<223> OTHER INFORMATION: synthetic polynucleotides

<400> SEQUENCE: 50
ttgtcctgtg cagcttctgg cttcaccatt agtggttctt ggatacactg        50
ggtgcgtcag gccccgggta agggcctgga atgggttgct gggatttatc       100
cttatgacgg ttatacttac tatgccgata gcgtcaaggg ccgtttcact       150
ataagcgcag acacatccaa aaacacagcc tacctacaaa tgaacagctt       200
aagagctgag gacactgccg tctattattg tgctcgtgag gccgagggcc       250
tgtaccagtc cgggatctac gacgcgggta tggactactg gggtcaa          297

<210> SEQ ID NO 51
<211> LENGTH: 279
<212> TYPE: DNA
<213> ORGANISM: Artificial sequence
<220> FEATURE:
<223> OTHER INFORMATION: synthetic polynucleotides

<400> SEQUENCE: 51
ttgtcctgtg cagcttctgg cttcaccatt actagttact atatacactg        50
ggtgcgtcag gccccgggta agggcctgga atgggttgct tggatttatc       100
```

```
ctgctgacgg tgctacttac tatgccgata gcgtcaaggg ccgtttcact          150
ataagcgcag acacatccaa aaacacagcc tacctacaaa tgaacagctt          200
aagagctgag gacactgccg tctattattg tgctcgtggg tcctacttcg          250
ggggctacga tatggactac  tggggtcaa                                279

<210> SEQ ID NO 52
<211> LENGTH: 276
<212> TYPE: DNA
<213> ORGANISM: Artificial sequence
<220> FEATURE:
<223> OTHER INFORMATION: synthetic polynucleotides

<400> SEQUENCE: 52
ttgtcctgtg cagcttctgg cttcaccatt aatgattctg atatacactg           50
ggtgcgtcag gccccgggta agggcctgga atgggttggt attatttatc          100
cttatgacgg ttatacttac tatgccgata gcgtcaaggg ccgtttcact          150
ataagcgcag acacatccaa aaacacagcc tacctacaaa tgaacagctt          200
aagagctgag gacactgccg tctattattg tgcaagaagc aacctggaca          250
acaacttgtt cgactactgg  ggtcaa                                    276

<210> SEQ ID NO 53
<211> LENGTH: 294
<212> TYPE: DNA
<213> ORGANISM: Artificial sequence
<220> FEATURE:
<223> OTHER INFORMATION: synthetic polynucleotides

<400> SEQUENCE: 53
ttgtcctgtg cagcttctgg cttcaccatt aatggttact ggatacactg           50
ggtgcgtcag gccccgggta agggcctgga atgggttgct gatattaatc          100
ctaatggcgg ttctactaac tatgccgata gcgtcaaggg ccgtttcact          150
ataagcgcag acacatccaa aaacacagcc tacctacaaa tgaacagctt          200
aagagctgag gacactgccg tctattattg tgctcgtgcc taccggtgcg          250
gcgggctcgc cgactgggcc ggggctatgg actactgggg  tcaa                294

<210> SEQ ID NO 54
<211> LENGTH: 294
<212> TYPE: DNA
<213> ORGANISM: Artificial sequence
<220> FEATURE:
<223> OTHER INFORMATION: synthetic polynucleotides

<400> SEQUENCE: 54
ttgtcctgtg cagcttctgg cttcaccatt agtggttctt ggatacactg           50
ggtgcgtcag gccccgggta agggcctgga atgggttgct attattactc          100
cttctggcgg taatactgac tatgccgata gcgtcaaggg ccgtttcact          150
ataagcgcag acacatccaa aaacacagcc tacctacaaa tgaacagctt          200
aagagctgag gacactgccg tctattattg tgctcgtgag gtcttcgccg          250
tgtcgaccgc cggctacccc tgggttatgg actactgggg  tcaa                294

<210> SEQ ID NO 55
<211> LENGTH: 288
<212> TYPE: DNA
```

<213> ORGANISM: Artificial sequence
<220> FEATURE:
<223> OTHER INFORMATION: synthetic polynucleotides

<400> SEQUENCE: 55

```
ttgtcctgtg cagcttctgg cttcaccatt actgattctt ggatacactg      50
ggtgcgtcag gccccgggta agggcctgga atgggttggt tctattactc     100
cttataacgg taatactgac tatgccgata gcgtcaaggg ccgtttcact     150
ataagcgcag acacatccaa aaacacagcc tacctacaaa tgaacagctt     200
aagagctgag gacactgccg tctattattg tgctcgcagg ggggagtccg     250
acgaggccta cgccgcggtt atggactact  ggggtcaa                288
```

<210> SEQ ID NO 56
<211> LENGTH: 291
<212> TYPE: DNA
<213> ORGANISM: Artificial sequence
<220> FEATURE:
<223> OTHER INFORMATION: synthetic polynucleotides

<400> SEQUENCE: 56

```
ttgtcctgtg cagcttctgg cttcaccatt agtagttccg atatacactg      50
ggtgcgtcag gccccgggta agggcctgga atgggttggt actattaatc     100
ctgctagcgg ttctactgac tatgccgata gcgtcaaggg ccgtttcact     150
ataagcgcag acacatccaa aaacacagcc tacctacaaa tgaacagctt     200
aagagctgag gacactgccg tctattattg tgctcgcggc gccaacagca     250
gcttctacgc gctccagtac gttatggact actggggtca a              291
```

<210> SEQ ID NO 57
<211> LENGTH: 294
<212> TYPE: DNA
<213> ORGANISM: Artificial sequence
<220> FEATURE:
<223> OTHER INFORMATION: synthetic polynucleotides

<400> SEQUENCE: 57

```
ttgtcctgtg cagcttctgg cttcaccatt actgataatt atatacactg      50
ggtgcgtcag gccccgggta agggcctgga atgggttggt tggatttctc     100
cttatagcgg ttatacttac tatgccgata gcgtcaaggg ccgtttcact     150
ataagcgcag acacatccaa aaacacagcc tacctacaaa tgaacagctt     200
aagagctgag gacactgccg tctattattg tgctcgtgag accctcttct     250
acgacaagga ccagtactcc tacgttatgg actactgggg tcaa           294
```

<210> SEQ ID NO 58
<211> LENGTH: 282
<212> TYPE: DNA
<213> ORGANISM: Artificial sequence
<220> FEATURE:
<223> OTHER INFORMATION: synthetic polynucleotides

<400> SEQUENCE: 58

```
ttgtcctgtg cagcttctgg cttcaccatt agtagttctt atatacactg      50
ggtgcgtcag gccccgggta agggcctgga atgggttgct tggatttctc     100
cttatagcgg ttatactgac tatgccgata gcgtcaaggg ccgtttcact     150
ataagcgcag acacatccaa aaacacagcc tacctacaaa tgaacagctt     200
```
aagagctgag gacactgccg tctattattg tgctcgtgag gggctcctgc      250
ggtggggcta cgctatggac tactggggtc aa                         282

<210> SEQ ID NO 59
<211> LENGTH: 291
<212> TYPE: DNA
<213> ORGANISM: Artificial sequence
<220> FEATURE:
<223> OTHER INFORMATION: synthetic polynucleotides

<400> SEQUENCE: 59
ttgtcctgtg cagcttctgg cttcaccatt actgataatg ggatacactg      50
ggtgcgtcag gccccgggta agggcctgga atgggttggt tggattactc      100
ctactagcgg ttatactaac tatgccgata gcgtcaaggg ccgtttcact      150
ataagcgcag acacatccaa aaacacagcc tacctacaaa tgaacagctt      200
aagagctgag gacactgccg tctattattg tgctcgcgac ggggacacct      250
ggaagtggga cgccccgtac gttatggact actggggtca a               291

<210> SEQ ID NO 60
<211> LENGTH: 291
<212> TYPE: DNA
<213> ORGANISM: Artificial sequence
<220> FEATURE:
<223> OTHER INFORMATION: synthetic polynucleotides

<400> SEQUENCE: 60
ttgtcctgtg cagcttctgg cttcaccatt actaatactt atatacactg      50
ggtgcgtcag gccccgggta agggcctgga atgggttgct tggatttctc      100
cttatagcgg ttatactgac tatgccgata gcgtcaagga ccgtttcact      150
ataagcgcag acacatccaa aaacacagcc tacctacaaa tgaacagctt      200
aagagctgag gacactgccg tctattattg tgctcgcgag atcttgctgg      250
actacggttc cgcgggctac gctatggact actggggtca a               291

<210> SEQ ID NO 61
<211> LENGTH: 291
<212> TYPE: DNA
<213> ORGANISM: Artificial sequence
<220> FEATURE:
<223> OTHER INFORMATION: synthetic polynucleotides

<400> SEQUENCE: 61
ttgtcctgtg cagcttctgg cttcaccatt actagtacct ggatacactg      50
ggtgcgtcag gccccgggta agggcctgga atgggttggt gttattactc      100
ctactaacgg ttctacttac tatgccgata gcgtcaaggg ccgtttcact      150
ataagcgcag acacatccaa aaacacagcc tacctacaaa tgaacagctt      200
aagagctgag gacactgccg tctattattg tgctcgcgag gtgtggtggt      250
ggggcgacgg ccacggctac gttatggact actggggtca a               291

<210> SEQ ID NO 62
<211> LENGTH: 288
<212> TYPE: DNA
<213> ORGANISM: Artificial sequence
<220> FEATURE:
<223> OTHER INFORMATION: synthetic polynucleotides

<400> SEQUENCE: 62

| | |
|---|---|
| ttgtcctgtg cagcttctgg cttcaccatt agtagttctg ctatacactg | 50 |
| ggtgcgtcag gccccgggta agggcctgga atgggttggt gggattactc | 100 |
| ctgctagcgg ttatacttac tatgccgata gcgtcaaggg ccgtttcact | 150 |
| ataagcgcag acacatccaa aaacacagcc tacctacaaa tgaacagctt | 200 |
| aagagctgag gacactgccg tctattattg tgctcgctcg cccggcgggg | 250 |
| tgttcgtcga cggcggggtt atggactact ggggtcaa | 288 |

<210> SEQ ID NO 63
<211> LENGTH: 303
<212> TYPE: DNA
<213> ORGANISM: Artificial sequence
<220> FEATURE:
<223> OTHER INFORMATION: synthetic polynucleotides

<400> SEQUENCE: 63

| | |
|---|---|
| ttgtcctgtg cagcttctgg cttcaccatt aatagtactg atatacactg | 50 |
| ggtgcgtcag gccccgggta agggcctgga atgggttggt aggattaatc | 100 |
| cttctggcgg ttctactaac tatgccgata gcgtcaaggg ccgtttcact | 150 |
| ataagcgcag acacatccaa aaacacagcc tacctacaaa tgaacagctt | 200 |
| aagagctgag gacactgccg tctattattg tgctcgtacc agcgcgtaca | 250 |
| ccacgtgggc ggtcgactgg ttcatcggct acgttatgga ctactggggt | 300 |
| caa | 303 |

<210> SEQ ID NO 64
<211> LENGTH: 303
<212> TYPE: DNA
<213> ORGANISM: Artificial sequence
<220> FEATURE:
<223> OTHER INFORMATION: synthetic polynucleotides

<400> SEQUENCE: 64

| | |
|---|---|
| ttgtcctgtg cagcttctgg cttcaccatt actggttacg ggatacactg | 50 |
| ggtgcgtcag gccccgggta agggcctgga atgggttgct tggatttctc | 100 |
| cttctaacgg ttatacttac tatgccgata gcgtcaaggg ccgtttcact | 150 |
| ataagcgcag acacatccaa aaacacagcc tacctacaaa tgaacagctt | 200 |
| aagagctgag gacactgccg tctattattg tgctcgtcgc gtcagctact | 250 |
| acgtctacag gcacgactgg gtcaggggct acgttatgga ctactggggt | 300 |
| caa | 303 |

<210> SEQ ID NO 65
<211> LENGTH: 267
<212> TYPE: DNA
<213> ORGANISM: Artificial sequence
<220> FEATURE:
<223> OTHER INFORMATION: synthetic polynucleotides

<400> SEQUENCE: 65

| | |
|---|---|
| ttgtcctgtg cagcttctgg cttcaccatt actgatacct ggatacactg | 50 |
| ggtgcgtcag gccccgggta agggcctgga atgggttggt gttattactc | 100 |
| cttatggcgg ttatacttac tatgccgata gcgtcaaggg ccgtttcact | 150 |
| ataagcgcag acacatccaa aaacacagcc tacctacaaa tgaacagctt | 200 | aagagctgag gacactgccg tctattattg tgcaagagac gggggcttct        250 tcgattactg gggtcaa        267

<210> SEQ ID NO 66
<211> LENGTH: 282
<212> TYPE: DNA
<213> ORGANISM: Artificial sequence
<220> FEATURE:
<223> OTHER INFORMATION: synthetic polynucleotides

<400> SEQUENCE: 66
ttgtcctgtg cagcttctgg cttcaccatt agtgattcct ctatacactg        50
ggtgcgtcag gccccgggta agggcctgga atgggttgct tttatttatc        100
ctactagcgg ttctacttac tatgccaata gcgtcaaggg ccgtttcact        150
ataagcgcag acacatccaa aaacacagcc tacctacaaa tgaacagctt        200
aagagctgag gacactgccg tctattattg tgcacgtgcc tcgtacgggg        250
tgagcaagtg gaccttgac tactggggtc aa        282

<210> SEQ ID NO 67
<211> LENGTH: 303
<212> TYPE: DNA
<213> ORGANISM: Artificial sequence
<220> FEATURE:
<223> OTHER INFORMATION: synthetic polynucleotides

<400> SEQUENCE: 67
ttgtcctgtg cagcttctgg cttcaccatt actggttacg ggatacactg        50
ggtgcgtcag gccccgggta agggcctgga atgggttgct tggatttctc        100
cttctaacgg ttatacttac tatgccgata gcgtcaagg ccgtttcact        150 ataagcgcat acacatccaa aaacacagcc tacctacaaa tgaacagctt        200
aagagctgag gacactgccg tctattattg tgctcgtcgc gtcagctact        250
acgtctacag gcacgactgg gtcaggggct acgttatgga ctactggggt        300
caa  303

<210> SEQ ID NO 68
<211> LENGTH: 288
<212> TYPE: DNA
<213> ORGANISM: Artificial sequence
<220> FEATURE:
<223> OTHER INFORMATION: synthetic polynucleotides

<400> SEQUENCE: 68
ttgtcctgtg cagcttctgg cttcaccatt actggtactt atatacactg        50
ggtgcgtcag gccccgggta agggcctgga atgggttgct tggatttctc        100
cttatagcgg ttatactaac tatgccgata gcgtcaaggg ccgtttcact        150
ataagcgcag acacatccaa aaacacagcc tacctacaaa tgaacagctt        200
aagagctgag gacactgccg tctattattg tgcaagagag gcccgctcct        250
cgttgagcgc ggactacgct atggactact ggggtcaa        288

<210> SEQ ID NO 69
<211> LENGTH: 294
<212> TYPE: DNA
<213> ORGANISM: Artificial sequence
<220> FEATURE:

<223> OTHER INFORMATION: synthetic polynucleotides

<400> SEQUENCE: 69

| ttgtcctgtg cagcttctgg cttcaccatt actgataatt atatacactg | 50 |
| ggtgcgtcag gccccgggta agggcctgga atgggttgct tggatttctc | 100 |
| cttatagcgg ttatacttac tatgccgata gcgtcaaggg ccgtttcact | 150 |
| ataagcgcag acacatccaa aaacacagcc tacctacaaa tgaacagctt | 200 |
| aagagctgag gacactgccg tctattattg tgctcgtgag tccggcttct | 250 |
| ccgcgtgcaa cacgcgggcg tacgctatgg actactgggg tcaa | 294 |

<210> SEQ ID NO 70
<211> LENGTH: 288
<212> TYPE: DNA
<213> ORGANISM: Artificial sequence
<220> FEATURE:
<223> OTHER INFORMATION: synthetic polynucleotides

<400> SEQUENCE: 70

| ttgtcctgtg cagcttctgg cttcaccatt actgattctt ggatacactg | 50 |
| ggtgcgtcag gccccgggta agggcctgga atgggttggt tctattactc | 100 |
| cttataacgg taatactgac tatgccgata gcgtcaaggg ccgtttcact | 150 |
| ataagcgcag acacatccaa aaacacagcc tacctacaaa tgaacagctt | 200 |
| aagagctgag gacactgccg tctattattg tgctcgcagg ggggagtccg | 250 |
| acgaggccta ccccgcggtt atggactact ggggtcaa | 288 |

<210> SEQ ID NO 71
<211> LENGTH: 280
<212> TYPE: DNA
<213> ORGANISM: Artificial sequence
<220> FEATURE:
<223> OTHER INFORMATION: synthetic polynucleotides

<400> SEQUENCE: 71

| ttgtcctgtg cagcttctgg cttcaccatt actagtaccg ctatacactg | 50 |
| ggtgcgtcag gccccgggta agggcctgga atgggttgct tggattactc | 100 |
| cttatgacgg ttatactgac tatgccgata gcgtcaaggg ccgtttcact | 150 |
| ataagcgcag acacatccaa aaacacagcc tacctactaa tgaacagctt | 200 |
| aagagctgag gacactgccg tctattattg tgctcgtacg tggttcacgc | 250 |
| tggcctcggc tatggaacta ctggggtcaa | 280 |

<210> SEQ ID NO 72
<211> LENGTH: 303
<212> TYPE: DNA
<213> ORGANISM: Artificial sequence
<220> FEATURE:
<223> OTHER INFORMATION: synthetic polynucleotides

<400> SEQUENCE: 72

| ttgtcctgtg cagcttctgg cttcaccatt actggtaatg gatacactg | 50 |
| ggtgcgtcag gccccgggta agggcctgga atgggttgct tggatttctc | 100 |
| ctactaacgg ttctacttac tatgccgata gcgtcaaggg ccgtttcact | 150 |
| ataagcgcag acacatccaa aaacacagcc tacctacaaa tgaacagctt | 200 |
| aagagctgag gacactgccg tctattattg tgctcgtagg gtcgactacc | 250 | aggtctacca cgaccgcttc gaggaggggt acgctatgga ctactggggt    300 caa    303

<210> SEQ ID NO 73
<211> LENGTH: 282
<212> TYPE: DNA
<213> ORGANISM: Artificial sequence
<220> FEATURE:
<223> OTHER INFORMATION: synthetic polynucleotides

<400> SEQUENCE: 73
ttgtcctgtg cagcttctgg cttcaccatt aatagttatt ggatacactg    50
ggtgcgtcag gccccgggta agggcctgga atgggttggt tggatttctc    100
ctgataacgg tgctactaac tatgccgata gcgtcaaggg ccgtttcact    150
ataagcgcag acacatccaa aaacacagcc tacctacaaa tgaacagctt    200
aagagctgag gacactgccg tctattattg tgctcgtaag ttctggggct    250
gggactgggg gggtatggac tactggggtc aa    282

<210> SEQ ID NO 74
<211> LENGTH: 282
<212> TYPE: DNA
<213> ORGANISM: Artificial sequence
<220> FEATURE:
<223> OTHER INFORMATION: synthetic polynucleotides

<400> SEQUENCE: 74
ttgtcctgtg cagcttctgg cttcaccatt agtgattctt atatacactg    50
ggtgcgtcag gccccgggta agggcctgga atgggttggt gatattactc    100
ctactgacgg ttatactgac tatgccgata gcgtcaaggg ccgtttcact    150
ataagcgcag acacatccaa aaacacagcc tacctacaaa tgaacagctt    200
aagagctgag gacactgccg tctattattg tgctcgtaac ttgatgtggt    250
gggactcgtc ggctatggac tactggggtc aa    282

<210> SEQ ID NO 75
<211> LENGTH: 282
<212> TYPE: DNA
<213> ORGANISM: Artificial sequence
<220> FEATURE:
<223> OTHER INFORMATION: synthetic polynucleotides

<400> SEQUENCE: 75
ttgtcctgtg cagcttctgg cttcaccatt agtgattctg gatacactg    50 ggtgcgtcag gccccgggta agggcctgga atgggttggt tttatttatc    100
ctaatggcgg ttctacttac tatgccgata gcgtcaaggg ccgtttcact    150
ataagcgcag acacatccaa aaacacagcc tacctacaaa tgaacagctt    200
aagagctgag gacactgccg tctattattg tgctcgtatg tcgttgatcg    250
ggttctcgta cgctatggac tactggggtc aa    282

<210> SEQ ID NO 76
<211> LENGTH: 279
<212> TYPE: DNA
<213> ORGANISM: Artificial sequence
<220> FEATURE:
<223> OTHER INFORMATION: synthetic polynucleotides

<400> SEQUENCE: 76

```
ttgtcctgtg cagcttctgg cttcaccatt aatagtacct ggatacactg         50
ggtgcgtcag gccccgggta agggcctgga atgggttgct tggattaatc        100
cttataacgg ttctacttac tatgccgata gcgtcaaggg ccgtttcact        150
ataagcgcag acacatccaa aaacacagcc tacctacaaa tgaacagctt        200
aagagctgag gacactgccg tctattattg tgcaagagac ttgtacgact        250
acgacatcgg cttcgactac  tggggtcaa                              279
```

<210> SEQ ID NO 77
<211> LENGTH: 133
<212> TYPE: PRT
<213> ORGANISM: Homo sapiens

<400> SEQUENCE: 77

```
Arg Lys Ile Pro Lys Val Gly His Thr Phe Phe Gln Lys Pro Glu
 1               5                  10                  15

Ser Cys Pro Pro Val Pro Gly Gly Ser Met Lys Leu Asp Ile Gly
                20                  25                  30

Ile Ile Asn Glu Asn Gln Arg Val Ser Met Ser Arg Asn Ile Glu
            35                  40                  45

Ser Arg Ser Thr Ser Pro Trp Asn Tyr Thr Val Thr Trp Asp Pro
        50                  55                  60

Asn Arg Tyr Pro Ser Glu Val Val Gln Ala Gln Cys Arg Asn Leu
    65                  70                  75

Gly Cys Ile Asn Ala Gln Gly Lys Glu Asp Ile Ser Met Asn Ser
80                  85                  90

Val Pro Ile Gln Gln Glu Thr Leu Val Val Arg Arg Lys His Gln
                95                 100                 105

Gly Cys Ser Val Ser Phe Gln Leu Glu Lys Val Leu Val Thr Val
            110                 115                 120

Gly Cys Thr Cys Val Thr Pro Val Ile His His Val Gln
        125                 130
```

<210> SEQ ID NO 78
<211> LENGTH: 132
<212> TYPE: PRT
<213> ORGANISM: Homo sapiens

<400> SEQUENCE: 78

```
Gly Ile Thr Ile Pro Arg Asn Pro Gly Cys Pro Asn Ser Glu Asp
 1               5                  10                  15

Lys Asn Phe Pro Arg Thr Val Met Val Asn Leu Asn Ile His Asn
                20                  25                  30

Arg Asn Thr Asn Thr Asn Pro Lys Arg Ser Ser Asp Tyr Tyr Asn
            35                  40                  45

Arg Ser Thr Ser Pro Trp Asn Leu His Arg Asn Glu Asp Pro Glu
        50                  55                  60

Arg Tyr Pro Ser Val Ile Trp Glu Ala Lys Cys Arg His Leu Gly
    65                  70                  75

Cys Ile Asn Ala Asp Gly Asn Val Asp Tyr His Met Asn Ser Val
80                  85                  90

Pro Ile Gln Gln Glu Ile Leu Val Leu Arg Arg Glu Pro Pro His
                95                 100                 105

Cys Pro Asn Ser Phe Arg Leu Glu Lys Ile Leu Val Ser Val Gly
```

```
                    110                 115                 120
Cys Thr Cys Val Thr Pro Ile Val His His Val Ala
                125                 130

<210> SEQ ID NO 79
<211> LENGTH: 10
<212> TYPE: PRT
<213> ORGANISM: Homo sapiens

<400> SEQUENCE: 79

Glu Pro Pro His Cys Pro Asn Ser Phe Arg
                  5                  10

<210> SEQ ID NO 80
<211> LENGTH: 10
<212> TYPE: PRT
<213> ORGANISM: Homo sapiens

<400> SEQUENCE: 80

Asn Pro Gly Cys Pro Asn Ser Glu Asp Lys
                  5                  10
```

ANTIBODIES DIRECTED TO IL-17A/IL-17F HETERODIMERS

CROSS-REFERENCE TO RELATED APPLICATIONS

This application is a Continuation of U.S. application Ser. No. 11/953,733, filed Dec. 10, 2007, which is a Division of U.S. application Ser. No. 10/860,824, filed Jun. 2, 2004, now abandoned, which claims the benefit under 35 U.S.C. 119(h) of provisional application Ser. No. 60/486,457, filed Jul. 11, 2003 and provisional application Ser. No. 60/485,599, filed Jul. 8, 2003, which are incorporated by reference herein in their entireties.

SUBMISSION OF COMPUTER PROGRAM LISTING ON ASCII TEXT FILE

The content of the following submission on ASCII text file is incorporated herein by reference in its entirety: a computer readable form (CRF) of the Computer Program Listing (file name: 146392032402table1.txt, date recorded: Mar. 8, 2018, size: 32 kb).

FIELD OF THE INVENTION

The present invention relates generally to the identification and isolation of a novel human cytokine designated herein as interleukin-17A/F (IL-17A/F).

BACKGROUND OF THE INVENTION

Extracellular proteins play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. These secreted polypeptides or signaling molecules normally pass through the cellular secretory pathway to reach their site of action in the extracellular environment.

Secreted proteins have various industrial applications, including as pharmaceuticals, diagnostics, biosensors and bioreactors. Most protein drugs available at present, such as thrombolytic agents, interferons, interleukins, erythropoietins, colony stimulating factors, and various other cytokines, are secretory proteins. Their receptors, which are membrane proteins, also have potential as therapeutic or diagnostic agents.

Membrane-bound proteins and receptors can play important roles in, among other things, the formation, differentiation and maintenance of multicellular organisms. The fate of many individual cells, e.g., proliferation, migration, differentiation, or interaction with other cells, is typically governed by information received from other cells and/or the immediate environment. This information is often transmitted by secreted polypeptides (for instance, mitogenic factors, survival factors, cytotoxic factors, differentiation factors, neuropeptides, and hormones) which are, in turn, received and interpreted by diverse cell receptors or membrane-bound proteins. Such membrane-bound proteins and cell receptors include, but are not limited to, cytokine receptors, receptor kinases, receptor phosphatases, receptors involved in cell-cell interactions, and cellular adhesin molecules like selectins and integrins. For instance, transduction of signals that regulate cell growth and differentiation is regulated in part by phosphorylation of various cellular proteins. Protein tyrosine kinases, enzymes that catalyze that process, can also act as growth factor receptors. Examples include fibroblast growth factor receptor and nerve growth factor receptor.

Similarly to secreted proteins, membrane-bound proteins and receptor molecules have various industrial applications, including as pharmaceutical and diagnostic agents. Receptor immunoadhesins, for instance, can be employed as therapeutic agents to block receptor-ligand interactions. The membrane-bound proteins can also be employed for screening of potential peptide or small molecule inhibitors of the relevant receptor/ligand interaction.

Efforts are being undertaken by both industry and academia to identify new, native secreted proteins and native receptor or membrane-bound proteins. Many efforts are focused on the screening of mammalian recombinant DNA libraries to identify the coding sequences for novel secreted proteins. Examples of screening methods and techniques are described in the literature [see, for example, Klein et al., *Proc. Natl. Acad. Sci.*, 93:7108-7113 (1996); U.S. Pat. No. 5,536,637)].

In this regard, the present invention relates to identifying novel secreted polypeptides of the interleukin-17 (IL-17) family which have been shown to be related to immune-mediated and inflammatory disease. Immune related and inflammatory diseases are the manifestation or consequence of fairly complex, often multiple interconnected biological pathways which in normal physiology are critical to respond to insult or injury, initiate repair from insult or injury, and mount innate and acquired defense against foreign organisms. Disease or pathology occurs when these normal physiological pathways cause additional insult or injury either as directly related to the intensity of the response, as a consequence of abnormal regulation or excessive stimulation, as a reaction to self, or as a combination of these.

Though the genesis of these diseases often involves multi-step pathways and often multiple different biological systems/pathways, intervention at critical points in one or more of these pathways can have an ameliorative or therapeutic effect. Therapeutic intervention can occur by either antagonism of a detrimental process/pathway or stimulation of a beneficial process/pathway.

Many immune related diseases are known and have been extensively studied. Such diseases include immune-mediated inflammatory diseases (such as rheumatoid arthritis, immune mediated renal disease, hepatobiliary diseases, inflammatory bowel disease (IBD), psoriasis, and asthma), non-immune-mediated inflammatory diseases, infectious diseases, immunodeficiency diseases, neoplasia, etc.

T lymphocytes (T cells) are an important component of a mammalian immune response. T cells recognize antigens which are associated with a self-molecule encoded by genes within the major histocompatibility complex (MHC). The antigen may be displayed together with MHC molecules on the surface of antigen presenting cells, virus infected cells, cancer cells, grafts, etc. The T cell system eliminates these altered cells which pose a health threat to the host mammal. T cells include helper T cells and cytotoxic T cells. Helper T cells proliferate extensively following recognition of an antigen-MHC complex on an antigen presenting cell. Helper T cells also secrete a variety of cytokines i.e., lymphokines, which play a central role in the activation of B cells, cytotoxic T cells and a variety of other cells which participate in the immune response.

A central event in both humoral and cell mediated immune responses is the activation and clonal expansion of helper T cells. Helper T cell activation is initiated by the interaction of the T cell receptor (TCR)-CD3 complex with an antigen-MHC on the surface of an antigen presenting cell. This interaction mediates a cascade of biochemical events that induce the resting helper T cell to enter a cell cycle (the G0 to G1 transition) and results in the expression of a high affinity receptor for IL-2 and sometimes IL-4. The activated T cell progresses through the cycle proliferating and differentiating into memory cells or effector cells.

In addition to the signals mediated through the TCR, activation of T cells involves additional costimulation induced by cytokines released by the antigen presenting cell or through interactions with membrane bound molecules on the antigen presenting cell and the T cell. The cytokines IL-1 and IL-6 have been shown to provide a costimulatory signal. Also, the interaction between the B7 molecule expressed on the surface of an antigen presenting cell and CD28 and CTLA-4 molecules expressed on the T cell surface effect T cell activation. Activated T cells express an increased number of cellular adhesion molecules, such as ICAM-1, integrins, VLA-4, LFA-1, CD56, etc.

T-cell proliferation in a mixed lymphocyte culture or mixed lymphocyte reaction (MLR) is an established indication of the ability of a compound to stimulate the immune system. In many immune responses, inflammatory cells infiltrate the site of injury or infection. The migrating cells may be neutrophilic, eosinophilic, monocytic or lymphocytic as can be determined by histologic examination of the affected tissues. *Current Protocols in Immunology*, ed. John E. Coligan, 1994, John Wiley & Sons, Inc.

Immune related diseases could be treated by suppressing the immune response. Using neutralizing antibodies that inhibit molecules having immune stimulatory activity would be beneficial in the treatment of immune-mediated and inflammatory diseases. Molecules which inhibit the immune response can be utilized (proteins directly or via the use of antibody agonists) to inhibit the immune response and thus ameliorate immune related disease.

Interleukin-17 (IL-17) is a T-cell derived pro-inflammatory molecule that stimulates epithelial, endothelial and fibroblastic cells to produce other inflammatory cytokines and chemokines including IL-6, IL-8, G-CSF, and MCP-1 [see, Yao, Z. et al., *J. Immunol.*, 122(12):5483-5486 (1995); Yao, Z. et al., *Immunity*, 3(6):811-821 (1995); Fossiez, F., et al., *J. Exp. Med.*, 183(6): 2593-2603 (1996); Kennedy, J., et al., *J. Interferon Cytokine Res.*, 16(8):611-7 (1996); Cai, X. Y., et al., *Immunol. Lett*, 62(1):51-8 (1998); Jovanovic, D. V., et al., *J. Immunol.*, 160(7):3513-21 (1998); Laan, M., et al., *J. Immunol.*, 162(4):2347-52 (1999); Linden, A., et al., *Eur Respir J*, 15(5):973-7 (2000); and Aggarwal, S. and Gurney, A. L., *J Leukoc Biol*, 71(1):1-8 (2002)]. IL-17 also synergizes with other cytokines including TNF-α and IL-1β to further induce chemokine expression (Chabaud, M., et al., *J. Immunol.* 161(1):409-14 (1998)). Interleukin 17 (IL-17) exhibits pleitropic biological activities on various types of cells. IL-17 also has the ability to induce ICAM-1 surface expression, proliferation of T cells, and growth and differentiation of CD34$^+$ human progenitors into neutrophils. IL-17 has also been implicated in bone metabolism, and has been suggested to play an important role in pathological conditions characterized by the presence of activated T cells and TNF-α production such as rheumatoid arthritis and loosening of bone implants (Van Bezooijen et al., *J. Bone Miner. Res.*, 14: 1513-1521 [1999]). Activated T cells of synovial tissue derived from rheumatoid arthritis patients were found to secrete higher amounts of IL-17 than those derived from normal individuals or osteoarthritis patients (Chabaud et al., *Arthritis Rheum.*, 42: 963-970 [1999]). It was suggested that this proinflammatory cytokine actively contributes to synovial inflammation in rheumatoid arthritis. Apart from its proinflammatory role, IL-17 seems to contribute to the pathology of rheumatoid arthritis by yet another mechanism. For example, IL-17 has been shown to induce the expression of osteoclast differentiation factor (ODF) mRNA in osteoblasts (Kotake et al., *J. Clin. Invest.*, 103: 1345-1352 [1999]). ODF stimulates differentiation of progenitor cells into osteoclasts, the cells involved in bone resorption. Since the level of IL-17 is significantly increased in synovial fluid of rheumatoid arthritis patients, it appears that IL-17 induced osteoclast formation plays a crucial role in bone resorption in rheumatoid arthritis. IL-17 is also believed to play a key role in certain other autoimmune disorders such as multiple sclerosis (Matusevicius et al., *Mult. Scler.*, 5: 101-104 (1999); Kurasawa, K., et al., *Arthritis Rheu* 43(11):2455-63 (2000)) and psoriasis (Teunissen, M. B., et al., *J Invest Dermatol* 111(4):645-9 (1998); Albanesi, C., et al., *J Invest Dermatol* 115(1):81-7 (2000); and Homey, B., et al., *J. Immunol.* 164(12:6621-32 (2000)).

IL-17 has further been shown, by intracellular signalling, to stimulate Ca$^{2+}$ influx and a reduction in [cAMP], in human macrophages (Jovanovic et al., *J. Immunol.*, 160: 3513 [1998]). Fibroblasts treated with IL-17 induce the activation of NF-κB, [Yao et al., *Immunity*, 3:811 (1995), Jovanovic et al., supra], while macrophages treated with it activate NF-κB and mitogen-activated protein kinases (Shalom-Barek et al., *J. Biol. Chem.*, 273:27467 [1998]). Additionally, IL-17 also shares sequence similarity with mammalian cytokine-like factor 7 that is involved in bone and cartilage growth. Other proteins with which IL-17 polypeptides share sequence similarity are human embryo-derived interleukin-related factor (EDIRF) and interleukin-20.

Consistent with IL-17's wide-range of effects, the cell surface receptor for IL-17 has been found to be widely expressed in many tissues and cell types (Yao et al., *Cytokine*, 9:794 [1997]). While the amino acid sequence of the human IL-17 receptor (IL-R) (866 amino acids) predicts a protein with a single transmembrane domain and a long, 525 amino acid intracellular domain, the receptor sequence is unique and is not similar to that of any of the receptors from the cytokine/growth factor receptor family. This coupled with the lack of similarity of IL-17 itself to other known proteins indicates that IL-17 and its receptor may be part of a novel family of signaling proteins and receptors. It has been demonstrated that IL-17 activity is mediated through binding to its unique cell surface receptor (designated herein as human IL-17R), wherein previous studies have shown that contacting T cells with a soluble form of the IL-17 receptor polypeptide inhibited T cell proliferation and IL-2 production induced by PHA, concanavalin A and anti-TCR monoclonal antibody (Yao et al., *J. Immunol.*, 155:5483-5486 [1995]). As such, there is significant interest in identifying and characterizing novel polypeptides having homology to the known cytokine receptors, specifically IL-17 receptors.

Interleukin 17 is now recognized as the prototype member of an emerging family of cytokines. The large scale sequencing of the human and other vertebrate genomes has revealed the presence of additional genes encoding proteins clearly related to IL-17, thus defining a new family of cytokines. There are at least 6 members of the IL-17 family in humans and mice including IL-17B, IL-17C, IL-17D, IL-17E and IL-17F as well as novel receptors IL-17RH1, IL-17RH2, IL-17RH3 and IL-17RH4 (see WO01/46420 published Jun. 28, 2001). One such IL-17 member (designated as IL-17F) has been demonstrated to bind to the human IL-17 receptor (IL-17R) (Yao et al., *Cytokine*, 9(11):794-800 (1997)). Initial characterization suggests that, like IL-17, several of these newly identified molecules have the ability to modulate immune function. The potent inflammatory actions that have been identified for several of these factors and the emerging associations with major human diseases suggest that these proteins may have significant roles in inflammatory processes and may offer opportunities for therapeutic intervention.

The gene encoding human IL-17F is located adjacent to IL-17 (Hymowitz, S. G., et al., *Embo J*, 20(19):5332-41 (2001)). IL-17 and IL-17F share 44% amino acid identity whereas the other members of the IL-17 family share a more limited 15-27% amino acid identity suggesting that IL-17 and IL-17F form a distinct subgroup within the IL-17 family (Starnes, T., et al., *J Immunol*. 167(8):4137-40 (2001); Aggarwal, S. and Gurney, A. L., *J. Leukoc Biol*, 71(1):1-8 (2002)). IL-17F appears to have similar biological actions as IL-17, and is able to promote the production of IL-6, IL-8, and G-CSF from a wide variety of cells. Similar to IL-17, it is able to induce cartilage matrix release and inhibit new cartilage matrix synthesis (see US-2002-0177188-A1 published Nov. 28, 2002). Thus, like IL-17, IL-17F may potentially contribute to the pathology of inflammatory disorders. Recently, these authors have observed that both IL-17 and IL-17F are induced in T cells by the action of interleukin 23 (IL-23) (Aggarwal, S., et al., *J. Biol. Chem.*, 278(3):1910-4 (2003)). The observation that IL-17 and IL-17F share similar chromosomal localization and significant sequence similarity sd well as the observation that IL-17 and IL-17F appear to be induced with the same cell population in response to a specific stimuli has lead to the identification of a new human cytokine that is comprised of a covalent heterodimer of IL-17 and IL-17F (herein designated IL-17A/F). Human IL-17A/F is a distinctly new cytokine, distinguishable from human IL-17 and IL-17F in both protein structure and in cell-based activity assays. Through the use of purified recombinant human IL-17A/F as a standard, a human IL-17AF-specific ELISA has been developed. Through the use of this specific ELISA, the induced expression of human IL-17A/F was detected, confirming that IL-17A/F is naturally produced from activated human T cells in culture. Hence, IL-17A/F is a distinctly new cytokine, detectable as a natural product of isolated activated human T cells, whose recombinant form has been characterized, in both protein structure and cell-based assays, as to be different and distinguishable from related cytokines. Thus, these studies provide and identify a novel immune stimulant (i.e. IL-17A/F) that can boost the immune system to respond to a particular antigen that may not have been immunologically active previously. As such, the newly identified immune stimulant has important clinical applications. This novel IL-17A/F cytokine or agonists thereof, would therefore find practical utility as an immune stimulant, whereas molecules which inhibit IL-17A/F activity (antagonists) would be expected to find practical utility when an inhibition of the immune response is desired, such as in autoimmune diseases. Specifically, antibodies to this new cytokine which either mimic (agonist antibodies) or inhibit (antagonist antibodies) the immunological activities of IL-17A/F would possess therapeutic qualities. Small molecules which act to inhibit the activity of this novel cytokine would also have potential therapeutic uses.

SUMMARY OF THE INVENTION

A. Embodiments

The present invention concerns compositions and methods useful for the diagnosis and treatment of immune related disease in mammals, including humans. The present invention is based on the identification of proteins (including agonist and antagonist antibodies) which either stimulate or inhibit the immune response in mammals. Immune related diseases can be treated by suppressing or enhancing the immune response. Molecules that enhance the immune response stimulate or potentiate the immune response to an antigen. Molecules which stimulate the immune response can be used therapeutically where enhancement of the immune response would be beneficial. Alternatively, molecules that suppress the immune response attenuate or reduce the immune response to an antigen (e.g., neutralizing antibodies) can be used therapeutically where attenuation of the immune response would be beneficial (e.g., inflammation). Accordingly, the IL-17A/F polypeptides of the present invention and agonists and antagonists thereof are also useful to prepare medicines and medicaments for the treatment of immune-related and inflammatory diseases. In a specific aspect, such medicines and medicaments comprise a therapeutically effective amount of an IL-17A/F polypeptide, agonist or antagonist thereof with a pharmaceutically acceptable carrier. Preferably, the admixture is sterile.

In a further embodiment, the invention concerns a method of identifying agonists of or antagonists to an IL-17A/F polypeptide which comprises contacting the IL-17A/F polypeptide with a candidate molecule and monitoring a biological activity mediated by said IL-17A/F polypeptide. Preferably, the IL-17A/F polypeptide is a native sequence IL-17A/F polypeptide. In a specific aspect, the IL-17A/F agonist or antagonist is an anti-IL-17A/F antibody.

In another embodiment, the invention concerns a composition of matter comprising an IL-17A/F polypeptide or an agonist or antagonist antibody which binds the polypeptide in admixture with a carrier or excipient. In one aspect, the composition comprises a therapeutically effective amount of the polypeptide or antibody. In another aspect, when the composition comprises an immune stimulating molecule, the composition is useful for: (a) enhancing infiltration of inflammatory cells into a tissue of a mammal in need thereof, (b) stimulating or enhancing an immune response in a mammal in need thereof, (c) increasing the proliferation of T-lymphocytes in a mammal in need thereof in response to an antigen, (d) stimulating the activity of T-lymphocytes or (e) increasing the vascular permeability. In a further aspect, when the composition comprises an immune inhibiting molecule, the composition is useful for: (a) decreasing infiltration of inflammatory cells into a tissue of a mammal in need thereof, (b) inhibiting or reducing an immune response in a mammal in need thereof, (c) decreasing the activity of T-lymphocytes or (d) decreasing the proliferation of T-lymphocytes in a mammal in need thereof in response to an antigen. In another aspect, the composition comprises a further active ingredient, which may, for example, be a further antibody or a cytotoxic or chemotherapeutic agent. Preferably, the composition is sterile.

In another embodiment, the invention concerns a method of treating an immune related disorder in a mammal in need thereof, comprising administering to the mammal a therapeutically effective amount of an IL-17A/F polypeptide, an agonist thereof, or an antagonist thereto. In a preferred aspect, the immune related disorder is selected form the group consisting of: systemic lupus erythematosis, rheumatoid arthritis, osteoarthritis, juvenile chronic arthritis, spondyloarthropathies, systemic sclerosis, idiopathic inflammatory myopathies, Sjögren's syndrome, systemic vasculitis, sarcoidosis, autoimmune hemolytic anemia, autoimmune thrombocytopenia, thyroiditis, diabetes mellitus, immune-mediated renal disease, demyelinating diseases of the central and peripheral nervous systems such as multiple sclerosis, idiopathic demyelinating polyneuropathy or Guillain-Barré syndrome, and chronic inflammatory demyelinating polyneuropathy, hepatobiliary diseases such as infectious, autoimmune chronic active hepatitis, primary biliary cirrhosis, granulomatous hepatitis, and sclerosing cholangitis, inflammatory bowel disease, gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonia, idiopathic pulmonary fibrosis and hypersensitivity pneumonitis, transplantation associated diseases including graft rejection and graft-versus-host-disease.

In another embodiment, the invention provides an antibody which specifically binds to any of the above or below described polypeptides. Optionally, the antibody is a monoclonal antibody, humanized antibody, antibody fragment or single-chain antibody. In one aspect, the present invention concerns an isolated antibody which binds an IL-17A/F polypeptide. In another aspect, the antibody mimics the activity of an IL-17A/F polypeptide (an agonist antibody) or conversely the antibody inhibits or neutralizes the activity of an IL-17A/F polypeptide (an antagonist antibody). In another aspect, the antibody is a monoclonal antibody, which preferably has nonhuman complementarity determining region (CDR) residues and human framework region (FR) residues. The antibody may be labeled and may be immobilized on a solid support. In a further aspect, the antibody is an antibody fragment, a monoclonal antibody, a single-chain antibody, or an anti-idiotypic antibody. In another aspect, the antibody fragment or single-chain antibody comprises a Fab fragment selected from the group consisting of the amino acid sequence shown in FIG. 6 as SEQ ID NO:9, SEQ ID NO:10; SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, and SEQ ID NO:42, wherein said Fab fragment further comprises three heavy chain variable regions containing CDR-H1 consisting of amino acid residues 7 to 16 of SEQ ID NOs:9-42, CDR-H2 consisting of amino acid residues 30 to 46 of SEQ ID NOs:9-42, and CDR-H3 consisting of amino acid residue 78 to at least amino acid residue 96 of SEQ ID NOs:9-42, wherein said Fab fragment is capable of binding IL-17A/F. In another aspect, the antibody fragment or single-chain antibody comprises a Fab fragment selected from the group consisting of the amino acid sequence shown in FIG. 6 as SEQ ID NO:9, SEQ ID NO:10; SEQ ID NO: 11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, and SEQ ID NO:42, wherein said Fab fragment further comprises at least heavy chain variable region containing CDR-H1 consisting of amino acid residues 7 to 16 of SEQ ID NOs:9-42, and CDR-H2 consisting of amino acid residues 30 to 46 of SEQ ID NOs:9-42, wherein said Fab fragment is capable of binding IL-17A/F. In another aspect, the antibody fragment or single-chain antibody comprises a Fab fragment selected from the group consisting of the amino acid sequence shown in FIG. 6 as SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, and SEQ ID NO:42, wherein said Fab fragment further comprises at least heavy chain variable regions containing CDR-H1 consisting of amino acid residues 7 to 16 of SEQ ID NOs:9-42 and CDR-H3 consisting of amino acid residue 78 to at least amino acid residue 96 of SEQ ID NOs:9-42, wherein said Fab fragment is capable of binding IL-17A/F. In another aspect, the antibody fragment or single-chain antibody comprises a Fab fragment selected from the group consisting of the amino acid sequence shown in FIG. 6 as SEQ ID NO:9, SEQ ID NO:10; SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, and SEQ ID NO:42, wherein said Fab fragment further comprises at least heavy chain variable regions containing CDR-H2 consisting of amino acid residues 30 to 46 of SEQ ID NOs:9-42, and CDR-H3 consisting of amino acid residue 78 to at least amino acid residue 96 of SEQ ID NOs:9-42, wherein said Fab fragment is capable of binding IL-17A/F. In another aspect, the antibody fragment or single-chain antibody comprises a Fab fragment selected from the group consisting of the amino acid sequence shown in FIG. 6 as SEQ ID NO:9, SEQ ID NO:10; SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, and SEQ ID NO:42, wherein said Fab fragment further comprises at least one of heavy chain variable region containing CDR-H1 consisting of amino acid residues 7 to 16 of SEQ ID NOs:9-42, CDR-H2 consisting of amino acid residues 30 to 46 of SEQ ID NOs:9-42, or CDR-H3 consisting of amino acid residue 78 to at least amino acid residue 96 of SEQ ID NOs:9-42, wherein said Fab fragment is capable of binding IL-17A/F. In another aspect, said CDR-H1 region of SEQ ID NO:9, SEQ ID NO:10; SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, or SEQ ID NO:42 comprises at least amino acid residues 7-10 corresponding to the amino sequence GFTI (designated herein as SEQ ID NO:77), wherein said SEQ ID NO:77 is capable of binding IL-17A/F. In another aspect, said CDR-H2 region of SEQ ID NO:9, SEQ ID NO:10; SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, or SEQ ID NO:42 comprises at least amino acid residues 41-46 corresponding to amino acid sequence YADSVK (designated herein as SEQ ID NO:78), wherein said SEQ ID NO:78 is capable of binding IL-17A/F.

In still another embodiment, the invention concerns an isolated nucleic acid molecule selected from the group consisting of the nucleotide sequence of SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75 and SEQ ID NO:76, wherein said nucleic acid molecule encodes the Fab fragment shown as SEQ ID NO:9, SEQ ID NO: 10; SEQ ID NO: 11, SEQ ID NO: 12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, or SEQ ID NO:42, wherein said Fab fragment is capable of binding to IL-17A/F.

In a another aspect, the invention provides an isolated Fab fragment capable of binding IL-17A/F encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of said Fab fragment and recovering said Fab fragment from the cell culture.

In yet another embodiment, the present invention provides a composition comprising an anti-IL-17A/F antibody in admixture with a pharmaceutically acceptable carrier. In one aspect, the composition comprises a therapeutically effective amount of the antibody. Preferably, the composition is sterile. The composition may be administered in the form of a liquid pharmaceutical formulation, which may be preserved to achieve extended storage stability. Alternatively, the antibody is a monoclonal antibody, an antibody fragment, a humanized antibody, or a single-chain antibody.

In a further embodiment, the invention concerns an article of manufacture, comprising:

(a) a composition of matter comprising an IL-17A/F polypeptide or agonist, antagonist, or an antibody that specifically binds to said polypeptide thereof;

(b) a container containing said composition; and (c) a label affixed to said container, or a package insert included in said container referring to the use of said IL-17A/F polypeptide or agonist or antagonist thereof in the treatment of an immune related disease. The composition may comprise a therapeutically effective amount of the IL-17A/F polypeptide or the agonist or antagonist thereof.

In yet another embodiment, the present invention concerns a method of diagnosing an immune related disease in a mammal, comprising detecting the level of expression of a gene encoding an IL-17A/F polypeptide (a) in a test sample of tissue cells obtained from the mammal, and (b) in a control sample of known normal tissue cells of the same cell type, wherein a higher or lower expression level in the test sample as compared to the control sample indicates the presence of immune related disease in the mammal from which the test tissue cells were obtained.

In another embodiment, the present invention concerns a method of diagnosing an immune disease in a mammal, comprising (a) contacting an anti-IL-17A/F antibody with a test sample of tissue cells obtained from the mammal, and (b) detecting the formation of a complex between the antibody and an IL-17A/F polypeptide, in the test sample; wherein the formation of said complex is indicative of the presence or absence of said disease. The detection may be qualitative or quantitative, and may be performed in comparison with monitoring the complex formation in a control sample of known normal tissue cells of the same cell type. A larger quantity of complexes formed in the test sample indicates the presence or absence of an immune disease in the mammal from which the test tissue cells were obtained. The antibody preferably carries a detectable label. Complex formation can be monitored, for example, by light microscopy, flow cytometry, fluorimetry, or other techniques known in the art. The test sample is usually obtained from an individual suspected of having a deficiency or abnormality of the immune system.

In another embodiment, the invention provides a method for determining the presence of an IL-17A/F polypeptide in a sample comprising exposing a test sample of cells suspected of containing the IL-17A/F polypeptide to an anti-IL-17A/F antibody and determining the binding of said antibody to said cell sample. In a specific aspect, the sample comprises a cell suspected of containing the IL-17A/F polypeptide and the antibody binds to the cell. The antibody is preferably detectably labeled and/or bound to a solid support.

In another embodiment, the present invention concerns an immune-related disease diagnostic kit, comprising an anti-IL-17A/F antibody and a carrier in suitable packaging. The kit preferably contains instructions for using the antibody to detect the presence of the IL-17A/F polypeptide. Preferably the carrier is pharmaceutically acceptable.

In another embodiment, the present invention concerns a diagnostic kit, containing an anti-IL-17A/F antibody in suitable packaging. The kit preferably contains instructions for using the antibody to detect the IL-17A/F polypeptide.

In another embodiment, the invention provides a method of diagnosing an immune-related disease in a mammal which comprises detecting the presence or absence or an IL-17A/F polypeptide in a test sample of tissue cells obtained from said mammal, wherein the presence or absence of the IL-17A/F polypeptide in said test sample is indicative of the presence of an immune-related disease in said mammal.

In another embodiment, the present invention concerns a method for identifying an agonist of an IL-17A/F polypeptide comprising:
(a) contacting cells and a test compound to be screened under conditions suitable for the induction of a cellular response normally induced by an IL-17A/F polypeptide; and
(b) determining the induction of said cellular response to determine if the test compound is an effective agonist, wherein the induction of said cellular response is indicative of said test compound being an effective agonist.

In another embodiment, the invention concerns a method for identifying a compound capable of inhibiting the activity of an IL-17A/F polypeptide comprising contacting a candidate compound with an IL-17A/F polypeptide under conditions and for a time sufficient to allow these two components to interact and determining whether the activity of the IL-17A/F polypeptide is inhibited. In a specific aspect, either the candidate compound or the IL-17A/F polypeptide is immobilized on a solid support. In another aspect, the non-immobilized component carries a detectable label. In a preferred aspect, this method comprises the steps of:
(a) contacting cells and a test compound to be screened in the presence of an IL-17A/F polypeptide under conditions suitable for the induction of a cellular response normally induced by an IL-17A/F polypeptide; and
(b) determining the induction of said cellular response to determine if the test compound is an effective antagonist.

In another embodiment, the invention provides a method for identifying a compound that inhibits the expression of an IL-17A/F polypeptide in cells that normally express the polypeptide, wherein the method comprises contacting the cells with a test compound and determining whether the expression of the IL-17A/F polypeptide is inhibited. In a preferred aspect, this method comprises the steps of:
(a) contacting cells and a test compound to be screened under conditions suitable for allowing expression of the IL-17A/F polypeptide; and (b) determining the inhibition of expression of said polypeptide.

In yet another embodiment, the present invention concerns a method for treating an immune-related disorder in a mammal that suffers therefrom comprising administering to the mammal a nucleic acid molecule that codes for either (a) an IL-17A/F polypeptide, (b) an agonist of an IL-17A/F polypeptide or (c) an antagonist of an IL-17A/F polypeptide, wherein said agonist or antagonist may be an anti-IL-17A/F antibody. In a preferred embodiment, the mammal is human. In another preferred embodiment, the nucleic acid is administered via ex vivo gene therapy. In a further preferred embodiment, the nucleic acid is comprised within a vector, more preferably an adenoviral, adeno-associated viral, lentiviral or retroviral vector.

In yet another aspect, the invention provides a recombinant viral particle comprising a viral vector consisting essentially of a promoter, nucleic acid encoding (a) an IL-17A/F polypeptide, (b) an agonist polypeptide of an IL-17A/F polypeptide, or (c) an antagonist polypeptide of an IL-17A/F polypeptide, and a signal sequence for cellular secretion of the polypeptide, wherein the viral vector is in association with viral structural proteins. Preferably, the signal sequence is from a mammal, such as from a native IL-17A/F polypeptide.

In a still further embodiment, the invention concerns an ex vivo producer cell comprising a nucleic acid construct that expresses retroviral structural proteins and also comprises a retroviral vector consisting essentially of a promoter, nucleic acid encoding (a) an IL-17A/F polypeptide, (b) an agonist polypeptide of an IL-17A/F polypeptide or (c) an antagonist polypeptide of an IL-17A/F polypeptide, and a signal sequence for cellular secretion of the polypeptide, wherein said producer cell packages the retroviral vector in association with the structural proteins to produce recombinant retroviral particles.

In a still further embodiment, the invention provides a method for enhancing the infiltration of inflammatory cells from the vasculature into a tissue of a mammal comprising administering to said mammal (a) an IL-17A/F polypeptide or (b) an agonist of an IL-17A/F polypeptide, wherein the infiltration of inflammatory cells from the vasculature in the mammal is enhanced.

In a still further embodiment, the invention provides a method for decreasing the infiltration of inflammatory cells from the vasculature into a tissue of a mammal comprising administering to said mammal (a) an IL-17A/F polypeptide or (b) an antagonist of an IL-17A/F polypeptide, wherein the infiltration of inflammatory cells from the vasculature in the mammal is decreased.

In a still further embodiment, the invention provides a method of increasing the activity of T-lymphocytes in a mammal comprising administering to said mammal (a) an IL-17A/F polypeptide or (b) an agonist of an IL-17A/F polypeptide, wherein the activity of T-lymphocytes in the mammal is increased.

In a still further embodiment, the invention provides a method of decreasing the activity of T-lymphocytes in a mammal comprising administering to said mammal (a) an IL-17A/F polypeptide or (b) an antagonist of an IL-17A/F polypeptide, wherein the activity of T-lymphocytes in the mammal is decreased.

In a still further embodiment, the invention provides a method of increasing the proliferation of T-lymphocytes in a mammal comprising administering to said mammal (a) an IL-17A/F polypeptide or (b) an agonist of an IL-17A/F polypeptide, wherein the proliferation of T-lymphocytes in the mammal is increased.

In a still further embodiment, the invention provides a method of decreasing the proliferation of T-lymphocytes in a mammal comprising administering to said mammal (a) an IL-17A/F polypeptide or (b) an antagonist of an IL-17A/F polypeptide, wherein the proliferation of T-lymphocytes in the mammal is decreased.

In still a further embodiment, the invention concerns the use of an IL-17A/F polypeptide, or an agonist or antagonist thereof as hereinbefore described, or an anti-IL-17A/F antibody, for the preparation of a medicament useful in the treatment of a condition which is responsive to the IL-17A/F polypeptide or an agonist or antagonist thereof (e.g., anti-IL-17A/F). In a particular aspect, the invention concerns the use of an IL-17A/F polypeptide, or an agonist or antagonist thereof in a method for treating a degenerative cartilaginous disorder.

In still a further embodiment, the invention relates to a method of treating a degenerative cartilaginous disorder in a mammal comprising administering a therapeutically effective amount of an IL-17A/F polypeptide, agonist, or antagonist thereof, to said mammal suffering from said disorder.

In still a further embodiment, the invention relates to a kit comprising a composition comprising an IL-17A/F polypeptide, or an agonist or antagonist thereof, in admixture with a pharmaceutically acceptable carrier, a container containing said composition; and a label affixed to said container, referring to the use of said composition, in the treatment of a degenerative cartilaginous disorder.

B. Additional Embodiments

In other embodiments of the present invention, the invention provides an isolated nucleic acid molecule comprising a nucleotide sequence that encodes an IL-17A/F polypeptide.

In one aspect, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule encoding an IL-17A/F polypeptide having a full-length amino acid sequence as disclosed herein, an amino acid sequence lacking the signal peptide as disclosed herein, or any other specifically defined fragment of the full-length amino acid sequence as disclosed herein, or (b) the complement of the DNA molecule of (a).

In other aspects, the isolated nucleic acid molecule comprises a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule comprising the coding sequence of a full-length IL-17A/F polypeptide cDNA as disclosed herein, the coding sequence of an IL-17A/F polypeptide lacking the signal peptide as disclosed herein, or the coding sequence of any other specifically defined fragment of the full-length amino acid sequence as disclosed herein, or (b) the complement of the DNA molecule of (a).

In a further aspect, the invention concerns an isolated nucleic acid molecule comprising a nucleotide sequence having at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity to (a) a DNA molecule that encodes the same mature polypeptide encoded by any of the human protein cDNAs deposited with the ATCC as disclosed herein, or (b) the complement of the DNA molecule of (a).

Another embodiment is directed to fragments of an IL-17A/F polypeptide coding sequence, or the complement thereof, that may find use as, for example, hybridization probes, for encoding fragments of an IL-17A/F polypeptide that may optionally encode a polypeptide comprising a binding site for an anti-IL-17A/F antibody or as antisense oligonucleotide probes. Such nucleic acid fragments are usually at least about 20 nucleotides in length, alternatively at least about 30 nucleotides in length, alternatively at least about 40 nucleotides in length, alternatively at least about 50 nucleotides in length, alternatively at least about 60 nucleotides in length, alternatively at least about 70 nucleotides in length, alternatively at least about 80 nucleotides in length, alternatively at least about 90 nucleotides in length, alternatively at least about 100 nucleotides in length, alternatively at least about 110 nucleotides in length, alternatively at least about 120 nucleotides in length, alternatively at least about 130 nucleotides in length, alternatively at least about 140 nucleotides in length, alternatively at least about 150 nucleotides in length, alternatively at least about 160 nucleotides in length, alternatively at least about 170 nucleotides in length, alternatively at least about 180 nucleotides in length, alternatively at least about 190 nucleotides in length, alternatively at least about 200 nucleotides in length, alternatively at least about 250 nucleotides in length, alternatively at least about 300 nucleotides in length, alternatively at least about 350 nucleotides in length, alternatively at least about 400 nucleotides in length, alternatively at least about 450 nucleotides in length, alternatively at least about 500 nucleotides in length, alternatively at least about 600 nucleotides in length, alternatively at least about 700 nucleotides in length, alternatively at least about 800 nucleotides in length, alternatively at least about 900 nucleotides in length and alternatively at least about 1000 nucleotides in length, wherein in this context the term "about" means the referenced nucleotide sequence length plus or minus 10% of that referenced length. It is noted that novel fragments of an IL-17A/F polypeptide-encoding nucleotide sequence may be determined in a routine manner by aligning the IL-17A/F polypeptide-encoding nucleotide sequence with other known nucleotide sequences using any of a number of well known sequence alignment programs and determining which polypeptide-encoding nucleotide sequence fragment(s) are novel. All of such polypeptide-encoding nucleotide sequences are contemplated herein. Also contemplated are the polypeptide fragments encoded by these nucleotide molecule fragments, preferably those IL-17A/F polypeptide fragments that comprise a binding site for an anti-IL-17A/F antibody.

In another embodiment, the invention provides an isolated IL-17A/F polypeptide encoded by any of the isolated nucleic acid sequences hereinabove identified.

In a certain aspect, the invention concerns an isolated IL-17A/F polypeptide, comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to an IL-17A/F polypeptide having a full-length amino acid sequence as disclosed herein, an amino acid sequence lacking the signal peptide as disclosed herein, as disclosed herein or any other specifically defined fragment of the full-length amino acid sequence as disclosed herein.

In a further aspect, the invention concerns an isolated IL-17A/F polypeptide comprising an amino acid sequence having at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to an amino acid sequence encoded by any of the human protein cDNAs deposited with the ATCC as disclosed herein.

In a further aspect, the invention concerns an isolated IL-17A/F polypeptide comprising an amino acid sequence scoring at least about 80% positives, alternatively at least about 81% positives, alternatively at least about 82% positives, alternatively at least about 83% positives, alternatively at least about 84% positives, alternatively at least about 85% positives, alternatively at least about 86% positives, alternatively at least about 87% positives, alternatively at least about 88% positives, alternatively at least about 89% positives, alternatively at least about 90% positives, alternatively at least about 91% positives, alternatively at least about 92% positives, alternatively at least about 93% positives, alternatively at least about 94% positives, alternatively at least about 95% positives, alternatively at least about 96% positives, alternatively at least about 97% positives, alternatively at least about 98% positives and alternatively at least about 99% positives when compared with the amino acid sequence of an IL-17A/F polypeptide having a full-length amino acid sequence as disclosed herein, an amino acid sequence lacking the signal peptide as disclosed herein, or any other specifically defined fragment of the full-length amino acid sequence as disclosed herein.

In a specific aspect, the invention provides an isolated IL-17A/F polypeptide without the N-terminal signal sequence and/or the initiating methionine and is encoded by a nucleotide sequence that encodes such an amino acid sequence as hereinbefore described. Processes for producing the same are also herein described, wherein those processes comprise culturing a host cell comprising a vector which comprises the appropriate encoding nucleic acid molecule under conditions suitable for expression of the IL-17A/F polypeptide and recovering the IL-17A/F polypeptide from the cell culture.

In yet another embodiment, the invention concerns agonists and antagonists of a native IL-17A/F polypeptide as defined herein. In a particular embodiment, the agonist or antagonist is an anti-IL-17A/F antibody or a small molecule.

In a further embodiment, the invention concerns a method of identifying agonists or antagonists to an IL-17A/F polypeptide which comprise contacting the IL-17A/F polypeptide with a candidate molecule and monitoring a biological activity mediated by said IL-17A/F polypeptide. Preferably, the IL-17A/F polypeptide is a native IL-17A/F polypeptide.

In a still further embodiment, the invention concerns a composition of matter comprising an IL-17A/F polypeptide, or an agonist or antagonist of an IL-17A/F polypeptide as herein described, or an anti-IL-17A/F antibody, in combination with a carrier. Optionally, the carrier is a pharmaceutically acceptable carrier.

Another embodiment of the present invention is directed to the use of an IL-17A/F polypeptide, or an agonist or antagonist thereof as hereinbefore described, or an anti-IL-17A/F antibody, for the preparation of a medicament useful in the treatment of a condition which is responsive to the IL-17A/F polypeptide, an agonist or antagonist thereof or an anti-IL-17A/F antibody.

In additional embodiments of the present invention, the invention provides vectors comprising DNA encoding any of the herein described polypeptides. Host cell comprising any such vector are also provided. By way of example, the host cells may be CHO cells, E. coli, yeast, or Baculovirus-infected insect cells. An process for producing any of the herein described polypeptides is further provided and comprises culturing host cells under conditions suitable for expression of the desired polypeptide and recovering the desired polypeptide from the cell culture.

In other embodiments, the invention provides chimeric molecules comprising any of the herein described polypeptides fused to a heterologous polypeptide or amino acid sequence. Example of such chimeric molecules comprise any of the herein described polypeptides fused to an epitope tag sequence or a Fc region of an immunoglobulin.

In yet another embodiment, the invention provides an antibody which specifically binds to any of the above or below described polypeptides. Optionally, the antibody is a monoclonal antibody, humanized antibody, antibody fragment or single-chain antibody.

In yet other embodiments, the invention provides oligonucleotide probes useful for isolating genomic and cDNA nucleotide sequences or as antisense probes, wherein those probes may be derived from any of the above or below described nucleotide sequences.

BRIEF DESCRIPTION OF THE DRAWINGS

FIG. 1A and FIG. 1B show the results of expressing and isolating a novel human cytokine designated IL-17A/F. Human 293 kidney cells were transfected with cDNA expression vectors encoding human IL-17 and IL-17F alone or in combination as indicated in FIG. 1A and FIG. 1B. Conditioned media from transfected cells was immunoprecipitated (IP) utilizing antibodies that are able to recognize IL-17 (lanes 1-5), or IL-17F (lanes 6-10) as indicated in FIG. 1A and FIG. 1B. Western Blot analysis is shown demonstrating the presence of a dimeric IL-17A/F complex in lane 8 of FIG. 1A and in lane 3 of FIG. 1B. The dimeric IL-17A/F complex is consistent in size with a covalent heterodimeric species comprised of one polypeptide chain of IL-17 and one polypeptide chain of IL-17F.

FIG. 2A-2G show the purification of recombinant IL-17A/F.

FIG. 2A shows the results of silver stained SDS-PAGE of protein fractions from initial fractionation to fraction 11 of EL-I 7A/F on an S-Sepharose column.

FIG. 2B shows the results of silver stained SDS-PAGE of protein fractions from fraction 12 to 24 of EL-I 7A/F on an S-Sepharose column.

FIG. 2C shows the results of silver stained SDS-PAGE of protein fractions from fraction 25 to 37 of EL-I 7A/F on an S-Sepharose column.

FIG. 2D shows the results of silver stained SDS-PAGE of protein fractions from fraction 38 to 50 of EL-I 7A/F on an S-Sepharose column.

Fractions 31 and 32 contain a protein with an apparent molecular mass of approximately 33 kD consistent with IL-17A/F. FIG. 2E-F show the results of further purification of IL-17A/F using Vydac C4 column 35 chromatography. Shown is the chromatograph of eluted proteins measured at 214 nm and 280 nm. FIG. 2G demonstrates that purified IL-17A/F protein fractions from the Vydac C4 purification column induce IL-8 production in TK-10 cells.

FIG. 3A-C show the results of amino acid sequence analysis of IL-17A/F. FIG. 3A shows the non-reducing SDS-PAGE analysis of purified IL-17A/F. Resolved protein was transferred to a PVDF membrane and stained with Coomassie blue protein stain. The positions of molecular weight markers are indicated on the right side. FIG. 3B shows the results of N-terminal sequence analysis of isolated IL-17A/F (amino acid residues detected from an N-terminal sequence analysis of the band shown in FIG. 3A). The sequence analysis reveals two N-terminal sequences (Sequence 1 is designated SEQ ID NO:1 and Sequence 2 is designated SEQ ID NO:2, respectively). FIG. 3C shows the amino acid sequence of human IL-17 (shown in both FIG. 3C and FIG. 8, designated SEQ ID NO:3) and the amino acid sequence of human IL-17F (shown both in FIG. 3C and FIG. 10, designated SEQ ID NO:4). The signal sequences of IL-17 and IL-17F are underlined. The sequences that have identity to the two N-terminal peptide sequences (SEQ ID NO:1 and SEQ ID NO:2) present in IL-17A/F are highlighted in bold for the shown IL-17 and IL-17F polypeptide sequences.

FIG. 4A-G show mass spectrometry analysis of 11-17A/F. FIG. 4A is a schematic showing the amino acid sequence with its interchain and intrachain disulfide bonds of mature IL-17A/F heterodimer (SEQ ID NO:77). The cysteines involved in disulfide linkages are indicated by bullet, (●), and residue number. The disulfide bonds are indicated by black lines connecting the bonded cysteines. Those disulfide bonds that form interchain disulfide linkages are highlighted by bold black lines. FIG. 4B shows the schematic of IL-17A/F peptide fragments #1 and #2 containing disulfide bonds between the IL-17 chain and the IL-17F chain that would be anticipated to be produced by digestion of IL-17A/F with trypsin [IL-17AlF disulfide bond fragment #1 is designated SEQ ID NO:7; IL-17A/F disulfide bond fragment #2 is designated SEQ ID NO:8, respectively]. The amino acids contained within these fragments are indicated and numbered relative to the initiating methionine of each chain. Also indicated is the calculated approximate molecular mass of these fragments that would be expected to be observed by mass spectrometry. FIG. 4C and FIG. 4D shows the matrix-assisted laser desorption/ionization time of flight mass spectrometry (MALDI-TOF) peptide map of IL-17A/F. The resulting peptide map contains peaks with [M+1−1]+ =2420.12 Da and 3410.60 Da, consistent with the disulfide linked peptides. FIG. 4E and FIG. 4F demonstrate further characterization of non-reduced samples of IL17A/F by liquid-chromatography electrospray ionization ion trap mass spectrometry (LC-ESI-MS). The ion chromatograms represent (from top to bottom) the total ion chromatogram, reconstructed ion chromatogram (MC) of EL-17AJF disulfide bond fragment #2 [M+2H]2+, and IL-17A/F disulfide bond fragment #1 [M+2H]3+. Peaks consistent with both heterodimers were observed whereas no peaks above background chemical noise were observed at the anticipated masses for homodimeric peptides.

FIG. 6 shows the amino acid sequence of the region of the heavy chain variable region containing CDR H1-H3 from Fab that bind IL-17A/F. Shown is an alignment of a region of the predicted amino acid sequence of thirty four (34) clones (SEQ ID NO:9 to SEQ ID NO:42, respectively) that encode distinct antibody heavy chain sequences that are able to bind to IL-17A/F. The three heavy chain CDR regions (CDR-H1, CDR-1-12, CDR-H3) are shaded.

FIG. 7 shows a nucleotide sequence (SEQ ID NO:5) of a native sequence IL-17 cDNA.

FIG. 8 shows the amino acid sequence (SEQ ID NO:3) derived from the coding sequence of SEQ ID NO:5 shown in FIG. 7.

FIG. 9 shows a nucleotide sequence (SEQ ID NO:6) of a native sequence IL-17F cDNA.

FIG. 10 shows the amino acid sequence (SEQ ID NO:4) derived from the coding sequence of SEQ 5 ID NO:6 shown in FIG. 9.

DETAILED DESCRIPTION OF THE PREFERRED EMBODIMENTS

I. Definitions

Figure 2E:
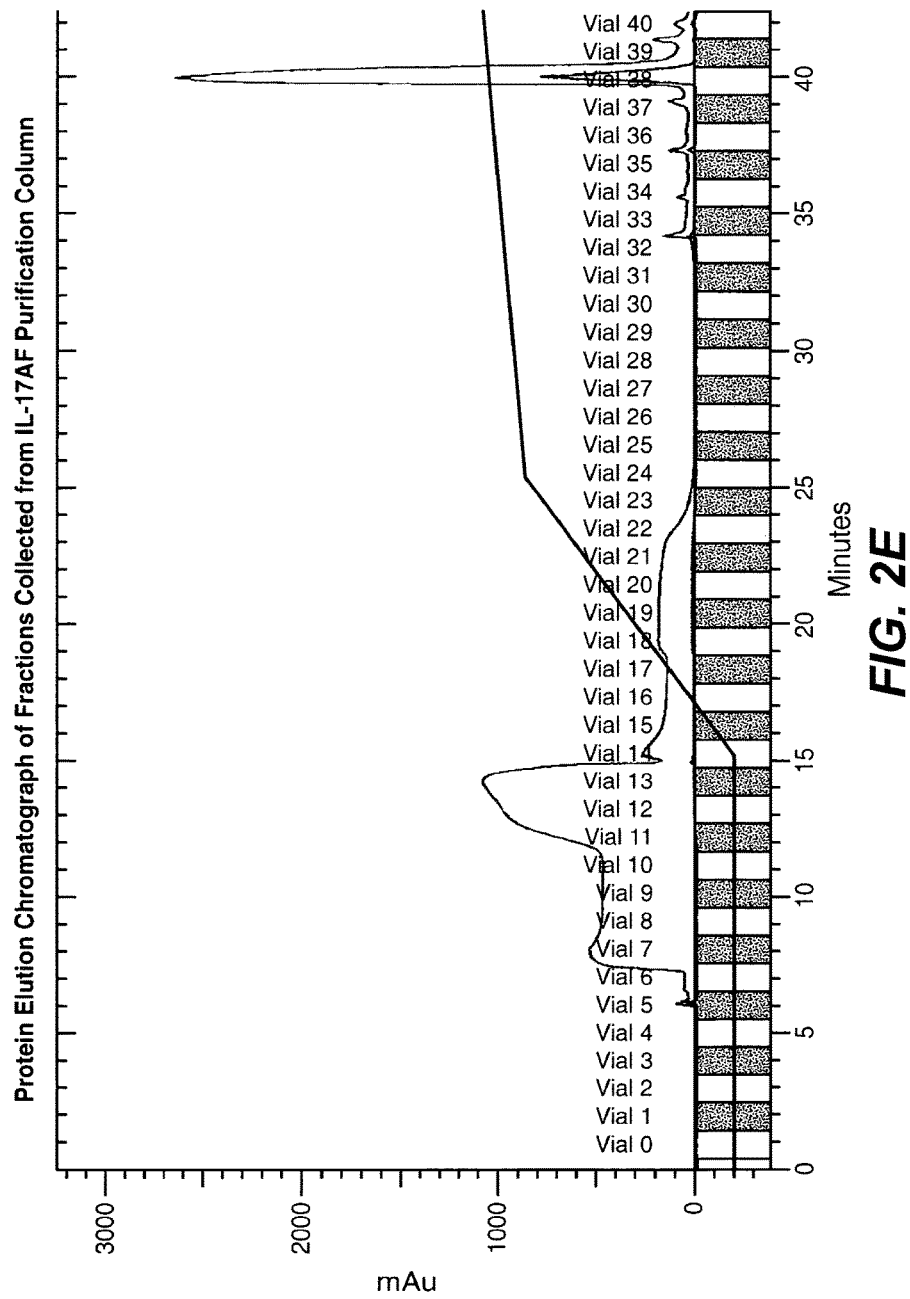

A "native sequence IL-17A/F polypeptide" comprises a polypeptide having the same amino acid sequence as the corresponding IL-17A/F polypeptide derived from nature. Such native sequence IL-17A/F polypeptides can be isolated from nature or can be produced by recombinant or synthetic means. The term "native sequence IL-17A/F polypeptide" specifically encompasses naturally-occurring truncated or secreted forms of the specific IL-17A/F polypeptide (e.g., an extracellular domain sequence), naturally-occurring variant forms (e.g., alternatively spliced forms) and naturally-occurring allelic variants of the polypeptide. In various embodiments of the invention, the native sequence IL-17A/F polypeptides disclosed herein are mature or full-length native sequence polypeptides comprising the full-length amino acid sequences shown in the accompanying figures. Start and stop codons are shown in bold font and underlined in the figures. However, while the IL-17A/F polypeptides disclosed in the accompanying figures are shown to begin with methionine residues designated herein as amino acid position 1 in the figures, it is conceivable and possible that other methionine residues located either upstream or downstream from the amino acid position 1 in the figures may be employed as the starting amino acid residue for the IL-17A/F polypeptides.

The approximate location of the "signal peptides" of the various IL-17A/F polypeptides disclosed herein are shown in the present specification and/or the accompanying figures. It is noted, however, that the C-terminal boundary of a signal peptide may vary, but most likely by no more than about 5 amino acids on either side of the signal peptide C-terminal boundary as initially identified herein, wherein the C-terminal boundary of the signal peptide may be identified pursuant to criteria routinely employed in the art for identifying that type of amino acid sequence element (e.g., Nielsen et al., Prot. Eng., 10:1-6 (1997) and von Heinje et al., Nucl. Acids. Res., 1:4683-4690 (1986)). Moreover, it is also recognized that, in some cases, cleavage of a signal sequence from a secreted polypeptide is not entirely uniform, resulting in more than one secreted species. These mature polypeptides, where the signal peptide is cleaved within no more than about 5 amino acids on either side of the C-terminal boundary of the signal peptide as identified herein, and the polynucleotides encoding them, are contemplated by the present invention.

"IL-17A/F polypeptide variant" means an active IL-17A/F polypeptide as defined above or below having at least about 80% amino acid sequence identity with a full-length native sequence IL-17A/F polypeptide sequence as disclosed herein, an IL-17A/F polypeptide sequence lacking the signal peptide as disclosed herein, or any other fragment of a full-length IL-17A/F polypeptide sequence as disclosed herein. Such IL-17A/F polypeptide variants include, for instance, IL-17A/F polypeptides wherein one or more amino acid residues are added, or deleted, at the – or C-terminus of the full-length native amino acid sequence. Ordinarily, an IL-17A/F polypeptide variant will have at least about 80% amino acid sequence identity, alternatively at least about 81% amino acid sequence identity, alternatively at least about 82% amino acid sequence identity, alternatively at least about 83% amino acid sequence identity, alternatively at least about 84% amino acid sequence identity, alternatively at least about 85% amino acid sequence identity, alternatively at least about 86% amino acid sequence identity, alternatively at least about 87% amino acid sequence identity, alternatively at least about 88% amino acid sequence identity, alternatively at least about 89% amino acid sequence identity, alternatively at least about 90% amino acid sequence identity, alternatively at least about 91% amino acid sequence identity, alternatively at least about 92% amino acid sequence identity, alternatively at least about 93% amino acid sequence identity, alternatively at least about 94% amino acid sequence identity, alternatively at least about 95% amino acid sequence identity, alternatively at least about 96% amino acid sequence identity, alternatively at least about 97% amino acid sequence identity, alternatively at least about 98% amino acid sequence identity and alternatively at least about 99% amino acid sequence identity to a full-length native sequence IL-17A/F polypeptide sequence as disclosed herein, an IL-17A/F polypeptide sequence lacking the signal peptide as disclosed herein, or any other specifically defined fragment of a full-length IL-17A/F polypeptide sequence as disclosed herein. Ordinarily, IL-17A/F variant polypeptides are at least about 10 amino acids in length, alternatively at least about 20 amino acids in length, alternatively at least about 30 amino acids in length, alternatively at least about 40 amino acids in length, alternatively at least about 50 amino acids in length, alternatively at least about 60 amino acids in length, alternatively at least about 70 amino acids in length, alternatively at least about 80 amino acids in length, alternatively at least about 90 amino acids in length, alternatively at least about 100 amino acids in length, alternatively at least about 150 amino acids in length, alternatively at least about 200 amino acids in length, alternatively at least about 300 amino acids in length, or more.

"Percent (%) amino acid sequence identity" with respect to the IL-17A/F polypeptide sequences identified herein is defined as the percentage of amino acid residues in a candidate sequence that are identical with the amino acid residues in the specific IL-17A/F polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. As examples of % amino acid sequence identity calculations using this method, Tables 2 and 3 demonstrate how to calculate the % amino acid sequence identity of the amino acid sequence designated "Comparison Protein" to the amino acid sequence of a hypothetical polypeptide of interest. "Comparison Protein" represents the amino acid sequence of a polypeptide against which the polypeptide of interest is being compared, and "X, "Y" and "Z" each represent different hypothetical amino acid residues.

Unless specifically stated otherwise, all % amino acid sequence identity values used herein are obtained as described in the immediately preceding paragraph using the ALIGN-2 computer program. However, % amino acid sequence identity values may also be obtained as described below by using the WU-BLAST-2 computer program (Altschul et al., *Methods in Enzymology* 266:460-480 (1996)). Most of the WU-BLAST-2 search parameters are set to the default values. Those not set to default values, i.e., the adjustable parameters, are set with the following values: overlap span=1, overlap fraction=0.125, word threshold (T)=11, and scoring matrix=BLOSUM62. When WU-BLAST-2 is employed, a % amino acid sequence identity value is determined by dividing (a) the number of matching identical amino acid residues between the amino acid sequence of the polypeptide of interest having a sequence derived from the native polypeptide and the comparison amino acid sequence of interest (i.e., the sequence against which the polypeptide of interest is being compared which may be an IL-17A/F variant polypeptide) as determined by WU-BLAST-2 by (b) the total number of amino acid residues of the polypeptide of interest. For example, in the statement "a polypeptide comprising an the amino acid sequence A which has or having at least 80% amino acid sequence identity to the amino acid sequence B", the amino acid sequence A is the comparison amino acid sequence of the "Comparison Protein" of interest and the amino acid sequence B is the amino acid sequence of the polypeptide of interest.

Percent amino acid sequence identity may also be determined using the sequence comparison program NCBI-BLAST2 (Altschul et al., *Nucleic Acids Res.* 25:3389-3402 (1997)). The NCBI-BLAST2 sequence comparison program may be downloaded from http://www.ncbi.nlm.nih.gov or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program NCBI-BLAST2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

"IL-17A/F variant polynucleotide" or "IL-17A/F variant nucleic acid sequence" means a nucleic acid molecule which encodes an active IL-17A/F polypeptide as defined below and which has at least about 80% nucleic acid sequence identity with a nucleotide acid sequence encoding a full-length native sequence IL-17A/F polypeptide sequence as disclosed herein, a full-length native sequence IL-17A/F polypeptide sequence lacking the signal peptide as disclosed herein, or any other fragment of a full-length IL-17A/F polypeptide sequence as disclosed herein. Ordinarily, an IL-17A/F variant polynucleotide will have at least about 80% nucleic acid sequence identity, alternatively at least about 81% nucleic acid sequence identity, alternatively at least about 82% nucleic acid sequence identity, alternatively at least about 83% nucleic acid sequence identity, alternatively at least about 84% nucleic acid sequence identity, alternatively at least about 85% nucleic acid sequence identity, alternatively at least about 86% nucleic acid sequence identity, alternatively at least about 87% nucleic acid sequence identity, alternatively at least about 88% nucleic acid sequence identity, alternatively at least about 89% nucleic acid sequence identity, alternatively at least about 90% nucleic acid sequence identity, alternatively at least about 91% nucleic acid sequence identity, alternatively at least about 92% nucleic acid sequence identity, alternatively at least about 93% nucleic acid sequence identity, alternatively at least about 94% nucleic acid sequence identity, alternatively at least about 95% nucleic acid sequence identity, alternatively at least about 96% nucleic acid sequence identity, alternatively at least about 97% nucleic acid sequence identity, alternatively at least about 98% nucleic acid sequence identity and alternatively at least about 99% nucleic acid sequence identity with a nucleic acid sequence encoding a full-length native sequence IL-17A/F polypeptide sequence as disclosed herein, a full-length native sequence IL-17A/F polypeptide sequence lacking the signal peptide as disclosed herein, or any other fragment of a full-length IL-17A/F polypeptide sequence as disclosed herein. Variants do not encompass the native nucleotide sequence.

Ordinarily, IL-17A/F variant polynucleotides are at least about 30 nucleotides in length, alternatively at least about 60 nucleotides in length, alternatively at least about 90 nucleotides in length, alternatively at least about 120 nucleotides in length, alternatively at least about 150 nucleotides in length, alternatively at least about 180 nucleotides in length, alternatively at least about 210 nucleotides in length, alternatively at least about 240 nucleotides in length, alternatively at least about 270 nucleotides in length, alternatively at least about 300 nucleotides in length, alternatively at least about 450 nucleotides in length, alternatively at least about 600 nucleotides in length, alternatively at least about 900 nucleotides in length, or more.

"Percent (%) nucleic acid sequence identity" with respect to IL-17A/F-encoding nucleic acid sequences identified herein is defined as the percentage of nucleotides in a candidate sequence that are identical with the nucleotides in the IL-17A/F nucleic acid sequence of interest, after aligning the sequences and introducing gaps, if necessary, to achieve the maximum percent sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. For purposes herein, however, % nucleic acid sequence identity values are generated using the sequence comparison computer program ALIGN-2, wherein the complete source code for the ALIGN-2 program is provided in Table 1 below. The ALIGN-2 sequence comparison computer program was authored by Genentech, Inc. and the source code shown in Table 1 below has been filed with user documentation in the U.S. Copyright Office, Washington D.C., 20559, where it is registered under U.S. Copyright Registration No. TXU510087. The ALIGN-2 program is publicly available through Genentech. Inc., South San Francisco, Calif. or may be compiled from the source code provided in Table 1 below. The ALIGN-2 program should be compiled for use on a UNIX operating system, preferably digital UNIX V4.0D. All sequence comparison parameters are set by the ALIGN-2 program and do not vary.

In situations where ALIGN-2 is employed for nucleic acid sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program ALIGN-2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C. As examples of % nucleic acid sequence identity calculations, Tables 4 and 5, demonstrate how to calculate the % nucleic acid sequence identity of the nucleic acid sequence designated "Comparison DNA" to the nucleic acid sequence designated "IL-17A/F-DNA", wherein "IL-17A/F-DNA" represents a hypothetical IL-17A/F-encoding nucleic acid sequence of interest, "Comparison DNA" represents the nucleotide sequence of a nucleic acid molecule against which the "IL-17A/F-DNA" nucleic acid molecule of interest is being compared, and "N", "L" and "V" each represent different hypothetical nucleotides.

Unless specifically stated otherwise, all % nucleic acid sequence identity values used herein are obtained as described in the immediately preceding paragraph using the ALIGN-2 computer program. However, % nucleic acid sequence identity values may also be obtained as described below by using the WU-BLAST-2 computer program (Altschul et al., *Methods in Enzymology* 266:460-480 (1996)). Most of the WU-BLAST-2 search parameters are set to the default values. Those not set to default values, i.e., the adjustable parameters, are set with the following values: overlap span=1, overlap fraction=0.125, word threshold (T)=1, and scoring matrix=BLOSUM62. When WU-BLAST-2 is employed, a % nucleic acid sequence identity value is determined by dividing (a) the number of matching identical nucleotides between the nucleic acid sequence of the IL-17A/F polypeptide-encoding nucleic acid molecule of interest having a sequence derived from the native sequence IL-17A/F polypeptide-encoding nucleic acid and the comparison nucleic acid molecule of interest (i.e., the sequence against which the IL-17A/F polypeptide-encoding nucleic acid molecule of interest is being compared which may be a variant IL-17A/F polynucleotide) as determined by WU-BLAST-2 by (b) the total number of nucleotides of the IL-17A/F polypeptide-encoding nucleic acid molecule of interest. For example, in the statement "an isolated nucleic acid molecule comprising a nucleic acid sequence A which has or having at least 80% nucleic acid sequence identity to the nucleic acid sequence B", the nucleic acid sequence A is the comparison nucleic acid molecule of interest and the nucleic acid sequence B is the nucleic acid sequence of the IL-17A/F polypeptide-encoding nucleic acid molecule of interest.

Percent nucleic acid sequence identity may also be determined using the sequence comparison program NCBI-BLAST2 (Altschul et al., *Nucleic Acids Res.* 25:3389-3402 (1997)). The NCBI-BLAST2 sequence comparison program may be downloaded from http://www.ncbi.nlm.nih.gov or otherwise obtained from the National Institute of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25 and scoring matrix=BLOSUM62.

In situations where NCBI-BLAST2 is employed for sequence comparisons, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) is calculated as follows:

100 times the fraction W/Z where W is the number of nucleotides scored as identical matches by the sequence alignment program NCBI-BLAST2 in that program's alignment of C and D, and where Z is the total number of nucleotides in D. It will be appreciated that where the length of nucleic acid sequence C is not equal to the length of nucleic acid sequence D, the % nucleic acid sequence identity of C to D will not equal the % nucleic acid sequence identity of D to C.

In other embodiments, IL-17A/F variant polynucleotides are nucleic acid molecules that encode an active IL-17A/F polypeptide and which are capable of hybridizing, preferably under stringent hybridization and wash conditions, to nucleotide sequences encoding a full-length IL-17A/F polypeptide as disclosed herein. IL-17A/F variant polypeptides may be those that are encoded by an IL-17A/F variant polynucleotide.

"Isolated," when used to describe the various polypeptides disclosed herein, means polypeptide that has been identified and separated and/or recovered from a component of its natural environment. Contaminant components of its natural environment are materials that would typically interfere with diagnostic or therapeutic uses for the polypeptide, and may include enzymes, hormones, and other proteinaceous or nonproteinaceous solutes. In preferred embodiments, the polypeptide will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated polypeptide includes polypeptide in situ within recombinant cells, since at least one component of the IL-17A/F polypeptide natural environment will not be present. Ordinarily, however, isolated polypeptide will be prepared by at least one purification step.

An "isolated" IL-17A/F polypeptide-encoding nucleic acid or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

The term "control sequences" refers to DNA sequences necessary for the expression of an operably linked coding sequence in a particular host organism. The control sequences that are suitable for prokaryotes, for example, include an promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; an promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology*, Wiley Interscience Publishers, (1995).

"Stringent conditions" or "high stringency conditions", as defined herein, may be identified by those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

The term "epitope tagged" when used herein refers to a chimeric polypeptide comprising an IL-17A/F polypeptide fused to a "tag polypeptide". The tag polypeptide has enough residues to provide an epitope against which an antibody can be made, yet is short enough such that it does not interfere with activity of the polypeptide to which it is fused. The tag polypeptide preferably also is fairly unique so that the antibody does not substantially cross-react with other epitopes. Suitable tag polypeptides generally have at least six amino acid residues and usually between about 8 and 50 amino acid residues (preferably, between about 10 and 20 amino acid residues).

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

The term "antagonist" is used in the broadest sense, and includes any molecule that partially or fully blocks, inhibits, or neutralizes a biological activity of a native IL-17A/F polypeptide disclosed herein. In a similar manner, the term "agonist" is used in the broadest sense and includes any molecule that mimics a biological activity of a native IL-17A/F polypeptide disclosed herein. Suitable agonist or antagonist molecules specifically include agonist or antagonist antibodies or antibody fragments, fragments or amino acid sequence variants of native IL-17A/F polypeptides, peptides, antisense oligonucleotides, small organic molecules, etc. Methods for identifying agonists or antagonists of an IL-17A/F polypeptide may comprise contacting an IL-17A/F polypeptide with a candidate agonist or antagonist molecule and measuring a detectable change in one or more biological activities normally associated with the IL-17A/F polypeptide.

"Treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

"Chronic" administration refers to administration of the agent(s) in a continuous mode as opposed to an acute mode, so as to maintain the initial therapeutic effect (activity) for an extended period of time. "Intermittent" administration is treatment that is not consecutively done without interruption, but rather is cyclic in nature.

"Mammal" for purposes of treatment refers to any animal classified as a mammal, including humans, domestic and farm animals, and zoo, sports, or pet animals, such as dogs, cats, cattle, horses, sheep, pigs, goats, rabbits, etc. Preferably, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers which are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "antibody" is used in the broadest sense and specifically covers, for example, single anti-IL-17A/F monoclonal antibodies (including agonist, antagonist, and neutralizing antibodies), anti-IL-17A/F antibody compositions with polyepitopic specificity, polyclonal antibodies, single chain anti-IL-17A/F antibodies, and fragments of anti-IL-17A/F antibodies (see below) as long as they exhibit the desired biological or immunological activity. The term "immunoglobulin" (Ig) is used interchangeable with antibody herein.

An "isolated antibody" is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The basic 4-chain antibody unit is a heterotetrameric glycoprotein composed of two identical light (L) chains and two identical heavy (H) chains (an IgM antibody consists of 5 of the basic heterotetramer unit along with an additional polypeptide called J chain, and therefore contain 10 antigen binding sites, while secreted IgA antibodies can polymerize to form polyvalent assemblages comprising 2-5 of the basic 4-chain units along with J chain). In the case of IgGs, the 4-chain unit is generally about 150,000 daltons. Each L chain is linked to a H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and ε isotypes. Each L chain has at the N-terminus, a variable domain ($V_L$) followed by a constant domain ($C_L$) at its other end. The $V_L$ is aligned with the $V_H$ and the $C_L$ is aligned with the first constant domain of the heavy chain ($C_H$ 1). Particular amino acid residues are believed to form an interface between the light chain and heavy chain variable domains. The pairing of a $V_H$ and $V_L$ together forms a single antigen-binding site. For the structure and properties of the different classes of antibodies, see, e.g., *Basic and Clinical Immunology*, 8th edition, Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated α, δ, ε, γ, and μ, respectively. The γ and α classes are further divided into subclasses on the basis of relatively minor differences in $C_H$ sequence and function, e.g., humans express the following subclasses: IgG1, IgG2, IgG3, IgG4, IgA1, and IgA2.

The term "variable" refers to the fact that certain segments of the variable domains differ extensively in sequence among antibodies. The V domain mediates antigen binding and define specificity of a particular antibody for its particular antigen. However, the variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g. around about residues 24-34 (L1), 50-56 (L2) and 89-97 (L3) in the $V_L$, and around about 1-35 (H1), 50-65 (H2) and 95-102 (H3) in the $V_H$; Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the $V_L$, and 26-32 (H1), 53-55 (H2) and 96-101 (H3) in the $V_H$; Chothia and Lesk *J. Mol. Biol.* 196:901-917 (1987)).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present invention may be prepared by the hybridoma methodology first described by Kohler et al., *Nature*, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., *Nature*, 352:624-628 (1991) and Marks et al., *J. Mol. Biol.*, 222: 581-597 (1991), for example.

The monoclonal antibodies herein include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see U.S. Pat. No. 4,816,567; and Morrison et al., *Proc. Natl. Acad. Sci. USA*, 81:6851-6855 (1984)). Chimeric antibodies of interest herein include "primatized" antibodies comprising variable domain antigen-binding sequences derived from a non-human primate (e.g. Old World Monkey, Ape etc), and human constant region sequences.

An "intact" antibody is one which comprises an antigen-binding site as well as a $C_L$ and at least heavy chain constant domains, $C_H 1$, $C_H 2$ and $C_H 3$. The constant domains may be native sequence constant domains (e.g. human native sequence constant domains) or amino acid sequence variant thereof. Preferably, the intact antibody has one or more effector functions.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (see U.S. Pat. No. 5,641,870, Example 2; Zapata et al., *Protein Eng.* 8(10): 1057-1062 [1995]); single-chain antibody molecules; and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H 1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the $C_H 1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 5-10 residues) between the $V_H$ and $V_L$ domains such that interchain but not intrachain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., *Proc. Natl. Acad. Sci. USA*, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

A "species-dependent antibody," e.g., a mammalian antihuman IgE antibody, is an antibody which has a stronger binding affinity for an antigen from a first mammalian species than it has for a homologue of that antigen from a second mammalian species. Normally, the species-dependent antibody "bind specifically" to a human antigen (i.e., has a binding affinity (Kd) value of no more than about $1 \times 10^{-7}$ M, preferably no more than about $1 \times 10^{-8}$ and most preferably no more than about $1 \times 10^{-9}$ M) but has a binding affinity for a homologue of the antigen from a second non-human mammalian species which is at least about 50 fold, or at least about 500 fold, or at least about 1000 fold, weaker than its binding affinity for the human antigen. The species-dependent antibody can be of any of the various types of antibodies as defined above, but preferably is a humanized or human antibody.

An "IL-17A/F binding oligopeptide" is an oligopeptide that binds, preferably specifically, to an IL-17A/F polypeptide as described herein. IL-17A/F binding oligopeptides may be chemically synthesized using known oligopeptide synthesis methodology or may be prepared and purified using recombinant technology. IL-17A/F binding oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to an IL-17A/F polypeptide as described herein. IL-17A/F binding oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., *Proc. Natl. Acad. Sci. U.S.A.*, 81:3998-4002 (1984); Geysen et al., *Proc. Natl. Acad. Sci. U.S.A.*, 82:178-182 (1985); Geysen et al., in *Synthetic Peptides as Antigens*, 130-149 (1986); Geysen et al., *J. Immunol. Meth.*, 102:259-274 (1987); Schoofs et al., *J. Immunol.*, 140:611-616 (1988), Cwirla, S. E. et al. (1990) *Proc. Natl. Acad. Sci. USA*, 87:6378; Lowman, H. B. et al. (1991) *Biochemistry*, 30:10832; Clackson, T. et al. (1991) *Nature*, 352: 624; Marks, J. D. et al. (1991), *J. Mol. Biol.*, 222:581; Kang, A. S. et al. (1991) *Proc. Natl. Acad. Sci. USA*, 88:8363, and Smith, G. P. (1991) *Current Opin. Biotechnol.*, 2:668).

An "IL-17A/F binding organic molecule" is an organic molecule other than an oligopeptide or antibody as defined herein that binds, preferably specifically, to an IL-17A/F polypeptide as described herein. IL-17A/F binding organic molecules may be identified and chemically synthesized using known methodology (see, e.g., PCT Publication Nos. WO00/00823 and WO00/39585). IL-17A/F binding organic molecules are usually less than about 2000 daltons in size, alternatively less than about 1500, 750, 500, 250 or 200 daltons in size, wherein such organic molecules that are capable of binding, preferably specifically, to an IL-17A/F polypeptide as described herein may be identified without undue experimentation using well known techniques. In this regard, it is noted that techniques for screening organic molecule libraries for molecules that are capable of binding to a polypeptide target are well known in the art (see, e.g., PCT Publication Nos. WO00/00823 and WO00/39585).

An antibody, oligopeptide or other organic molecule "which binds" an antigen of interest, e.g. a tumor-associated polypeptide antigen target, is one that binds the antigen with sufficient affinity such that the antibody, oligopeptide or other organic molecule is useful as a diagnostic and/or therapeutic agent in targeting a cell or tissue expressing the antigen, and does not significantly cross-react with other proteins. In such embodiments, the extent of binding of the antibody, oligopeptide or other organic molecule to a "non-target" protein will be less than about 10% of the binding of the antibody, oligopeptide or other organic molecule to its particular target protein as determined by fluorescence activated cell sorting (FACS) analysis or radioimmunoprecipitation (RIA). With regard to the binding of an antibody, oligopeptide or other organic molecule to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about $10^{-4}$ M, alternatively at least about $10^{-5}$ M, alternatively at least about $10^{-6}$ M, alternatively at least about $10^{-7}$ M, alternatively at least about $10^{-8}$ M, alternatively at least about $10^{-9}$ M, alternatively at least about $10^{-10}$ M, alternatively at least about $10^{-11}$ M, alternatively at least about $10^{-12}$ M, or greater. In one embodiment, the term "specific binding" refers to binding where a molecule binds to a particular polypeptide or epitope on a particular polypeptide without substantially binding to any other polypeptide or polypeptide epitope.

An antibody, oligopeptide or other organic molecule that "inhibits the growth of tumor cells expressing an "IL-17A/F polypeptide" or a "growth inhibitory" antibody, oligopeptide or other organic molecule is one which results in measurable growth inhibition of cancer cells expressing or overexpressing the appropriate IL-17A/F polypeptide. Preferred growth inhibitory anti-IL-17A/F antibodies, oligopeptides or organic molecules inhibit growth of IL-17A/F-expressing tumor cells by greater than 20%, preferably from about 20% to about 50% and even more preferably, by greater than 50% (e.g., from about 50% to about 100%) as compared to the appropriate control, the control typically being tumor cells not treated with the antibody, oligopeptide or other organic molecule being tested. In one embodiment, growth inhibition can be measured at an antibody concentration of about 0.1 to 30 μg/ml or about 0.5 nM to 200 nM in cell culture, where the growth inhibition is determined 1-10 days after exposure of the tumor cells to the antibody. Growth inhibition of tumor cells in vivo can be determined in various ways. The antibody is growth inhibitory in vivo if administration of the anti-IL-17A/F antibody at about 1 μg/kg to about 100 mg/kg body weight results in reduction in tumor size or tumor cell proliferation within about 5 days to 3 months from the first administration of the antibody, preferably within about 5 to 30 days.

An antibody, oligopeptide or other organic molecule which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses an IL-17A/F polypeptide. Preferably the cell is a tumor cell, e.g., a prostate, breast, ovarian, stomach, endometrial, lung, kidney, colon, bladder cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody, oligopeptide or other organic molecule which induces apoptosis is one which results in about 2 to 50 fold, preferably about 5 to 50 fold, and most preferably about 10 to 50 fold, induction of annexin binding relative to untreated cell in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-92 (1991). To assess ADCC activity of a molecule of interest, an in vitro ADCC assay, such as that described in U.S. Pat. Nos. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. *Proc. Natl. Acad. Sci. U.S.A.* 95:652-656 (1998).

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, *Annu. Rev. Immunol.* 9:457-492 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *J. Immunol. Methods* 202:163 (1996), may be performed.

The word "label" when used herein refers to a detectable compound or composition which is conjugated directly or indirectly to the antibody so as to generate a "labeled" antibody. The label may be detectable by itself (e.g. radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as an IL-17A/F polypeptide or antibody thereto) to a mammal. The components of the liposome are commonly arranged in a bilayer formation, similar to the lipid arrangement of biological membranes.

A "small molecule" is defined herein to have a molecular weight below about 500 Daltons.

The term "modulate" means to affect (e.g., either upregulate, downregulate or otherwise control) the level of a signaling pathway. Cellular processes under the control of signal transduction include, but are not limited to, transcription of specific genes, normal cellular functions, such as metabolism, proliferation, differentiation, adhesion, apoptosis and survival, as well as abnormal processes, such as transformation, blocking of differentiation and metastasis.

"Active" or "activity" for the purposes herein refers to form(s) of an IL-17A/F polypeptide which retain a biological and/or an immunological activity of native or naturally-occurring IL-17A/F polypeptides, wherein "biological" activity refers to a biological function (either inhibitory or stimulatory) caused by a native or naturally-occurring IL-17A/F polypeptide other than the ability to induce the production of an antibody against an antigenic epitope possessed by a native or naturally-occurring IL-17A/F polypeptide and an "immunological" activity refers to the ability to induce the production of an antibody against an antigenic epitope possessed by a native or naturally-occurring IL-17A/F polypeptide. One preferred biological activity includes inducing activation of NF-κB and stimulation of the production of the proinflammatory chemokines IL-8 and IL-6. Another preferred biological activity includes stimulation of peripheral blood mononuclear cells or CD4+ cells. Another preferred biological activity includes stimulation of the proliferation of T-lymphocytes. Another preferred biological activity includes, for example, the release of TNF-α from THP1 cells. Another activity includes an enhancement of matrix synthesis in articular cartilage. Alternatively, another activity includes promoting breakdown of articular cartilage matrix as well as inhibiting matrix synthesis. Another preferred biological activity includes modulating the level of the interleukin-17 signalling pathway during mild to severe stages of inflammatory bowel disease or during stroke.

An "immunological" activity refers only to the ability to induce the production of an antibody against an antigenic epitope possessed by a native or naturally-occurring IL-17A/F polypeptide.

"Degenerative cartilagenous disorder" describes a host of disorders that is characterized principally by the destruction of the cartilage matrix. Additional pathologies includes nitric oxide production, and elevated proteoglycan breakdown. Exemplary disorders encompassed within this definition, include, for example, arthritis (e.g., osteoarthritis, rheumatoid arthritis, psoriatic arthritis).

The term "immune related disease" means a disease in which a component of the immune system of a mammal causes, mediates or otherwise contributes to a morbidity in the mammal. Also included are diseases in which stimulation or intervention of the immune response has an ameliorative effect on progression of the disease. Included within this term are immune-mediated inflammatory diseases, non-immune-mediated inflammatory diseases, infectious diseases, immunodeficiency diseases, neoplasia, etc.

The term "T cell mediated disease" means a disease in which T cells directly or indirectly mediate or otherwise contribute to a morbidity in a mammal. The T cell mediated disease may be associated with cell mediated effects, lymphokine mediated effects, etc., and even effects associated with B cells if the B cells are stimulated, for example, by the lymphokines secreted by T cells.

Examples of immune-related and inflammatory diseases, some of which are immune or T cell mediated, which can be treated according to the invention include systemic lupus erythematosis, rheumatoid arthritis, juvenile chronic arthritis, spondyloarthropathies, systemic sclerosis (scleroderma), idiopathic inflammatory myopathies (dermatomyositis, polymyositis), Sjögren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barré syndrome, and chronic inflammatory demyclinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonia, idiopathic pulmonary fibrosis and hypersensitivity pneumonitis, transplantation associated diseases including graft rejection and graft-versus-host-disease. Infectious diseases including viral diseases such as AIDS (HIV infection), hepatitis A, B, C, D. and E, herpes, etc., bacterial infections, fungal infections, protozoal infections and parasitic infections. The term "effective amount" is a concentration or amount of an IL-17A/F polypeptide and/or agonist/antagonist which results in achieving a particular stated purpose. An "effective amount" of an IL-17A/F polypeptide or agonist or antagonist thereof may be determined empirically. Furthermore, a "therapeutically effective amount" is a concentration or amount of an IL-17A/F polypeptide and/or agonist/antagonist which is effective for achieving a stated therapeutic effect. This amount may also be determined empirically.

The term "cytotoxic agent" as used herein refers to a substance that inhibits or prevents the function of cells and/or causes destruction of cells. The term is intended to include radioactive isotopes (e.g., $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include adriamycin, doxorubicin, epirubicin, 5-fluorouracil, cytosine arabinoside ("Ara-C"), cyclophosphamide, thiotepa, busulfan, cytoxin, taxoids, e.g., paclitaxel (Taxol, Bristol-Myers Squibb Oncology, Princeton, N.J.), and doxetaxel (Taxotere, Rhône-Poulenc Rorer, Antony, France), toxotere, methotrexate, cisplatin, melphalan, vinblastine, bleomycin, etoposide, ifosfamide, mitomycin C, mitoxantrone, vincristine, vinorelbine, carboplatin, teniposide, daunomycin, carminomycin, aminopterin, dactinomycin, mitomycins, esperamicins (see U.S. Pat. No. 4,675,187), melphalan and other related nitrogen mustards. Also included in this definition are hormonal agents that act to regulate or inhibit hormone action on tumors such as tamoxifen and onapristone.

A "growth inhibitory agent" when used herein refers to a compound or composition which inhibits growth of a cell, especially cancer cell overexpressing any of the genes identified herein, either in vitro or in vivo. Thus, the growth inhibitory agent is one which significantly reduces the percentage of cells overexpressing such genes in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxol, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogens, and antineoplastic drugs" by Murakami et al., (WB Saunders: Philadelphia, 1995), especially p. 13.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor, fibroblast growth factor, prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor, transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, IL-6, IL-7, IL-8, IL-9, IL-10, IL-11, IL-12, or IL-17; a tumor necrosis factor such as TNF-α or TNF-β; and other polypeptide factors including leukemia inhibitory factor (LIF) and kit ligand (KL). As used herein, the term cytokine includes proteins from natural sources or from recombinant cell culture and biologically active equivalents of the native sequence cytokines.

TABLE 2

| IL-17A/F Protein | XXXXXXXXXXXXXXX | (Length = 15 amino acids) |
|---|---|---|
| Comparison Protein | XXXXXYYYYYYY | (Length = 12 amino acids) |

% amino acid sequence identity = (the number of identically matching amino acid residues between the two polypeptide sequences as determined by ALIGN-2) divided by (the total number of amino acid residues of the IL-17A/F protein) = 5 divided by 15 = 33.3%

TABLE 3

| IL-17A/F Protein | XXXXXXXXXX | (Length = 10 amino acids) |
|---|---|---|
| Comparison Protein |  | XXXXXYYYYYZZYZ |
|  |  | (Length = 15 amino acids) |

% amino acid sequence identity = (the number of identically matching amino acid residues between the two polypeptide sequences as determined by ALIGN-2) divided by (the total number of amino acid residues of the IL-17A/F protein) = 5 divided by 10 = 50%

TABLE 4

| IL-17A/F-DNA | NNNNNNNNNNNNNN | (Length = 14 nucleotides) |
|---|---|---|
| Comparison DNA |  | NNNNNNLLLLLLLLL |
|  |  | (Length = 16 nucleotides) |

% nucleic acid sequence identity = (the number of identically matching nucleotides between the two nucleic acid sequences as determined by ALIGN-2) divided by (the total number of nucleotides of the IL-17A/F-DNA nucleic acid sequence) = 6 divided by 14 = 42.9%

TABLE 5

| IL-17A/F-DNA | NNNNNNNNNNNN | (Length = 12 nucleotides) |
|---|---|---|
| Comparison DNA | NNNNLLLVV | (Length = 9 nucleotides) |

% nucleic acid sequence identity = (the number of identically matching nucleotides between the two nucleic acid sequences as determined by ALIGN-2) divided by (the total number of nucleotides of the IL-17A/F-DNA nucleic acid sequence) = 4 divided by 12 = 33.3%

II. Compositions and Methods of the Invention

A. Full-Length IL-17A/F Polypeptides

The present invention provides newly identified and isolated nucleotide sequences encoding polypeptides referred to in the present application as IL-17A/F polypeptides. In particular, cDNAs encoding various IL-17A/F polypeptides have been identified and isolated, as disclosed in further detail in the Examples below.

B. IL-17A/F Polypeptide Variants

In addition to the full-length native sequence IL-17A/F polypeptides described herein, it is contemplated that IL-17A/F variants can be prepared. IL-17A/F variants can be prepared by introducing appropriate nucleotide changes into the IL-17A/F DNA, and/or by synthesis of the desired IL-17A/F polypeptide. Those skilled in the art will appreciate that amino acid changes may alter post-translational processes of the IL-17A/F, such as changing the number or position of glycosylation sites or altering the membrane anchoring characteristics.

Variations in the native full-length sequence IL-17A/F or in various domains of the IL-17A/F described herein, can be made, for example, using any of the techniques and guidelines for conservative and non-conservative mutations set forth, for instance, in U.S. Pat. No. 5,364,934. Variations may be a substitution, deletion or insertion of one or more codons encoding the IL-17A/F that results in a change in the amino acid sequence of the IL-17A/F as compared with the native sequence IL-17A/F. Optionally the variation is by substitution of at least one amino acid with any other amino acid in one or more of the domains of the IL-17A/F. Guidance in determining which amino acid residue may be inserted, substituted or deleted without adversely affecting the desired activity may be found by comparing the sequence of the IL-17A/F with that of homologous known protein molecules and minimizing the number of amino acid sequence changes made in regions of high homology. Amino acid substitutions can be the result of replacing one amino acid with another amino acid having similar structural and/or chemical properties, such as the replacement of a leucine with a serine, i.e., conservative amino acid replacements. Insertions or deletions may optionally be in the range of about 1 to 5 amino acids. The variation allowed may be determined by systematically making insertions, deletions or substitutions of amino acids in the sequence and testing the resulting variants for activity exhibited by the full-length or mature native sequence.

IL-17A/F polypeptide fragments are provided herein. Such fragments may be truncated at the N-terminus or C-terminus, or may lack internal residues, for example, when compared with a full length native protein. Certain fragments lack amino acid residues that are not essential for a desired biological activity of the IL-17A/F polypeptide.

IL-17A/F fragments may be prepared by any of a number of conventional techniques. Desired peptide fragments may be chemically synthesized. An alternative approach involves generating IL-17A/F fragments by enzymatic digestion, e.g., by treating the protein with an enzyme known to cleave proteins at sites defined by particular amino acid residues, or by digesting the DNA with suitable restriction enzymes and isolating the desired fragment. Yet another suitable technique involves isolating and amplifying a DNA fragment encoding a desired polypeptide fragment, by polymerase chain reaction (PCR). Oligonucleotides that define the desired termini of the DNA fragment are employed at the 5' and 3' primers in the PCR. Preferably, IL-17A/F polypeptide fragments share at least one biological and/or immunological activity with the native IL-17A/F polypeptide disclosed herein.

In particular embodiments, conservative substitutions of interest are shown in Table 6 under the heading of preferred substitutions. If such substitutions result in a change in biological activity, then more substantial changes, denominated exemplary substitutions in Table 6, or as further described below in reference to amino acid classes, are introduced and the products screened.

TABLE 6

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly(G) | pro; ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | leu |
| Pro (P) | ala | ala |
| Ser (S) | thr | thr |
| Thr (T) | ser | ser |
| Trp (W) | tyr; phe | tyr |
| Tyr(Y) | trp; phe; thr; ser | phe |
| Val (V) | ile; leu; met; phe; ala; norleucine | leu |

Substantial modifications in function or immunological identity of the IL-17A/F polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gin, his, lys, arg;
(5) residues that influence chain orientation: gly, pro; and
(6) aromatic: trp, tyr, phe.

Non-conservative substitutions will entail exchanging a member of one of these classes for another class. Such substituted residues also may be introduced into the conservative substitution sites or, more preferably, into the remaining (non-conserved) sites.

The variations can be made using methods known in the art such as oligonucleotide-mediated (site-directed) mutagenesis, alanine scanning, and PCR mutagenesis. Site-directed mutagenesis [Carter et al., *Nucl. Acids Res.*, 13:4331 (1986); Zoller et al., *Nucl. Acids Res.*, 10:6487 (1987)], cassette mutagenesis (Wells et al., *Gene*, 34:315 [1985]), restriction selection mutagenesis (Wells et al., *Philos. Trans. R. Soc. London SerA.* 317:415 [1986]) or other known techniques can be performed on the cloned DNA to produce the IL-17A/F variant DNA.

Scanning amino acid analysis can also be employed to identify one or more amino acids along a contiguous sequence. Among the preferred scanning amino acids are relatively small, neutral amino acids. Such amino acids include alanine, glycine, serine, and cysteine. Alanine is typically a preferred scanning amino acid among this group because it eliminates the side-chain beyond the beta-carbon and is less likely to alter the main-chain conformation of the variant (Cunningham and Wells, Science, 244: 1081-1085 [1989]). Alanine is also typically preferred because it is the most common amino acid. Further, it is frequently found in both buried and exposed positions (Creighton, the Proteins, (W.H. Freeman & Co., N.Y.); Chothia, J. Mol. Biol., 150:1 [1976]). If alanine substitution does not yield adequate amounts of variant, an isoteric amino acid can be used.

C. Modifications of IL-17A/F

Covalent modifications of IL-17A/F are included within the scope of this invention. One type of covalent modification includes reacting targeted amino acid residues of an IL-17A/F polypeptide with an organic derivatizing agent that is capable of reacting with selected side chains or the N- or C-terminal residues of the IL-17A/F. Derivatization with bifunctional agents is useful, for instance, for crosslinking IL-17A/F to a water-insoluble support matrix or surface for use in the method for purifying anti-IL-17A/F antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains [T. E. Creighton, Proteins: Structure and Molecular Properties, W.H. Freeman & Co., San Francisco, pp. 79-86 (1983)], acetylation of the N-terminal amine, and amidation of any C-terminal carboxyl group.

Another type of covalent modification of the IL-17A/F polypeptide included within the scope of this invention comprises altering the native glycosylation pattern of the polypeptide. "Altering the native glycosylation pattern" is intended for purposes herein to mean deleting one or more carbohydrate moieties found in native sequence IL-17A/F (either by removing the underlying glycosylation site or by deleting the glycosylation by chemical and/or enzymatic means), and/or adding one or more glycosylation sites that are not present in the native sequence IL-17A/F. In addition, the phrase includes qualitative changes in the glycosylation of the native proteins, involving a change in the nature and proportions of the various carbohydrate moieties present.

Addition of glycosylation sites to the IL-17A/F polypeptide may be accomplished by altering the amino acid sequence. The alteration may be made, for example, by the addition of, or substitution by, one or more serine or threonine residues to the native sequence IL-17A/F (for O-linked glycosylation sites). The IL-17A/F amino acid sequence may optionally be altered through changes at the DNA level, particularly by mutating the DNA encoding the IL-17A/F polypeptide at preselected bases such that codons are generated that will translate into the desired amino acids.

Another means of increasing the number of carbohydrate moieties on the IL-17A/F polypeptide is by chemical or enzymatic coupling of glycosides to the polypeptide. Such methods are described in the art, e.g., in WO 87/05330 published 11 Sep. 1987, and in Aplin and Wriston, CRC Crit. Rev. Biochem., pp. 259-306 (1981).

Removal of carbohydrate moieties present on the IL-17A/F polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo- and exo-glycosidases as described by Thotakura et al., Meth. Enzymol., 138:350 (1987).

Another type of covalent modification of IL-17A/F comprises linking the IL-17A/F polypeptide to one of a variety of nonproteinaceous polymers, e.g., polyethylene glycol (PEG), polypropylene glycol, or polyoxyalkylenes, in the manner set forth in U.S. Pat. Nos. 4,640,835; 4,496,689; 4,301,144; 4,670,417; 4,791,192 or 4,179,337.

The IL-17A/F of the present invention may also be modified in a way to form a chimeric molecule comprising IL-17A/F fused to another, heterologous polypeptide or amino acid sequence.

In one embodiment, such a chimeric molecule comprises a fusion of the IL-17A/F with a tag polypeptide which provides an epitope to which an anti-tag antibody can selectively bind. The epitope tag is generally placed at the amino- or carboxyl-terminus of the IL-17A/F. The presence of such epitope-tagged forms of the IL-17A/F can be detected using an antibody against the tag polypeptide. Also, provision of the epitope tag enables the IL-17A/F to be readily purified by affinity purification using an anti-tag antibody or another type of affinity matrix that binds to the epitope tag. Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., Mol. Cell. Biol., 8:2159-2165 (1988)]; the c-myc tag and the 8F9, 3C7, 6E10, G4, B7 and 9E10 antibodies thereto [Evan et al., Molecular and Cellular Biology, 5:3610-3616 (1985)]; and the Herpes Simplex virus glycoprotein D (gD) tag and its antibody [Paborsky et al., Protein Engineering, 3(6):547-553 (1990)]. Other tag polypeptides include the Flag-peptide [Hopp et al., BioTechnology, 6:1204-1210 (1988)]; the KT3 epitope peptide [Martin et al., Science, 255:192-194 (1992)]; an α-tubulin epitope peptide [Skinner et al., J. Biol. Chem., 266:15163-15166 (1991)]; and the T7 gene 10 protein peptide tag [Lutz-Freyermuth et al., Proc. Natl. Acad. Sci. USA, 87:6393-6397 (1990)].

In an alternative embodiment, the chimeric molecule may comprise a fusion of the IL-17A/F with an immunoglobulin or a particular region of an immunoglobulin. For a bivalent form of the chimeric molecule (also referred to as an "immunoadhesin"), such a fusion could be to the Fc region of an IgG molecule. The Ig fusions preferably include the substitution of a soluble (transmembrane domain deleted or inactivated) form of an IL-17A/F polypeptide in place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995.

In yet a further embodiment, the IL-17A/F polypeptides of the present invention may also be modified in a way to form a chimeric molecule comprising an IL-17A/F polypeptide fused to a leucine zipper. Various leucine zipper polypeptides have been described in the art. See, e.g., Landschulz et al., *Science*, 240:1759 (1988); WO 94/10308; Hoppe et al., *FEBS Letters*. 344:1991 (1994); Maniatis et al., *Nature*, 341:24 (1989). It is believed that use of a leucine zipper fused to an IL-17A/F polypeptide may be desirable to assist in dimerizing or trimerizing soluble IL-17A/F polypeptide in solution. Those skilled in the art will appreciate that the leucine zipper may be fused at either the N- or C-terminal end of the IL-17A/F molecule.

D. Preparation of IL-17A/F

The description below relates primarily to production of IL-17A/F by culturing cells transformed or transfected with a vector containing IL-17A/F nucleic acid. It is, of course, contemplated that alternative methods, which are well known in the art, may be employed to prepare IL-17A/F. For instance, the IL-17A/F sequence, or portions thereof, may be produced by direct peptide synthesis using solid-phase techniques [see, e.g., Stewart et al., *Solid-Phase Peptide Synthesis*, W.H. Freeman Co., San Francisco, Calif. (1969); Merrifield, *J. Am. Chem. Soc.*, 85:2149-2154 (1963)]. In vitro protein synthesis may be performed using manual techniques or by automation. Automated synthesis may be accomplished, for instance, using an Applied Biosystems Peptide Synthesizer (Foster City, Calif.) using manufacturer's instructions. Various portions of the IL-17A/F may be chemically synthesized separately and combined using chemical or enzymatic methods to produce the full-length IL-17A/F.

1. Isolation of DNA Encoding IL-17A/F

DNA encoding IL-17A/F may be obtained from a cDNA library prepared from tissue believed to possess the IL-17A/F mRNA and to express it at a detectable level. Accordingly, human IL-17A/F DNA can be conveniently obtained from a cDNA library prepared from human tissue, such as described in the Examples. The IL-17A/F-encoding gene may also be obtained from a genomic library or by known synthetic procedures (e.g., automated nucleic acid synthesis).

Libraries can be screened with probes (such as antibodies to the IL-17A/F or oligonucleotides of at least about 20-80 bases) designed to identify the gene of interest or the protein encoded by it. Screening the cDNA or genomic library with the selected probe may be conducted using standard procedures, such as described in Sambrook et al., *Molecular Cloning: A Laboratory Manual* (New York: Cold Spring Harbor Laboratory Press, 1989). An alternative means to isolate the gene encoding IL-17A/F is to use PCR methodology [Sambrook et al., supra; Dieffenbach et al., *PCR Primer: A Laboratory Manual* (Cold Spring Harbor Laboratory Press, 1995)].

The Examples below describe techniques for screening a cDNA library. The oligonucleotide sequences selected as probes should be of sufficient length and sufficiently unambiguous that false positives are minimized. The oligonucleotide is preferably labeled such that it can be detected upon hybridization to DNA in the library being screened. Methods of labeling are well known in the art, and include the use of radiolabels like $^{32}$P-labeled ATP, biotinylation or enzyme labeling. Hybridization conditions, including moderate stringency and high stringency, are provided in Sambrook et al., supra.

Sequences identified in such library screening methods can be compared and aligned to other known sequences deposited and available in public databases such as GenBank or other private sequence databases. Sequence identity (at either the amino acid or nucleotide level) within defined regions of the molecule or across the full-length sequence can be determined using methods known in the art and as described herein.

Nucleic acid having protein coding sequence may be obtained by screening selected cDNA or genomic libraries using the deduced amino acid sequence disclosed herein for the first time, and, if necessary, using conventional primer extension procedures as described in Sambrook et al., supra, to detect precursors and processing intermediates of mRNA that may not have been reverse-transcribed into cDNA.

2. Selection and Transformation of Host Cells

Host cells are transfected or transformed with expression or cloning vectors described herein for IL-17A/F production and cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in *Mammalian Cell Biotechnology: a Practical Approach*, M. Butler, ed. (IRL Press, 1991) and Sambrook et al., supra.

Methods of eukaryotic cell transfection and prokaryotic cell transformation are known to the ordinarily skilled artisan, for example, $CaCl_2$, $CaPO_4$, liposome-mediated and electroporation. Depending on the host cell used, transformation is performed using standard techniques appropriate to such cells. The calcium treatment employing calcium chloride, as described in Sambrook et al., supra, or electroporation is generally used for prokaryotes. Infection with *Agrobacterium tumefaciens* is used for transformation of certain plant cells, as described by Shaw et al., *Gene* 23:315 (1983) and WO 89/05859 published 29 Jun. 1989. For mammalian cells without such cell walls, the calcium phosphate precipitation method of Graham and van der Eb, *Virology*, 52:456-457 (1978) can be employed. General aspects of mammalian cell host system transfections have been described in U.S. Pat. No. 4,399,216. Transformations into yeast are typically carried out according to the method of Van Solingen et al., *J. Bact.*, 130:946 (1977) and Hsiao et al., *Proc. Natl. Acad. Sci. (USA)*, 76:3829 (1979). However, other methods for introducing DNA into cells, such as by nuclear microinjection, electroporation, bacterial protoplast fusion with intact cells, or polycations, e.g., polybrene, polyornithine, may also be used. For various techniques for transforming mammalian cells, see Keown et al., *Methods in Enzymology*, 185:527-537 (1990) and Mansour et al., *Nature*, 336:348-352 (1988).

Suitable host cells for cloning or expressing the DNA in the vectors herein include prokaryote, yeast, or higher eukaryote cells. Suitable prokaryotes include but are not limited to eubacteria, such as Gram-negative or Gram-positive organisms, for example, Enterobacteriaceae such as E coll. Various *E. coli* strains are publicly available, such as *E. coli* K12 strain MM294 (ATCC 31,446); *E. coli* X1776 (ATCC 31,537); *E. coli* strain W3110 (ATCC 27,325) and K5 772 (ATCC 53,635). Other suitable prokaryotic host cells include Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli* such as *B. subtilis* and *B. licheniformis* (e.g., *B. licheniformis* 41P disclosed in DD 266,710 published 12 Apr. 1989),

*Pseudomonas* such as *P. aeruginosa*, and *Streptomyces*. These examples are illustrative rather than limiting. Strain W3110 is one particularly preferred host or parent host because it is a common host strain for recombinant IL-17A/F duct fermentations. Preferably, the host cell secretes minimal amounts of proteolytic enzymes. For example, strain W3110 may be modified to effect a genetic mutation in the genes encoding proteins endogenous to the host, with examples of such hosts including *E. coli* W3110 strain 1A2, which has the complete genotype tonA; *E. coli* W3110 strain 9E4, which has the complete genotype tonA ptr3; *E. coli* W3110 strain 27C7 (ATCC 55,244), which has the complete genotype tonA ptr3 phoA E15 (argF-lac)169 degP ompT kan$^r$; *E. coli* W3110 strain 37D6, which has the complete genotype tonA ptr3 phoA E15 (argF-lac)169 degP ompT rbs7 ilvG kan$^r$; *E. coli* W3110 strain 40B4, which is strain 37D6 with a non-kanamycin resistant degP deletion mutation; and an *E. coli* strain having mutant periplasmic protease disclosed in U.S. Pat. No. 4,946,783 issued 7 Aug. 1990. Alternatively, in vitro methods of cloning, e.g., PCR or other nucleic acid polymerase reactions, are suitable.

In addition to prokaryotes, eukaryotic microbes such as filamentous fungi or yeast are suitable cloning or expression hosts for IL-17A/F-encoding vectors. *Saccharomyces cerevisiae* is a commonly used lower eukaryotic host microorganism. Others include *Schizosaccharomyces pombe* [Beach and Nurse, *Nature*, 290: 140 (1981); EP 139,383 published 2 May 1985]; *Kluyveromyces* hosts (U.S. Pat. No. 4,943,529; Fleer et al., *Bio/Technology*, 9:968-975 [1991]) such as, e.g., *K. lactis* (MW98-8C, CBS683, CBS4574; Louvencourt et al., *J. Bacteriol.*, 154(2):737-742 [1983]), *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906; Van den Berg et al., *Bio/Technology*, 8:135 [1990]), *K. thermotolerans*, and *K. marxianus*; *yarrowia* (EP 402,226); *Pichia pastoris* (EP 183,070; Sreekrishna et al., *J. Basic Microbiol.*, 28:265-278 [1988]); *Candida*; *Trichoderma reesia* (EP 244,234); *Neurospora crassa* (Case et al., *Proc. Natl. Acad. Sci. USA*, 76:5259-5263 [1979]); *Schwanniomyces* such as *Schwanniomyces occidentalis* (EP 394,538 published 31 Oct. 1990); and filamentous fungi such as, e.g., *Neurospora*, *Penicillium*, *Tolypocladium* (WO 91/00357 published 10 Jan. 1991), and *Aspergillus* hosts such as *A. nidulans* (Ballance et al., *Biochem. Biophys. Res. Commun.*, 112:284-289 [1983]; Tilburn et al., *Gene*, 26:205-221 [1983]; Yelton et al., *Proc. Natl. Acad. Sci. USA*. 81:1470-1474 [1984]) and *A. niger* (Kelly and Hynes, *EMBO J.*, 4:475-479 [1985]). Methylotropic yeasts are suitable herein and include, but are not limited to, yeast capable of growth on methanol selected from the genera consisting of *Hansenula, Candida, Kloeckera, Pichia, Saccharomyces. Torulopsis*, and *Rhodotorula*. A list of specific species that are exemplary of this class of yeasts may be found in C. Anthony, *The Biochemistry of Methylotrophs*, 269 (1982).

Suitable host cells for the expression of glycosylated IL-17A/F are derived from multicellular organisms. Examples of invertebrate cells include insect cells such as *Drosophila* S2 and *Spodoptera* Sf9 or *Spodoptera* High 5 cells, as well as plant cells. Examples of useful mammalian host cell lines include Chinese hamster ovary (CHO) and COS cells. More specific examples include monkey kidney CV1 line transformed by SV40 (COS-7, ATCC CRL 1651); human embryonic kidney line (293 or 293 cells subcloned for growth in suspension culture, Graham et al., *J. Gen Virol.*, 36:59 (1977)); Chinese hamster ovary cells/-DHFR (CHO, Urlaub and Chasin, *Proc. Natl. Acad. Sci. USA*, 77:4216 [1980]); mouse sertoli cells (TM4, Mather, *Biol. Prod.*, 23:243-251 [1980]); human lung cells (W138, ATCC CCL 75); human liver cells (Hep G2, HB 8065); and mouse mammary tumor (MMT 060562, ATCC CCL51). The selection of the appropriate host cell is deemed to be within the skill in the art.

3. Selection and Use of a Replicable Vector

The nucleic acid (e.g., cDNA or genomic DNA) encoding IL-17A/F may be inserted into a replicable vector for cloning (amplification of the DNA) or for expression. Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, an promoter, and a transcription termination sequence. Construction of suitable vectors containing one or more of these components employs standard ligation techniques which are known to the skilled artisan.

The IL-17A/F may be produced recombinantly not only directly, but also as a fusion polypeptide with a heterologous polypeptide, which may be a signal sequence or other polypeptide having a specific cleavage site at the N-terminus of the mature protein or polypeptide. In general, the signal sequence may be a component of the vector, or it may be a part of the IL-17A/F-encoding DNA that is inserted into the vector. The signal sequence may be a prokaryotic signal sequence selected, for example, from the group of the alkaline phosphatase, penicillinase, lpp, or heat-stable enterotoxin II leaders. For yeast secretion the signal sequence may be, e.g., the yeast invertase leader, alpha factor leader (including *Saccharomyces* and *Kluyveromyces* α-factor leaders, the latter described in U.S. Pat. No. 5,010,182), or acid phosphatase leader, the *C. albicans* glucoamylase leader (EP 362,179 published 4 Apr. 1990), or the signal described in WO 90/13646 published 15 Nov. 1990. In mammalian cell expression, mammalian signal sequences may be used to direct secretion of the protein, such as signal sequences from secreted polypeptides of the same or related species, as well as viral secretory leaders.

Both expression and cloning vectors contain a nucleic acid sequence that enables the vector to replicate in one or more selected host cells. Such sequences are well known for a variety of bacteria, yeast, and viruses. The origin of replication from the plasmid pBR322 is suitable for most Gram-negative bacteria, the 2μ plasmid origin is suitable for yeast, and various viral origins (SV40, polyoma, adenovirus, VSV or BPV) are useful for cloning vectors in mammalian cells.

Expression and cloning vectors will typically contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for *Bacilli*.

An example of suitable selectable markers for mammalian cells are those that enable the identification of cells competent to take up the IL-17A/F-encoding nucleic acid, such as DHFR or thymidine kinase. An appropriate host cell when wild-type DHFR is employed is the CHO cell line deficient in DHFR activity, prepared and propagated as described by Urlaub et al., *Proc. Natl. Acad. Sci. USA*, 77:4216 (1980). A suitable selection gene for use in yeast is the trp1 gene present in the yeast plasmid YRp7 [Stinchcomb et al., *Nature*, 282:39 (1979); Kingsman et al., *Gene*, 7:141 (1979); Tschemper et al., *Gene*, 10:157 (1980)]. The trp1 gene provides a selection marker for a mutant strain of yeast lacking the ability to grow in tryptophan, for example, ATCC No. 44076 or PEP4-1 [Jones, *Genetics*, 85:12 (1977)].

Expression and cloning vectors usually contain a promoter operably linked to the IL-17A/F-encoding nucleic acid sequence to direct mRNA synthesis. Promoters recognized by a variety of potential host cells are well known. Promoters suitable for use with prokaryotic hosts include the β-lactamase and lactose promoter systems [Chang et al., *Nature*, 275:615 (1978); Goeddel et al., *Nature*, 281:544 (1979)], alkaline phosphatase, a tryptophan (trp) promoter system [Goeddel, *Nucleic Acids Res.*, 8:4057 (1980); EP 36,776], and hybrid promoters such as the tac promoter [deBoer et al., *Proc. Natl. Acad. Sci. USA*, 80:21-25 (1983)]. Promoters for use in bacterial systems also will contain a Shine-Dalgarno (S.D.) sequence operably linked to the DNA encoding IL-17A/F.

Examples of suitable promoting sequences for use with yeast hosts include the promoters for 3-phosphoglycerate kinase [Hitzeman et al., *J. Biol. Chem.*, 255:2073 (1980)] or other glycolytic enzymes [Hess et al., *J. Adv. Enzyme Reg.*, 7:149 (1968); Holland, *Biochemistry*, 17:4900 (1978)], such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657.

IL-17A/F transcription from vectors in mammalian host cells is controlled, for example, by promoters obtained from the genomes of viruses such as polyoma virus, fowlpox virus (UK 2,211,504 published 5 Jul. 1989), adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, and from heat-shock promoters, provided such promoters are compatible with the host cell systems.

Transcription of a DNA encoding the IL-17A/F by higher eukaryotes may be increased by inserting an enhancer sequence into the vector. Enhancers are cis-acting elements of DNA, usually about from 10 to 300 bp, that act on a promoter to increase its transcription. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. The enhancer may be spliced into the vector at a position 5' or 3' to the IL-17A/F coding sequence, but is preferably located at a site 5' from the promoter.

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding IL-17A/F.

Still other methods, vectors, and host cells suitable for adaptation to the synthesis of IL-17A/F in recombinant vertebrate cell culture are described in Gething et al., *Nature*, 293:620-625 (1981); Mantel et al., *Nature*, 281:40-46 (1979); EP 117,060; and EP 117,058.

4. Detecting Gene Amplification/Expression

Gene amplification and/or expression may be measured in a sample directly, for example, by conventional Southern blotting, Northern blotting to quantitate the transcription of mRNA (Thomas, *Proc. Natl. Acad. Sci. USA*, 77:5201-5205 [1980]), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of cells or tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence IL-17A/F polypeptide or against a synthetic peptide based on the DNA sequences provided herein or against exogenous sequence fused to IL-17A/F DNA and encoding a specific antibody epitope.

5. Purification of Polypeptide

Forms of IL-17A/F may be recovered from culture medium or from host cell lysates. If membrane-bound, it can be released from the membrane using a suitable detergent solution (e.g., Triton-X 100) or by enzymatic cleavage. Cells employed in expression of IL-17A/F can be disrupted by various physical or chemical means, such as freeze-thaw cycling, sonication, mechanical disruption, or cell lysing agents.

It may be desired to purify IL-17A/F from recombinant cell proteins or polypeptides. The following procedures are exemplary of suitable purification procedures: by fractionation on an ion-exchange column; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; protein A Sepharose columns to remove contaminants such as IgG; and metal chelating columns to bind epitope-tagged forms of the IL-17A/F. Various methods of protein purification may be employed and such methods are known in the art and described for example in Deutscher, *Methods in Enzymology,* 182 (1990); Scopes, *Protein Purification: Principles and Practice*, Springer-Verlag, New York (1982). The purification step(s) selected will depend, for example, on the nature of the production process used and the particular IL-17A/F produced.

E. Uses for IL-17A/F

Nucleotide sequences (or their complement) encoding IL-17A/F have various applications in the art of molecular biology, including uses as hybridization probes, in chromosome and gene mapping and in the generation of anti-sense RNA and DNA. IL-17A/F nucleic acid will also be useful for the preparation of IL-17A/F polypeptides by the recombinant techniques described herein.

The full-length native sequence IL-17A/F gene, or portions thereof, may be used as hybridization probes for a cDNA library to isolate the full-length IL-17A/F cDNA or to isolate still other cDNAs (for instance, those encoding naturally-occurring variants of IL-17A/F or IL-17A/F from other species) which have a desired sequence identity to the native IL-17A/F sequence disclosed herein. Optionally, the length of the probes will be about 20 to about 50 bases. The hybridization probes may be derived from at least partially novel regions of the full length native nucleotide sequence wherein those regions may be determined without undue experimentation or from genomic sequences including promoters, enhancer elements and introns of native sequence IL-17A/F. By way of example, a screening method will comprise isolating the coding region of the IL-17A/F gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the IL-17A/F gene of the present invention can be used to screen libraries of human cDNA, genomic DNA or mRNA to determine which members of such libraries the probe hybridizes to. Hybridization techniques are described in further detail in the Examples below.

Any EST sequences disclosed in the present application may similarly be employed as probes, using the methods disclosed herein.

Other useful fragments of the IL-17A/F nucleic acids include antisense or sense oligonucleotides comprising a singe-stranded nucleic acid sequence (either RNA or DNA) capable of binding to target IL-17A/F mRNA (sense) or IL-17A/F DNA (antisense) sequences. Antisense or sense oligonucleotides, according to the present invention, comprise a fragment of the coding region of IL-17A/F DNA. Such a fragment generally comprises at least about 14 nucleotides, preferably from about 14 to 30 nucleotides. The ability to derive an antisense or a sense oligonucleotide, based upon a cDNA sequence encoding a given protein is described in, for example, Stein and Cohen (*Cancer Res.* 48:2659, [1988]) and van der Krol et al. (*BioTechniques,* 6:958, [1988]).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of IL-17A/F proteins. Antisense or sense oligonucleotides further comprise oligonucleotides having modified sugar-phosphodiester backbones (or other sugar linkages, such as those described in WO 91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences.

Other examples of sense or antisense oligonucleotides include those oligonucleotides which are covalently linked to organic moieties, such as those described in WO 90/10048, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. In a preferred procedure, an antisense or sense oligonucleotide is inserted into a suitable retroviral vector. A cell containing the target nucleic acid sequence is contacted with the recombinant retroviral vector, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see WO 90/13641).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

Antisense or sense RNA or DNA molecules are generally at least about 5 bases in length, about 10 bases in length, about 15 bases in length, about 20 bases in length, about 25 bases in length, about 30 bases in length, about 35 bases in length, about 40 bases in length, about 45 bases in length, about 50 bases in length, about 55 bases in length, about 60 bases in length, about 65 bases in length, about 70 bases in length, about 75 bases in length, about 80 bases in length, about 85 bases in length, about 90 bases in length, about 95 bases in length, about 100 bases in length, or more.

The probes may also be employed in PCR techniques to generate a pool of sequences for identification of closely related IL-17A/F coding sequences.

Nucleotide sequences encoding an IL-17A/F can also be used to construct hybridization probes for mapping the gene which encodes that IL-17A/F and for the genetic analysis of individuals with genetic disorders. The nucleotide sequences provided herein may be mapped to a chromosome and specific regions of a chromosome using known techniques such as in situ hybridization, linkage analysis against known chromosomal markers, and hybridization screening with libraries.

When the coding sequences for IL-17A/F encode a protein which binds to another protein (example, where the protein is a receptor), the protein can be used in assays to identify the other proteins or molecules involved in the binding interaction. By such methods, inhibitors of the receptor/ligand binding interaction can be identified. Proteins involved in such binding interactions can also be used to screen for peptide or small molecule inhibitors or agonists of the binding interaction. Also, the receptor protein can be used to isolate correlative ligand(s). Screening assays can be designed to find lead compounds that mimic the biological activity of a native IL-17A/F or a receptor for IL-17A/F. Such screening assays will include assays amenable to high-throughput screening of chemical libraries, making them particularly suitable for identifying small molecule drug candidates. Small molecules contemplated include synthetic organic or inorganic compounds. The assays can be performed in a variety of formats, including protein-protein binding assays, biochemical screening assays, immunoassays and cell based assays, which are well characterized in the art.

Nucleic acids which encode IL-17A/F or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding IL-17A/F can be used to clone genomic DNA encoding IL-17A/F in accordance with established techniques and the genomic sequences used to generate transgenic animals that contain cells which express DNA encoding IL-17A/F. Methods for generating transgenic animals, particularly animals such as mice or rats, have become conventional in the art and are described, for example, in U.S. Pat. Nos. 4,736,866 and 4,870,009. Typically, particular cells would be targeted for IL-17A/F transgene incorporation with tissue-specific enhancers. Transgenic animals that include a copy of a transgene encoding IL-17A/F introduced into the germ line of the animal at an embryonic stage can be used to examine the effect of increased expression of DNA encoding IL-17A/F. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of IL-17A/F can be used to construct an IL-17A/F "knock out" animal which has a defective or altered gene encoding IL-17A/F as a result of homologous recombination between the endogenous gene encoding IL-17A/F and altered genomic DNA encoding IL-17A/F introduced into an embryonic stem cell of the animal. For example, cDNA encoding IL-17A/F can be used to clone genomic DNA encoding IL-17A/F in accordance with established techniques. A portion of the genomic DNA encoding IL-17A/F can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell*, 51:503 (1987) for a description of homologous recombination vectors]. The vector is introduced into an embryonic stem cell line (e.g., by electroporation) and cells in which the introduced DNA has homologously recombined with the endogenous DNA are selected [see, e.g., Li et al., *Cell*, 69:915 (1992)]. The selected cells are then injected into a blastocyst of an animal (e.g., a mouse or rat) to form aggregation chimeras [see, e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the IL-7A/F polypeptide.

Nucleic acid encoding the IL-17A/F polypeptides may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA*, 83:4143-4146 [1986]). The oligonucleotides can be modified to enhance their uptake, e.g., by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vive in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology*, 11: 205-210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g., capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al., *J. Biol. Chem.*, 262: 4429-4432 (1987); and Wagner et al., *Proc. Natl. Acad. Sci. USA*, 87: 3410-3414 (1990). For review of gene marking and gene therapy protocols see Anderson et al., *Science*, 256: 808-813 (1992).

The IL-17A/F polypeptides described herein may also be employed as molecular weight markers for protein electrophoresis purposes and the isolated nucleic acid sequences may be used for recombinantly expressing those markers.

The nucleic acid molecules encoding the IL-17A/F polypeptides or fragments thereof described herein are useful for chromosome identification. In this regard, there exists an ongoing need to identify new chromosome markers, since relatively few chromosome marking reagents, based upon actual sequence data are presently available. Each IL-17A/F nucleic acid molecule of the present invention can be used as a chromosome marker.

The IL-17A/F polypeptides and nucleic acid molecules of the present invention may also be used diagnostically for tissue typing, wherein the IL-17A/F polypeptides of the present invention may be differentially expressed in one tissue as compared to another, preferably in a diseased tissue as compared to a normal tissue of the same tissue type. IL-17A/F nucleic acid molecules will find use for generating probes for PCR, Northern analysis, Southern analysis and Western analysis.

The IL-17A/F polypeptides described herein may also be employed as therapeutic agents. The IL-17A/F polypeptides of the present invention can be formulated according to known methods to prepare pharmaceutically useful compositions, whereby the IL-17A/F product hereof is combined in admixture with a pharmaceutically acceptable carrier vehicle. Therapeutic formulations are prepared for storage by mixing the active ingredient having the desired degree of purity with optional physiologically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients or stabilizers are nontoxic to recipients at the dosages and concentrations employed, and include buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagine, arginine or lysine; monosaccharides, disaccharides and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™ or PEG.

The formulations to be used for in vivo administration must be sterile. This is readily accomplished by filtration through sterile filtration membranes, prior to or following lyophilization and reconstitution.

Therapeutic compositions herein generally are placed into a container having a sterile access port, for example, an intravenous solution bag or vial having a stopper pierceable by a hypodermic injection needle.

The route of administration is in accord with known methods, e.g., injection or infusion by intravenous, intraperitoneal, intracerebral, intramuscular, intraocular, intraarterial or intralesional routes, topical administration, or by sustained release systems.

Dosages and desired drug concentrations of pharmaceutical compositions of the present invention may vary depending on the particular use envisioned. The determination of the appropriate dosage or route of administration is well within the skill of an ordinary physician. Animal experiments provide reliable guidance for the determination of effective doses for human therapy. Interspecies scaling of effective doses can be performed following the principles laid down by Mordenti, J. and Chappell, W. "The use of interspecies scaling in toxicokinetics" In *Toxicokinetics and New Drug Development*, Yacobi et al., Eds., Pergamon Press, New York 1989, pp. 42-96.

When in vivo administration of an IL-17A/F polypeptide or agonist or antagonist thereof is employed, normal dosage amounts may vary from about 10 ng/kg to up to 100 mg/kg of mammal body weight or more per day, preferably about 1 µg/kg/day to 10 mg/kg/day, depending upon the route of administration. Guidance as to particular dosages and methods of delivery is provided in the literature; see, for example, U.S. Pat. Nos. 4,657,760; 5,206,344; or 5,225,212. It is anticipated that different formulations will be effective for different treatment compounds and different disorders, that administration targeting one organ or tissue, for example, may necessitate delivery in a manner different from that to another organ or tissue.

Where sustained-release administration of an IL-17A/F polypeptide is desired in a formulation with release characteristics suitable for the treatment of any disease or disorder requiring administration of the IL-17A/F polypeptide, microencapsulation of the IL-17A/F polypeptide is contemplated. Microencapsulation of recombinant proteins for sustained release has been successfully performed with human growth hormone (rhGH), interferon-(rhIFN-), interleukin-2, and MN rgp120. Johnson et al., *Nat. Med.*, 2:795-799 (1996); Yasuda, *Biomed. Ther.*, 27:1221-1223 (1993); Hora et al., *Bio/Technology*, 8:755-758 (1990); Cleland, "Design and Production of Single Immunization Vaccines Using Polylactide Polyglycolide Microsphere Systems," in *Vaccine Design: The Subunit and Adjuvant Approach*, Powell and Newman, eds, (Plenum Press: New York, 1995), pp. 439-462; WO 97/03692, WO 96/40072, WO 96/07399; and U.S. Pat. No. 5,654,010.

The sustained-release formulations of these proteins were developed using poly-lactic-coglycolic acid (PLGA) polymer due to its biocompatibility and wide range of biodegradable properties. The degradation products of PLGA, lactic and glycolic acids, can be cleared quickly within the human body. Moreover, the degradability of this polymer can be adjusted from months to years depending on its molecular weight and composition. Lewis, "Controlled release of bioactive agents from lactide/glycolide polymer," in: M. Chasin and R. Langer (Eds.), *Biodegradable Polymers as Drug Delivery Systems* (Marcel Dekker: New York, 1990), pp. 1-41.

This invention encompasses methods of screening compounds to identify those that mimic the IL-17A/F polypeptide (agonists) or prevent the effect of the IL-17A/F polypeptide (antagonists). Screening assays for antagonist drug candidates are designed to identify compounds that bind or complex with the IL-17A/F polypeptides encoded by the genes identified herein, or otherwise interfere with the interaction of the encoded polypeptides with other cellular proteins. Such screening assays will include assays amenable to high-throughput screening of chemical libraries, making them particularly suitable for identifying small molecule drug candidates.

The assays can be performed in a variety of formats, including protein-protein binding assays, biochemical screening assays, immunoassays, and cell-based assays, which are well characterized in the art.

All assays for antagonists are common in that they call for contacting the drug candidate with an IL-17A/F polypeptide encoded by a nucleic acid identified herein under conditions and for a time sufficient to allow these two components to interact.

In binding assays, the interaction is binding and the complex formed can be isolated or detected in the reaction mixture. In a particular embodiment, the IL-17A/F polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the IL-17A/F polypeptide and drying. Alternatively, an immobilized antibody, e.g., a monoclonal antibody, specific for the IL-17A/F polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labeled antibody specifically binding the immobilized complex.

If the candidate compound interacts with but does not bind to a particular IL-17A/F polypeptide encoded by a gene identified herein, its interaction with that polypeptide can be assayed by methods well known for detecting protein-protein interactions. Such assays include traditional approaches, such as, e.g., cross-linking, co-immunoprecipitation, and co-purification through gradients or chromatographic columns. In addition, protein-protein interactions can be monitored by using a yeast-based genetic system described by Fields and co-workers (Fields and Song, *Nature (London)*, 340:245-246 [1989]); Chien et al., *Proc. Natl. Acad. Sci. USA,* 88:9578-9582 [1991]) as disclosed by Chevray and Nathans, *Proc. Natl. Acad. Sci. USA,* 89:5789-5793 (1991). Many transcriptional activators, such as yeast GAL4, consist of two physically discrete modular domains, one acting as the DNA-binding domain, the other one functioning as the transcription-activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

Compounds that interfere with the interaction of a gene encoding an IL-17A/F polypeptide identified herein and other intra- or extracellular components can be tested as follows: usually a reaction mixture is prepared containing the product of the gene and the intra- or extracellular component under conditions and for a time allowing for the interaction and binding of the two products. To test the ability of a candidate compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described herein above. The formation of a complex in the control reaction(s) but not in the reaction mixture containing the test compound indicates that the test compound interferes with the interaction of the test compound and its reaction partner.

To assay for antagonists, the IL-17A/F polypeptide may be added to a cell along with the compound to be screened for a particular activity and the ability of the compound to inhibit the activity of interest in the presence of the IL-17A/F polypeptide indicates that the compound is an antagonist to the IL-17A/F polypeptide. Alternatively, antagonists may be detected by combining the IL-17A/F polypeptide and a potential antagonist with membrane-bound IL-17A/F polypeptide receptors or recombinant receptors under appropriate conditions for a competitive inhibition assay. The IL-17A/F polypeptide can be labeled, such as by radioactivity, such that the number of IL-17A/F polypeptide molecules bound to the receptor can be used to determine the effectiveness of the potential antagonist. The gene encoding the receptor can be identified by numerous methods known to those of skill in the art, for example, ligand panning and FACS sorting. Coligan et al., *Current Protocols in Immun.,* 1(2): Chapter 5 (1991). Preferably, expression cloning is employed wherein polyadenylated RNA is prepared from a cell responsive to the IL-17A/F polypeptide and a cDNA library created from this RNA is divided into pools and used to transfect COS cells or other cells that are not responsive to the IL-17A/F polypeptide. Transfected cells that are grown on glass slides are exposed to labeled IL-17A/F polypeptide. The IL-17A/F polypeptide can be labeled by a variety of means including iodination or inclusion of a recognition site for a site-specific protein kinase. Following fixation and incubation, the slides are subjected to autoradiographic analysis. Positive pools are identified and sub-pools are prepared and re-transfected using an interactive sub-pooling and re-screening process, eventually yielding a single clone that encodes the putative receptor.

As an alternative approach for receptor identification, labeled IL-17A/F polypeptide can be photoaffinity-linked with cell membrane or extract preparations that express the receptor molecule. Cross-linked material is resolved by PAGE and exposed to X-ray film. The labeled complex containing the receptor can be excised, resolved into peptide fragments, and subjected to protein micro-sequencing. The amino acid sequence obtained from micro-sequencing would be used to design a set of degenerate oligonucleotide probes to screen a cDNA library to identify the gene encoding the putative receptor.

In another assay for antagonists, mammalian cells or a membrane preparation expressing the receptor would be incubated with labeled IL-17A/F polypeptide in the presence of the candidate compound. The ability of the compound to enhance or block this interaction could then be measured.

More specific examples of potential antagonists include an oligonucleotide that binds to the fusions of immunoglobulin with IL-17A/F polypeptide, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. Alternatively, a potential antagonist may be a closely related protein, for example, a mutated form of the IL-17A/F polypeptide that recognizes the receptor but imparts no effect, thereby competitively inhibiting the action of the IL-17A/F polypeptide.

Another potential IL-17A/F polypeptide antagonist is an antisense RNA or DNA construct prepared using antisense technology, where, e.g., an antisense RNA or DNA molecule acts to block directly the translation of mRNA by hybridizing to targeted mRNA and preventing protein translation. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature IL-17A/F polypeptides herein, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.,* 6:3073 (1979); Cooney et al., *Science,* 241:456 (1988); Dervan et al., *Science,* 251:1360 (1991)), thereby preventing transcription and the production of the IL-17A/F polypeptide. The antisense RNA oligonucleotide hybridizes to the mRNA in vivo and blocks translation of the mRNA molecule into the IL-17A/F polypeptide (antisense—Okano, *Neurochem.,* 56:560 (1991); *Oligodeoxynucleotides as Antisense Inhibitors of Gene Expression* (CRC Press: Boca Raton, Fla., 1988). The oligonucleotides described above can also be delivered to cells such that the antisense RNA or DNA may be expressed in vivo to inhibit production of the IL-17A/F polypeptide. When antisense DNA is used, oligodeoxyribonucleotides derived from the translation-initiation site, e.g., between about −10 and +10 positions of the target gene nucleotide sequence, are preferred.

Potential antagonists include small molecules that bind to the active site, the receptor binding site, or growth factor or other relevant binding site of the IL-17A/F polypeptide, thereby blocking the normal biological activity of the IL-17A/F polypeptide. Examples of small molecules include, but are not limited to, small peptides or peptide-like molecules, preferably soluble peptides, and synthetic non-peptidyl organic or inorganic compounds.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology,* 4:469-471 (1994), and PCT publication No. WO 97/33551 (published Sep. 18, 1997).

Nucleic acid molecules in triple-helix formation used to inhibit transcription should be single-stranded and composed of deoxynucleotides. The base composition of these oligonucleotides is designed such that it promotes triple-helix formation via Hoogsteen base-pairing rules, which generally require sizeable stretches of purines or pyrimidines on one strand of a duplex. For further details see, e.g., PCT publication No. WO 97/33551, supra.

These small molecules can be identified by any one or more of the screening assays discussed herein above and/or by any other screening techniques well known for those skilled in the art.

Diagnostic and therapeutic uses of the herein disclosed molecules may also be based upon the positive functional assay hits disclosed and described below F. Tissue Distribution The location of tissues expressing the IL-17A/F can be identified by determining mRNA expression in various human tissues. The location of such genes provides information about which tissues are most likely to be affected by the stimulating and inhibiting activities of the IL-17A/F polypeptides. The location of a gene in a specific tissue also provides sample tissue for the activity blocking assays discussed below.

As noted before, gene expression in various tissues may be measured by conventional Southern blotting. Northern blotting to quantitate the transcription of mRNA (Thomas, *Proc. Natl. Acad. Sci. USA,* 77:5201-5205 [1980]), dot blotting (DNA analysis), or in situ hybridization, using an appropriately labeled probe, based on the sequences provided herein. Alternatively, antibodies may be employed that can recognize specific duplexes, including DNA duplexes, RNA duplexes, and DNA-RNA hybrid duplexes or DNA-protein duplexes.

Gene expression in various tissues, alternatively, may be measured by immunological methods, such as immunohistochemical staining of tissue sections and assay of cell culture or body fluids, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence of an IL-17A/F polypeptide or against a synthetic peptide based on the DNA sequences encoding the IL-17A/F polypeptide or against an exogenous sequence fused to a DNA encoding an IL-17A/F polypeptide and encoding a specific antibody epitope. General techniques for generating antibodies, and special protocols for Northern blotting and in situ hybridization are provided below.

G. Antibody Binding Studies

The activity of the IL-17A/F polypeptides can be further verified by antibody binding studies, in which the ability of anti-IL-17A/F antibodies to inhibit the effect of the IL-17A/F polypeptides, respectively, on tissue cells is tested. Exemplary antibodies include polyclonal, monoclonal, humanized, bispecific, and heteroconjugate antibodies, the preparation of which will be described herein below.

Antibody binding studies may be carried out in any known assay method, such as competitive binding assays, direct and indirect sandwich assays, and immunoprecipitation assays. Zola, *Monoclonal Antibodies: A Manual of Techniques,* pp. 147-158 (CRC Press, Inc., 1987).

Competitive binding assays rely on the ability of a labeled standard to compete with the test sample analyte for binding with a limited amount of antibody. The amount of target protein in the test sample is inversely proportional to the amount of standard that becomes bound to the antibodies. To facilitate determining the amount of standard that becomes bound, the antibodies preferably are insolubilized before or after the competition, so that the standard and analyte that are bound to the antibodies may conveniently be separated from the standard and analyte which remain unbound.

Sandwich assays involve the use of two antibodies, each capable of binding to a different immunogenic portion, or epitope, of the protein to be detected. In a sandwich assay, the test sample analyte is bound by a first antibody which is immobilized on a solid support, and thereafter a second antibody binds to the analyte, thus forming an insoluble three-part complex. See, e.g., U.S. Pat. No. 4,376,110. The second antibody may itself be labeled with a detectable moiety (direct sandwich assays) or may be measured using an anti-immunoglobulin antibody that is labeled with a detectable moiety (indirect sandwich assay). For example, one type of sandwich assay is an ELISA assay, in which case

H. Cell-Based Assays

Cell-based assays and animal models for immune related diseases can be used to further understand the relationship between the genes and polypeptides identified herein and the development and pathogenesis of immune related disease.

In a different approach, cells of a cell type known to be involved in a particular immune related disease are transfected with the cDNAs described herein, and the ability of these cDNAs to stimulate or inhibit immune function is analyzed. Suitable cells can be transfected with the desired gene, and monitored for immune function activity. Such transfected cell lines can then be used to test the ability of poly- or monoclonal antibodies or antibody compositions to inhibit or stimulate immune function, for example to modulate T-cell proliferation or inflammatory cell infiltration. Cells transfected with the coding sequences of the genes identified herein can further be used to identify drug candidates for the treatment of immune related diseases.

In addition, primary cultures derived from transgenic animals (as described below) can be used in the cell-based assays herein, although stable cell lines are preferred. Techniques to derive continuous cell lines from transgenic animals are well known in the art (see. e.g., Small et al., *Mol. Cell. Biol.*, 5: 642-648 [1985]).

One suitable cell based assay is the mixed lymphocyte reaction (MLR). *Current Protocols in Immunology*, unit 3.12; edited by J E Coligan, A M Kruisbeek, D H Marglies, E M Shevach, W Strober, National Institutes of Health, Published by John Wiley & Sons, Inc. In this assay, the ability of a test compound to stimulate or inhibit the proliferation of activated T cells is assayed. A suspension of responder T cells is cultured with allogeneic stimulator cells and the proliferation of T cells is measured by uptake of tritiated thymidine. This assay is a general measure of T cell reactivity. Since the majority of T cells respond to and produce IL-2 upon activation, differences in responsiveness in this assay in part reflect differences in IL-2 production by the responding cells. The MLR results can be verified by a standard lymphokine (IL-2) detection assay. *Current Protocols in Immunology, above,* 3.15, 6.3.

A proliferative T cell response in an MLR assay may be due to direct mitogenic properties of an assayed molecule or to external antigen induced activation. Additional verification of the T cell stimulatory activity of the IL-17A/F polypeptides can be obtained by a costimulation assay. T cell activation requires an antigen specific signal mediated through the T-cell receptor (TCR) and a costimulatory signal mediated through a second ligand binding interaction, for example, the B7 (CD80, CD86)/CD28 binding interaction. CD28 crosslinking increases lymphokine secretion by activated T cells. T cell activation has both negative and positive controls through the binding of ligands which have a negative or positive effect. CD28 and CTLA-4 are related glycoproteins in the Ig superfamily which bind to B7. CD28 binding to B7 has a positive costimulation effect of T cell activation; conversely, CTLA-4 binding to B7 has a negative T cell deactivating effect. Chambers, C. A. and Allison, *J. P., Curr. Opin. Immunol.*, (1997) 9:396. Schwartz, R. H., *Cell* (1992) 71:1065; Linsley, P. S. and Ledbetter, J. A., *Annu. Rev. Immunol.* (1993) 11:191; June, C. H. et al., *Immunol. Today* (1994) 15:321; Jenkins, M. K., *Immunity* (1994) 1:405. In a costimulation assay, the IL-17A/F polypeptides are assayed for T cell costimulatory or inhibitory activity.

IL-17A/F polypeptides, as well as other compounds of the invention, which are stimulators (costimulators) of T cell proliferation and agonists, e.g., agonist antibodies, thereto as determined by MLR and costimulation assays, for example, are useful in treating immune related diseases characterized by poor, suboptimal or inadequate immune function. These diseases are treated by stimulating the proliferation and activation of T cells (and T cell mediated immunity) and enhancing the immune response in a mammal through administration of a stimulatory compound, such as the stimulating IL-17A/F polypeptides. The stimulating polypeptide may, for example, be an IL-17A/F polypeptide or an agonist antibody thereof.

Direct use of a stimulating compound as in the invention has been validated in experiments with 4-1BB glycoprotein, a member of the tumor necrosis factor receptor family, which binds to a ligand (4-1BBL) expressed on primed T cells and signals T cell activation and growth. Alderson, M. E. et al., *J. Immunol.*, 24:2219 (1994).

The use of an agonist stimulating compound has also been validated experimentally. Activation of 4-1BB by treatment with an agonist anti-4-1BB antibody enhances eradication of tumors. Hellstrom, I. and Hellstrom, K. E., *Crit. Rev. Immunol.*, 18:1 (1998). Immunoadjuvant therapy for treatment of tumors, described in more detail below, is another example of the use of the stimulating compounds of the invention. An immune stimulating or enhancing effect can also be achieved by antagonizing or blocking the activity of an IL-17A/F which has been found to be inhibiting in the MLR assay. Negating the inhibitory activity of the compound produces a net stimulatory effect. Suitable antagonists/blocking compounds are antibodies or fragments thereof which recognize and bind to the inhibitory protein, thereby blocking the effective interaction of the protein with its receptor and inhibiting signaling through the receptor. This effect has been validated in experiments using anti-CTLA-4 antibodies which enhance T cell proliferation, presumably by removal of the inhibitory signal caused by CTLA-4 binding. Walunas, T. L. et al., *Immunity*, 1:405 (1994).

Alternatively, an immune stimulating or enhancing effect can also be achieved by administration of an IL-17A/F polypeptide which has vascular permeability enhancing properties. Enhanced vacuolar permeability would be beneficial to disorders which can be attenuated by local infiltration of immune cells (e.g., monocytes, eosinophils, PMNs) and inflammation.

On the other hand, IL-17A/F polypeptides, as well as other compounds of the invention, which are direct inhibitors of T cell proliferation/activation, lymphokine secretion, and/or vascular permeability can be directly used to suppress the immune response. These compounds are useful to reduce the degree of the immune response and to treat immune related diseases characterized by a hyperactive, superoptimal, or autoimmune response. This use of the compounds of the invention has been validated by the experiments described above in which CTLA-4 binding to receptor B7 deactivates T cells. The direct inhibitory compounds of the invention function in an analogous manner. The use of compound which suppress vascular permeability would be expected to reduce inflammation. Such uses would be beneficial in treating conditions associated with excessive inflammation.

Alternatively, compounds, e.g., antibodies, which bind to stimulating IL-17A/F polypeptides and block the stimulating effect of these molecules produce a net inhibitory effect and can be used to suppress the T cell mediated immune response by inhibiting T cell proliferation/activation and/or lymphokine secretion. Blocking the stimulating effect of the polypeptides suppresses the immune response of the mammal. This use has been validated in experiments using an anti-IL2 antibody. In these experiments, the antibody binds to IL2 and blocks binding of IL2 to its receptor thereby achieving a T cell inhibitory effect.

I. Animal Models

The results of the cell based in vitro assays can be further verified using in vivo animal models and assays for T-cell function. A variety of well known animal models can be used to further understand the role of the genes identified herein in the development and pathogenesis of immune related disease, and to test the efficacy of candidate therapeutic agents, including antibodies, and other antagonists of the native polypeptides, including small molecule antagonists. The in vivo nature of such models makes them predictive of responses in human patients. Animal models of immune related diseases include both non-recombinant and recombinant (transgenic) animals. Non-recombinant animal models include, for example, rodent, e.g., murine models. Such models can be generated by introducing cells into syngeneic mice using standard techniques, e.g., subcutaneous injection, tail vein injection, spleen implantation, intraperitoneal implantation, implantation under the renal capsule, etc.

Graft-versus-host disease occurs when immunocompetent cells are transplanted into immunosuppressed or tolerant patients. The donor cells recognize and respond to host antigens. The response can vary from life threatening severe inflammation to mild cases of diarrhea and weight loss. Graft-versus-host disease models provide a means of assessing T cell reactivity against MHC antigens and minor transplant antigens. A suitable procedure is described in detail in *Current Protocols in Immunology*, above, unit 4.3.

An animal model for skin allograft rejection is a means of testing the ability of T cells to mediate in vivo tissue destruction and a measure of their role in transplant rejection. The most common and accepted models use murine tail-skin grafts. Repeated experiments have shown that skin allograft rejection is mediated by T cells, helper T cells and killer-effector T cells, and not antibodies. Auchincloss, H. Jr. and Sachs, D. H., *Fundamental Immunology*, 2nd ed., W. E. Paul ed., Raven Press, NY, 889-992 (1989). A suitable procedure is described in detail in *Current Protocols in Immunology*, above, unit 4.4. Other transplant rejection models which can be used to test the compounds of the invention are the allogeneic heart transplant models described by Tanabe, M. et al., *Transplantation* 58:23 (1994) and Tinubu, S. A. et al., *J. Immunol.*, 4330-4338 (1994).

Animal models for delayed type hypersensitivity provides an assay of cell mediated immune function as well. Delayed type hypersensitivity reactions are a T cell mediated in vivo immune response characterized by inflammation which does not reach a peak until after a period of time has elapsed after challenge with an antigen. These reactions also occur in tissue specific autoimmune diseases such as multiple sclerosis (MS) and experimental autoimmune encephalomyelitis (EAE, a model for MS). A suitable procedure is described in detail in *Current Protocols in Immunology*, above, unit 4.5.

EAE is a T cell mediated autoimmune disease characterized by T cell and mononuclear cell inflammation and subsequent demyelination of axons in the central nervous system. EAE is generally considered to be a relevant animal model for MS in humans. Bolton, C., *Multile Sclerosis*, 1:143 (1995). Both acute and relapsing-remitting models have been developed. The compounds of the invention can be tested for T cell stimulatory or inhibitory activity against immune mediated demyelinating disease using the protocol described in *Current Protocols in Immunology*, above, units 15.1 and 15.2. See also the models for myelin disease in which oligodendrocytes or Schwann cells are grafted into the central nervous system as described in Duncan, I. D. et al., *Molec. Med. Today*, 554-561 (1997).

Contact hypersensitivity is a simple delayed type hypersensitivity in vivo assay of cell mediated immune function. In this procedure, cutaneous exposure to exogenous haptens which gives rise to a delayed type hypersensitivity reaction which is measured and quantitated. Contact sensitivity involves an initial sensitizing phase followed by an elicitation phase. The elicitation phase occurs when the T lymphocytes encounter an antigen to which they have had previous contact. Swelling and inflammation occur, making this an excellent model of human allergic contact dermatitis. A suitable procedure is described in detail in *Current Protocols in Immunology*, Eds. J. E. Cologan, A. M. Kruisbeek, D. H. Margulies, E. M. Shevach and W. Strober, John Wiley & Sons. Inc., unit 4.2 (1994). I also Grabbe, S. and Schwarz, T, *Immun. Today*, 19(1): 37-44 (1998).

An animal model for arthritis is collagen-induced arthritis. This model shares clinical, histological and immunological characteristics of human autoimmune rheumatoid arthritis and is an acceptable model for human autoimmune arthritis. Mouse and rat models are characterized by synovitis erosion of cartilage and subchondral bone. The compounds of the invention can be tested for activity against autoimmune arthritis using the protocols described in *Current Protocols in Immunology*, above, units 15.5. See also the model using a monoclonal antibody to CD18 and VLA-4 integrins described in Issekutz, A. C. et al., *Immunology*, 88:569 (1996).

A model of asthma has been described in which antigen-induced airway hyper-reactivity, pulmonary eosinophilia and inflammation are induced by sensitizing an animal with ovalbumin and then challenging the animal with the same protein delivered by aerosol. Several animal models (guinea pig, rat, non-human primate) show symptoms similar to atopic asthma in humans upon challenge with aerosol antigens. Murine models have many of the features of human asthma. Suitable procedures to test the compounds of the invention for activity and effectiveness in the treatment of asthma are described by Wolyniec, W. W. et al., *Am. J. Respir. Cell Mol. Biol.*, 18:777 (1998) and the references cited therein.

Additionally, the compounds of the invention can be tested on animal models for psoriasis like diseases. Evidence suggests a T cell pathogenesis for psoriasis. The compounds of the invention can be tested in the scid/scid mouse model described by Schon, M. P. et al., *Nat. Med.*, 3:183 (1997), in which the mice demonstrate histopathologic skin lesions resembling psoriasis. Another suitable model is the human skin/scid mouse chimera prepared as described by Nickoloff, B. J. et al., *Am. J. Path.*, 146:580 (1995).

Recombinant (transgenic) animal models can be engineered by introducing the coding portion of the genes identified herein into the genome of animals of interest, using standard techniques for producing transgenic animals. Animals that can serve as a target for transgenic manipulation include, without limitation, mice, rats, rabbits, guinea pigs, sheep, goats, pigs, and non-human primates, e.g., baboons, chimpanzees and monkeys. Techniques known in the art to introduce a transgene into such animals include pronucleic microinjection (Hoppe and Wanger, U.S. Pat. No. 4,873,191); retrovirus-mediated gene transfer into germ lines (e.g., Van der Putten et al., *Proc. Natl. Acad. Sci. USA*, 82, 6148-615 [1985]); gene targeting in embryonic stem cells (Thompson et al., *Cell,* 56, 313-321 [1989]); electroporation of embryos (Lo, *Mol. Cel. Biol.,* 3, 1803-1814 [1983]); sperm-mediated gene transfer (Lavitrano et al., *Cell,* 57, 717-73 [1989]). For review, see, for example, U.S. Pat. No. 4,736,866.

For the purpose of the present invention, transgenic animals include those that carry the transgene only in part of their cells ("mosaic animals"). The transgene can be integrated either as a single transgene, or in concatamers, e.g., head-to-head or head-to-tail tandems. Selective introduction of a transgene into a particular cell type is also possible by following, for example, the technique of Lasko et al., *Proc. Natl. Acad. Sci. USA,* 89, 6232-636 (1992).

The expression of the transgene in transgenic animals can be monitored by standard techniques. For example, Southern blot analysis or PCR amplification can be used to verify the integration of the transgene. The level of mRNA expression can then be analyzed using techniques such as in situ hybridization, Northern blot analysis, PCR, or immunocytochemistry.

The animals may be further examined for signs of immune disease pathology, for example by histological examination to determine infiltration of immune cells into specific tissues. Blocking experiments can also be performed in which the transgenic animals are treated with the compounds of the invention to determine the extent of the T cell proliferation stimulation or inhibition of the compounds. In these experiments, blocking antibodies which bind to the IL-17A/F polypeptide, prepared as described above, are administered to the animal and the effect on immune function is determined.

Alternatively, "knock out" animals can be constructed which have a defective or altered gene encoding a polypeptide identified herein, as a result of homologous recombination between the endogenous gene encoding the polypeptide and altered genomic DNA encoding the same polypeptide introduced into an embryonic cell of the animal. For example, cDNA encoding a particular polypeptide can be used to clone genomic DNA encoding that polypeptide in accordance with established techniques. A portion of the genomic DNA encoding a particular polypeptide can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, *Cell,* 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., *Cell,* 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach*, E. J. Robertson, ed. (IRL, Oxford, 1987), pp. 113-152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knock-out animals can be characterized for instance, for their ability to defend against certain pathological conditions and for their development of pathological conditions due to absence of the polypeptide.

J. ImmunoAdjuvant Therapy

In one embodiment, the immunostimulating compounds of the invention can be used in immunoadjuvant therapy for the treatment of tumors (cancer). It is now well established that T cells recognize human tumor specific antigens. One group of tumor antigens, encoded by the MAGE, BAGE and GAGE families of genes, are silent in all adult normal tissues, but are expressed in significant amounts in tumors, such as melanomas, lung tumors, head and neck tumors, and bladder carcinomas. DeSmet, C. et al., *Proc. Natl. Acad. Sci. USA,* 93:7149 (1996). It has been shown that costimulation of T cells induces tumor regression and an antitumor response both in vitro and in vivo. Melero, I. et al., *Nature Medicine,* 3:682 (1997); Kwon, E. D. et al., *Proc. Natl. Acad. Sci. USA,* 94: 8099 (1997); Lynch, D. H. et al., *Nature Medicine,* 3:625 (1997); Finn, O. J. and Lotze, M. T., *J. Immunol.,* 21:114 (1998). The stimulatory compounds of the invention can be administered as adjuvants, alone or together with a growth regulating agent, cytotoxic agent or chemotherapeutic agent, to stimulate T cell proliferation/activation and an antitumor response to tumor antigens. The growth regulating, cytotoxic, or chemotherapeutic agent may be administered in conventional amounts using known administration regimes. Immunostimulating activity by the compounds of the invention allows reduced amounts of the growth regulating, cytotoxic, or chemotherapeutic agents thereby potentially lowering the toxicity to the patient.

K. Screening Assays for Drug Candidates

Screening assays for drug candidates are designed to identify compounds that bind to or complex with the polypeptides encoded by the genes identified herein or a biologically active fragment thereof, or otherwise interfere with the interaction of the encoded polypeptides with other cellular proteins. Such screening assays will include assays amenable to high-throughput screening of chemical libraries, making them particularly suitable for identifying small molecule drug candidates. Small molecules contemplated include synthetic organic or inorganic compounds, including peptides, preferably soluble peptides, (poly)peptide-immunoglobulin fusions, and, in particular, antibodies including, without limitation, poly- and monoclonal antibodies and antibody fragments, single-chain antibodies, anti-idiotypic antibodies, and chimeric or humanized versions of such antibodies or fragments, as well as human antibodies and antibody fragments. The assays can be performed in a variety of formats, including protein-protein binding assays, biochemical screening assays, immunoassays and cell based assays, which are well characterized in the art. All assays are common in that they call for contacting the drug candidate with a polypeptide encoded by a nucleic acid identified herein under conditions and for a time sufficient to allow these two components to interact.

In binding assays, the interaction is binding and the complex formed can be isolated or detected in the reaction mixture. In a particular embodiment, the polypeptide encoded by the gene identified herein or the drug candidate is immobilized on a solid phase, e.g., on a microtiter plate, by covalent or non-covalent attachments. Non-covalent attachment generally is accomplished by coating the solid surface with a solution of the polypeptide and drying. Alternatively, an immobilized antibody, e.g., a monoclonal antibody, specific for the polypeptide to be immobilized can be used to anchor it to a solid surface. The assay is performed by adding the non-immobilized component, which may be labeled by a detectable label, to the immobilized component, e.g., the coated surface containing the anchored component. When the reaction is complete, the non-reacted components are removed, e.g., by washing, and complexes anchored on the solid surface are detected. When the originally non-immobilized component carries a detectable label, the detection of label immobilized on the surface indicates that complexing occurred. Where the originally non-immobilized component does not carry a label, complexing can be detected, for example, by using a labelled antibody specifically binding the immobilized complex.

If the candidate compound interacts with but does not bind to a particular protein encoded by a gene identified herein, its interaction with that protein can be assayed by methods well known for detecting protein-protein interactions. Such assays include traditional approaches, such as, cross-linking, co-immunoprecipitation, and co-purification through gradients or chromatographic columns. In addition, protein-protein interactions can be monitored by using a yeast-based genetic system described by Fields and co-workers [Fields and Song, *Nature (London)*, 340, 245-246 (1989); Chien et al., *Proc. Natl. Acad. Sci. USA*, 88, 9578-9582 (1991)] as disclosed by Chevray and Nathans, *Proc. Natl. Acad. Sci. USA*, 89, 5789-5793 (1991). Many transcriptional activators, such as yeast GAL4, consist of two physically discrete modular domains, one acting as the DNA-binding domain, while the other one functioning as the transcription activation domain. The yeast expression system described in the foregoing publications (generally referred to as the "two-hybrid system") takes advantage of this property, and employs two hybrid proteins, one in which the target protein is fused to the DNA-binding domain of GAL4, and another, in which candidate activating proteins are fused to the activation domain. The expression of a GAL1-lacZ reporter gene under control of a GAL4-activated promoter depends on reconstitution of GAL4 activity via protein-protein interaction. Colonies containing interacting polypeptides are detected with a chromogenic substrate for β-galactosidase. A complete kit (MATCHMAKER™) for identifying protein-protein interactions between two specific proteins using the two-hybrid technique is commercially available from Clontech. This system can also be extended to map protein domains involved in specific protein interactions as well as to pinpoint amino acid residues that are crucial for these interactions.

In order to find compounds that interfere with the interaction of a gene identified herein and other intra- or extracellular components can be tested, a reaction mixture is usually prepared containing the product of the gene and the intra- or extracellular component under conditions and for a time allowing for the interaction and binding of the two products. To test the ability of a test compound to inhibit binding, the reaction is run in the absence and in the presence of the test compound. In addition, a placebo may be added to a third reaction mixture, to serve as positive control. The binding (complex formation) between the test compound and the intra- or extracellular component present in the mixture is monitored as described above. The formation of a complex in the control reaction(s) but not in the reaction mixture containing the test compound indicates that the test compound interferes with the interaction of the test compound and its reaction partner.

L. Compositions and Methods for the Treatment of Immune Related Diseases

The compositions useful in the treatment of immune related diseases include, without limitation, proteins, antibodies, small organic molecules, peptides, phosphopeptides, antisense and ribozyme molecules, triple helix molecules, etc. that inhibit or stimulate immune function, for example, T cell proliferation/activation, lymphokine release, or immune cell infiltration.

For example, antisense RNA and RNA molecules act to directly block the translation of mRNA by hybridizing to targeted mRNA and preventing protein translation. When antisense DNA is used, oligodeoxyribonucleotides derived from the translation initiation site, e.g., between about −10 and +10 positions of the target gene nucleotide sequence, are preferred.

Ribozymes are enzymatic RNA molecules capable of catalyzing the specific cleavage of RNA. Ribozymes act by sequence-specific hybridization to the complementary target RNA, followed by endonucleolytic cleavage. Specific ribozyme cleavage sites within a potential RNA target can be identified by known techniques. For further details see, e.g., Rossi, *Current Biology*, 4, 469-471 (1994), and PCT publication No. WO 97/33551 (published Sep. 18, 1997).

Nucleic acid molecules in triple helix formation used to inhibit transcription should be single-stranded and composed of deoxynucleotides. The base composition of these oligonucleotides is designed such that it promotes triple helix formation via Hoogsteen base pairing rules, which generally require sizeable stretches of purines or pyrimidines on one strand of a duplex. For further details see, e.g., PCT publication No. WO 97/33551, supra.

These molecules can be identified by any or any combination of the screening assays discussed above and/or by any other screening techniques well known for those skilled in the art.

M. Anti-IL-17A/F Antibodies

In one embodiment, the present invention provides anti-IL-17A/F antibodies which may find use herein as therapeutic and/or diagnostic agents. Exemplary antibodies include polyclonal, monoclonal, humanized, bispecific, and heteroconjugate antibodies.

1. Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen (especially when synthetic peptides are used) to a protein that is immunogenic in the species to be immunized. For example, the antigen can be conjugated to keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later, the animals are boosted with ⅕ to 1/10 the original amount of peptide or conjugate in Freund's complete adjuvant by subcutaneous injection at multiple sites. Seven to 14 days later, the animals are bled and the serum is assayed for antibody titer. Animals are boosted until the titer plateaus. Conjugates also can be made in recombinant cell culture as protein fusions. Also, aggregating agents such as alum are suitably used to enhance the immune response.

2. Monoclonal Antibodies

Monoclonal antibodies may be made using the hybridoma method first described by Kohler et al., *Nature,* 256:495 (1975), or may be made by recombinant DNA methods (U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, *Monoclonal Antibodies: Principles and Practice,* pp. 59-103 (Academic Press, 1986)).

The hybridoma cells thus prepared are seeded and grown in a suitable culture medium which medium preferably contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Preferred fusion partner myeloma cells are those that fuse efficiently, support stable high-level production of antibody by the selected antibody-producing cells, and are sensitive to a selective medium that selects against the unfused parental cells. Preferred myeloma cell lines are murine myeloma lines, such as those derived from MOPC-21 and MPC-11 mouse tumors available from the Salk Institute Cell Distribution Center, San Diego, Calif. USA, and SP-2 and derivatives e.g., X63-Ag8-653 cells available from the American Type Culture Collection, Manassas, Va., USA. Human myeloma and mouse-human heteromyeloma cell lines also have been described for the production of human monoclonal antibodies (Kozbor, *J. Immunol.,* 133:3001 (1984); and Brodeur et al., *Monoclonal Antibody Production Techniques and Applications,* pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The binding affinity of the monoclonal antibody can, for example, be determined by the Scatchard analysis described in Munson et al., *Anal. Biochem.,* 107:220 (1980).

Once hybridoma cells that produce antibodies of the desired specificity, affinity, and/or activity are identified, the clones may be subcloned by limiting dilution procedures and grown by standard methods (Goding, *Monoclonal Antibodies: Principles and Practice,* pp. 59-103 (Academic Press, 1986)). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.,* 5:256-262 (1993) and Plückthun, *Immunol. Revs.* 130:151-188 (1992).

In a further embodiment, monoclonal antibodies or antibody fragments can be isolated from antibody phage libraries generated using the techniques described in McCafferty et al., *Nature,* 348:552-554 (1990). Clackson et al., *Nature,* 352:624-628 (1991) and Marks et al., *J. Mol. Biol.,* 222:581-597 (1991) describe the isolation of murine and human antibodies, respectively, using phage libraries. Subsequent publications describe the production of high affinity (nM range) human antibodies by chain shuffling (Marks et al., *Bio/Technology,* 10:779-783 (1992)), as well as combinatorial infection and in vivo recombination as a strategy for constructing very large phage libraries (Waterhouse et al., *Nuc. Acids. Res.* 21:2265-2266 (1993)). Thus, these techniques are viable alternatives to traditional monoclonal antibody hybridoma techniques for isolation of monoclonal antibodies.

The DNA that encodes the antibody may be modified to produce chimeric or fusion antibody polypeptides, for example, by substituting human heavy chain and light chain constant domain ($C_H$ and $C_L$) sequences for the homologous murine sequences (U.S. Pat. No. 4,816,567; and Morrison, et al., *Proc. Natl Acad. Sci. USA,* 81:6851 (1984)), or by fusing the immunoglobulin coding sequence with all or part of the coding sequence for a non-immunoglobulin polypeptide (heterologous polypeptide). The non-immunoglobulin polypeptide sequences can substitute for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

3. Human and Humanized Antibodies

The anti-IL-17A/F antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522-525 (1986); Riechmann et al., *Nature*, 332:323-329 (1988); and Presta, *Curr. Op. Struct. Biol.*, 2:593-596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522-525 (1986); Riechmann et al., *Nature*, 332:323-327 (1988); Verhoeyen et al., *Science*, 239:1534-1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity and HAMA response (human anti-mouse antibody) when the antibody is intended for human therapeutic use. According to the so-called "best-fit" method, the sequence of the variable domain of a rodent antibody is screened against the entire library of known human variable domain sequences. The human V domain sequence which is closest to that of the rodent is identified and the human framework region (FR) within it accepted for the humanized antibody (Sims et al., *J. Immunol.* 151:2296 (1993); Chothia et al., *J. Mol. Biol.*, 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.* 151:2623 (1993)).

It is further important that antibodies be humanized with retention of high binding affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Various forms of a humanized anti-IL-17A/F antibody are contemplated. For example, the humanized antibody may be an antibody fragment, such as a Fab, which is optionally conjugated with one or more cytotoxic agent(s) in order to generate an immunoconjugate. Alternatively, the humanized antibody may be an intact antibody, such as an intact IgG1 antibody.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *Proc. Natl. Acad. Sci. USA*, 90:2551 (1993); Jakobovits et al., *Nature*, 362:255-258 (1993); Bruggemann et al., *Year in Immuno.* 7:33 (1993); U.S. Pat. Nos. 5,545,806, 5,569,825, 5,591,669 (all of GenPharm); U.S. Pat. No. 5,545,807; and WO 97/17852.

Alternatively, phage display technology (McCafferty et al., *Nature* 348:552-553 [1990]) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, reviewed in, e.g., Johnson, Kevin S. and Chiswell, David J., *Current Opinion in Structural Biology* 3:564-571 (1993). Several sources of V-gene segments can be used for phage display. Clackson et al., *Nature*, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

4. Antibody Fragments

In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science,* 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Fab and F(ab')$_2$ fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See *Antibody Engineering*, ed. Borrebaeck, supra. The antibody fragment may also be a "linear antibody", e.g., as described in U.S. Pat. No. 5,641,870 for example. Such linear antibody fragments may be monospecific or bispecific.

5. Bispecific Antibodies

Bispecific antibodies are antibodies that have binding specificities for at least two different epitopes. Exemplary bispecific antibodies may bind to two different epitopes of an IL-17A/F protein as described herein. Other such antibodies may combine an IL-17A/F binding site with a binding site for another protein. Alternatively, an anti-IL-17A/F arm may be combined with an arm which binds to a triggering molecule on a leukocyte such as a T-cell receptor molecule (e.g. CD3), or Fc receptors for IgG (FcγR), such as FcγRI (CD64), FcγRII (CD32) and FcγRIII (CDI6), so as to focus and localize cellular defense mechanisms to the IL-17A/F-expressing cell. Bispecific antibodies may also be used to localize cytotoxic agents to cells which express IL-17A/F. These antibodies possess an IL-17A/F-binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab')$_2$ bispecific antibodies).

WO 96/16673 describes a bispecific anti-ErbB2/anti-FcγRIII antibody and U.S. Pat. No. 5,837,234 discloses a bispecific anti-ErbB2/anti-FcγRI antibody. A bispecific anti-ErbB2/Fcα antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., *Nature* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.* 10:3655-3659 (1991).

According to a different approach, antibody variable domains with the desired binding specificities (antibody-antigen combining sites) are fused to immunoglobulin constant domain sequences. Preferably, the fusion is with an Ig heavy chain constant domain, comprising at least part of the hinge, $C_H2$, and $C_H3$ regions. It is preferred to have the first heavy-chain constant region ($C_H1$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant affect on the yield of the desired chain combination.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology* 121:210(1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.* 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets. Various techniques for making and isolating bispecific antibody fragments directly from recombinant cell culture have also been described. For example, bispecific antibodies have been produced using leucine zippers. Kostelny et al., *J. Immunol.* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a $V_H$ connected to a $V_L$ by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al., *J. Immunol.* 147:60 (1991).

6. Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

7. Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)$_n$-VD2-(X2)$_n$-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

8. Effector Function Engineering

It may be desirable to modify the antibody of the invention with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al., *Cancer Research* 53:2560-2565 (1993). Alternatively, an antibody can be engineered which has dual Fc regions and may thereby have enhanced complement lysis and ADCC capabilities. See Stevenson et al., *Anti-Cancer Drug Design* 3:219-230 (1989). To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Pc region of an IgG molecule (e.g., IgG$_1$, IgG$_2$, IgG$_3$, or IgG$_4$) that is responsible for increasing the in vivo serum half-life of the IgG molecule.

9. Immunoconjugates

The invention also pertains to immunoconjugates comprising an antibody conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, a trichothene, and CC1065, and the derivatives of these toxins that have toxin activity, are also contemplated herein.

Maytansine and Maytansinoids

In one preferred embodiment, an anti-IL-17A/F antibody (full length or fragments) of the invention is conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

Maytansinoid-Antibody Conjugates

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., *Proc. Natl. Acad. Sci. USA* 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., *Cancer Research* 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansonid drug, which could be increased by increasing the number of maytansinoid molecules per antibody molecule. The A7-maytansinoid conjugate showed low systemic cytotoxicity in mice.

Anti-IL-17A/F Polypeptide Antibody-Maytansinoid Conjugates (Immunoconjugates)

Anti-IL-17A/F antibody-maytansinoid conjugates are prepared by chemically linking an anti-IL-17A/F antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, and Chari et al., *Cancer Research* 52:127-131 (1992). The linking groups include disufide groups, thioether groups, acid labile groups, photolabile groups, peptidase labile groups, or esterase labile groups, as disclosed in the above-identified patents, disulfide and thioether groups being preferred.

Conjugates of the antibody and maytansinoid may be made using a variety of bifunctional protein coupling agents such as N-succinimidyl-3-(2-pyridyldithio) propionate (SPDP, succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., *Biochem. J.* 173:723-737 [1978]) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hyrdoxymethyl, the C-15 position modified with a hydroxyl group, and the C-20 position having a hydroxyl group. In a preferred embodiment, the linkage is formed at the C-3 position of maytansinol or a maytansinol analogue.

Calicheamicin

Another immunoconjugate of interest comprises an anti-IL-17A/F antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta^I_1$ (Hinman et al., *Cancer Research* 53:3336-3342 (1993), Lode et al., *Cancer Research* 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the anti-IL-17A/F antibodies of the invention include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated anti-IL-17A/F antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for diagnosis, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2, 4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., *Cancer Research* 52:127-131 (1992); U.S. Pat. No. 5,208,020) may be used.

Alternatively, a fusion protein comprising the anti-IL-17A/F antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

10. Immunoliposomes

The anti-IL-17A/F antibodies disclosed herein may also be formulated as immunoliposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody are prepared by methods known in the art, such as described in Epstein et al., *Proc. Natl. Acad. Sci. USA* 82:3688 (1985); Hwang et al., *Proc. Natl Acad. Sci. USA* 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., *J. Biol. Chem.* 257:286-288 (1982) via a disulfide interchange reaction. A chemotherapeutic agent is optionally contained within the liposome. See Gabizon et al., *J. National Cancer Ins.* 81(19):1484(1989).

N. IL-17A/F Binding Oligopeptides

IL-17A/F binding oligopeptides of the present invention are oligopeptides that bind, preferably specifically, to an IL-17A/F polypeptide as described herein. IL-17A/F binding oligopeptides may be chemically synthesized using known oligopeptide synthesis methodology or may be prepared and purified using recombinant technology. IL-17A/F binding oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such oligopeptides that are capable of binding, preferably specifically, to an IL-17A/F polypeptide as described herein. IL-17A/F binding oligopeptides may be identified without undue experimentation using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., Proc. Natl. Acad. Sci. U.S.A., 81:3998-4002 (1984); Geysen et al., Proc. Natl. Acad. Sci. U.S.A., 82:178-182 (1985); Geysen et al., in Synthetic Peptides as Antigens, 130-149 (1986); Geysen et al., J. Immunol. Meth., 102:259-274 (1987); Schoofs et al., J. Immunol., 140:611-616 (1988), Cwirla, S. E. et al. (1990) Proc. Natl. Acad. Sci. USA. 87:6378; Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363, and Smith, G. P. (1991) Current Opin. Biotechnol., 2:668).

In this regard, bacteriophage (phage) display is one well known technique which allows one to screen large oligopeptide libraries to identify member(s) of those libraries which are capable of specifically binding to a polypeptide target. Phage display is a technique by which variant polypeptides are displayed as fusion proteins to the coat protein on the surface of bacteriophage particles (Scott, J. K. and Smith, G. P. (1990) Science 249: 386). The utility of phage display lies in the fact that large libraries of selectively randomized protein variants (or randomly cloned cDNAs) can be rapidly and efficiently sorted for those sequences that bind to a target molecule with high affinity. Display of peptide (Cwirla, S. E. et al. (1990) Proc. Natl. Acad. Sci. USA, 87:6378) or protein (Lowman, H. B. et al. (1991) Biochemistry, 30:10832; Clackson, T. et al. (1991) Nature, 352: 624; Marks, J. D. et al. (1991), J. Mol. Biol., 222:581; Kang, A. S. et al. (1991) Proc. Natl. Acad. Sci. USA, 88:8363) libraries on phage have been used for screening millions of polypeptides or oligopeptides for ones with specific binding properties (Smith, G. P. (1991) Current Opin. Biotechnol., 2:668). Sorting phage libraries of random mutants requires a strategy for constructing and propagating a large number of variants, a procedure for affinity purification using the target receptor, and a means of evaluating the results of binding enrichments. U.S. Pat. Nos. 5,223,409, 5,403,484, 5,571,689, and 5,663,143.

Although most phage display methods have used filamentous phage, lambdoid phage display systems (WO 95/34683; U.S. Pat. No. 5,627,024), T4 phage display systems (Ren, Z-J. et al. (1998) Gene 215:439; Zhu, Z. (1997) CAN 33:534; Jiang, J. et al. (1997) can 128:44380; Ren, Z-J. et al. (1997) CAN 127:215644; Ren, Z-J. (1996) Protein Sci. 5:1833; Efimov, V. P. et al. (1995) Virus Genes 10:173) and T7 phage display systems (Smith, G. P. and Scott, J. K. (1993) Methods in Enzymology, 217, 228☐257; U.S. Pat. No. 5,766,905) are also known.

Many other improvements and variations of the basic phage display concept have now been developed. These improvements enhance the ability of display systems to screen peptide libraries for binding to selected target molecules and to display functional proteins with the potential of screening these proteins for desired properties. Combinatorial reaction devices for phage display reactions have been developed (WO 98/14277) and phage display libraries have been used to analyze and control bimolecular interactions (WO 98/20169; WO 98/20159) and properties of constrained helical peptides (WO 98/20036). WO 97/35196 describes a method of isolating an affinity ligand in which a phage display library is contacted with one solution in which the ligand will bind to a target molecule and a second solution in which the affinity ligand will not bind to the target molecule, to selectively isolate binding ligands. WO 97/46251 describes a method of biopanning a random phage display library with an affinity purified antibody and then isolating binding phage, followed by a micropanning process using microplate wells to isolate high affinity binding phage. The use of *Staphlylococcus aureus* protein A as an affinity tag has also been reported (Li et al. (1998) Mol Biotech., 9:187). WO 97/47314 describes the use of substrate subtraction libraries to distinguish enzyme specificities using a combinatorial library which may be a phage display library. A method for selecting enzymes suitable for use in detergents using phage display is described in WO 97/09446. Additional methods of selecting specific binding proteins are described in U.S. Pat. Nos. 5,498,538, 5,432, 018, and WO 98/15833.

Methods of generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323.

O. IL-17A/F Binding Organic Molecules

IL-17A/F binding organic molecules are organic molecules other than oligopeptides or antibodies as defined herein that bind, preferably specifically, to an IL-17A/F polypeptide as described herein. IL-17A/F binding organic molecules may be identified and chemically synthesized using known methodology (see, e.g., PCT Publication Nos. WO00/00823 and WO00/39585). IL-17A/F binding organic molecules are usually less than about 2000 daltons in size, alternatively less than about 1500, 750, 500, 250 or 200 daltons in size, wherein such organic molecules that are capable of binding, preferably specifically, to an IL-17A/F polypeptide as described herein may be identified without undue experimentation using well known techniques. In this regard, it is noted that techniques for screening organic molecule libraries for molecules that are capable of binding to a polypeptide target are well known in the art (see, e.g., PCT Publication Nos. WO00/00823 and WO00/39585). IL-17A/F binding organic molecules may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, or the like.

P. Screening for Anti-IL-17A/F Antibodies, IL-17A/F Binding Oligopeptides and IL-17A/F Binding Organic Molecules with the Desired Properties Techniques for generating antibodies, oligopeptides and organic molecules that bind to IL-17A/F polypeptides have been described above. One may further select antibodies, oligopeptides or other organic molecules with certain biological characteristics, as desired.

The growth inhibitory effects of an anti-IL-17A/F antibody, oligopeptide or other organic molecule of the invention may be assessed by methods known in the art, e.g., using cells which express an IL-17A/F polypeptide either endogenously or following transfection with the IL-17A/F gene. For example, appropriate tumor cell lines and IL-17A/F-transfected cells may treated with an anti-IL-17A/F monoclonal antibody, oligopeptide or other organic molecule of the invention at various concentrations for a few days (e.g., 2-7) days and stained with crystal violet or MTT or analyzed by some other colorimetric assay. Another method of measuring proliferation would be by comparing $^3$H-thymidine uptake by the cells treated in the presence or absence an anti-IL-17A/F antibody, IL-17A/F binding oligopeptide or IL-17A/F binding organic molecule of the invention. After treatment, the cells are harvested and the amount of radioactivity incorporated into the DNA quantitated in a scintillation counter. Appropriate positive controls include treatment of a selected cell line with a growth inhibitory antibody known to inhibit growth of that cell line. Growth inhibition of tumor cells in vivo can be determined in various ways known in the art. Preferably, the tumor cell is one that overexpresses an IL-17A/F polypeptide. Preferably, the anti-IL-17A/F antibody, IL-17A/F binding oligopeptide or IL-17A/F binding organic molecule will inhibit cell proliferation of an IL-17A/F-expressing tumor cell in vitro or in vivo by about 25-100% compared to the untreated tumor cell, more preferably, by about 30-100%, and even more preferably by about 50-100% or 70-100%, in one embodiment, at an antibody concentration of about 0.5 to 30 µg/ml. Growth inhibition can be measured at an antibody concentration of about 0.5 to 30 µg/ml or about 0.5 nM to 200 nM in cell culture, where the growth inhibition is determined 1-10 days after exposure of the tumor cells to the antibody. The antibody is growth inhibitory in vivo if administration of the anti-IL-17A/F antibody at about 1 µg/kg to about 100 mg/kg body weight results in reduction in tumor size or reduction of tumor cell proliferation within about 5 days to 3 months from the first administration of the antibody, preferably within about 5 to 30 days.

To select for an anti-IL-17A/F antibody, IL-17A/F binding oligopeptide or IL-17A/F binding organic molecule which induces cell death, loss of membrane integrity as indicated by, e.g., propidium iodide (PI), trypan blue or 7AAD uptake may be assessed relative to control. A PI uptake assay can be performed in the absence of complement and immune effector cells. IL-17A/F polypeptide-expressing tumor cells are incubated with medium alone or medium containing the appropriate anti-IL-17A/F antibody (e.g, at about 10 µg/ml), IL-17A/F binding oligopeptide or IL-17A/F binding organic molecule. The cells are incubated for a 3 day time period. Following each treatment, cells are washed and aliquoted into 35 mm strainer-capped 12×75 tubes (1 ml per tube, 3 tubes per treatment group) for removal of cell clumps. Tubes then receive PI (10 µg/ml). Samples may be analyzed using a FACSCAN® flow cytometer and FACSCONVERT® CellQuest software (Becton Dickinson). Those anti-IL-17A/F antibodies, IL-17A/F binding oligopeptides or IL-17A/F binding organic molecules that induce statistically significant levels of cell death as determined by PI uptake may be selected as cell death-inducing anti-IL-17A/F antibodies, IL-17A/F binding oligopeptides or IL-17A/F binding organic molecules.

To screen for antibodies, oligopeptides or other organic molecules which bind to an epitope on an IL-17A/F polypeptide bound by an antibody of interest, a routine cross-blocking assay such as that described in *Antibodies, A Laboratory Manual*, Cold Spring Harbor Laboratory, Ed Harlow and David Lane (1988), can be performed. This assay can be used to determine if a test antibody, oligopeptide or other organic molecule binds the same site or epitope as a known anti-IL-17A/F antibody. Alternatively, or additionally, epitope mapping can be performed by methods known in the art. For example, the antibody sequence can be mutagenized such as by alanine scanning, to identify contact residues. The mutant antibody is initially tested for binding with polyclonal antibody to ensure proper folding. In a different method, peptides corresponding to different regions of an IL-17A/F polypeptide can be used in competition assays with the test antibodies or with a test antibody and an antibody with a characterized or known epitope.

Q. Pharmaceutical Compositions

The active IL-17A/F molecules of the invention (e.g., IL-17A/F polypeptides, anti-IL-17A/F antibodies, and/or variants of each) as well as other molecules identified by the screening assays disclosed above, can be administered for the treatment of immune related diseases, in the form of pharmaceutical compositions.

Therapeutic formulations of the active IL-17A/F molecule, preferably a polypeptide or antibody of the invention, are prepared for storage by mixing the active molecule having the desired degree of purity with optional pharmaceutically acceptable carriers, excipients or stabilizers (Remington's Pharmaceutical Sciences 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Compounds identified by the screening assays disclosed herein can be formulated in an analogous manner, using standard techniques well known in the art.

Lipofections or liposomes can also be used to deliver the IL-17A/F molecule into cells. Where antibody fragments are used, the smallest inhibitory fragment which specifically binds to the binding domain of the target protein is preferred. For example, based upon the variable region sequences of an antibody, peptide molecules can be designed which retain the ability to bind the target protein sequence. Such peptides can be synthesized chemically and/or produced by recombinant DNA technology (see, e.g., Marasco et al., *Proc. Natl. Acad. Sci. USA,* 90:7889-7893 [1993]).

The formulation herein may also contain more than one active compound as necessary for the particular indication being treated, preferably those with complementary activities that do not adversely affect each other. Alternatively, or in addition, the composition may comprise a cytotoxic agent, cytokine or growth inhibitory agent. Such molecules are suitably present in combination in amounts that are effective for the purpose intended.

The active IL-17A/F molecules may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration must be sterile. This is readily accomplished by filtration through sterile filtration membranes.

Sustained-release preparations or the IL-17A/F molecules may be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

R. Methods of Treatment

It is contemplated that the polypeptides, antibodies and other active compounds of the present invention may be used to treat various immune related diseases and conditions, such as T cell mediated diseases, including those characterized by infiltration of inflammatory cells into a tissue, stimulation of T-cell proliferation, inhibition of T-cell proliferation, increased or decreased vascular permeability or the inhibition thereof.

Exemplary conditions or disorders to be treated with the polypeptides, antibodies and other compounds of the invention, include, but are not limited to systemic lupus erythematosis, rheumatoid arthritis, juvenile chronic arthritis, osteoarthritis, spondyloarthropathies, systemic sclerosis (scleroderma), idiopathic inflammatory myopathies (dermatomyositis, polymyositis), Sjögren's syndrome, systemic vasculitis, sarcoidosis, autoimmune hemolytic anemia (immune pancytopenia, paroxysmal nocturnal hemoglobinuria), autoimmune thrombocytopenia (idiopathic thrombocytopenic purpura, immune-mediated thrombocytopenia), thyroiditis (Grave's disease, Hashimoto's thyroiditis, juvenile lymphocytic thyroiditis, atrophic thyroiditis), diabetes mellitus, immune-mediated renal disease (glomerulonephritis, tubulointerstitial nephritis), demyelinating diseases of the central and peripheral nervous systems such as multiple sclerosis, idiopathic demyelinating polyneuropathy or Guillain-Barré syndrome, and chronic inflammatory demyelinating polyneuropathy, hepatobiliary diseases such as infectious hepatitis (hepatitis A, B, C, D, E and other non-hepatotropic viruses), autoimmune chronic active hepatitis, primary biliary cirrhosis, granulomatous hepatitis, and sclerosing cholangitis, inflammatory bowel disease (ulcerative colitis: Crohn's disease), gluten-sensitive enteropathy, and Whipple's disease, autoimmune or immune-mediated skin diseases including bullous skin diseases, erythema multiforme and contact dermatitis, psoriasis, allergic diseases such as asthma, allergic rhinitis, atopic dermatitis, food hypersensitivity and urticaria, immunologic diseases of the lung such as eosinophilic pneumonia, idiopathic pulmonary fibrosis and hypersensitivity pneumonitis, transplantation associated diseases including graft rejection and graft-versus-host-disease.

In systemic lupus erythematosus, the central mediator of disease is the production of auto-reactive antibodies to self proteins/tissues and the subsequent generation of immune-mediated inflammation. Antibodies either directly or indirectly mediate tissue injury. Though T lymphocytes have not been shown to be directly involved in tissue damage, T lymphocytes are required for the development of auto-reactive antibodies. The genesis of the disease is thus T lymphocyte dependent. Multiple organs and systems are affected clinically including kidney, lung, musculoskeletal system, mucocutaneous, eye, central nervous system, cardiovascular system, gastrointestinal tract, bone marrow and blood.

Rheumatoid arthritis (RA) is a chronic systemic autoimmune inflammatory disease that mainly involves the synovial membrane of multiple joints with resultant injury to the articular cartilage. The pathogenesis is T lymphocyte dependent and is associated with the production of rheumatoid factors, auto-antibodies directed against self IgG, with the resultant formation of immune complexes that attain high levels in joint fluid and blood. These complexes in the joint may induce the marked infiltrate of lymphocytes and monocytes into the synovium and subsequent marked synovial changes; the joint space/fluid if infiltrated by similar cells with the addition of numerous neutrophils. Tissues affected are primarily the joints, often in symmetrical pattern. However, extra-articular disease also occurs in two major forms. One form is the development of extra-articular lesions with ongoing progressive joint disease and typical lesions of pulmonary fibrosis, vasculitis, and cutaneous ulcers. The second form of extra-articular disease is the so called Felty's syndrome which occurs late in the RA disease course, sometimes after joint disease has become quiescent, and involves the presence of neutropenia, thrombocytopenia and splenomegaly. This can be accompanied by vasculitis in multiple organs with formations of infarcts, skin ulcers and gangrene. Patients often also develop rheumatoid nodules in the subcutis tissue overlying affected joints; the nodules late stage have necrotic centers surrounded by a mixed inflammatory cell infiltrate. Other manifestations which can occur in RA include: pericarditis, pleuritis, coronary arteritis, interstitial pneumonitis with pulmonary fibrosis, keratoconjunctivitis sicca, and rheumatoid nodules.

Juvenile chronic arthritis is a chronic idiopathic inflammatory disease which begins often at less than 16 years of age. Its phenotype has some similarities to RA; some patients which are rheumatoid factor positive are classified as juvenile rheumatoid arthritis. The disease is sub-classified into three major categories: pauciarticular, polyarticular, and systemic. The arthritis can be severe and is typically destructive and leads to joint ankylosis and retarded growth. Other manifestations can include chronic anterior uveitis and systemic amyloidosis.

Spondyloarthropathies are a group of disorders with some common clinical features and the common association with the expression of HLA-B27 gene product. The disorders include: ankylosing spondylitis, Reiter's syndrome (reactive arthritis), arthritis associated with inflammatory bowel disease, spondylitis associated with psoriasis, juvenile onset spondyloarthropathy and undifferentiated spondyloarthropathy. Distinguishing features include sacroileitis with or without spondylitis; inflammatory asymmetric arthritis; association with HLA-B27 (a serologically defined allele of the HLA-B locus of class I MHC); ocular inflammation, and absence of autoantibodies associated with other rheumatoid disease. The cell most implicated as key to induction of the disease is the $CD8^+$ T lymphocyte, a cell which targets antigen presented by class I MHC molecules. $CD8^+$ T cells may react against the class I MHC allele HLA-B27 as if it were a foreign peptide expressed by MHC class I molecules. It has been hypothesized that an epitope of HLA-B27 may mimic a bacterial or other microbial antigenic epitope and thus induce a CD8' T cells response.

Systemic sclerosis (scleroderma) has an unknown etiology. A hallmark of the disease is induration of the skin; likely this is induced by an active inflammatory process. Scleroderma can be localized or systemic; vascular lesions are common and endothelial cell injury in the microvasculature is an early and important event in the development of systemic sclerosis; the vascular injury may be immune mediated. An immunologic basis is implied by the presence of mononuclear cell infiltrates in the cutaneous lesions and the presence of anti-nuclear antibodies in many patients. ICAM-1 is often upregulated on the cell surface of fibroblasts in skin lesions suggesting that T cell interaction with these cells may have a role in the pathogenesis of the disease. Other organs involved include: the gastrointestinal tract: smooth muscle atrophy and fibrosis resulting in abnormal peristalsis/motility; kidney: concentric subendothelial intimal proliferation affecting small arcuate and interlobular arteries with resultant reduced renal cortical blood flow, results in proteinuria, azotemia and hypertension; skeletal muscle: atrophy, interstitial fibrosis; inflammation; lung: interstitial pneumonitis and interstitial fibrosis; and heart: contraction band necrosis, scarring/fibrosis.

Idiopathic inflammatory myopathies including dermatomyositis, polymyositis and others are disorders of chronic muscle inflammation of unknown etiology resulting in muscle weakness. Muscle injury/inflammation is often symmetric and progressive. Autoantibodies are associated with most forms. These myositis-specific autoantibodies are directed against and inhibit the function of components, proteins and RNA's, involved in protein synthesis.

Sjögren's syndrome is due to immune-mediated inflammation and subsequent functional destruction of the tear glands and salivary glands. The disease can be associated with or accompanied by inflammatory connective tissue diseases. The disease is associated with autoantibody production against Ro and La antigens, both of which are small RNA-protein complexes. Lesions result in keratoconjunctivitis sicca, xerostomia, with other manifestations or associations including biliary cirrhosis, peripheral or sensory neuropathy, and palpable purpura.

Systemic vasculitis are diseases in which the primary lesion is inflammation and subsequent damage to blood vessels which results in ischemia/necrosis/degeneration to tissues supplied by the affected vessels and eventual end-organ dysfunction in some cases. Vasculitides can also occur as a secondary lesion or sequelae to other immune-inflammatory mediated diseases such as rheumatoid arthritis, systemic sclerosis, etc., particularly in diseases also associated with the formation of immune complexes. Diseases in the primary systemic vasculitis group include: systemic necrotizing vasculitis: polyarteritis nodosa, allergic angiitis and granulomatosis, polyangiitis; Wegener's granulomatosis; lymphomatoid granulomatosis; and giant cell arteritis. Miscellaneous vasculitides include: mucocutaneous lymph node syndrome (MLNS or Kawasaki's disease), isolated CNS vasculitis, Behet's disease, thromboangiitis obliterans (Buerger's disease) and cutaneous necrotizing venulitis. The pathogenic mechanism of most of the types of vasculitis listed is believed to be primarily due to the deposition of immunoglobulin complexes in the vessel wall and subsequent induction of an inflammatory response either via ADCC, complement activation, or both.

Sarcoidosis is a condition of unknown etiology which is characterized by the presence of epithelioid granulomas in nearly any tissue in the body; involvement of the lung is most common. The pathogenesis involves the persistence of activated macrophages and lymphoid cells at sites of the disease with subsequent chronic sequelae resultant from the release of locally and systemically active products released by these cell types.

Autoimmune hemolytic anemia including autoimmune hemolytic anemia, immune pancytopenia and paroxysmal noctural hemoglobinuria is a result of production of antibodies that react with antigens expressed on the surface of red blood cells (and in some cases other blood cells including platelets as well) and is a reflection of the removal of those antibody coated cells via complement mediated lysis and/or ADCC/Fc-receptor-mediated mechanisms.

In autoimmune thrombocytopenia including thrombocytopenic purpura, and immune-mediated thrombocytopenia in other clinical settings, platelet destruction/removal occurs as a result of either antibody or complement attaching to platelets and subsequent removal by complement lysis, ADCC or FC-receptor mediated mechanisms.

Thyroiditis including Grave's disease, Hashimoto's thyroiditis, juvenile lymphocytic thyroiditis, and atrophic thyroiditis, are the result of an autoimmune response against thyroid antigens with production of antibodies that react with proteins present in and often specific for the thyroid gland. Experimental models exist including spontaneous models: rats (BUF and BB rats) and chickens (obese chicken strain); inducible models: immunization of animals with either thyroglobulin, thyroid microsomal antigen (thyroid peroxidase).

Type I diabetes mellitus or insulin-dependent diabetes is the autoimmune destruction of pancreatic islet cells; this destruction is mediated by auto-antibodies and auto-reactive T cells. Antibodies to insulin or the insulin receptor can also produce the phenotype of insulin-non-responsiveness.

Immune mediated renal diseases, including glomerulonephritis and tubulointerstitial nephritis, are the result of antibody or T lymphocyte mediated injury to renal tissue either directly as a result of the production of autoreactive antibodies or T cells against renal antigens or indirectly as a result of the deposition of antibodies and/or immune complexes in the kidney that are reactive against other, non-renal antigens. Thus other immune-mediated diseases that result in the formation of immune-complexes can also induce immune mediated renal disease as an indirect sequelae. Both direct and indirect immune mechanisms result in inflammatory response that produces/induces lesion development in renal tissues with resultant organ function impairment and in some cases progression to renal failure. Both humoral and cellular immune mechanisms can be involved in the pathogenesis of lesions.

Demyelinating diseases of the central and peripheral nervous systems, including multiple sclerosis; idiopathic demyelinating polyneuropathy or Guillain-Barré syndrome; and chronic inflammatory demyelinating polyneuropathy, are believed to have an autoimmune basis and result in nerve demyelination as a result of damage caused to oligodendrocytes or to myelin directly. In MS there is evidence to suggest that disease induction and progression is dependent on T lymphocytes. Multiple sclerosis is a demyelinating disease that is T lymphocyte-dependent and has either a relapsing-remitting course or a chronic progressive course. The etiology is unknown; however, viral infections, genetic predisposition, environment, and autoimmunity all contribute. Lesions contain infiltrates of predominantly T lymphocyte mediated, microglial cells and infiltrating macrophages; $CD4^+$ T lymphocytes are the predominant cell type at lesions. The mechanism of oligodendrocyte cell death and subsequent demyelination is not known but is likely T lymphocyte driven.

Inflammatory and fibrotic lung disease, including eosinophilic pneumonia; idiopathic pulmonary fibrosis, and hypersensitivity pneumonitis may involve a disregulated immune-inflammatory response. Inhibition of that response would be of therapeutic benefit.

Autoimmune or immune-mediated skin disease including bullous skin diseases, erythema multiforme, and contact dermatitis are mediated by auto-antibodies, the genesis of which is T lymphocyte-dependent.

Psoriasis is a T lymphocyte-mediated inflammatory disease. Lesions contain infiltrates of T lymphocytes, macrophages and antigen processing cells, and some neutrophils.

Allergic diseases, including asthma; allergic rhinitis; atopic dermatitis; food hypersensitivity; and urticaria are T lymphocyte dependent. These diseases are predominantly mediated by T lymphocyte induced inflammation, IgE mediated-inflammation or a combination of both.

Transplantation associated diseases, including graft rejection and graft-versus-host-disease (GVHD) are T lymphocyte-dependent; inhibition of T lymphocyte function is ameliorative.

Other diseases in which intervention of the immune and/or inflammatory response have benefit are infectious disease including but not limited to viral infection (including but not limited to AIDS, hepatitis A, B, C, D, E and herpes) bacterial infection, fungal infections, and protozoal and parasitic infections (molecules (or derivatives/agonists) which stimulate the MLR can be utilized therapeutically to enhance the immune response to infectious agents), diseases of immunodeficiency (molecules/derivatives/agonists) which stimulate the MLR can be utilized therapeutically to enhance the immune response for conditions of inherited, acquired, infectious induced (as in HIV infection), or iatrogenic (i.e., as from chemotherapy) immunodeficiency, and neoplasia.

It has been demonstrated that some human cancer patients develop an antibody and/or T lymphocyte response to antigens on neoplastic cells. It has also been shown in animal models of neoplasia that enhancement of the immune response can result in rejection or regression of that particular neoplasm. Molecules that enhance the T lymphocyte response in the MLR have utility in vivo in enhancing the immune response against neoplasia. Molecules which enhance the T lymphocyte proliferative response in the MLR (or small molecule agonists or antibodies that affected the same receptor in an agonistic fashion) can be used therapeutically to treat cancer. Molecules that inhibit the lymphocyte response in the MLR also function in vivo during neoplasia to suppress the immune response to a neoplasm; such molecules can either be expressed by the neoplastic cells themselves or their expression can be induced by the neoplasm in other cells. Antagonism of such inhibitory molecules (either with antibody, small molecule antagonists or other means) enhances immune-mediated tumor rejection.

Additionally, inhibition of molecules with proinflammatory properties may have therapeutic benefit in reperfusion injury; stroke; myocardial infarction; atherosclerosis; acute lung injury; hemorrhagic shock; burn; sepsis/septic shock; acute tubular necrosis; endometriosis; degenerative joint disease and pancreatitis. The compounds of the present invention, e.g., polypeptides or antibodies, are administered to a mammal, preferably a human, in accord with known methods, such as intravenous administration as a bolus or by continuous infusion over a period of time, by intramuscular, intraperitoneal, intracerebral spinal, subcutaneous, intra-articular, intra synovial, intrathecal, oral, topical, or inhalation (intranasal, intrapulmonary) mutes. Intravenous or inhaled administration of polypeptides and antibodies is preferred.

In immunoadjuvant therapy, other therapeutic regimens, such administration of an anti-cancer agent, may be combined with the administration of the proteins antibodies or compounds of the instant invention. For example, the patient to be treated with a the immunoadjuvant of the invention may also receive an anti-cancer agent (chemotherapeutic agent) or radiation therapy. Preparation and dosing schedules for such chemotherapeutic agents may be used according to manufacturers' instructions or as determined empirically by the skilled practitioner. Preparation and dosing schedules for such chemotherapy are also described in *Chemotherapy Service*, Ed., M. C. Perry, Williams & Wilkins, Baltimore, Md. (1992). The chemotherapeutic agent may precede, or follow administration of the immunoadjuvant or may be given simultaneously therewith. Additionally, an anti-oestrogen compound such as tamoxifen or an anti-progesterone such as onapristone (see, EP 616812) may be given in dosages known for such molecules.

It may be desirable to also administer antibodies against other immune disease associated or tumor associated antigens, such as antibodies which bind to CD20, CD11a, CD18, ErbB2, EGFR, ErbB3, ErbB4, or vascular endothelial factor (VEGF). Alternatively, or in addition, two or more antibodies binding the same or two or more different antigens disclosed herein may be coadministered to the patient. Sometimes, it may be beneficial to also administer one or more cytokines to the patient. In one embodiment, the IL-17A/F polypeptides are coadministered with a growth inhibitory agent. For example, the growth inhibitory agent may be administered first, followed by an IL-17A/F polypeptide. However, simultaneous administration or administration first is also contemplated. Suitable dosages for the growth inhibitory agent are those presently used and may be lowered due to the combined action (synergy) of the growth inhibitory agent and the IL-17A/F polypeptide.

For the treatment or reduction in the severity of immune related disease, the appropriate dosage of an a compound of the invention will depend on the type of disease to be treated, as defined above, the severity and course of the disease, whether the agent is administered for preventive or therapeutic purposes, previous therapy, the patient's clinical history and response to the compound, and the discretion of the attending physician. The compound is suitably administered to the patient at one time or over a series of treatments.

For example, depending on the type and severity of the disease, about 1 mg/kg to 15 mg/kg (e.g., 0.1-20 mg/kg) of polypeptide or antibody is an initial candidate dosage for administration to the patient, whether, for example, by one or more separate administrations, or by continuous infusion. A typical daily dosage might range from about 1 mg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

S. Articles of Manufacture

In another embodiment of the invention, an article of manufacture containing materials (e.g., comprising an IL-17A/F molecule) useful for the diagnosis or treatment of the disorders described above is provided. The article of manufacture comprises a container and an instruction. Suitable containers include, for example, bottles, vials, syringes, and test tubes. The containers may be formed from a variety of materials such as glass or plastic. The container holds a composition which is effective for diagnosing or treating the condition and may have a sterile access port (for example the container may be an intravenous solution bag or a vial having a stopper pierceable by a hypodermic injection needle). The active agent in the composition is usually a polypeptide or an antibody of the invention. An instruction or label on, or associated with, the container indicates that the composition is used for diagnosing or treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

T. Diagnosis and Prognosis of Immune Related Disease

Cell surface proteins, such as proteins which are overexpressed in certain immune related diseases, are excellent targets for drug candidates or disease treatment. The same proteins along with secreted proteins encoded by the genes amplified in immune related disease states find additional use in the diagnosis and prognosis of these diseases. For example, antibodies directed against the protein products of genes amplified in multiple sclerosis, rheumatoid arthritis, inflammatory bowel disorder, or another immune related disease, can be used as diagnostics or prognostics.

For example, antibodies, including antibody fragments, can be used to qualitatively or quantitatively detect the expression of proteins encoded by amplified or overexpressed genes ("marker gene products"). The antibody preferably is equipped with a detectable, e.g., fluorescent label, and binding can be monitored by light microscopy, flow cytometry, fluorimetry, or other techniques known in the art. These techniques are particularly suitable, if the overexpressed gene encodes a cell surface protein Such binding assays are performed essentially as described above.

In situ detection of antibody binding to the marker gene products can be performed, for example, by immunofluorescence or immunoelectron microscopy. For this purpose, a histological specimen is removed from the patient, and a labeled antibody is applied to it, preferably by overlaying the antibody on a biological sample. This procedure also allows for determining the distribution of the marker gene product in the tissue examined. It will be apparent for those skilled in the art that a wide variety of histological methods are readily available for in situ detection.

The following examples are offered for illustrative purposes only, and are not intended to limit the scope of the present invention in any way.

All patent and literature references cited in the present specification are hereby incorporated by reference in their entirety.

EXAMPLES

Commercially available reagents referred to in the examples were used according to manufacturer's instructions unless otherwise indicated. The source of those cells identified in the following examples, and throughout the specification, by ATCC accession numbers is the American Type Culture Collection, Manassas, Va.

Example 1

Recombinant Expression of a Novel IL-17 Cytokine Identified as IL-17A/F

Human 293 Kidney Cells Transfection with cDNA Expression Vectors Encoding IL-17 and IL-17F Human 293 kidney cells were transfected with equal amounts of plasmids encoding the human IL-17, IL-17C and IL-17F genes, using a calcium phosphate precipitation procedure. For each 50%-80% confluent T-150 flask, 50 µg of each plasmid was mixed to form a precipitate to layer onto cells. One day after transfection, 50:50 F12:DMEM containing 10% FCS, 5 mM L-glutamine, penicillin-streptomycin was removed and replaced with serum-free PS24 media and cultured for an additional four days. After four days, conditioned media was collected centrifuged and sterile filtered, prior to purification.

Purification of Recombinant IL-17A/F

Figure 2F:
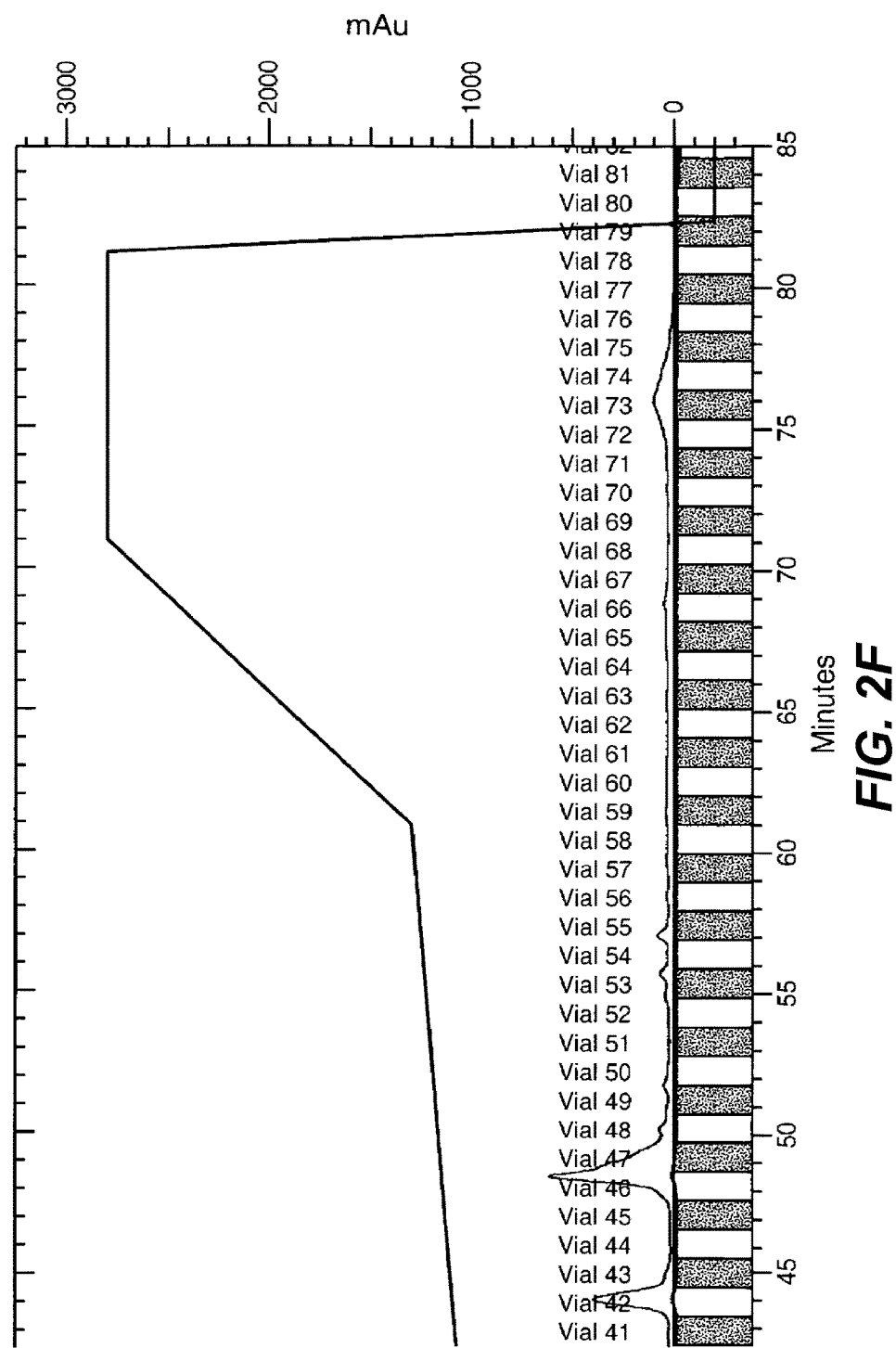
Figure 2G:
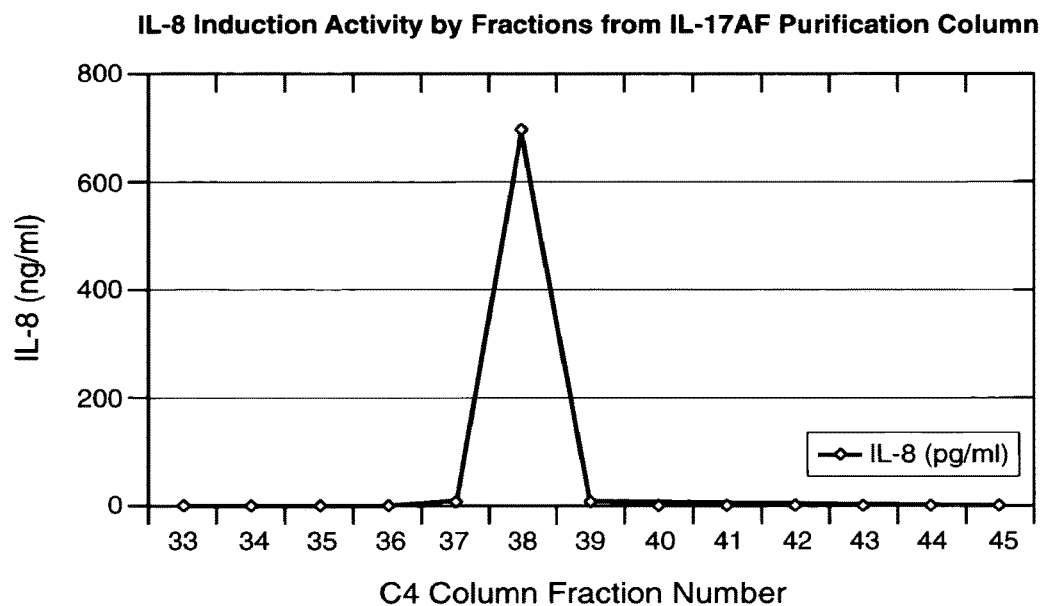

A. Initial Fractionation Step 1:

Two and a half liters of recombinant IL-17A/F conditioned media from human 293 kidney cell transient cultures was concentrated and dialyzed against 20 mM sodium acetate, pH 5.0, 1 mM sodium azide (Buffer A) using a 10 kilodalton cutoff membrane to a volume of 480 milliliters, then applied to a Pharmacia HiLoad S Sepharose 26/10 column at 6 ml/min. The column was eluted with a linear gradient to 100% Buffer B (20 mM sodium acetate, 1 M NaCl, 1 mM sodium azide, pH 5.0) at a rate of 1%/minute with a flow rate of 6 ml/min collecting 12 ml fractions. SDS PAGE analysis was performed on the fractions collected from this column. Proteins were revealed with silver staining. Molecular mass markers are labeled for gel containing fractions 25-37 (FIG. 2A-2D). Fractions 31 and 32 contained a protein with an apparent molecular mass of approximately 33 kD consistent with IL-17A/F:

B. Purification of IL-17A/F:

Four ml of fraction 32 (FIG. 2) was acidified with 0.1% trifluoroacetic acid then applied at 0.5 ml/min to a Vydac C4 column equilibrated in 0.1% trifluoroacetic acid (Buffer C) and gradient eluted to 100% Buffer D (0.1% trifluoroacetic acid in 100% acetonitrile) with a three step gradient (0-35% D over 10 minutes, 35-50% D over 35 minutes, 50-100% D over 10 minutes). FIG. 2 shows the chromatograph of eluted proteins measured at 214 nm and 280 nm. The acetonitrile step gradient is overlain over the profile. Protein concentration of fraction 38 was found to be 0.536 mg/ml by amino acid analysis. Gels, blots, amino acid sequence and activity assays were run on this fraction.

Fraction 31 and the remaining volume of fraction 32, from the HiLoad S Sepharose run were pooled and dialyzed against Buffer A for eight hours using a 10 kD cutoff membrane and passed through a 0.2 micron filter. This material was loaded on a Mono S column equilibrated in Buffer A at a flow rate of 1 ml/min and eluted with a three step gradient to 100% Buffer B (0-30% B over 10 column volumes, 30-75% B over 45 column volumes, 75-100% B over 10 column volumes) while collecting 1 ml/fraction. Fractions 26-43 were assayed and protein concentrations were determined by amino acid analysis. The concentration of fractions 31, 32 and 33 were 0.258, 0.359 and 0.291 mg/ml respectively. Gels, blots, amino acid sequence, mass spectrophotometry and activity assays were run primarily on fraction 32 and 33. Fractions generated by chromatography were assayed for IL-17 and IL-17F content through the use of Western blotting. One μg/ml of monoclonal antibody directed against either IL-17 or IL-17F was used to detect the presence of either IL-17 or IL-17F in the samples.

Mass Spectrometry Analysis of IL-17A/F

The amino acid sequence and interchain disulfide bonds of mature IL-17A/F were determined by mass spectrometry analysis (see FIG. 4A; IL-17A/F heterodimeric polypeptide shown with interchain and intrachain disulfide linkages). Two interchain disulfide linkages were detected between IL-17F and IL-17 polypeptide chains [between residue $47_{IL\text{-}17F}$ and residue $129_{IL\text{-}17}$; and between residue $137_{IL\text{-}17F}$ and residue $33_{IL\text{-}17}$, respectively (bold black lines in FIG. 4A). In addition, two intrachain disulfide links form in each of the homodimer polypeptide chains IL-17 [between residues 102 and 152; and between residues 107 to 154] and IL-17F[between residues 94 and 144; and between residues 99 and 146] (light black lines in FIG. 4A). The amino acids are numbered relative to the initiating methionine in each precursor polypeptide chain (FIG. 4A). FIG. 4B shows a schematic of the IL-17A/F peptide fragments containing disulfide bonds between the IL-17 and the IL-17F chain that would be anticipated by digestion of the IL-17A/F with trypsin [IL-17A/F disulfide bond fragment #1 is designated as SEQ ID NO:7; IL-17A/F disulfide bond fragment #2 is designated as SEQ ID NO:8, respectively]. The amino acids contained within these fragments are indicated and numbered relative to the initiating methionine of each chain.

The calculated approximate molecular mass of these fragments that would be observed by mass spectrometry is shown in FIG. 4B as 3410.58 Da and 2420.05 Da [IL-17A/F disulfide bond fragment #1 and #2 respectively]. Matrix-assisted laser desorption/ionization time of flight mass spectrometry (MALDI-TOF) peptide mapping was performed (FIG. 4C). 55 pmol of IL-17A/F in a buffer of 400 mM NaCl, 20 mM NaOAC buffer pH 5 was digested overnight at 37° C. with Promega sequencing grade trypsin. Matrix-assisted laser desorption/ionization time of flight mass spectrometry (MALDI-TOF) was performed with delayed extraction in positive ion reflectron mode using a 2', 4', 6'-trihydoxyacetophenone matrix. The resulting peptide map contained peaks with [M+H]+=2420.12 Da for fragment #2 and 3410.60 Da for fragment #1, consistent with the disulfide linked peptides (FIG. 4C-4F). A second sample aliquot was digested at pH 8 following reduction of disulfide bonds with dithiothreitol and alkylation of sulfhydryl groups with iodoacetamide. The MALDI-TOF spectrum of this sample lacked the peaks in question, supporting their assignment as disulfide-linked. The non-reduced sample was further characterized by liquid-chromatography electrospray ionization ion trap mass spectrometry (LC-ESI-MS) (FIG. 4D-4F). The ion chromatograms represent (from top to bottom) the total ion chromatogram, reconstructed ion chromatogram (RIC) of IL-17A/F disulfide bond fragment #2 [M+2H]2+, and IL-17A/F disulfide bond fragment #1 [M+2H]3+. Peaks consistent with both heterodimers were observed whereas no peaks above background chemical noise were observed at the anticipated masses of the homodimeric peptides thus indicating the absence of IL-17 or IL-17F homodimers. The composition of the disulfide-linked heterodimers was then confirmed by tandem mass spectrometry. Collision-induced dissociation of the doubly charged precursor at m/z 1210.9 corresponded to IL-17A/F disulfide bond fragment #2 and the triply charged precursor at m/z 1138.0 corresponds to IL-17A/F disulfide bond fragment #1. Predicted b- and y-ion series fragment peaks were observed in the corresponding spectra.

Phage Library Screening for Antibodies that Bind to IL-17A/F

In order to identify antibodies which bind to IL-17A/F, a phage library of synthetic Fab antibodies was screened. Thirty four (34) independent clones encoding distinct Fab antibody sequences were identified. Which were able to mediate binding to IL-17A/F. The phage library of human antibody sequences was prepared and screened for antigen specific Fab in a manner similar to that previously described (Gerstner, R. B. et al., *J. Mol. Biol.,* 321(5):851-62 (2002). Briefly, the humanized monoclonal antibody 4D5, an anti-HER2 antibody, was used as a scaffold to construct phage-displayed Fab libraries. These Fab are displayed on the phage monovalently and/or divalently by fusion to a homodimerizable leucine zipper. To generate library diversity, we chose to randomize surface exposed heavy chain CDR residues that were also found to be highly diverse in the Kabat database of natural antibody sequences and form a contiguous patch. Furthermore, we used site-directed mutagenesis with tailored degenerate codons to generate amino acid diversity that mimicked the natural immune repertoire at each CDR site. First two CDR of heavy chain, H1 and H2, were allowed limited diversity of same length as Herceptin, whereas H3 is designed to have high degeneracy with length ranged from 7 to 19. All antibodies generated from the initial library selection have the identical light chain. Full length IgG or Fab can be generated by one-step cloning of the heavy chain variable domain into vectors providing the desired isotype specific constant region sequence. To further improve the affinity of binders from the heavy chain library, a second-step randomization of light chain CDRs can be employed. The amino acid sequence of the region of the variable domain of the heavy chains that contains the three (3) CDRs [H1-H3] from Fab that bind IL-17A/F are shown in FIG. 6. Shown is the alignment of a region of the predicted amino acid sequence of 34 Fab clones that encode distinct antibody heavy chain sequences that are able to bind to IL-17A/F. The three heavy chain CDR regions are indicated as CDR-H1, CDR-H2 and CDR-H3, respectively are shaded. The corresponding SEQ ID NO for each clone is as follows:
Clone #1=SEQ ID NO:9; Clone #2=SEQ ID NO:10; Clone #3=SEQ ID NO:11; Clone #4=SEQ ID NO:12; Clone #5=SEQ ID NO:13; Clone #6=SEQ ID NO:14; Clone #7=SEQ ID NO:15; Clone #8=SEQ ID NO:16; Clone #9=SEQ ID NO:17; Clone #10=SEQ ID NO:18; Clone #11=SEQ ID NO:19; Clone #12=SEQ ID NO:20; Clone #13=SEQ ID NO:21; Clone #14=SEQ ID NO:22; Clone #15=SEQ ID NO:23; Clone #16=SEQ ID NO:24; Clone #17=SEQ ID NO:25; Clone #18=SEQ ID NO:26; Clone #19=SEQ ID NO:27; Clone #20=SEQ ID NO:28; Clone #21=SEQ ID NO:29; Clone #22=SEQ ID NO:30; Clone #23=SEQ ID NO:31; Clone #24=SEQ ID NO:32; Clone #25=SEQ ID NO:33; Clone #26=SEQ ID NO:34; Clone #27=SEQ ID NO:35; Clone #28=SEQ ID NO:36; Clone #29=SEQ ID NO:37; Clone #30=SEQ ID NO:38; Clone #31=SEQ ID NO:39; Clone #32=SEQ ID NO:40; Clone #33=SEQ ID NO:41; Clone #34=SEQ ID NO:42, respectively.

In addition, the corresponding encoding DNA sequences for each of the thirty four (34) clones is shown in Table 7 below (SEQ ID NO:43 to SEQ ID NO:76, respectively).

TABLE 7

SEQ ID NO: 43:
TTGTCCTGTGCAGCTTCTGGCTTCACCATTAGTGATTCCGCTATACA

CTGGGTGCGTCAGGCCCCGGGTAAGGGCCTGGAATGGGTTGCTGGGA

TTACTCCTTATAGCGGTTATACTGACTATGCCGATAGCGTCAAGGGC

CGTTTCACTATAAGCGCAGACACATCCAAAAACACAGCCTACCTACA

AATGAACAGCTTAAGAGCTGAGGACACTGCCGTCTATTATTGTGCAA

AAGAGGCCCGCGAGGGCTACGACGTCGGCTACGCTATGGACTACTGG

GGTCAA

SEQ ID NO: 44:
TTGTCCTGTGCAGCTTCTGGCTTCACCATTAGTGATTCCTATATACA

CTGGGTGCGTCAGGCCCCGGGTAAGGGCCTGGAATGGGTTGCTGAAA

TTTCTCCTCCTGGCGGCGATACTTACTATGCCGATAGCGTCAAGGGC

CGTTTCACTATAAGCGCAGACACATCCAAAAACACAGCCTACCTACA

AATGAACAGCTTAAGAGCTGAGGACACTGCCGTCTATTATTGTGCTC

GTCTCTTGTGGTGGTGGGACGGGGCTATGGACTACTGGGGTCAA

SEQ ID NO: 45:
TTGTCCTGTGCAGCTTCTGGCTTCACCATTACTAATACTTGGATACA

CTGGGTGCGTCAGGCCCCGGGTAAGGGCCTGGAATGGGTTGCTGTTA

TTACTCCTTATGGCGGTGCTACTTACTATGCCGATAGCGTCAAGGGC

CGTTTCACTATAAGCGCAGACACATCCAAAAACACAGCCTACCTACA

AATGAACAGCTTAAGAGCTGAGGACACTGCCGTCTATTATTGTGCAA

GAGAGAGTATGTGGAGTAAGTTCGACTACTGGGGTCAA

SEQ ID NO: 46:
TTGTCCTGTGCAGCTTCTGGCTTCACCATTAATAGTTCTGCTATACA

CTGGGTGCGTCAGGCCCCGGGTAAGGGCCTGGAATGGGTTGGTTATA

TTACTCCTGATAACGGTGATACTAACTATGCCGATAGCGTCAAGGGC

CGTTTCACTATAAGCGCAGACACATCCAAAAACACAGCCTACCTACA

AATGAACAGCTTAATAGCTGAGGATACTGCCGTCTATTATTGTGCTC

GCGGCCACGGCAACTTCTACGGTACCTGGGCGGCTATGGACTACTGG

GGTCAA

SEQ ID NO: 47:
TTGTCCTGTGCAGCTTCTGGCTTCACCATTAGTGGTTCTGATATACA

CTGGGTGCGTCAGGCCCCGGGTAAGGGCCTGGAATGGGTTGCTTATA

TTAATCCTTATGGCGGTTCTACTGACTATGCCGATAGCGTCAAGGGC

CGTTTCACTATAAGCGCAGACACATCCAAAAACACAGCCTACCTACA

AATGAACAGCTTAAGAGCTGAGGACACTGCCGTCTATTATTGTGCTC

GTGCGTACGAGATGTGGTACGTTATGGACTACTGGGGTCAA

SEQ ID NO: 48:
TTGTCCTGTGCAGCTTCTGGCTTCACCATTACTAATTCCTGGATACA

CTGGGTGCGTCAGGCCCCGGGTAAGGGCCTGGAATGGGTTGGTGTTA

TTACTCCTTCTAGCGGTTCTACTTACTATGCCGATAGCGTCAAGGGC

CGTTTCACTATAAGCGCAGACACATCCAAAAACACAGCCTACCTACA

AATGAACAGCTTAAGAGCTGAGGACACTGCCGTCTATTATTGTGCTC

GTGAGGTCTTCCCCGACATCGGGGACTGCAGCAACGCCTACTGCTAC

GCTATGGACTACTGGGGTCAA

SEQ ID NO: 49:
TTGTCCTGTGCAGCTTCTGGCTTCACCATTACTAGTACTTATATACA

CTGGGTGCGTCAGGCCCCGGGTAAGGGCCTGGAATGGGTTGCTTGGA

TTTCTCCTTATAGCGGTTATACTGACTATGCCGATAGCGTCAAGGGC

CGTTTCACTATAAGCGCAGACACATCCAAAAACACAGCCTACCTACA

AATGAACAGCTTAAGAGCTGAGGACACTGCCGTCTATTATTGTGCTC

GTGAGGTGGGTGGGGGACTCGTACGCTATGGACTACTGGGGTCAA

SEQ ID NO: 50:
TTGTCCTGTGCAGCTTCTGGCTTCACCATTAGTGGTTCTTGGATACA

CTGGGTGCGTCAGGCCCCGGGTAAGGGCCTGGAATGGGTTGCTGGGA

TTTATCCTTATGACGGTTATACTTACTATGCCGATAGCGTCAAGGGC

CGTTTCACTATAAGCGCAGACACATCCAAAAACACAGCCTACCTACA

AATGAACAGCTTAAGAGCTGAGGACACTGCCGTCTATTATTGTGCTC

GTGAGGCCGAGGGCCTGTACCAGTCCGGGATCTACGACGCGGGTATG

GACTACTGGGGTCAA

TABLE 7-continued

SEQ ID NO: 51:
TTGTCCTGTGCAGCTTCTGGCTTCACCATTACTAGTTACTATATACA
CTGGGTGCGTCAGGCCCCGGGTAAGGGCCTGGAATGGGTTGCTTGGA
TTTATCCTGCTGACGGTGCTACTTACTATGCCGATAGCGTCAAGGGC
CGTTTCACTATAAGCGCAGACACATCCAAAAACACAGCCTACCTACA
AATGAACAGCTTAAGAGCTGAGGACACTGCCGTCTATTATTGTGCTC
GTGGGTCCTACTTCGGGGGCTACGATATGGACTACTGGGGTCAA

SEQ ID NO: 52:
TTGTCCTGTGCAGCTTCTGGCTTCACCATTAATGATTCTGATATACA
CTGGGTGCGTCAGGCCCCGGGTAAGGGCCTGGAATGGGTTGGTATTA
TTTATCCTTATGACGGTTATACTTACTATGCCGATAGCGTCAAGGGC
CGTTTCACTATAAGCGCAGACACATCCAAAAACACAGCCTACCTACA
AATGAACAGCTTAAGAGCTGAGGACACTGCCGTCTATTATTGTGCAA
GAAGCAACCTGGACAACAACTTGTTCGACTACTGGGGTCAA

SEQ ID NO: 53:
TTGTCCTGTGCAGCTTCTGGCTTCACCATTAATGGTTACTGGATACA
CTGGGTGCGTCAGGCCCCGGGTAAGGGCCTGGAATGGGTTGCTGATA
TTAATCCTAATGGCGGTTCTACTAACTATGCCGATAGCGTCAAGGGC
CGTTTCACTATAAGCGCAGACACATCCAAAAACACAGCCTACCTACA
AATGAACAGCTTAAGAGCTGAGGACACTGCCGTCTATTATTGTGCTC
GTGCCTACCGGTGCGGCGGGCTCGCCGACTGGGCCGGGGCTATGGAC
TACTGGGGTCAA

SEQ ID NO: 54:
TTGTCCTGTGCAGCTTCTGGCTTCACCATTAGTGGTTCTTGGATACA
CTGGGTGCGTCAGGCCCCGGGTAAGGGCCTGGAATGGGTTGCTATTA
TTACTCCTTCTGGCGGTAATACTGACTATGCCGATAGCGTCAAGGGC
CGTTTCACTATAAGCGCAGACACATCCAAAAACACAGCCTACCTACA
AATGAACAGCTTAAGAGCTGAGGACACTGCCGTCTATTATTGTGCTC
GTGAGGTCTTCGCCGTGTCGACCGCCGGCTACCCCTGGGTTATGGAC
TACTGGGGTCAA

SEQ ID NO: 55:
TTGTCCTGTGCAGCTTCTGGCTTCACCATTACTGATTCTTGGATACA
CTGGGTGCGTCAGGCCCCGGGTAAGGGCCTGGAATGGGTTGGTTCTA
TTACTCCTTATAACGGTAATACTGACTATGCCGATAGCGTCAAGGGC
CGTTTCACTATAAGCGCAGACACATCCAAAAACACAGCCTACCTACA
AATGAACAGCTTAAGAGCTGAGGACACTGCCGTCTATTATTGTGCTC
GCAGGGGGGAGTCCGACGAGGCCTACGCCGCGGTTATGGACTACTGG
GGTCAA

SEQ ID NO: 56:
TTGTCCTGTGCAGCTTCTGGCTTCACCATTAGTAGTTCCGATATACA
CTGGGTGCGTCAGGCCCCGGGTAAGGGCCTGGAATGGGTTGGTACTA
TTAATCCTGCTAGCGGTTCTACTGACTATGCCGATAGCGTCAAGGGC
CGTTTCACTATAAGCGCAGACACATCCAAAAACACAGCCTACCTACA
AATGAACAGCTTAAGAGCTGAGGACACTGCCGTCTATTATTGTGCTC
GCGGCGCCAACAGCAGCTTCTACGCGCTCCAGTACGTTATGGACTAC
TGGGGTCAA

SEQ ID NO: 57:
TTGTCCTGTGCAGCTTCTGGCTTCACCATTACTGATAATTATATACA
CTGGGTGCGTCAGGCCCCGGGTAAGGGCCTGGAATGGGTTGGTTGGA
TTTCTCCTTATAGCGGTTATACTTACTATGCCGATAGCGTCAAGGGC
CGTTTCACTATAAGCGCAGACACATCCAAAAACACAGCCTACCTACA
AATGAACAGCTTAAGAGCTGAGGACACTGCCGTCTATTATTGTGCTC
GTGAGACCCTCTTCTACGACAAGGACCAGTACTCCTACGTTATGGAC
TACTGGGGTCAA

SEQ ID NO: 58:
TTGTCCTGTGCAGCTTCTGGCTTCACCATTAGTAGTTCTTATATACA
CTGGGTGCGTCAGGCCCCGGGTAAGGGCCTGGAATGGGTTGCTTGGA
TTTCTCCTTATAGCGGTTATACTGACTATGCCGATAGCGTCAAGGGC
CGTTTCACTATAAGCGCAGACACATCCAAAAACACAGCCTACCTACA
AATGAACAGCTTAAGAGCTGAGGACACTGCCGTCTATTATTGTGCTC
GTGAGGGGCTCCTGCGGTGGGGCTACGCTATGGACTACTGGGGTCAA

SEQ ID NO: 59:
TTGTCCTGTGCAGCTTCTGGCTTCACCATTACTGATAATGGGATACA
CTGGGTGCGTCAGGCCCCGGGTAAGGGCCTGGAATGGGTTGGTTGGA
TTACTCCTACTAGCGGTTATACTAACTATGCCGATAGCGTCAAGGGC
CGTTTCACTATAAGCGCAGACACATCCAAAAACACAGCCTACCTACA
AATGAACAGCTTAAGAGCTGAGGACACTGCCGTCTATTATTGTGCTC
GCGACGGGGACACCTGGAAGTGGGACGCCCCGTACGTTATGGACTAC
TGGGGTCAA

SEQ ID NO: 60:
TTGTCCTGTGCAGCTTCTGGCTTCACCATTACTAATACTTATATACA
CTGGGTGCGTCAGGCCCCGGGTAAGGGCCTGGAATGGGTTGCTTGGA
TTTCTCCTTATAGCGGTTATACTGACTATGCCGATAGCGTCAAGGAC
CGTTTCACTATAAGCGCAGACACATCCAAAAACACAGCCTACCTACA
AATGAACAGCTTAAGAGCTGAGGACACTGCCGTCTATTATTGTGCTC
GCGAGATCTTGCTGGACTACGGTTCCGCGGGCTACGCTATGGACTAC
TGGGGTCAA

SEQ ID NO: 61:
TTGTCCTGTGCAGCTTCTGGCTTCACCATTACTAGTACCTGGATACA
CTGGGTGCGTCAGGCCCCGGGTAAGGGCCTGGAATGGGTTGGTGTTA
TTACTCCTACTAACGGTTCTACTTACTATGCCGATAGCGTCAAGGGC
CGTTTCACTATAAGCGCAGACACATCCAAAAACACAGCCTACCTACA
AATGAACAGCTTAAGAGCTGAGGACACTGCCGTCTATTATTGTGCTC
GCGAGGTGTGGTGGTGGGCGACGGCCACGGCTACGTTATGGACTAC
TGGGGTCAA

TABLE 7-continued

SEQ ID NO: 62:
TTGTCCTGTGCAGCTTCTGGCTTCACCATTAGTAGTTCTGCTATACA
CTGGGTGCGTCAGGCCCCGGGTAAGGGCCTGGAATGGGTTGGTGGGA
TTACTCCTGCTAGCGGTTATACTTACTATGCCGATAGCGTCAAGGGC
CGTTTCACTATAAGCGCAGACACATCCAAAAACACAGCCTACCTACA
AATGAACAGCTTAAGAGCTGAGGACACTGCCGTCTATTATTGTGCTC
GCTCGCCCGGCGGGGTGTTCGTCGACGGCGGGGTTATGGACTACTGG
GGTCAA

SEQ ID NO: 63:
TTGTCCTGTGCAGCTTCTGGCTTCACCATTAATAGTACTGATATACA
CTGGGTGCGTCAGGCCCCGGGTAAGGGCCTGGAATGGGTTGGTAGGA
TTAATCCTTCTGGCGGTTCTACTAACTATGCCGATAGCGTCAAGGGC
CGTTTCACTATAAGCGCAGACACATCCAAAAACACAGCCTACCTACA
AATGAACAGCTTAAGAGCTGAGGACACTGCCGTCTATTATTGTGCTC
GTACCAGCGCGTACACCACGTGGGCGGTCGACTGGTTCATCGGCTAC
GTTATGGACTACTGGGGTCAA

SEQ ID NO: 64:
TTGTCCTGTGCAGCTTCTGGCTTCACCATTACTGGTTACGGGATACA
CTGGGTGCGTCAGGCCCCGGGTAAGGGCCTGGAATGGGTTGCTTGGA
TTTCTCCTTCTAACGGTTATACTTACTATGCCGATAGCGTCAAGGGC
CGTTTCACTATAAGCGCAGACACATCCAAAAACACAGCCTACCTACA
AATGAACAGCTTAAGAGCTGAGGACACTGCCGTCTATTATTGTGCTC
GTCGCGTCAGCTACTACGTCTACAGGCACGACTGGGTCAGGGCTAC
GTTATGGACTACTGGGGTCAA

SEQ ID NO: 65:
TTGTCCTGTGCAGCTTCTGGCTTCACCATTACTGATACCTGGATACA
CTGGGTGCGTCAGGCCCCGGGTAAGGGCCTGGAATGGGTTGGTGTTA
TTACTCCTTATGGCGGTTATACTTACTATGCCGATAGCGTCAAGGGC
CGTTTCACTATAAGCGCAGACACATCCAAAAACACAGCCTACCTACA
AATGAACAGCTTAAGAGCTGAGGACACTGCCGTCTATTATTGTGCAA
GAGACGGGGCTTCTTCGATTACTGGGGTCAA

SEQ ID NO: 66:
TTGTCCTGTGCAGCTTCTGGCTTCACCATTAGTGATTCCTCTATACA
CTGGGTGCGTCAGGCCCCGGGTAAGGGCCTGGAATGGGTTGCTTTTA
TTTATCCTACTAGCGGTTCTACTTACTATGCCAATAGCGTCAAGGGC
CGTTTCACTATAAGCGCAGACACATCCAAAAACACAGCCTACCTACA
AATGAACAGCTTAAGAGCTGAGGACACTGCCGTCTATTATTGTGCAC
GTGCCTCGTACGGGGTGAGCAAGTGGACCTTTGACTACTGGGGTCAA

SEQ ID NO: 67:
TTGTCCTGTGCAGCTTCTGGCTTCACCATTACTGGTTACGGGATACA
CTGGGTGCGTCAGGCCCCGGGTAAGGGCCTGGAATGGGTTGCTTGGA
TTTCTCCTTCTAACGGTTATACTTACTATGCCGATAGCGTCAAGGGC
CGTTTCACTATAAGCGCAGACACATCCAAAAACACAGCCTACCTACA
AATGAACAGCTTAAGAGCTGAGGACACTGCCGTCTATTATTGTGCTC
GTCGCGTCAGCTACTACGTCTACAGGCACGACTGGGTCAGGGCTAC
GTTATGGACTACTGGGGTCAA

SEQ ID NO: 68:
TTGTCCTGTGCAGCTTCTGGCTTCACCATTACTGGTACTTATATACA
CTGGGTGCGTCAGGCCCCGGGTAAGGGCCTGGAATGGGTTGCTTGGA
TTTCTCCTTATAGCGGTTATACTAACTATGCCGATAGCGTCAAGGGC
CGTTTCACTATAAGCGCAGACACATCCAAAAACACAGCCTACCTACA
AATGAACAGCTTAAGAGCTGAGGACACTGCCGTCTATTATTGTGCAA
GAGAGGCCCGCTCCTCGTTGAGCGCGGACTACGCTATGGACTACTGG
GGTCAA

SEQ ID NO: 69:
TTGTCCTGTGCAGCTTCTGGCTTCACCATTACTGATAATTATATACA
CTGGGTGCGTCAGGCCCCGGGTAAGGGCCTGGAATGGGTTGCTTGGA
TTTCTCCTTATAGCGGTTATACTTACTATGCCGATAGCGTCAAGGGC
CGTTTCACTATAAGCGCAGACACATCCAAAAACACAGCCTACCTACA
AATGAACAGCTTAAGAGCTGAGGACACTGCCGTCTATTATTGTGCTC
GTGAGTCCGGCTTCTCCGCGTGCAACACGCGGGCGTACGCTATGGAC
TACTGGGGTCAA

SEQ ID NO: 70:
TTGTCCTGTGCAGCTTCTGGCTTCACCATTACTGATTCTTGGATACA
CTGGGTGCGTCAGGCCCCGGGTAAGGGCCTGGAATGGGTTGGTTCTA
TTACTCCTTATAACGGTAATACTGACTATGCCGATAGCGTCAAGGGC
CGTTTCACTATAAGCGCAGACACATCCAAAAACACAGCCTACCTACA
AATGAACAGCTTAAGAGCTGAGGACACTGCCGTCTATTATTGTGCTC
GCAGGGGGGAGTCCGACGAGGCCTACCCCGCGGTTATGGACTACTGG
GGTCAA

SEQ ID NO: 71:
TTGTCCTGTGCAGCTTCTGGCTTCACCATTACTAGTACCGCTATACA
CTGGGTGCGTCAGGCCCCGGGTAAGGGCCTGGAATGGGTTGCTTGGA
TTACTCCTTATGACGGTTATACTGACTATGCCGATAGCGTCAAGGGC
CGTTTCACTATAAGCGCAGACACATCCAAAAACACAGCCTACCTACT
AATGAACAGCTTAAGAGCTGAGGACACTGCCGTCTATTATTGTGCTC
GTACGTGGTTCACGCTGGCCTCGGCTATGGAACTACTGGGGTCAA

SEQ ID NO: 72:
TTGTCCTGTGCAGCTTCTGGCTTCACCATTACTGGTAATGGGATACA
CTGGGTGCGTCAGGCCCCGGGTAAGGGCCTGGAATGGGTTGCTTGGA
TTTCTCCTACTAACGGTTCTACTTACTATGCCGATAGCGTCAAGGGC
CGTTTCACTATAAGCGCAGACACATCCAAAAACACAGCCTACCTACA
AATGAACAGCTTAAGAGCTGAGGACACTGCCGTCTATTATTGTGCTC
GTAGGGTCGACTACCAGGTCTACCACGACCGCTTCGAGGAGGGGTAC
GCTATGGACTACTGGGGTCAA

TABLE 7-continued

SEQ ID NO: 73:
TTGTCCTGTGCAGCTTCTGGCTTCACCATTAATAGTTATTGGATACA

CTGGGTGCGTCAGGCCCCGGGTAAGGGCCTGGAATGGGTTGGTTGGA

TTTCTCCTGATAACGGTGCTACTAACTATGCCGATAGCGTCAAGGGC

CGTTTCACTATAAGCGCAGACACATCCAAAAACACAGCCTACCTACA

AATGAACAGCTTAAGAGCTGAGGACACTGCCGTCTATTATTGTGCTC

GTAAGTTCTGGGGCTGGGACTGGGGGGTATGGACTACTGGGGTCAA

SEQ ID NO: 74:
TTGTCCTGTGCAGCTTCTGGCTTCACCATTAGTGATTCTTATATACA

CTGGGTGCGTCAGGCCCCGGGTAAGGGCCTGGAATGGGTTGGTGATA

TTACTCCTACTGACGGTTATACTGACTATGCCGATAGCGTCAAGGGC

CGTTTCACTATAAGCGCAGACACATCCAAAAACACAGCCTACCTACA

AATGAACAGCTTAAGAGCTGAGGACACTGCCGTCTATTATTGTGCTC

GTAACTTGATGTGGTGGGACTCGTCGGCTATGGACTACTGGGGTCAA

SEQ ID NO: 75:
TTGTCCTGTGCAGCTTCTGGCTTCACCATTAGTGATTCTGGGATACA

CTGGGTGCGTCAGGCCCCGGGTAAGGGCCTGGAATGGGTTGGTTTTA

TTTATCCTAATGGCGGTTCTACTTACTATGCCGATAGCGTCAAGGGC

CGTTTCACTATAAGCGCAGACACATCCAAAAACACAGCCTACCTACA

AATGAACAGCTTAAGAGCTGAGGACACTGCCGTCTATTATTGTGCTC

GTATGTCGTTGATCGGGTTCTCGTACGCTATGGACTACTGGGGTCAA

SEQ ID NO: 76:
TTGTCCTGTGCAGCTTCTGGCTTCACCATTAATAGTACCTGGATACA

CTGGGTGCGTCAGGCCCCGGGTAAGGGCCTGGAATGGGTTGCTTGGA

TTAATCCTTATAACGGTTCTACTTACTATGCCGATAGCGTCAAGGGC

CGTTTCACTATAAGCGCAGACACATCCAAAAACACAGCCTACCTACA

AATGAACAGCTTAAGAGCTGAGGACACTGCCGTCTATTATTGTGCAA

GAGACTTGTACGACTACGACATCGGCTTCGACTACTGGGGTCAA

Cell-Based Assays—IL-17A/F Induces the Production of IL-8 and IL-6

Figure 3A:
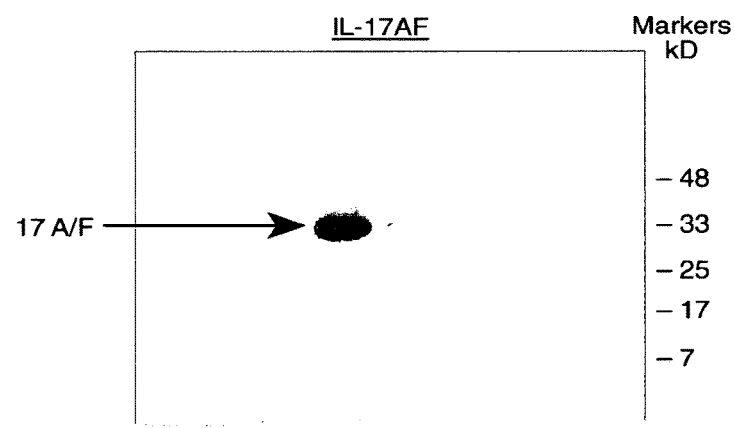
Figure 5A:
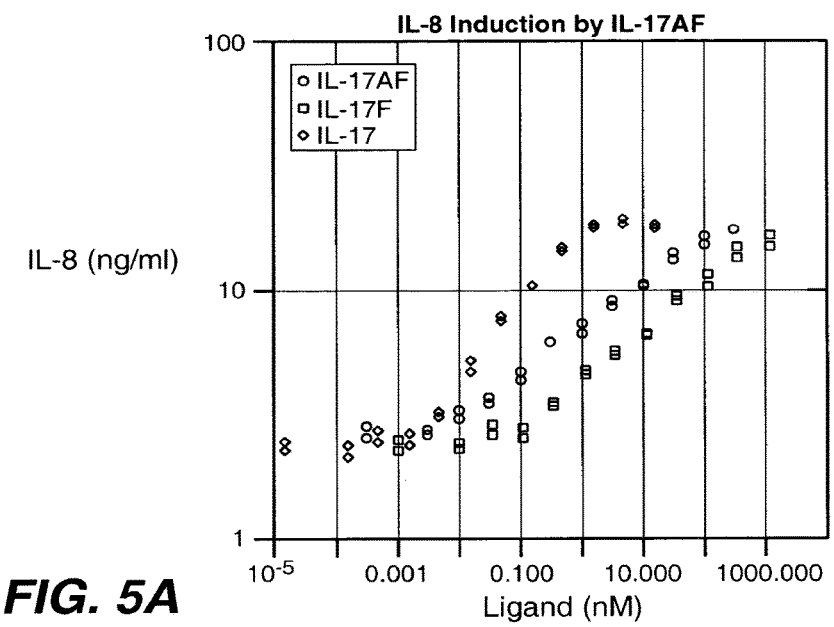
FIG. 5A shows the dose response curves comparing the proinflammatory response induced by IL-17A/F, IL-17 and IL-17F. IL-17A/F, IL-17 and IL-17F were incubated with TK-10 cells at the indicated concentrations for 24 hours. IL-17A/F was shown to have potent IL-8 inducing activity with substantial activity seen at sub-nM concentrations.
Figure 5B:
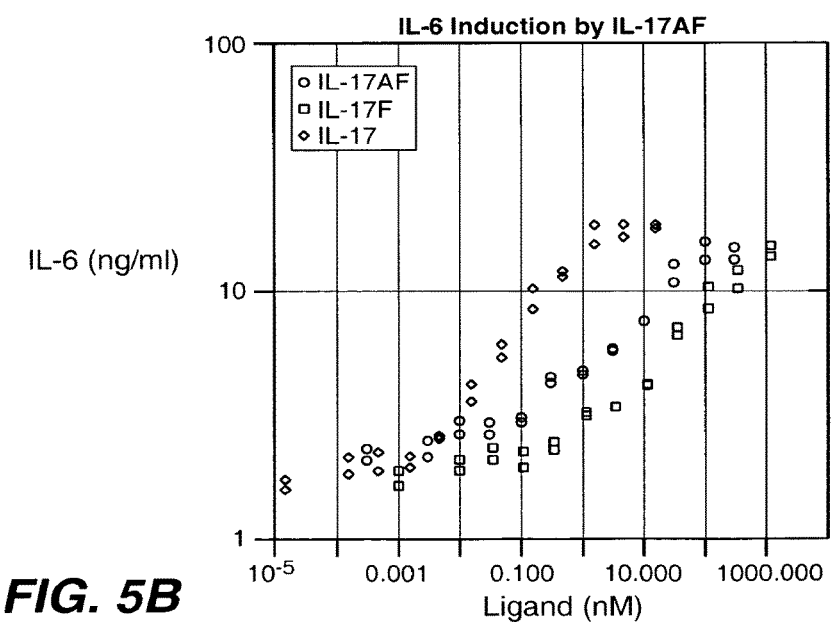
FIG. 5B shows the dose response curves comparing IL-6 induction by IL-17A/F, IL-17 and IL-17F. IL-17A/F, IL-17 and IL-17F were incubated with TK-I0 cells at the indicated concentrations for 24 hours. TK-I0 conditioned media was collected and analyzed by IL-6 ELISA.

Fractions isolated from the Vydac C4 purification step described above (FIG. 3A-3C) were assayed for the ability of IL-17A/F to induce the production of IL-8. Fractions were tested by incubation with TK-10 cells for 24 hours (0.033 microliters fraction/ml of cell culture media). Conditioned media was then collected and IL-8 and IL-6 concentration measurements were performed on each fraction by ELISA. Fraction 38 was found to have robust activity. Protein concentration of fraction 38 was found to be 0.536 mg/ml by amino acid analysis. Gels, blots, amino acid sequence and activity assays were run on this fraction (FIG. 3A-3C). Alternatively, fraction 31 and the remaining volume of fraction 32, from the HiLoad S Sepharose run were pooled and dialyzed against Buffer A for eight hours using a 10 kD cutoff membrane and passed through a 0.2 micron filter. This material was loaded on a Mono S column equilibrated in Buffer A at a flow rate of 1 ml/min and eluted with a three step gradient to 100% Buffer B (0-30% B over 10 column volumes, 30-75% B over 45 column volumes, 75-100% B over 10 column volumes) while collecting 1 ml/fraction. Fractions 26-43 were assayed and protein concentrations were determined by amino acid analysis. Pure IL-17A/F was identified in fractions 31-33 as a single protein with apparent molecular mass of 30-35 kD. The concentrations of fractions 31, 32 and 33 were 0.258, 0.359 and 0.291 mg/ml respectively. Gels and protein sequence analysis showed this material to be identical to IL-17A/F purified by C4 column (above). Dose response curves comparing IL-8 and IL-6 induction by IL-17A/F, IL-17 and IL-17F are shown in FIG. 5A-5B. IL-17A/F, IL-17 and IL-17F were incubated with TK-10 cells at the indicated concentrations for 24 hours. TK-10 conditioned media was collected and analyzed by IL-8 ELISA and IL-6 ELISA.

Discussion

Co-expression of mRNA for IL-17 and IL-17F leads to the secretion of a novel protein species that is able to bind with both certain antibodies that are capable of binding to IL-17 and certain antibodies that are capable of binding to IL-17F. This novel protein species is designated herein as interleukin-17A/F (IL-17A/F). This species is not observed when human kidney 293 cells are made to express either IL-17 or IL-17F in isolation. Conditioned media from transfected cells was immunoprecipitated (IP) utilizing antibodies that are able to recognize IL-17 (lanes 1-5) or IL-17F (lanes 6-10) as shown in FIG. 1A and FIG. 1B. Immunoprecipitated proteins were then resolved by Western blot analysis and blotted with antibodies to IL-17 (FIG. 1A) or IL-17F (FIG. 1B). Detection of IL-17A/F is indicated in lane 8 of FIG. 1A and in lane 3 of FIG. 1B by the presence of IL-17 in dimeric complex with IL-17F. The molecular mass of this species, as determined by non-reducing SDS-PAGE is approximately 30-35 kD, consistent with the species being comprised of one molecule of IL-17 and one molecule of IL-17F joined by covalent linkage. The existence of this new species (IL-17A/F) can also be recognized as protein of electrophoretic mobility that is distinct from that observed when either IL-17 or IL-17F is expressed in isolation. As such, this new species can also be visualized without the use of antibodies through the use of other protein detection methods such as conventional protein staining techniques.

The existence of a novel protein species produced by co-expression of IL-17 and IL-17F was also observed by resolving the secreted proteins present in conditioned media with reverse phase chromatography. Comparison of the protein fractions observed from the secreted proteins produced by cells co-expressing IL-17 and IL-17F with the patterns observed with cells producing either IL-17 or IL-17F revealed the presence of an additional protein species. This protein species. IL-17A/F, was purified and isolated to homogeneity by column chromatography (FIG. 2A-2G and FIG. 3A-3C).

Purified protein ran as a single band of approximately 30-35 kD as determined by non-reducing SDS-PAGE (FIG. 3A). However, under reducing conditions two clearly distinct bands were revealed with an apparent molecular mass of approximately 15-18 kD (not shown). Thus, IL-17A/F is a covalent dimer. An independent means of assessing the composition of the novel protein, N-terminal peptide sequence analysis, also clearly indicated that the isolated IL-17A/F contains both IL-17 and IL-17F peptides (FIG. 3B). The detected peptide sequences are identical to sequence contained within the N-terminal end of IL-17 and IL-17F (FIG. 3C). Western Blot analysis indicated that this novel protein species is also able to interact both with an antibody that is able to bind to IL-17 and with an antibody that is able to bind to IL-17F. Each of these observations and the distinct molecular mass of the novel isolated protein species suggest that the isolated protein IL-17A/F is a novel protein species comprised of a covalent association of IL-17 and IL-17F.

Figure 4D:
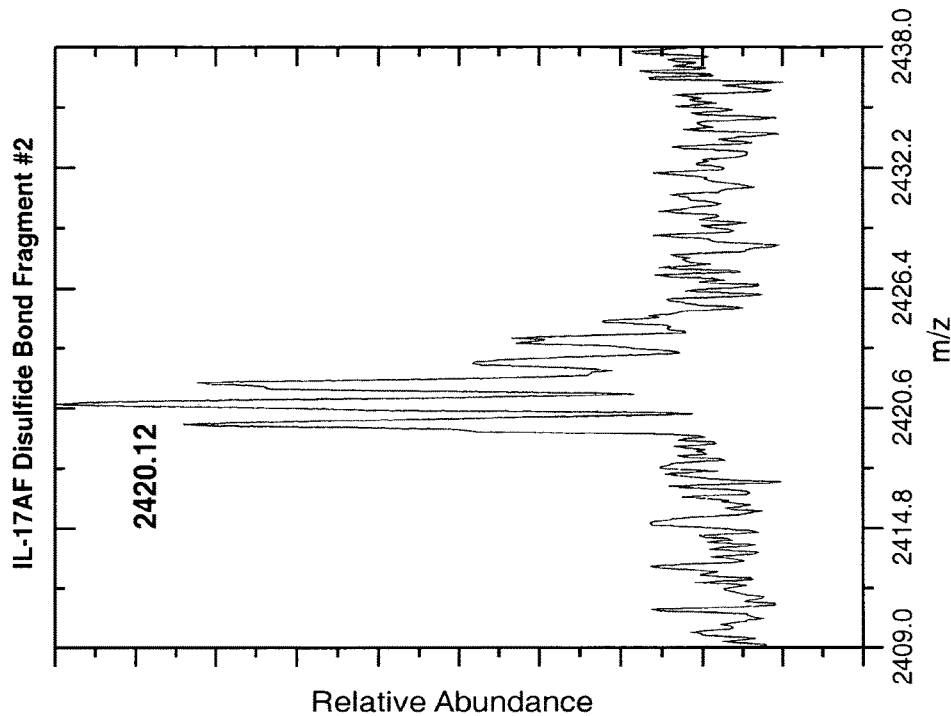
Figure 4C:
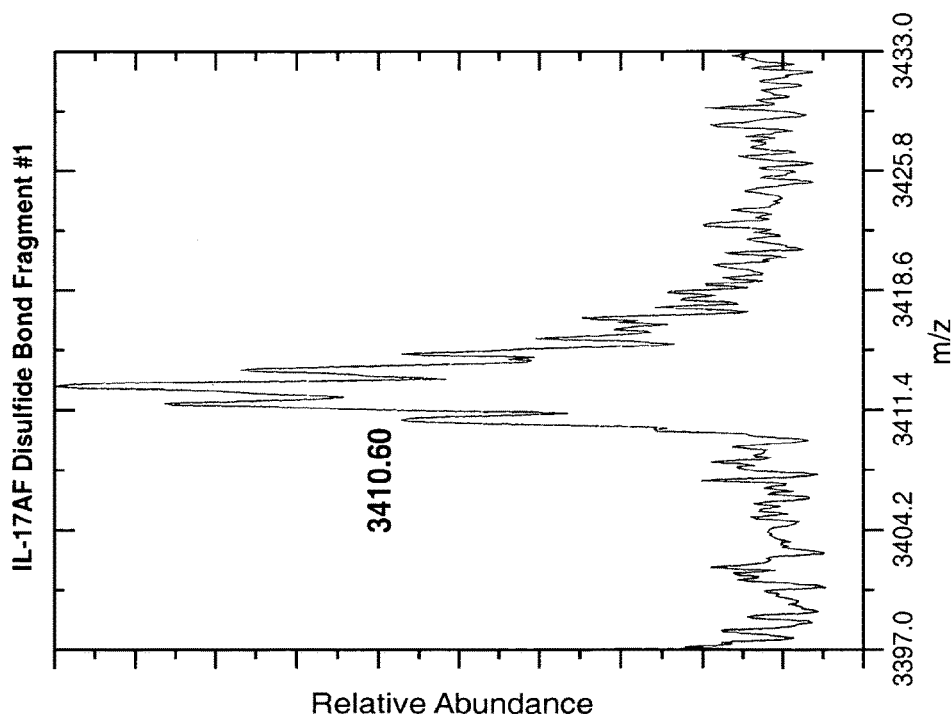
Figure 4E:
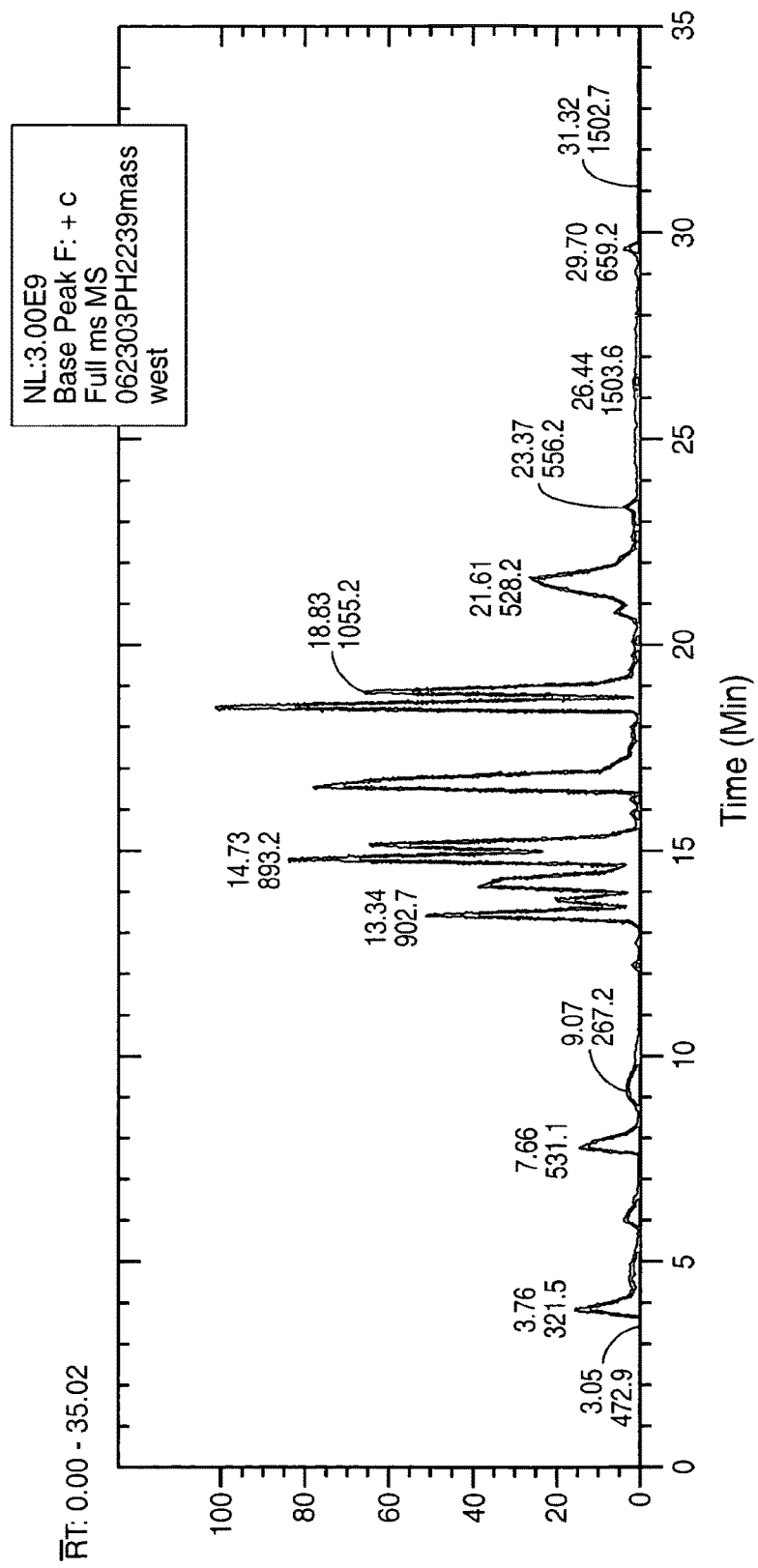
Figure 4F:
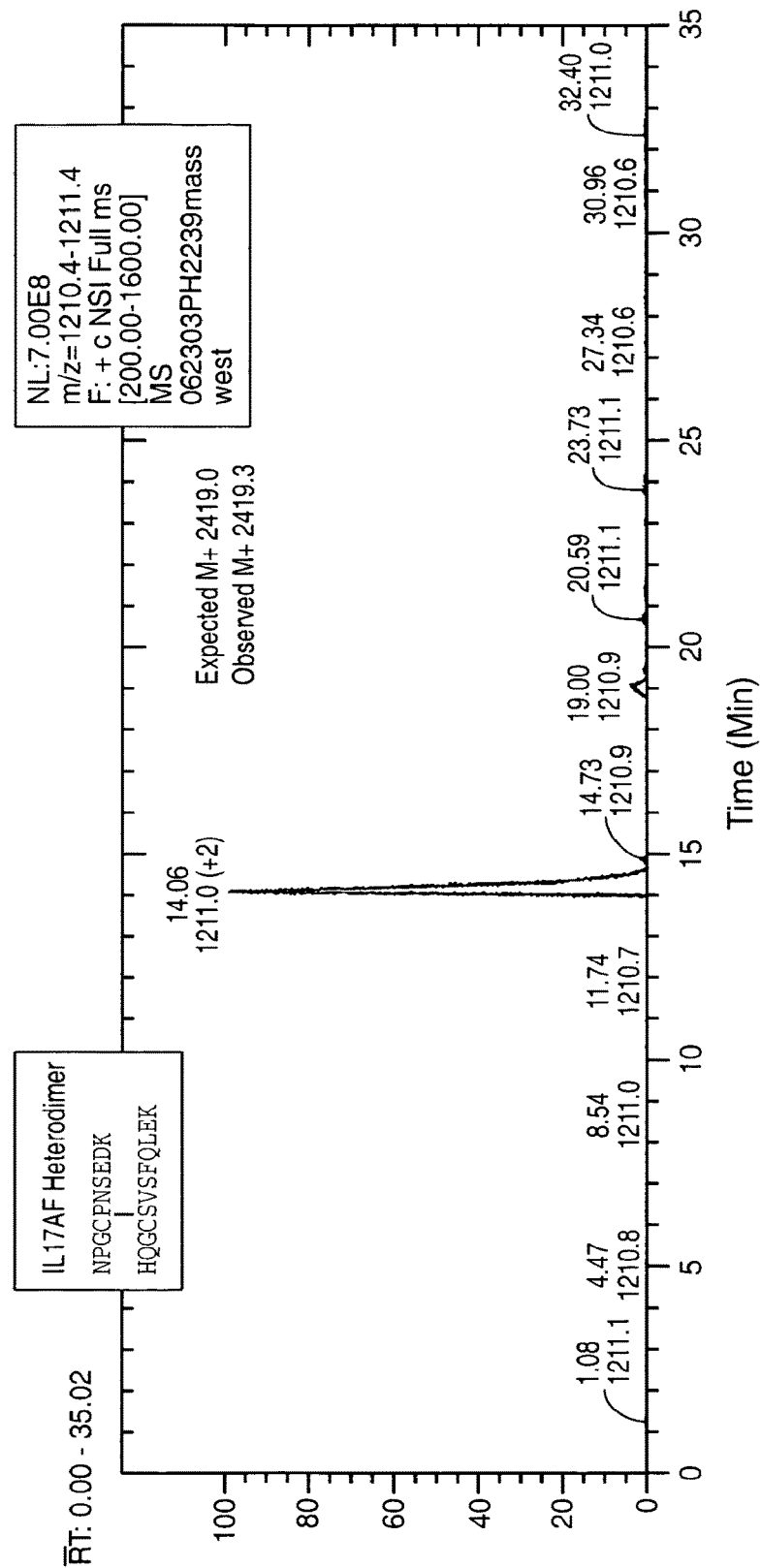
Figure 4G:
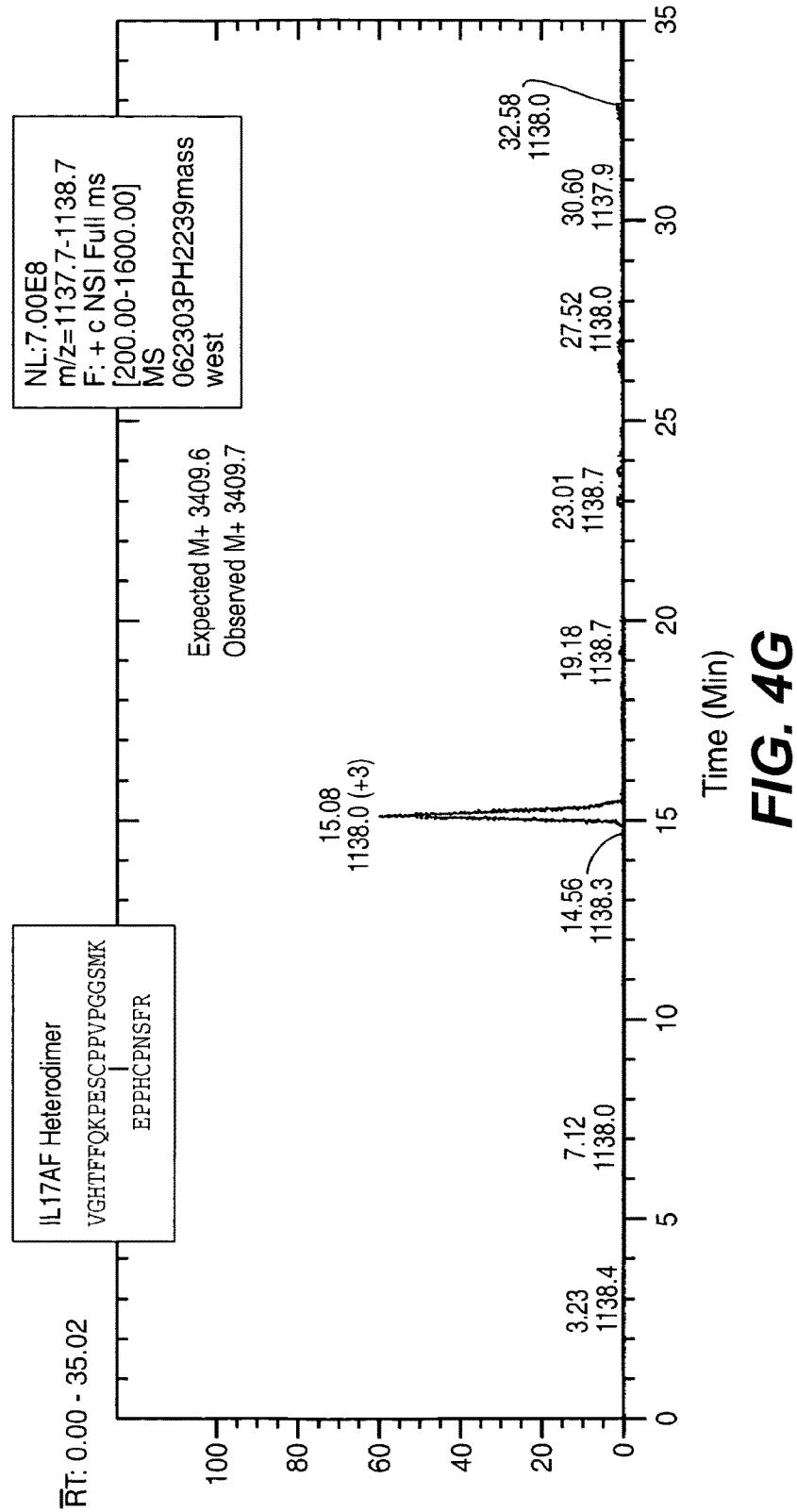

The existence and location of the disulfide bonds that link the IL-17 and IL-17F chains of IL-17A/F were further characterized by use of mass spectrometry. The position of disulfide linkages within IL-17A/F is shown in schematic FIG. 4A. Two interchain disulfide bonds link the IL-17 and IL-17F chains in IL-17A/F. Digestion of IL-17A/F with trypsin would be expected to produce two distinct peptide fragments containing the interchain disulfide bonds (IL-17A/F disulfide bond fragment #1 and #2; SEQ ID NOs:7 and 8, respectively. These peptides are shown schematically (FIG. 4B) together with the respective predicted molecular mass. These peptides were observed by Marix-assisted laser desorption/ionization time of flight mass spectrometry (MALDI-TOF) (4C-4D) and by liquid-chromatography electrospray ionization ion trap mass spectrometry (LC-ESI-MS) (4E-4G). Peptide peaks corresponding to homodimers of IL-17 or IL-17F were not detected, indicating that the purified IL-17A/F was comprised of covalent heterodimers of IL-17 and IL-17F chains and did not contain detectable levels of homodimers of either IL-17 or IL-17F.

In addition, antibodies which bind to IL-17A/F have been identified by screening a phage library of synthetic Fab antibodies. Thirty four (34) independent clones encoding distinct Fab antibody sequences were identified. Which were able to mediate binding to IL-17A/F. The amino acid sequence of the region of the variable domain of the heavy chains that contains the three (3) CDRs [H1-H3] from Fab that bind IL-17A/F are shown in FIG. 6. Shown is the alignment of a region of the predicted amino acid sequence of 34 Fab clones that encode distinct antibody heavy chain sequences that are able to bind to IL-17A/F. The three heavy chain CDR regions are indicated as CDR-H1, CDR-H2 and CDR-H3, respectively are highlighted in yellow. The corresponding amino acid sequences for each of the thirty four (34) clones are identified as SEQ ID NOs:9-42. In addition, the corresponding encoding DNA sequences for each of the identified thirty four (34) clones is shown in Table 7 below (SEQ ID NO:43 to SEQ ID NO:76, respectively). Thus, specific antibodies which bind selectively to the novel heterodimeric complex of IL-17A/F have been identified which may serve to modulate the activity of this novel cytokine.

IL-17A/F was analyzed for ability to stimulate a proinflammatory response using the TK-10 human kidney cell line (FIG. 5A-5B). This cell line responds to both IL-17 and IL-17F by production of IL-8. IL-17A/F also robustly induced IL-8 production in this cell line (FIG. 5A). Interestingly, IL-17A/F was observed to have a unique potency that differs from that of either IL-17 or IL-17F. The difference in activity differs from IL-17 and IL-17F by roughly an order of magnitude in each case. The substantially greater activity of IL-17A/F than IL-17F in this assay suggests that IL-17A/F may comprise a critical component of the cytokine activity resulting from the IL-17F gene product. This unique potency may enable the molecule to possess distinct range of actions in vivo. IL-17A/F also induced production of IL-6 from this cell line (FIG. 5B). Additionally, it is likely that IL-17A/F may possess additional characteristics not present in either IL-17 or IL-17F as a result of its novel heterodimeric composition that may alter the kinetics and utilization of receptor subunits in vivo, resulting in unique biological consequences.

Example 2

Identification of a Novel IL-17 Cytokine Produced in Activated Human T Cells

A novel human IL-17 cytokine (herein identified as human IL-17A/F) is herein described for the first time as being naturally produced in activated human T-lymphocyte cells. Isolation and activation of human T-lymphocyte cells was performed and IL-17A/F production was detected and quantitatively measured by IL-7A/F ELISA as demonstrated below:

Isolation and Activation of Human T-Cells

Heparinized (0.5 ml/50 cc) freshly-drawn human blood from a normal healthy donor was diluted 1:1 with physiological saline, then layered onto LSM Lymphcyte Separation Media (ICN) and centrifuged as recommended by the manufacturer (ICN). Recovered mononuclear lymphocytes were plated in tissue culture flasks in complete RPMI (RPMI, I0% FCS, 2 mM L-Glutamine, Penicillin/Streptomycin (GIBCO)), for one hour at 37 degrees C. to deplete monocytes. Culture supernates were centrifuged to pellet the remaining cells. Human T lymphocytes were then isolated by negative selection using a CD4+ T cell isolation kit (MACS). To activate the isolated T lymphocytes, tissue culture flasks were coated with 5 ug/ml each of anti-CD3 (BD Bioscience) and anti-CD28 (BD Bioscience) in PBS overnight at 4 degrees C. After removing the coat media, isolated human T lymphocytes were plated in complete RPMI at an approximate density of 2 million cells per milliliter of media. Samples of media were collected at various time points following plating and assayed for IL-17A/F by ELISA. Non-activated control supernates were collected from cell supernatants from flasks not coated with anti-CD3 and anti-CD28.

Figure 12:
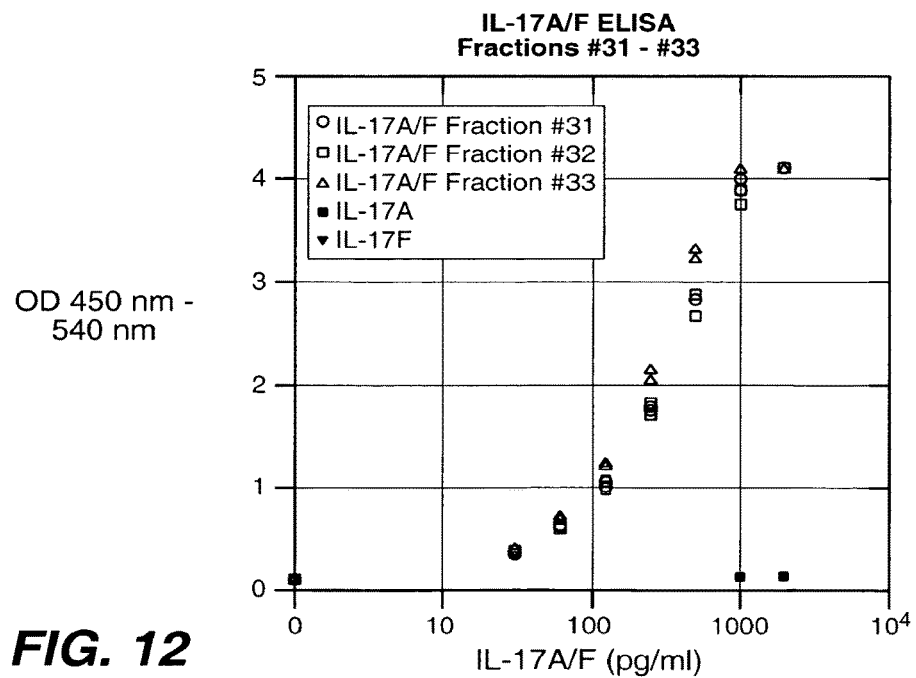
FIG. 12 shows the specificity of the IL-17A/F ELISA wherein three fractions #31-#33 assayed in parallel were shown to contain nearly equivalent quantities of IL-17A/F (IL-17A and IL-17F were used as controls).

ELISA Measurement of Human IL-17A/F Production in Anti-CD3/Anti-CD28 Activated Human T-Cells Human IL-17A/F levels were measured by ELISA. Mouse anti-human IL-17 was diluted in coat buffer (0.05 M sodium carbonate buffer, pH 9.6) and coated on 96-well microtiter plates (Nunc), for 12-15 hours at 2-8° C. All subsequent steps were performed at room temperature. Non-specific binding was blocked by emptying the wells and adding block buffer (PBS, 0.5% BSA, 10 ppm Proclin 300). After a 1-hour incubation, the wells were washed with wash buffer (PBS, 0.05% Tween 20, 10 ppm Proclin 300). Human IL-17A/F reference standards and samples, diluted in assay buffer (PBS, 0.5% BSA, 0.05% Tween 20, 10 ppm Proclin 300) were then added. Following a 2-hour incubation, the wells were washed with wash buffer. Biotinylated mouse anti-human IL-17F, diluted in assay buffer, was added and allowed to incubate for 1 hour. After washing the plates with wash buffer, Streptavidin-HRP (horseradish peroxidase) (Amersham), diluted in assay buffer, was added and allowed to incubate for 1 hour. After washing the plates with wash buffer, the substrate solution, TMB (tetra methyl benzidine)-Peroxidase (R & D Systems) was added. Color development was stopped by adding 2 N sulphuric acid. The plates were then read on a microtiter plate reader (SLT) at 450 nm with a subtracted blank at 540 nm. A four-parameter curve-fitting program was used to generate a standard curve, and sample concentrations were derived by interpolation from the linear portion of the curve. IL-17A and IL-17F were included as controls in the ELISA to illustrate the assay specificity for IL-17A/F (FIG. 12).

Figure 11:
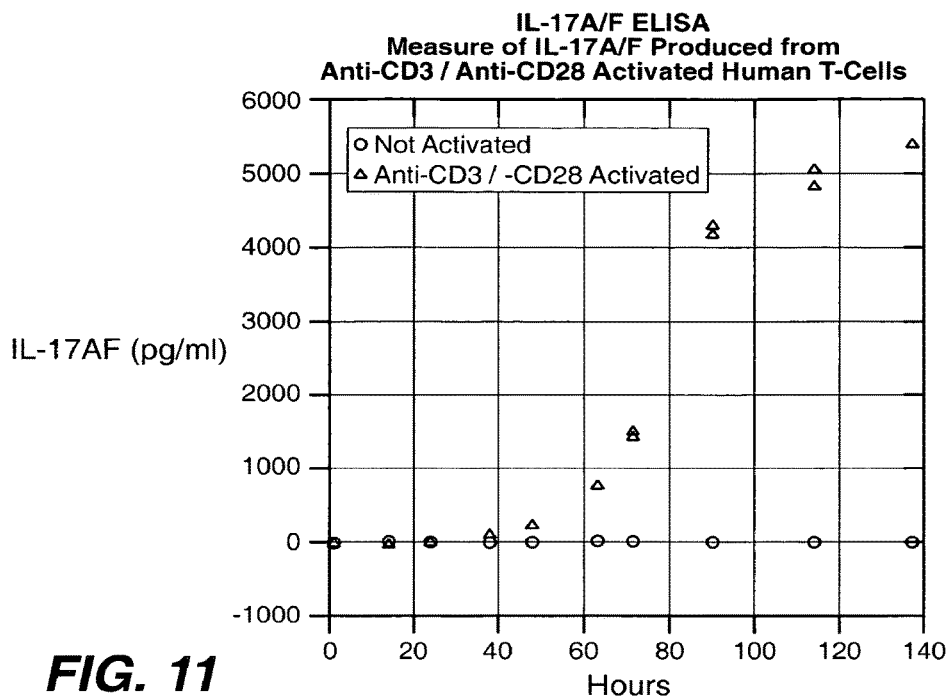
FIG. 11 shows IL-17A/F ELISA measurements of IL-17A/F produced from anti-CD3/anti-CD28 activated human T-cells.

Results:

The results of ELISA measurements of IL-17A/F production is shown in FIG. 11. These studies demonstrate the production of a novel cytokine IL-17A/F from anti-CD3/anti-CD28 activated human T lymphocyte cells compared to non-activated human T-cells wherein no production of IL-17A/F was detected. These results show for the first time the natural occurrence of a novel cytokine which is produced and released in response to the activation of human T lymphocytes. In addition, the specificity of the ELISA assay was demonstrated by observing nearly equivalent quantities of IL-17A/F in three samples (#31-33) when assayed in parallel. Negligible amounts of IL-17A or IL-17F were detected in this IL-17A/F specific ELISA (FIG. 12).

The studies described herein in both Example 1 and 2 establish that recombinant human IL-17A/F is a distinctly new cytokine, distinguishable from human IL-17 and IL-17F in both protein structure and in cell-based activity assays. Through the use of purified recombinant human IL-17A/F as a standard, a human IL-17AF-specific ELISA has been developed (shown in FIG. 11). Through the use of this specific ELISA, the induced expression of human IL-17A/F was detected, confirming that IL-17A/F is naturally produced from activated human T cells in culture. Hence, IL-17A/F is a distinctly new cytokine, detectable as a natural product of isolated activated human T cells, whose recombinant form has been characterized, in both protein structure and cell-based assays, as to be different and distinguishable from related cytokines.

This new cytokine can act to modulate the activity of IL-17 in vivo, acting as a competitive inhibitor to binding sites for IL-17 or other related cytokines. IL-17A/F can also modulate the activity of other related cytokines by down regulation of binding sites for itself and/or binding sites for other related cytokines. IL-17A/F can exhibit activity through intracellular adapters or signaling molecules which act to affect its own signaling activity or that of other related cytokines. IL-17A/F has the ability to affect the pairing of receptors and co-receptors found at the surface of cells or within the intracellular compartment.

Thus, these studies provide and identify a novel immune stimulant (i.e. IL-17A/F) that can boost the immune system to respond to a particular antigen that may not have been immunologically active previously. As such, the newly identified immune stimulant has important clinical applications. Other known immune stimulants such as IL-12 have been identified. [see Gubler et al. *PNAS*, 88, 4143 (1991)]. In a recent cancer vaccine trial, researchers from the University of Chicago and Genetics Institute (Cambridge, Mass.) have relyed upon the immune stimulatory activity of IL-12, for the treatment of melanoma. [Peterson et al. Journal of Clinical Oncology 21 (12). 2342-48 (2003)] They extracted circulating white blood cells carrying one or more markers of melanoma cells, isolated the antigen, and returned them to the patients. Normally patients would not have an immune response to his or her own human antigens. The patients were then treated with different doses of IL-12, an immune stimulant capable of inducing the proliferation of T cells that have been co-stimulated by dendritic cells. Due to the immune stimulatory effect of IL-12, the treatment provided superior results in comparison to earlier work, where patients' own dendritic cells were prepared from peripheral blood mononuclear cells (PBMCs), treated with antigens, then cultured in vitro and returned to the patient to stimulate anti-cancer response. [Thurner et al. J. Exp. Med. 190 (11), 1669-78 (1999)] Likewise, this novel IL-17A/F cytokine or agonists thereof, would therefore find practical utility as an immune stimulant. Whereas molecules which inhibit IL-17A/F activity (antagonists) would be expected to find practical utility when an inhibition of the immune response is desired, such as in autoimmune diseases.

Thus, antibodies to this new cytokine which either mimic (agonist antibodies) or inhibit (antagonist antibodies) the immunological activities of IL-17A/F would possess therapeutic qualities. Small molecules which act to inhibit the activity of this novel cytokine would also have potential therapeutic uses.

Example 3

Use of IL-17A/F as a Hybridization Probe

The following method describes use of a nucleotide sequence encoding IL-17A/F as a hybridization probe.

DNA comprising the coding sequence of full-length or mature IL-17A/F as disclosed herein is employed as a probe to screen for homologous DNAs (such as those encoding naturally-occurring variants of IL-17A/F) in human tissue cDNA libraries or human tissue genomic libraries.

Hybridization and washing of filters containing either library DNAs is performed under the following high stringency conditions. Hybridization of radiolabeled IL-17A/F-derived probe to the filters is performed in a solution of 50% formamide, 5×SSC, 0.1% SDS, 0.1% sodium pyrophosphate, 50 mM sodium phosphate, pH 6.8, 2×Denhardt's solution, and 10% dextran sulfate at 42° C. for 20 hours. Washing of the filters is performed in an aqueous solution of 0.1×SSC and 0.1% SDS at 42° C.

DNAs having a desired sequence identity with the DNA encoding full-length native sequence IL-17A/F can then be identified using standard techniques known in the art.

Example 4

Expression of IL-17A/F in *E. coli*

This example illustrates preparation of an unglycosylated form of IL-17A/F polypeptides by recombinant expression in *E. coli*.

The DNA sequence encoding an IL-17A/F polypeptide is initially amplified using selected PCR primers. The primers should contain restriction enzyme sites which correspond to the restriction enzyme sites on the selected expression vector. A variety of expression vectors may be employed. An example of a suitable vector is pBR322 (derived from *E. coli*; see Bolivar et al., *Gene*, 2:95 (1977)) which contains genes for ampicillin and tetracycline resistance. The vector is digested with restriction enzyme and dephosphorylated. The PCR amplified sequences are then ligated into the vector. The vector will preferably include sequences which encode for an antibiotic resistance gene, a trp promoter, a polyHis leader (including the first six STII codons, polyHis sequence, and enterokinase cleavage site), the IL-17A/F polypeptide coding region, lambda transcriptional terminator, and an argU gene.

The ligation mixture is then used to transform a selected *E. coli* strain using the methods described in Sambrook et al., supra. Transformants are identified by their ability to grow on LB plates and antibiotic resistant colonies are then selected. Plasmid DNA can be isolated and confirmed by restriction analysis and DNA sequencing.

Selected clones can be grown overnight in liquid culture medium such as LB broth supplemented with antibiotics. The overnight culture may subsequently be used to inoculate a larger scale culture. The cells are then grown to a desired optical density, during which the expression promoter is turned on.

After culturing the cells for several more hours, the cells can be harvested by centrifugation. The cell pellet obtained by the centrifugation can be solubilized using various agents known in the art, and the solubilized IL-17A/F protein can then be purified using a metal chelating column under conditions that allow tight binding of the protein.

IL-17A/F polypeptides may be expressed in *E. coli* in a poly-His tagged form, using the following procedure. The DNA encoding an IL-17A/F polypeptide is initially amplified using selected PCR primers. The primers will contain restriction enzyme sites which correspond to the restriction enzyme sites on the selected expression vector, and other useful sequences providing for efficient and reliable translation initiation, rapid purification on a metal chelation column, and proteolytic removal with enterokinase. The PCR-amplified, poly-His tagged sequences are then ligated into an expression vector, which is used to transform an *E. coli* host based on strain 52 (W3110 fuhA(tonA) lon galE rpoHts(htpRts) clpP(lacIq)). Transformants are first grown in LB containing 50 mg/ml carbenicillin at 30° C. with shaking until an O.D.600 of 3-5 is reached. Cultures are then diluted 50-100 fold into CRAP media (prepared by mixing 3.57 g $(NH_4)_2SO_4$, 0.71 g sodium citrate.2H2O, 1.07 g KCl, 5.36 g Difco yeast extract, 5.36 g Sheffield hycase SF in 500 mL water, as well as 110 mM MPOS, pH 7.3, 0.55% (w/v) glucose and 7 mM $MgSO_4$) and grown for approximately 20-30 hours at 30° C. with shaking. Samples are removed to verify expression by SDS-PAGE analysis, and the bulk culture is centrifuged to pellet the cells. Cell pellets are frozen until purification and refolding.

*E. coli* paste from 0.5 to 1 L fermentations (6-10 g pellets) is resuspended in 10 volumes (w/v) in 7 M guanidine, 20 mM Tris, pH 8 buffer. Solid sodium sulfite and sodium tetrathionate is added to make final concentrations of 0. M and 0.02 M, respectively, and the solution is stirred overnight at 4° C. This step results in a denatured protein with all cysteine residues blocked by sulfitolization. The solution is centrifuged at 40,000 rpm in a Beckman Ultracentrifuge for 30 min. The supernatant is diluted with 3-5 volumes of metal chelate column buffer (6 M guanidine, 20 mM Tris, pH 7.4) and filtered through 0.22 micron filters to clarify. The clarified extract is loaded onto a 5 ml Qiagen Ni-NTA metal chelate column equilibrated in the metal chelate column buffer. The column is washed with additional buffer containing 50 mM imidazole (Calbiochem, Utrol grade), pH 7.4. The protein is eluted with buffer containing 250 mM imidazole. Fractions containing the desired protein are pooled and stored at 4° C. Protein concentration is estimated by its absorbance at 280 nm using the calculated extinction coefficient based on its amino acid sequence.

The proteins are refolded by diluting the sample slowly into freshly prepared refolding buffer consisting of: 20 mM Tris, pH 8.6, 0.3 M NaCl, 2.5 M urea, 5 mM cysteine, 20 mM glycine and 1 mM EDTA. Refolding volumes are chosen so that the final protein concentration is between 50 to 100 micrograms/ml. The refolding solution is stirred gently at 4° C. for 12-36 hours. The refolding reaction is quenched by the addition of TFA to a final concentration of 0.4% (pH of approximately 3). Before further purification of the protein, the solution is filtered through a 0.22 micron filter and acetonitrile is added to 2-10% final concentration. The refolded protein is chromatographed on a Poros R1/H reversed phase column using a mobile buffer of 0.1% TFA with elution with a gradient of acetonitrile from 10 to 80% Aliquots of fractions with A280 absorbance are analyzed on SDS polyacrylamide gels and fractions containing homogeneous refolded protein are pooled. Generally, the properly refolded species of most proteins are eluted at the lowest concentrations of acetonitrile since those species are the most compact with their hydrophobic interiors shielded from interaction with the reversed phase resin. Aggregated species are usually eluted at higher acetonitrile concentrations. In addition to resolving misfolded forms of proteins from the desired form, the reversed phase step also removes endotoxin from the samples.

Fractions containing the desired folded IL-17A/F polypeptide are pooled and the acetonitrile removed using a gentle stream of nitrogen directed at the solution. Proteins are formulated into 20 mM Hepes, pH 6.8 with 0.14 M sodium chloride and 4% mannitol by dialysis or by gel filtration using G25 Superfine (Pharmacia) resins equilibrated in the formulation buffer and sterile filtered.

Example 5

Expression of IL-17A/F in Mammalian Cells

This example illustrates preparation of a potentially glycosylated form of IL-17A/F polypeptides by recombinant expression in mammalian cells.

The vector, pRK5 (see EP 307,247, published Mar. 15, 1989), is employed as the expression vector. Optionally, the IL-17A/F DNA is ligated into pRK5 with selected restriction enzymes to allow insertion of the IL-17A/F DNA using ligation methods such as described in Sambrook et al., supra. The resulting vector is called pRK5-IL-17A/F.

In one embodiment, the selected host cells may be 293 cells. Human 293 cells (ATCC CCL 1573) are grown to confluence in tissue culture plates in medium such as DMEM supplemented with fetal calf serum and optionally, nutrient components and/or antibiotics. About 10 μg pRK5-IL-17A/F DNA is mixed with about 1 μg DNA encoding the VA RNA gene [Thimmappaya et al., *Cell*, 31:543 (1982)] and dissolved in 500 μl of 1 mM Tris-HCl, 0.1 mM EDTA, 0.227 M $CaCl_2$. To this mixture is added, dropwise, 500 μl of 50 mM HEPES (pH 7.35), 280 mM NaCl, 1.5 mM $NaPO_4$, and a precipitate is allowed to form for 10 minutes at 25° C. The precipitate is suspended and added to the 293 cells and allowed to settle for about four hours at 37° C. The culture medium is aspirated off and 2 ml of 20% glycerol in PBS is added for 30 seconds. The 293 cells are then washed with serum free medium, fresh medium is added and the cells are incubated for about 5 days.

Approximately 24 hours after the transfections, the culture medium is removed and replaced with culture medium (alone) or culture medium containing 200 μCi/ml $^{35}$S-cysteine and 200 μCi/ml $^{35}$S-methionine. After a 12 hour incubation, the conditioned medium is collected, concentrated on a spin filter, and loaded onto a 15% SDS gel. The processed gel may be dried and exposed to film for a selected period of time to reveal the presence of the IL-17A/F polypeptide. The cultures containing transfected cells may undergo further incubation (in serum free medium) and the medium is tested in selected bioassays.

In an alternative technique, IL-17A/F may be introduced into 293 cells transiently using the dextran sulfate method described by Somparyrac et al., *Proc. Natl. Acad. Sci.*, 12:7575 (1981). 293 cells are grown to maximal density in a spinner flask and 700 μg pRK5-IL-17A/F DNA is added. The cells are first concentrated from the spinner flask by centrifugation and washed with PBS. The DNA-dextran precipitate is incubated on the cell pellet for four hours. The cells are treated with 20% glycerol for 90 seconds, washed with tissue culture medium, and re-introduced into the spinner flask containing tissue culture medium, 5 µg/ml bovine insulin and 0.1 µg/ml bovine transferrin. After about four days, the conditioned media is centrifuged and filtered to remove cells and debris. The sample containing the expressed IL-17A/F polypeptide can then be concentrated and purified by any selected method, such as dialysis and/or column chromatography.

In another embodiment, IL-17A/F polypeptides can be expressed in CHO cells. The pRK5-IL-17A/F can be transfected into CHO cells using known reagents such as $CaPO_4$ or DEAE-dextran. As described above, the cell cultures can be incubated, and the medium replaced with culture medium (alone) or medium containing a radiolabel such as $^{35}$S-methionine. After determining the presence of the IL-17A/F polypeptide, the culture medium may be replaced with serum free medium. Preferably, the cultures are incubated for about 6 days, and then the conditioned medium is harvested. The medium containing the expressed IL-17A/F polypeptide can then be concentrated and purified by any selected method.

Epitope-tagged IL-17A/F may also be expressed in host CHO cells. The IL-17A/F may be subcloned out of the pRK5 vector. The subclone insert can undergo PCR to fuse in frame with a selected epitope tag such as a poly-His tag into a Baculovirus expression vector. The poly-His tagged IL-17A/F insert can then be subcloned into a SV40 driven vector containing a selection marker such as DHFR for selection of stable clones. Finally, the CHO cells can be transfected (as described above) with the SV40 driven vector. Labeling may be performed, as described above, to verify expression. The culture medium containing the expressed poly-His tagged IL-17A/F can then be concentrated and purified by any selected method, such as by $Ni^{2+}$-chelate affinity chromatography.

IL-17A/F polypeptides may also be expressed in CHO and/or COS cells by a transient expression procedure or in CHO cells by another stable expression procedure.

Stable expression in CHO cells is performed using the following procedure. The proteins are expressed as an IgG construct (immunoadhesin), in which the coding sequences for the soluble forms (e.g., extracellular domains) of the respective proteins are fused to an IgG1 constant region sequence containing the hinge, CH2 and CH2 domains, and/or as a poly-His tagged form.

Following PCR amplification, the respective DNAs are subcloned in a CHO expression vector using standard techniques as described in Ausubel et al., *Current Protocols of Molecular Biology*, Unit 3.16, John Wiley and Sons (1997). CHO expression vectors are constructed to have compatible restriction sites 5' and 3' of the DNA of interest to allow the convenient shuttling of cDNA's. The vector used in expression in CHO cells is as described in Lucas et al., *Nucl. Acids Res.*, 24:9 (1774-1779 (1996), and uses the SV40 early promoter/enhancer to drive expression of the cDNA of interest and dihydrofolate reductase (DHFR). DHFR expression permits selection for stable maintenance of the plasmid following transfection.

Twelve micrograms of the desired plasmid DNA is introduced into approximately 10 million CHO cells using commercially available transfection reagents Superfect® (Qiagen), Dosper® or Fugene® (Boehringer Mannheim). The cells are grown as described in Lucas et al., supra. Approximately $3\times10^7$ cells are frozen in an ampule for further growth and production as described below.

The ampules containing the plasmid DNA are thawed by placement into water bath and mixed by vortexing. The contents are pipetted into a centrifuge tube containing 10 mLs of media and centrifuged at 1000 rpm for 5 minutes. The supernatant is aspirated and the cells are resuspended in 10 mL of selective media (0.2 µm filtered PS20 with 5% 0.2 µm diafiltered fetal bovine serum). The cells are then aliquoted into a 100 mL spinner containing 90 mL of selective media. After 1-2 days, the cells are transferred into a 250 mL spinner filled with 150 mL selective growth medium and incubated at 37° C. After another 2-3 days, 250 mL, 500 mL and 2000 mL spinners are seeded with $3\times10^5$ cells/mL. The cell media is exchanged with fresh media by centrifugation and resuspension in production medium. Although any suitable CHO media may be employed, a production medium described in U.S. Pat. No. 5,122,469, issued Jun. 16, 1992 may actually be used. A 3 L production spinner is seeded at $1.2\times10^6$ cells/mL. On day 0, the cell number pH ie determined. On day 1, the spinner is sampled and sparging with filtered air is commenced. On day 2, the spinner is sampled, the temperature shifted to 33° C., and 30 mL of 500 g/L glucose and 0.6 mL of 10% antifoam (e.g., 35% polydimethylsiloxane emulsion, Dow Corning 365 Medical Grade Emulsion) taken. Throughout the production, the pH is adjusted as necessary to keep it at around 7.2. After 10 days, or until the viability dropped below 70%, the cell culture is harvested by centrifugation and filtering through a 0.22 µm filter. The filtrate was either stored at 4° C. or immediately loaded onto columns for purification.

For the poly-His tagged constructs, the proteins are purified using a Ni-NTA column (Qiagen). Before purification, imidazole is added to the conditioned media to a concentration of 5 mM. The conditioned media is pumped onto a 6 ml Ni-NTA column equilibrated in 20 mM Hepes, pH 7.4, buffer containing 0.3 M NaCl and 5 mM imidazole at a flow rate of 4-5 ml/min. at 4° C. After loading, the column is washed with additional equilibration buffer and the protein eluted with equilibration buffer containing 0.25 M imidazole. The highly purified protein is subsequently desalted into a storage buffer containing 10 mM Hepes, 0.14 M NaCl and 4% mannitol, pH 6.8, with a 25 ml G25 Superfine (Pharmacia) column and stored at −80° C.

Immunoadhesin (Fc-containing) constructs are purified from the conditioned media as follows. The conditioned medium is pumped onto a 5 ml Protein A column (Pharmacia) which had been equilibrated in 20 mM Na phosphate buffer, pH 6.8. After loading, the column is washed extensively with equilibration buffer before elution with 100 mM citric acid, pH 3.5. The eluted protein is immediately neutralized by collecting 1 ml fractions into tubes containing 275 µL of 1 M Tris buffer, pH 9. The highly purified protein is subsequently desalted into storage buffer as described above for the poly-His tagged proteins. The homogeneity is assessed by SDS polyacrylamide gels and by N-terminal amino acid sequencing by Edman degradation.

Example 6

Expression of IL-17A/F in Yeast

The following method describes recombinant expression of IL-17A/F polypeptides in yeast.

First, yeast expression vectors are constructed for intracellular production or secretion of IL-17A/F from the ADH2/GAPDH promoter. DNA encoding the IL-17A/F polypeptide and the promoter is inserted into suitable restriction enzyme sites in the selected plasmid to direct intracellular expression of the IL-17A/F polypeptide. For secretion, DNA encoding IL-17A/F can be cloned into the selected plasmid, together with DNA encoding the ADH2/GAPDH promoter, a native IL-17A/F signal peptide or other mammalian signal peptide, or, for example, a yeast alpha-factor or invertase secretory signal/leader sequence, and linker sequences (if needed) for expression of IL-17A/F.

Yeast cells, such as yeast strain AB110, can then be transformed with the expression plasmids described above and cultured in selected fermentation media. The transformed yeast supernatants can be analyzed by precipitation with 10% trichloroacetic acid and separation by SDS-PAGE, followed by staining of the gels with Coomassie Blue stain.

Recombinant IL-17A/F polypeptides can subsequently be isolated and purified by removing the yeast cells from the fermentation medium by centrifugation and then concentrating the medium using selected cartridge filters. The concentrate containing the IL-17A/F polypeptide may further be purified using selected column chromatography resins.

Example 7

Expression of IL-17A/F in Baculovirus-Infected Insect Cells

The following method describes recombinant expression of IL-17A/F polypeptides in Baculovirus-infected insect cells.

The sequence coding for IL-17A/F is fused upstream of an epitope tag contained within a Baculovirus expression vector. Such epitope tags include poly-His tags and immunoglobulin tags (like Fc regions of IgG). A variety of plasmids may be employed, including plasmids derived from commercially available plasmids such as pVL1393 (Novagen). Briefly, the sequence encoding IL-17A/F or the desired portion of the coding sequence of IL-17A/F such as the sequence encoding the extracellular domain of a transmembrane protein or the sequence encoding the mature protein if the protein is extracellular is amplified by PCR with primers complementary to the 5' and 3' regions. The 5' primer may incorporate flanking (selected) restriction enzyme sites. The product is then digested with those selected restriction enzymes and subcloned into the expression vector.

Recombinant baculovirus is generated by co-transfecting the above plasmid and BaculoGold™ virus DNA (Pharmingen) into *Spodoptera frugiperda* ("Sf9") cells (ATCC CRL 1711) using lipofectin (commercially available from GIBCO-BRL). After 4-5 days of incubation at 28° C., the released viruses are harvested and used for further amplifications. Viral infection and protein expression are performed as described by O'Reilley et al., *Baculovirus expression vectors: A Laboratory Manual*, Oxford: Oxford University Press (1994).

Expressed poly-His tagged IL-17A/F can then be purified, for example, by $Ni^{2+}$-chelate affinity chromatography as follows. Extracts are prepared from recombinant virus-infected Sf9 cells as described by Rupert et al., *Nature*, 362:175-179 (1993). Briefly. Sf9 cells are washed, resuspended in sonication buffer (25 mL Hepes, pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate, 300 mM NaCl, 10% glycerol, pH 7.8) and filtered through a 0.45 µm filter. A $Ni^{2+}$-NTA agarose column (commercially available from Qiagen) is prepared with a bed volume of 5 mL, washed with 25 mL of water and equilibrated with 25 mL of loading buffer. The filtered cell extract is loaded onto the column at 0.5 mL per minute. The column is washed to baseline $A_{280}$ with loading buffer, at which point fraction collection is started. Next, the column is washed with a secondary wash buffer (50 mM phosphate; 300 mM NaCl, 10% glycerol, pH 6.0), which elutes nonspecifically bound protein. After reaching $A_{280}$ baseline again, the column is developed with a 0 to 500 mM Imidazole gradient in the secondary wash buffer. One mL fractions are collected and analyzed by SDS-PAGE and silver staining or Western blot with $Ni^{2+}$-NTA-conjugated to alkaline phosphatase (Qiagen). Fractions containing the eluted $His_{10}$-tagged IL-17A/F are pooled and dialyzed against loading buffer.

Alternatively, purification of the IgG tagged (or Fc tagged) IL-17A/F can be performed using known chromatography techniques, including for instance, Protein A or Protein G column chromatography.

Example 8

Preparation of Antibodies that Bind IL-17A/F

This example illustrates preparation of monoclonal antibodies which can specifically bind IL-17A/F.

Techniques for producing the monoclonal antibodies are known in the art and are described, for instance, in Goding, supra. Immunogens that may be employed include purified IL-17A/F polypeptides, fusion proteins containing IL-17A/F polypeptides, and cells expressing recombinant IL-17A/F polypeptides on the cell surface. Selection of the immunogen can be made by the skilled artisan without undue experimentation.

Mice, such as BALB/c, are immunized with the IL-17A/F immunogen emulsified in complete Freund's adjuvant and injected subcutaneously or intraperitoneally in an amount from 1-100 micrograms. Alternatively, the immunogen is emulsified in MPL-TDM adjuvant (Ribi Immunochemical Research, Hamilton, Mont.) and injected into the animal's hind foot pads. The immunized mice are then boosted 10 to 12 days later with additional immunogen emulsified in the selected adjuvant. Thereafter, for several weeks, the mice may also be boosted with additional immunization injections. Serum samples may be periodically obtained from the mice by retro-orbital bleeding for testing in ELISA assays to detect anti-IL-17A/F antibodies.

After a suitable antibody titer has been detected, the animals "positive" for antibodies can be injected with a final intravenous injection of IL-17A/F. Three to four days later, the mice are sacrificed and the spleen cells are harvested. The spleen cells are then fused (using 35% polyethylene glycol) to a selected murine myeloma cell line such as P3X63AgU.1, available from ATCC, No. CRL 1597. The fusions generate hybridoma cells which can then be plated in 96 well tissue culture plates containing HAT (hypoxanthine, aminopterin, and thymidine) medium to inhibit proliferation of non-fused cells, myeloma hybrids, and spleen cell hybrids.

The hybridoma cells will be screened in an ELISA for reactivity against IL-17A/F. Determination of "positive" hybridoma cells secreting the desired monoclonal antibodies against IL-17A/F is within the skill in the art.

The positive hybridoma cells can be injected intraperitoneally into syngeneic BALB/c mice to produce ascites containing the anti-IL-17A/F monoclonal antibodies. Alternatively, the hybridoma cells can be grown in tissue culture flasks or roller bottles. Purification of the monoclonal antibodies produced in the ascites can be accomplished using ammonium sulfate precipitation, followed by gel exclusion chromatography. Alternatively, affinity chromatography based upon binding of antibody to protein A or protein G can be employed.

Example 9

Purification of IL-17A/F Polypeptides Using Specific Antibodies

Native or recombinant IL-17A/F polypeptides may be purified by a variety of standard techniques in the art of protein purification. For example, pro-IL-17A/F polypeptide, mature IL-17A/F polypeptide, or pre-IL-17A/F polypeptide is purified by immunoaffinity chromatography using antibodies specific for the IL-17A/F polypeptide of interest. In general, an immunoaffinity column is constructed by covalently coupling the anti-IL-17A/F polypeptide antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, monoclonal antibodies are prepared from mouse ascites fluid by ammonium sulfate precipitation or chromatography on immobilized Protein A. Partially purified immunoglobulin is covalently attached to a chromatographic resin such as CnBr-activated SEPHAROSE™ (Pharmacia LKB Biotechnology). The antibody is coupled to the resin, the resin is blocked, and the derivative resin is washed according to the manufacturer's instructions.

Such an immunoaffinity column is utilized in the purification of IL-17A/F polypeptide by preparing a fraction from cells containing IL-17A/F polypeptide in a soluble form. This preparation is derived by solubilization of the whole cell or of a subcellular fraction obtained via differential centrifugation by the addition of detergent or by other methods well known in the art. Alternatively, soluble IL-17A/F polypeptide containing a signal sequence may be secreted in useful quantity into the medium in which the cells are grown.

A soluble IL-17A/F polypeptide-containing preparation is passed over the immunoaffinity column, and the column is washed under conditions that allow the preferential absorbance of IL-17A/F polypeptide (e.g., high ionic strength buffers in the presence of detergent). Then, the column is eluted under conditions that disrupt antibody/IL-17A/F polypeptide binding (e.g., a low pH buffer such as approximately pH 2-3, or a high concentration of a chaotrope such as urea or thiocyanate ion), and IL-17A/F polypeptide is collected.

Example 10

Drug Screening

This invention is particularly useful for screening compounds by using IL-17A/F polypeptides or binding fragment thereof in any of a variety of drug screening techniques. The IL-17A/F polypeptide or fragment employed in such a test may either be free in solution, affixed to a solid support, borne on a cell surface, or located intracellularly. One method of drug screening utilizes eukaryotic or prokaryotic host cells which are stably transformed with recombinant nucleic acids expressing the IL-17A/F polypeptide or fragment. Drugs are screened against such transformed cells in competitive binding assays. Such cells, either in viable or fixed form, can be used for standard binding assays. One may measure, for example, the formation of complexes between IL-17A/F polypeptide or a fragment and the agent being tested. Alternatively, one can examine the diminution in complex formation between the IL-17A/F polypeptide and its target cell or target receptors caused by the agent being tested.

Thus, the present invention provides methods of screening for drugs or any other agents which can affect an IL-17A/F polypeptide-associated disease or disorder. These methods comprise contacting such an agent with an IL-17A/F polypeptide or fragment thereof and assaying (i) for the presence of a complex between the agent and the IL-17A/F polypeptide or fragment, or (ii) for the presence of a complex between the IL-17A/F polypeptide or fragment and the cell, by methods well known in the art. In such competitive binding assays, the IL-17A/F polypeptide or fragment is typically labeled. After suitable incubation, free IL-17A/F polypeptide or fragment is separated from that present in bound form, and the amount of free or uncomplexed label is a measure of the ability of the particular agent to bind to IL-17A/F polypeptide or to interfere with the IL-17A/F polypeptide/cell complex.

Another technique for drug screening provides high throughput screening for compounds having suitable binding affinity to a polypeptide and is described in detail in WO 84/03564, published on Sep. 13, 1984. Briefly stated, large numbers of different small peptide test compounds are synthesized on a solid substrate, such as plastic pins or some other surface. As applied to an IL-17A/F polypeptide, the peptide test compounds are reacted with IL-17A/F polypeptide and washed. Bound IL-17A/F polypeptide is detected by methods well known in the art. Purified IL-17A/F polypeptide can also be coated directly onto plates for use in the aforementioned drug screening techniques. In addition, non-neutralizing antibodies can be used to capture the peptide and immobilize it on the solid support.

This invention also contemplates the use of competitive drug screening assays in which neutralizing antibodies capable of binding IL-17A/F polypeptide specifically compete with a test compound for binding to IL-17A/F polypeptide or fragments thereof. In this manner, the antibodies can be used to detect the presence of any peptide which shares one or more antigenic determinants with IL-17A/F polypeptide.

Example 11

Rational Drug Design

The goal of rational drug design is to produce structural analogs of biologically active polypeptide of interest (i.e., an IL-17A/F polypeptide) or of small molecules with which they interact, e.g., agonists, antagonists, or inhibitors. Any of these examples can be used to fashion drugs which are more active or stable forms of the IL-17A/F polypeptide or which enhance or interfere with the function of the IL-17A/F polypeptide in vivo (c.f. Hodgson, *Bio/Technology,* 9: 19-21 (1991)).

In one approach, the three-dimensional structure of the IL-17A/F polypeptide, or of an IL-17A/F polypeptide-inhibitor complex, is determined by x-ray crystallography, by computer modeling or, most typically, by a combination of the two approaches. Both the shape and charges of the IL-17A/F polypeptide must be ascertained to elucidate the structure and to determine active site(s) of the molecule. Less often, useful information regarding the structure of the IL-17A/F polypeptide may be gained by modeling based on the structure of homologous proteins. In both cases, relevant structural information is used to design analogous IL-17A/F polypeptide-like molecules or to identify efficient inhibitors. Useful examples of rational drug design may include molecules which have improved activity or stability as shown by Braxton and Wells, *Biochemistry,* 31:7796-7801 (1992) or which act as inhibitors, agonists, or antagonists of native peptides as shown by Athauda et al., *J. Biochem.,* 113:742-746 (1993).

It is also possible to isolate a target-specific antibody, selected by functional assay, as described above, and then to solve its crystal structure. This approach, in principle, yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced peptides. The isolated peptides would then act as the pharmacore.

By virtue of the present invention, sufficient amounts of the IL-7A/F polypeptide may be made available to perform such analytical studies as X-ray crystallography. In addition, knowledge of the IL-17A/F polypeptide amino acid sequence provided herein will provide guidance to those employing computer modeling techniques in place of or in addition to x-ray crystallography.

What is claimed is:

1. An isolated humanized monoclonal antibody that binds to an IL-17A/IL-17F heterodimer comprising the polypeptide of SEQ ID NO: 3 and the polypeptide of SEQ ID NO: 4 with or without their associated signal peptides.

2. The isolated antibody of claim 1, wherein said antibody is an antigen-binding fragment or a single-chain antibody.

3. The isolated antibody of claim 2, wherein the antigen-binding antibody fragment is an Fab, Fab', F(ab')$_2$, or Fv fragment.

4. The isolated antibody of claim 1, wherein the antibody is an IgG isotype.

5. The isolated antibody of claim 4, wherein the antibody is an IgG1, IgG2 or IgG4 isotype.

6. The isolated antibody of claim 1, which is labeled and is immobilized on a solid support.

7. A pharmaceutical composition comprising the isolated antibody of claim 1.

* * * * *

(12) POST-GRANT REVIEW CERTIFICATE (178th)

United States Patent
Arnott et al.

(10) Number: US 10,011,654 J1
(45) Certificate Issued: May 17, 2021

(54) ANTIBODIES DIRECTED TO IL-17A/IL-17F HETERODIMERS

(71) Applicant: GENENTECH, INC.

(72) Inventors: David P. Arnott; Austin L. Gurney; Philip E. Hass; James M. Lee; Yan Wu

(73) Assignee: Genentech, Inc.

Trial Numbers:

PGR2019-00044 filed Apr. 1, 2019
PGR2019-00043 filed Apr. 2, 2019

Post-Grant Review Certificate for:

Patent No.: 10,011,654
Issued: Jul. 3, 2018
Appl. No.: 14/491,641
Filed: Sep. 19, 2014

The results of PGR2019-00044 and PGR2019-00043 are reflected in this post-grant review certificate under 35 U.S.C. 328(b).

POST-GRANT REVIEW CERTIFICATE
U.S. Patent 10,011,654 J1
Trial No. PGR2019-00044
Certificate Issued May 17, 2021

AS A RESULT OF THE POST-GRANT REVIEW PROCEEDING, IT HAS BEEN DETERMINED THAT:

Claims 1-7 are cancelled.

\* \* \* \* \*